(12) United States Patent
Aissaoui et al.

(10) Patent No.: US 9,242,970 B2
(45) Date of Patent: Jan. 26, 2016

(54) LACTAM DERIVATIVES USEFUL AS OREXIN RECEPTOR ANTAGONISTS

(75) Inventors: Hamed Aissaoui, Pulversheim (FR);
Christoph Boss, Allschwil (CH);
Christine Brotschi, Allschwil (CH);
Bibia Heidmann, Altkirch (FR);
Thierry Sifferlen, Wentzwiller (FR);
Jodi T. Williams, Basel (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 304 days.

(21) Appl. No.: 13/884,741

(22) PCT Filed: Nov. 9, 2011

(86) PCT No.: PCT/IB2011/054993
§ 371 (c)(1),
(2), (4) Date: May 10, 2013

(87) PCT Pub. No.: WO2012/063207
PCT Pub. Date: May 18, 2012

(65) Prior Publication Data
US 2013/0237525 A1    Sep. 12, 2013

(30) Foreign Application Priority Data
Nov. 10, 2010    (WO) .................. PCT/IB2010/055105

(51) Int. Cl.
*A61K 31/365*    (2006.01)
*C07D 413/10*    (2006.01)
*C07D 207/26*    (2006.01)
*C07D 207/273*    (2006.01)
*C07D 211/76*    (2006.01)
*C07D 215/08*    (2006.01)
*C07D 215/14*    (2006.01)
*C07D 223/10*    (2006.01)
*C07D 241/06*    (2006.01)
*C07D 401/06*    (2006.01)
*C07D 401/10*    (2006.01)
*C07D 401/14*    (2006.01)
*C07D 405/06*    (2006.01)
*C07D 405/14*    (2006.01)
*C07D 407/04*    (2006.01)
*C07D 409/06*    (2006.01)
*C07D 413/06*    (2006.01)
*C07D 417/06*    (2006.01)
*C07D 417/10*    (2006.01)
*C07D 417/14*    (2006.01)

(52) U.S. Cl.
CPC ............ *C07D 413/10* (2013.01); *A61K 31/365* (2013.01); *C07D 207/26* (2013.01); *C07D 207/273* (2013.01); *C07D 211/76* (2013.01); *C07D 215/08* (2013.01); *C07D 215/14* (2013.01); *C07D 223/10* (2013.01); *C07D 241/06* (2013.01); *C07D 401/06* (2013.01); *C07D 401/10* (2013.01); *C07D 401/14* (2013.01); *C07D 405/06* (2013.01); *C07D 405/14* (2013.01); *C07D 407/04* (2013.01); *C07D 409/06* (2013.01); *C07D 413/06* (2013.01); *C07D 417/06* (2013.01); *C07D 417/10* (2013.01); *C07D 417/14* (2013.01)

(58) Field of Classification Search
CPC .................................................... A61K 31/365
See application file for complete search history.

(56) References Cited

U.S. PATENT DOCUMENTS

| | | | |
|---|---|---|---|
| 7,763,638 B2 | 7/2010 | Aissaoui et al. | |
| 8,329,706 B2 | 12/2012 | Aissaoui et al. | |
| 2009/0082394 A1 | 3/2009 | Jenck | |
| 2010/0234420 A1 | 9/2010 | Jenck | |
| 2012/0088759 A1 | 4/2012 | Aissaoui et al. | |

OTHER PUBLICATIONS

Denhez, C. et al., "Asymmetric Synthesis of Di- and Trisubstituted Pyrrolidinones via Zirconium-Mediated Intramolecular Coupling of N-3-Alkenyl Carbamates", Tetrahedron: Asymmetry, vol. 18, pp. 424-434, (2007).
Oudir, Souhila et al., "A Convenient Method for the Conversion of a Carboxy Group into a 4,6-Di-methoxy-1,3,5-triazine Group: Application to N-Benzylpyroglutamic Acids", Synthesis, No. 17, pp. 2845-2848, (2006).
Sakurai, T. et al., "Orexins and Orexin Receptors: A Family of Hypothalamic Neuropeptides and G Protein-Coupled Receptors that Regulate Feeding Behavior", Cell. vol. 92, pp. 573-585, (Feb. 20, 1998).
Chemelli, R.M. et al., "Narcolepsy in Orexin Knockout Mice: Molecular Genetics of Sleep Regulation", Cell. vol. 98, pp. 437-451, (Aug. 20, 1999).
Borgland, S.L. et al., "Orexin A in the VTA is Critical for the Induction of Synaptic Plasticity and Behavioral Sensitization to Cocaine", Neuron., vol. 49, pp. 589-601, (Feb. 16, 2006).
Gould, P.L., "Salt Selection for Basic Drugs", International Journal of Phamaceutics, vol. 33, pp. 201-217, (1986).

(Continued)

*Primary Examiner* — Yong Chong
(74) *Attorney, Agent, or Firm* — Hoxie & Associates, LLC

(57) ABSTRACT

The present invention relates to lactam derivatives of formula (I)

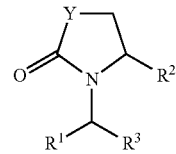

Formula (I)

wherein Y, $R^1$, $R^2$ and $R^3$ are as described in the description, to their preparation, to pharmaceutically acceptable salts thereof, and to their use as pharmaceuticals, to pharmaceutical compositions containing one or more compounds of formula (I), and especially to their use as orexin receptor antagonists.

12 Claims, No Drawings

(56) References Cited

OTHER PUBLICATIONS

Gennaro, A.R., Editor, "Remington: The Science and Practice of Pharmacy", 21st Edition, Philadelphia College of Pharmacy and Science, Table of Contents, (2005).

Greene, T.W., et al., Protective Groups in Organic Synthesis, 3rd Edition, Table of Contents, (1999).

Jenck, F. et al., "Promotion of Sleep by Targeting the Orexin System in Rats, Dogs and Humans", Nature Medicine, vol. 13, pp. 150-155, Advance Online Publication, http://www.nature.com/naturemedicine, (published online Jan. 28, 2007).

LACTAM DERIVATIVES USEFUL AS OREXIN RECEPTOR ANTAGONISTS

CROSS REFERENCE TO RELATED APPLICATIONS

This application is a United States National Stage Application under 35 U.S.C. 371 of PCT Application No. PCT/IB2011/054993, filed on Nov. 9, 2011, which claims the benefit of PCT Application No. PCT/IB2010/055105, filed Nov. 10, 2010.

The present invention relates to novel lactam derivatives of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451). Furthermore, in vitro and in vivo evidence for a critical role of orexin signaling in the ventral tegmental area in neural plasticity relevant to addiction has been published (S. L. Borgland et al. Neuron, 2006, 49, 589-601).

Thus, orexin receptors may have numerous implications in pathologies as known from the literature, such as dysthymic, mood, psychotic and anxiety disorders; diabetes and appetite, taste, eating, or drinking disorders; hypothalamic diseases; disturbed biological and circadian rhythms; sleep disturbances associated with diseases such as neurological disorders, neuropathic pain and restless leg syndrome; insomnias related to psychiatric disorders; sleep apnea; narcolepsy; idiopathic insomnias; parasomnias; benign prostatic hypertrophy; all dementias and cognitive dysfunctions in the healthy population and in psychiatric and neurologic disorders; and other diseases related to general orexin system dysfunctions. The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548) is currently in clinical development for primary insomnia. In the rat, the compound has been shown for example to decrease alertness, characterized by decreases in both active wake and locomotion; and to dose-dependently increase the time spent in both REM and NREM sleep (F. Jenck et al., Nature Medicine 2007, 13, 150-155). The compound has also been shown to enhance memory function in a rat model (WO2007/105177) and is also active in a rat model of post-traumatic stress disorder (WO2009/047723).

The present invention provides novel lactam derivatives, which are non-peptide antagonists of human orexin receptors. These compounds are in particular of potential use in the treatment of diseases related to the orexin system, especially comprising all types of sleep disorders, of stress-related syndromes, of addictions (especially psychoactive substance use, abuse, seeking and reinstatement), of cognitive dysfunctions in the healthy population and in psychiatric and neurologic disorders, of eating or drinking disorders.

1) A first aspect of the invention relates to compounds of the formula (I)

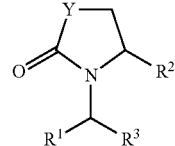

Formula (I)

wherein

Y represents a group —$(CH_2)_m$—, wherein m represents the integer 1, 2, or 3, wherein said group is optionally substituted with one or two substituents independently selected from the group consisting of ($C_{1-3}$)alkyl, ($C_{1-3}$)alkoxy, hydroxy, and halogen; or Y represents *—$CH_2$—O—, *—$CH_2$—NH—, or *—$CH_2$—N(($C_{1-3}$)alkyl)-; wherein the asterisks indicate the bond which is attached to the carbonyl group of the ring;

$R^1$ represents aryl or heteroaryl, wherein the aryl or heteroaryl independently is:

substituted with one, two, or three substituents, wherein the substituents are independently selected from the group consisting of:

($C_{1-4}$)alkyl, ($C_{1-4}$)alkoxy, ($C_{3-6}$)cycloalkyl, halogen, cyano, ($C_{1-3}$)fluoroalkyl, ($C_{1-3}$)fluoroalkoxy, ($C_{1-3}$)fluoroalkyl-thio-, ($C_{1-4}$)alkyl-sulfonyl, ($C_{3-6}$)cycloalkyl-($C_{1-4}$)alkoxy, ($C_{1-4}$)alkoxy-($C_{1-4}$)alkoxy;

—$NR^4R^5$, wherein $R^4$ and $R^5$ are independently hydrogen or ($C_{1-4}$)alkyl, or, $R^4$ and $R^5$ together with the nitrogen atom to which they are attached form a saturated 5-, 6-, or 7-membered ring optionally containing an oxygen atom;

phenyl or 5- or 6-membered heteroaryl, wherein said phenyl or 5- or 6-membered heteroaryl is independently unsubstituted, or mono-, di-, or tri-substituted, wherein the substituents are independently selected from the group consisting of ($C_{1-4}$)alkyl, ($C_{1-4}$)alkoxy, halogen, cyano, ($C_{1-3}$)fluoroalkyl, and ($C_{1-3}$)fluoroalkoxy; and phenyloxy or 5- or 6-membered heteroaryloxy, wherein said phenyl or 5- or 6-membered heteroaryl is independently unsubstituted, or mono-, di-, or tri-substituted, wherein the substituents are independently selected from the group consisting of ($C_{1-4}$)alkyl, ($C_{1-4}$)alkoxy, halogen, cyano, ($C_{1-3}$)fluoroalkyl, and ($C_{1-3}$)fluoroalkoxy;

wherein at maximum one substituent selected from phenyl or 5- or 6-membered heteroaryl, and phenyloxy or 5- or 6-membered heteroaryloxy is present;

or said aryl or heteroaryl is fused to a non-aromatic 5- or 6-membered ring, wherein said ring optionally contains one or two heteroatoms independently selected from oxygen and nitrogen; wherein said ring is optionally substituted with one or two substituents independently selected from ($C_{1-3}$)alkyl, oxo, and halogen;

or, in the specific case wherein said aryl is naphthyl, or said heteroaryl is a bicyclic or tricyclic ring, said aryl or heteroaryl may additionally be unsubstituted;

$R^2$ represents aryl or 5- to 10-membered heteroaryl, wherein the aryl or heteroaryl is independently substituted with one, two, or three substituents, wherein at least one substituent is attached in ortho-position to the point of attachment of $R^2$ to the rest of the molecule; wherein the substituents are independently selected from the group consisting of:

($C_{1-4}$)alkyl, ($C_{1-4}$)alkoxy, halogen, cyano, ($C_{1-3}$)fluoroalkyl, ($C_{1-3}$)fluoroalkoxy; hydroxy-($C_{1-4}$)alkoxy, dihydroxy-($C_{1-4}$)alkoxy, ($C_{3-6}$)cycloalkyl-($C_{1-4}$)alkoxy, ($C_{1-4}$)alkoxy-($C_{1-4}$)alkoxy; and phenyl or 5- or 6-membered heteroaryl, wherein said phenyl or 5- or 6-membered heteroaryl is independently unsubstituted, or mono-, di-, or tri-substituted, wherein the substituents are independently selected from the group consisting of ($C_{1-4}$)alkyl, ($C_{1-4}$)alkoxy, halogen, cyano, ($C_{1-3}$)fluoroalkyl, and ($C_{1-3}$)fluoroalkoxy;

wherein at maximum one phenyl or 5- or 6-membered heteroaryl substituent is present;

or two of said substituents form a non-aromatic 5- or 6-membered ring fused to said aryl or heteroaryl, wherein said ring optionally contains one or two heteroatoms independently selected from oxygen and nitrogen, wherein said ring in turn is optionally substituted with one or two substituents independently selected from ($C_{1-3}$)alkyl, oxo, and halogen;

and the remaining of said substituents, if present, is selected from the group consisting of ($C_{1-4}$)alkyl, ($C_{1-4}$)alkoxy, halogen, cyano, ($C_{1-3}$)fluoroalkyl, ($C_{1-3}$)fluoroalkoxy, hydroxy-($C_{1-4}$)alkoxy, dihydroxy-($C_{1-4}$)alkoxy, ($C_{3-6}$)cycloalkyl-($C_{1-4}$)alkoxy, and ($C_{1-4}$)alkoxy-($C_{1-4}$)alkoxy; and $R^3$ represents hydrogen, methyl or ethyl;

with the exception of the following compound:

5-(2-Methoxyphenyl)-1-[(4-methoxyphenyl)methyl]-3-methyl-2-pyrrolidinone (CAS Registry No. 936228-35-2).

The latter compound (especially the (3R*,5R*)-diastereoisomer) is known from Denhez et al., "Asymmetric synthesis of di- and trisubstituted pyrrolidinones via zirconium-mediated intramolecular coupling of N-3-alkenyl carbamates"; Tetrahedron: Asymmetry 2007, 18 (3), 424-434.

2) A second embodiment of the invention relates to compounds according to embodiment 1), which are also compounds of formula ($I_{E1}$) wherein the stereocenter at position 2 of the ring moiety is in absolute (S)-configuration:

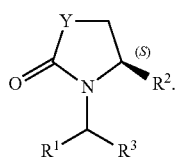

Formula ($I_{E1}$)

3) A further embodiment relates to compounds according to embodiment 1), which are also compounds of formula ($I_{E2}$) wherein the stereocenter at position 2 of the ring moiety is in absolute (R)-configuration:

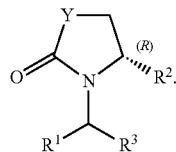

Formula ($I_{E2}$)

4) A further embodiment relates to compounds according to any one of embodiments 1) to 3), wherein, in case Y represents a group —$(CH_2)_m$—, said optional substitutent(s), if present, is/are attached to the carbon atom which is in alpha position to the carbonyl group of the ring. In a sub-embodiment, said optional substitutent(s), if present, are especially methyl or fluoro.

5) A further embodiment relates to compounds according to any one of embodiments 1) to 3), wherein Y represents —$CH_2$—, —$CH(CH_3)$—, —$CH(C_2H_5)$—, —CHF—, —CHCl—, —$CH(OCH_3)$—, —CH(OH)—, —$C(CH_3)_2$—, —$CF_2$—, —$CH_2$—$CH_2$—, *—$CH(CH_3)$—$CH_2$—, *—$CH_2$—$CH(CH_3)$—, *—$C(CH_3)_2$—$CH_2$—, *—$CH_2$—$C(CH_3)_2$—, —$CH_2$—$CH_2$—$CH_2$—, *—$CH_2$—O—, *—$CH_2$—NH—, or *—$CH_2$—$N(CH_3)$— [in one sub-embodiment Y represents —$CH_2$—, —$CH(CH_3)$—, —CHF—, CHCl—, —$CH_2$—$CH_2$—, *—$CH(CH_3)$—$CH_2$—, or —$CH_2$—$CH_2$—$CH_2$—; in another sub-embodiment Y represents —$CH(CH_3)$—, —CHF—, —CHCl—, —CH(OH)—, —$C(CH_3)_2$—, or —$CF_2$—]; wherein the asterisks indicate the bond which is attached to the carbonyl group of the ring.

6) A further embodiment relates to compounds according to any one of embodiments 1) to 3), wherein Y represents a group —$(CH_2)_m$—, wherein m represents the integer 1, 2, or 3.

7) A further embodiment relates to compounds according to any one of embodiments 1) to 3), wherein Y represents *—$CH_2$—O—, *—$CH_2$—NH—, or *—$CH_2$—$N(CH_3)$—; wherein the asterisks indicate the bond which is attached to the carbonyl group of the ring.

8) A further embodiment relates to compounds according to any one of embodiments 1) to 7), wherein $R^1$ represents $Ar^1$ or $Ar^3$—X—$Ar^2$—* wherein the asterisk indicates the bond that is attached to the rest of the molecule; wherein $Ar^1$ represents aryl or heteroaryl, wherein the aryl or heteroaryl independently is:

substituted with one, two, or three substituents, wherein the substituents are independently selected from the group consisting of:

($C_{1-4}$)alkyl, ($C_{1-4}$)alkoxy, ($C_{3-6}$)cycloalkyl, halogen, cyano, ($C_{1-3}$)fluoroalkyl, ($C_{1-3}$)fluoroalkoxy, ($C_{1-3}$)fluoroalkyl-thio-, ($C_{1-4}$)alkyl-sulfonyl, ($C_{3-6}$)cycloalkyl-($C_{1-4}$)alkoxy, ($C_{1-4}$)alkoxy-($C_{1-4}$)alkoxy; and —$NR^4R^5$, wherein $R^4$ and $R^5$ are independently selected from hydrogen, ($C_{1-4}$)alkyl, or, $R^4$ and $R^5$ together with the nitrogen atom to which they are attached form a saturated 5-, 6-, or 7-membered ring optionally containing an oxygen atom;

or said aryl or heteroaryl is fused to a non-aromatic 5- or 6-membered ring, wherein said ring optionally contains one or two heteroatoms independently selected from oxygen and nitrogen; wherein said ring is optionally substituted with one or two substituents independently selected from ($C_{1-3}$)alkyl, oxo, and halogen;

or, in the specific case wherein said aryl is naphthyl, or said heteroaryl is a bicyclic or tricyclic ring, said aryl or heteroaryl may additionally be unsubstituted;

Ar² represents phenyl or 5- or 6-membered heteroaryl; wherein the phenyl or 5- or 6-membered heteroaryl independently is
  unsubstituted, or substituted with one, or two substituents, wherein the substituents are independently selected from the group consisting of:
    $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, $(C_{1-3})$fluoroalkyl-thio-, $(C_{1-4})$alkyl-sulfonyl, $(C_{3-6})$cycloalkyl-$(C_{1-4})$alkoxy, $(C_{1-4})$alkoxy-$(C_{1-4})$alkoxy;
Ar³ represents phenyl or 5- or 6-membered heteroaryl, wherein said phenyl or 5- or 6-membered heteroaryl is independently unsubstituted, or mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy; and
X represents a bond, or oxygen.

9) A further embodiment relates to compounds according to embodiment 8), wherein
Ar¹ represents aryl, wherein the aryl is:
  substituted with one, two, or three substituents, wherein the substituents are independently selected from the group consisting of:
    $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, $(C_{1-3})$fluoroalkyl-thio-, $(C_{1-4})$alkyl-sulfonyl, $(C_{3-6})$cycloalkyl-$(C_{1-4})$alkoxy, $(C_{1-4})$alkoxy-$(C_{1-4})$alkoxy; and
    —$NR^4R^5$, wherein $R^4$ and $R^5$ are independently selected from hydrogen, $(C_{1-4})$alkyl, or, $R^4$ and $R^5$ together with the nitrogen atom to which they are attached form a saturated 5-, 6-, or 7-membered ring optionally containing an oxygen atom;
  or said aryl is fused to a non-aromatic 5- or 6-membered ring, wherein said ring optionally contains one or two heteroatoms independently selected from oxygen and nitrogen; wherein said ring is optionally substituted with one or two substituents independently selected from $(C_{1-3})$alkyl, oxo, and halogen;
  or, in the specific case wherein said aryl is naphthyl, it may additionally be unsubstituted;
or Ar¹ represents heteroaryl, wherein the heteroaryl is:
  substituted with one, two, or three substituents, wherein the substituents are independently selected from the group consisting of:
    $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, $(C_{1-3})$fluoroalkyl-thio-, $(C_{1-4})$alkyl-sulfonyl, $(C_{3-6})$cycloalkyl-$(C_{1-4})$alkoxy, $(C_{1-4})$alkoxy-$(C_{1-4})$alkoxy; and
    —$NR^4R^5$, wherein $R^4$ and $R^5$ are independently selected from hydrogen, $(C_{1-4})$alkyl, or, $R^4$ and $R^5$ together with the nitrogen atom to which they are attached form a saturated 5-, 6-, or 7-membered ring optionally containing an oxygen atom;
  or said heteroaryl is fused to a non-aromatic 5- or 6-membered ring, wherein said ring optionally contains one or two heteroatoms independently selected from oxygen and nitrogen; wherein said ring is optionally substituted with one or two substituents independently selected from $(C_{1-3})$alkyl, oxo, and halogen;
  or, in the specific case wherein said heteroaryl is a bicyclic or tricyclic ring, said heteroaryl may additionally be unsubstituted.

10) A further embodiment relates to compounds according to any one of embodiments 8) or 9), wherein
Ar¹ represents aryl, wherein the aryl is:
  substituted with one, or two substituents, wherein the substituents are independently selected from the group consisting of:
    $(C_{1-4})$alkoxy, halogen, $(C_{1-3})$fluoroalkyl, $(C_{1-3})$fluoroalkoxy, $(C_{1-4})$alkyl-sulfonyl, $(C_{1-3})$fluoroalkyl-thio-, $(C_{3-6})$cycloalkyl-$(C_{1-4})$alkoxy; and
    —$NR^4R^5$, wherein $R^4$ and $R^5$ together with the nitrogen atom to which they are attached form a saturated 5-, or 6-membered ring optionally containing an oxygen atom;
  or said aryl is fused to a non-aromatic 5- or 6-membered ring, wherein said ring optionally contains one or two heteroatoms independently selected from oxygen and nitrogen; wherein said ring is optionally substituted with two halogen substituents;
  or, in the specific case wherein said aryl is naphthyl, it may additionally be unsubstituted;
or Ar¹ represents heteroaryl, wherein the heteroaryl is:
  substituted with one, or two substituents, wherein the substituents are independently selected from the group consisting of:
    $(C_{1-4})$alkyl, $(C_{3-6})$cycloalkyl, halogen, $(C_{1-3})$fluoroalkoxy; and
    —$NR^4R^5$, wherein $R^4$ and $R^5$ together with the nitrogen atom to which they are attached form a pyrrolidine ring;
  or, in the specific case wherein said heteroaryl is a bicyclic or tricyclic ring, said heteroaryl may additionally be unsubstituted.

11) A further embodiment relates to compounds according to any one of embodiments 8) to 10), wherein
Ar¹ represents aryl or heteroaryl, wherein the aryl or heteroaryl independently is:
  substituted with one, or two substituents, wherein the substituents are independently selected from the group consisting of:
    $(C_{1-4})$alkyl, $(C_{1-4})$alkoxy, halogen, $(C_{1-3})$fluoroalkyl, $(C_{1-3})$fluoroalkoxy; and
    —$NR^4R^5$, wherein $R^4$ and $R^5$ together with the nitrogen atom to which they are attached form a saturated 5-, or 6-membered ring optionally containing an oxygen atom;
  or, in the specific case wherein said aryl is naphthyl, or said heteroaryl is a bicyclic or tricyclic ring, said aryl or heteroaryl may additionally be unsubstituted.

12) A further embodiment relates to compounds according to any one of embodiments 8) to 10), wherein
Ar¹ represents aryl or heteroaryl, wherein the aryl or heteroaryl independently is:
  phenyl, or a 5- or 6-membered heteroaryl, independently substituted with one, or two substituents, wherein
    one of the substituents is selected from the group consisting of: $(C_{1-4})$alkoxy, $(C_{1-3})$fluoroalkoxy; and
    —$NR^4R^5$, wherein $R^4$ and $R^5$ together with the nitrogen atom to which they are attached form a saturated 5-, or 6-membered ring optionally containing an oxygen atom;
    and the other, if present, is halogen;
  or said aryl is naphthyl, or said heteroaryl is a bicyclic or tricyclic ring, wherein said naphthyl or bicyclic or tricyclic heteroaryl independently are unsubstituted or substituted with a substituent independently selected from the group consisting of $(C_{1-4})$alkyl, and $(C_{1-4})$alkoxy.

13) A further embodiment relates to compounds according to any one of embodiments 1) to 12), wherein $Ar^1$ represents aryl.

14) A further embodiment relates to compounds according to any one of embodiments 1) to 12), wherein $Ar^1$ represents heteroaryl.

15) A further embodiment relates to compounds according to any one of embodiments 1) to 14), wherein $Ar^2$ represents phenyl or 5- or 6-membered heteroaryl; wherein the phenyl or 5- or 6-membered heteroaryl independently is unsubstituted, or substituted as explicitly defined (notably unsubstituted or substituted with one substituent, wherein the substituent is halogen).

16) A further embodiment relates to compounds according to any one of embodiments 1) to 15), wherein $Ar^2$ represents phenyl (notably phenyl-1,4-diyl, or phenyl-1,3-diyl); wherein said phenyl is preferably unsubstituted (notwithstanding the substituent —X—$Ar^3$), or substituted as explicitly defined.

17) A further embodiment relates to compounds according to any one of embodiments 1) to 15), wherein $Ar^2$ represents 5- or 6-membered heteroaryl (notably 5-membered heteroaryl wherein the group —X—$Ar^3$ and the rest of the molecule are attached in a 1,3-diyl arrangement; or 6-membered heteroaryl wherein the group —X—$Ar^3$ and the rest of the molecule are attached in a 1,3-diyl or 1,4-diyl arrangement); wherein said 5- or 6-membered heteroaryl is preferably unsubstituted (notwithstanding the substituent —X—$Ar^3$), or substituted as explicitly defined.

18) A further embodiment relates to compounds according to any one of embodiments 1) to 17), wherein $R^1$ represents $Ar^1$.

19) A further embodiment relates to compounds according to any one of embodiments 1) to 17), wherein $R^1$ represents $Ar^3$—X—$Ar^2$—* wherein the asterisk indicates the bond that is attached to the rest of the molecule.

20) A further embodiment relates to compounds according to any one of embodiments 1) to 8), wherein $R^1$ represents naphthyl, or bicyclic or tricyclic heteroaryl; wherein said naphthyl or bicyclic or tricyclic heteroaryl independently are unsubstituted or substituted with a substituent independently selected from the group consisting of $(C_{1-4})$alkyl, and $(C_{1-4})$alkoxy;

or $R^1$ represents a group selected from the group consisting of:

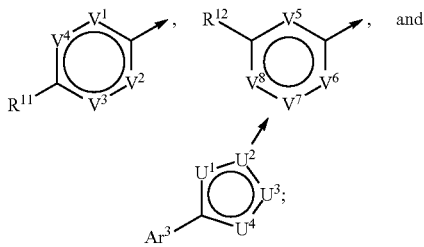

wherein
$R^{11}$ represents $Ar^3$—X, $(C_{1-3})$alkoxy, or $(C_{1-3})$fluoroalkoxy;
$R^{12}$ represents $Ar^3$—X, or —$NR^4R^5$, wherein $R^4$ and $R^5$ together with the nitrogen atom to which they are attached form a saturated 5-, or 6-membered ring optionally containing an oxygen atom;
independently one or two of $V^1$, $V^2$, $V^3$ and $V^4$ are N or CH, and the remaining are CH; wherein one of $V^1$, $V^2$, $V^3$ and $V^4$ being CH may optionally be substituted with halogen;
independently one or two of $V^5$, $V^6$, $V^7$ and $V^8$ are N or CH, and the remaining are CH; wherein one of $V^5$, $V^6$, $V^7$ and $V^8$ being CH (especially one of $V^5$, $V^7$ and $V^8$ being CH) may optionally be substituted with halogen;
$U^2$ is C or N, and $U^1$, $U^3$, and $U^4$ independently are CH, N, O, or S; provided that at least one of $U^2$, $U^1$, $U^3$, and $U^4$ is different from CH; wherein one of $U^1$, $U^3$, and $U^4$ being CH may optionally be substituted with methyl.

21) A further embodiment relates to compounds according to embodiment 20); wherein,
$R^{11}$ represents $Ar^3$—X, $(C_{2-3})$alkoxy, or (especially) $(C_{1-3})$fluoroalkoxy;
$R^{12}$ represents $Ar^3$—X, or —$NR^4R^5$, wherein $R^4$ and $R^5$ together with the nitrogen atom to which they are attached form a saturated 5-, or 6-membered ring optionally containing an oxygen atom;
independently one of $V^3$ and $V^4$ are N or CH, and the remaining of $V^1$, $V^2$, $V^3$ and $V^4$ are CH; wherein one of $V^1$, $V^2$, $V^3$ and $V^4$ being CH (especially one of $V^3$ and $V^4$ being CH) may optionally be substituted with halogen;
independently one of $V^5$ and $V^8$ are N or CH, and the remaining of $V^5$, $V^6$, $V^7$ and $V^8$ are CH; wherein one of $V^5$, $V^6$, $V^7$ and $V^8$ being CH (especially one of $V^5$, $V^7$ and $V^8$ being CH) may optionally be substituted with halogen;
$U^2$ is C or N, and $U^1$, $U^3$, and $U^4$ independently are CH, N, O, or S; provided that at least one of $U^2$, $U^1$, $U^3$, and $U^4$ is different from CH; wherein one of $U^1$, $U^3$, and $U^4$ being CH may optionally be substituted with methyl.

22) A further embodiment relates to compounds according to any one of embodiments 1) to 21), wherein
$Ar^3$ represents phenyl or 5- or 6-membered heteroaryl, wherein said phenyl or 5- or 6-membered heteroaryl is independently unsubstituted, or mono-substituted with $(C_{1-4})$alkyl, or halogen (notably $(C_{1-4})$alkyl, especially methyl). In a sub-embodiment, in case $Ar^3$ represents phenyl, said phenyl is notably unsubstituted; and, in case $Ar^3$ represents 5- or 6-membered heteroaryl, said heteroaryl is notably unsubstituted, or mono-substituted with methyl.

23) A further embodiment relates to compounds according to any one of embodiments 1) to 22), wherein X represents a bond.

24) A further embodiment relates to compounds according to any one of embodiments 1) to 22), wherein X represents oxygen.

25) A further embodiment relates to compounds according to any one of embodiments 1) to 17), or 19), wherein $Ar^3$—X—$Ar^2$—* is a group selected from the group consisting of 3-biphenyl, 3-(thiazolyl)-phenyl, 2-(thiazolyl)-pyridin-4-yl, 3-(pyrazolyl)-phenyl, 2-(pyrazolyl)-pyridin-4-yl, 3-(triazolyl)-phenyl, 3-(oxadiazolyl)-phenyl, 2-phenyl-thiazolyl, 3-(pyridinyl)-phenyl, 3-(pyrimidinyl)-phenyl, 2-phenyl-pyridin-4-yl, and 6-phenyl-pyridin-2-yl; wherein said groups are optionally mono-substituted with methyl or halogen. In a subembodiment, such groups $Ar^3$—X—$Ar^2$—* are especially selected from the group consisting of 3-thiazol-5-yl-phenyl, 3-thiazol-4-yl-phenyl, 3-thiazol-2-yl-phenyl, 3-(2-methyl-thiazol-4-yl)-phenyl, 3-(5-methyl-thiazol-2-yl)-phenyl, 2-thiazol-2-yl-pyridin-4-yl, 3-pyrazol-1-yl-phenyl, 2-pyrazol-1-yl-pyridin-4-yl, 3-[1,2,3]triazol-2-yl-phenyl, 3-(5-methyl-[1,2,4]oxadiazol-3-yl)-phenyl, 2-phenyl-thiazol-4-yl, 3-pyridin-2-yl-phenyl, 3-pyridin-3-yl-phenyl, 3-pyridin-4-yl-phenyl, 3-chloro-5-(pyridin-2-yl)-phenyl, 4-fluoro-3-(pyridin-2-yl)-phenyl, 2-fluoro-3-(pyridin-2-yl)-phenyl, 3-pyrimidin-2-yl-phenyl, 2-phenyl-pyridin-4-yl, and 6-phenyl-pyridin-2-yl.

26) A further embodiment relates to compounds according to any one of embodiments 1) to 25), wherein
$R^2$ represents aryl or 5- to 10-membered heteroaryl, wherein the aryl or heteroaryl is independently substituted with one, two, or three substituents, wherein at least one substituent is attached in ortho-position to the point of attachment of $R^2$ to the rest of the molecule; wherein
the substituents are independently selected from the group consisting of:
$(C_{1-4})$alkyl, $(C_{1-4})$alkoxy, halogen, $(C_{1-3})$fluoroalkyl, $(C_{1-3})$fluoroalkoxy; hydroxy-$(C_{1-4})$alkoxy, dihydroxy-$(C_{1-4})$alkoxy, $(C_{3-6})$cycloalkyl-$(C_{1-4})$alkoxy, $(C_{1-4})$alkoxy-$(C_{1-4})$alkoxy; and
phenyl, wherein said phenyl is independently unsubstituted, or mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;
wherein at maximum one phenyl substituent is present;
or two of said substituents form a non-aromatic 5- or 6-membered ring fused to said aryl or heteroaryl, wherein said ring optionally contains one or two heteroatoms independently selected from oxygen and nitrogen;
and the remaining of said substituents, if present, is selected from the group consisting of $(C_{1-4})$alkoxy, $(C_{1-3})$fluoroalkoxy, hydroxy-$(C_{1-4})$alkoxy, $(C_{3-6})$cycloalkyl-$(C_{1-4})$alkoxy, and $(C_{1-4})$alkoxy-$(C_{1-4})$alkoxy (notably $(C_{1-4})$alkoxy, especially methoxy).

27) A further embodiment relates to compounds according to any one of embodiments 1) to 25), wherein
$R^2$ represents phenyl or 5- or 6-membered heteroaryl, wherein the phenyl or 5- or 6-membered heteroaryl is independently substituted with one, two, or three substituents, wherein at least one substituent is attached in ortho-position to the point of attachment of $R^2$ to the rest of the molecule; wherein the substituents are independently selected from the group consisting of:
$(C_{1-4})$alkyl, $(C_{1-4})$alkoxy, halogen, $(C_{1-3})$fluoroalkyl, $(C_{1-3})$fluoroalkoxy; hydroxy-$(C_{1-4})$alkoxy, dihydroxy-$(C_{1-4})$alkoxy, $(C_{3-6})$cycloalkyl-$(C_{1-4})$alkoxy, $(C_{1-4})$alkoxy-$(C_{1-4})$alkoxy; and
phenyl or 5- or 6-membered heteroaryl, wherein said phenyl or 5- or 6-membered heteroaryl is independently unsubstituted, or mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;
wherein at maximum one phenyl or 5- or 6-membered heteroaryl substituent is present;
or $R^2$ represents naphthyl or 8- to 10-membered bicyclic heteroaryl, wherein the naphthyl or 8- to 10-membered bicyclic heteroaryl is preferably attached in alpha position to a bridgehead atom; and wherein the naphthyl or 8- to 10-membered bicyclic heteroaryl is independently substituted with one, or two substituents, wherein one substituent, selected from the group consisting of $(C_{1-4})$alkoxy, $(C_{1-3})$fluoroalkoxy, hydroxy-$(C_{1-4})$alkoxy, $(C_{3-6})$cycloalkyl-$(C_{1-4})$alkoxy, and $(C_{1-4})$alkoxy-$(C_{1-4})$alkoxy (notably $(C_{1-4})$alkoxy, especially methoxy), is attached in ortho-position to the point of attachment of $R^2$ to the rest of the molecule; and the remaining substituent, if present, is $(C_{1-4})$alkyl.

or $R^2$ represents a group selected from the group consisting of 2,3-dihydrobenzofuranyl, chromanyl, chromenyl, benzo[1,3]dioxolyl, 2,3-dihydro-benzo[1,4]dioxinyl, benzo[b][1,4]dioxinyl, and 2,3-dihydro-[1,4]dioxinopyridinyl; wherein said groups are attached to the rest of the molecule on the aromatic ring, in alpha position to a bridgehead atom; and wherein said groups are optionally substituted in the non-aromatic moiety with one or two substituents independently selected from $(C_{1-3})$alkyl, oxo, and halogen; and wherein said groups additionally are optionally substituted in the aromatic moiety (preferably in the other ortho-position) with a substituent selected from the group consisting of $(C_{1-4})$alkoxy, $(C_{1-3})$fluoroalkoxy, hydroxy-$(C_{1-4})$alkoxy, $(C_{3-6})$cycloalkyl-$(C_{1-4})$alkoxy, and $(C_{1-4})$alkoxy-$(C_{1-4})$alkoxy (notably $(C_{1-4})$alkoxy, especially methoxy). In a sub-embodiment these groups are unsubstituted in both the non-aromatic and the aromatic moiety.

28) A further embodiment relates to compounds according to any one of embodiments 1) to 25), wherein
$R^2$ represents phenyl or 5- or 6-membered heteroaryl, wherein the phenyl or 5- or 6-membered heteroaryl is independently substituted with one, two, or three substituents, wherein at least one substituent is attached in ortho-position to the point of attachment of $R^2$ to the rest of the molecule; herein the substituents are independently selected from the group consisting of:
$(C_{1-4})$alkyl, $(C_{1-4})$alkoxy, halogen, $(C_{1-3})$fluoroalkyl, $(C_{1-3})$fluoroalkoxy; hydroxy-$(C_{1-4})$alkoxy, dihydroxy-$(C_{1-4})$alkoxy, $(C_{3-6})$cycloalkyl-$(C_{1-4})$alkoxy, $(C_{1-4})$alkoxy-$(C_{1-4})$alkoxy; and
phenyl or 5- or 6-membered heteroaryl, wherein said phenyl or 5- or 6-membered heteroaryl is independently unsubstituted, or mono-substituted, wherein the substituent is independently selected from the group consisting of $(C_{1-4})$alkyl, $(C_{1-4})$alkoxy, halogen, cyano, $(C_{1-3})$fluoroalkyl, and $(C_{1-3})$fluoroalkoxy (preferably such phenyl or 5- or 6-membered heteroaryl is unsubstituted phenyl);
wherein at maximum one phenyl or 5- or 6-membered heteroaryl substituent is present;
or $R^2$ represents naphthyl or 8- to 10-membered bicyclic heteroaryl, wherein the naphthyl or 8- to 10-membered bicyclic heteroaryl is preferably attached in alpha position to a bridgehead atom; and wherein the naphthyl or 8- to 10-membered bicyclic heteroaryl is independently substituted with one, or two substituents, wherein one substituent is $(C_{1-4})$alkoxy (especially methoxy) which is attached in ortho-position to the point of attachment of $R^2$ to the rest of the molecule; and the remaining substituent, if present, is $(C_{1-4})$alkyl.
or $R^2$ represents a group selected from the group consisting of 2,3-dihydrobenzofuranyl, chromanyl, chromenyl, benzo[1,3]dioxolyl, 2,3-dihydro-benzo[1,4]dioxinyl, benzo[b][1,4]dioxinyl, and 2,3-dihydro-[1,4]dioxinopyridinyl; wherein said groups are attached to the rest of the molecule on the aromatic ring, in alpha position to a bridgehead atom; and wherein said groups are optionally substituted in the aromatic moiety (preferably in the other ortho-position) with a substituent selected from $(C_{1-4})$alkoxy (especially methoxy). In a sub-embodiment these groups are unsubstituted.

29) A further embodiment relates to compounds according to any one of embodiments 1) to 25), wherein R² represents phenyl or 6-membered heteroaryl, wherein the phenyl or 6-membered heteroaryl is independently substituted with two substituents which are both attached in ortho-position to the point of attachment of R² to the rest of the molecule; wherein the substituents are independently selected from the group consisting of:

$(C_{1-4})$alkyl, $(C_{1-4})$alkoxy, halogen, $(C_{1-3})$fluoroalkyl, $(C_{1-3})$fluoroalkoxy; hydroxy-$(C_{1-4})$alkoxy, dihydroxy-$(C_{1-4})$alkoxy, $(C_{3-6})$cycloalkyl-$(C_{1-4})$alkoxy, and $(C_{1-4})$alkoxy-$(C_{1-4})$alkoxy;

or R² represents naphthyl or 8- to 10-membered bicyclic heteroaryl (preferred), wherein the naphthyl or 8- to 10-membered bicyclic heteroaryl is preferably attached in alpha position to a bridgehead atom; and wherein the naphthyl or 8- to 10-membered bicyclic heteroaryl is independently substituted with one, or two substituents, wherein one substituent is $(C_{1-4})$alkoxy (especially methoxy) which is attached in ortho-position to the point of attachment of R² to the rest of the molecule; and the remaining substituent, if present, is $(C_{1-4})$alkyl.

or R² represents a group selected from the group consisting of benzo[1,3]dioxol-4-yl, and 2,3-dihydro-benzo[1,4]dioxin-5-yl; wherein said groups are optionally substituted in the aromatic moiety (preferably in the other ortho-position) with a $(C_{1-4})$alkoxy (especially methoxy) substituent. In a sub-embodiment these groups are unsubstituted.

30) A further embodiment relates to compounds according to any one of embodiments 1) to 29), wherein R² represents aryl or 5- to 10-membered heteroaryl (especially phenyl or 6-membered heteroaryl), wherein the aryl or heteroaryl is independently substituted with one, two, or three substituents, wherein at least one substituent is attached in ortho-position to the point of attachment of R² to the rest of the molecule; wherein said ortho-substituent is selected from the group consisting of:

$(C_{1-4})$alkoxy, $(C_{1-3})$fluoroalkoxy; hydroxy-$(C_{1-4})$alkoxy, dihydroxy-$(C_{1-4})$alkoxy, $(C_{3-6})$cycloalkyl-$(C_{1-4})$alkoxy, $(C_{1-4})$alkoxy-$(C_{1-4})$alkoxy; and phenyl or 5- or 6-membered heteroaryl, wherein said phenyl or 5- or 6-membered heteroaryl is independently unsubstituted, or mono-substituted, wherein the substituent is independently selected from the group consisting of $(C_{1-4})$alkyl, $(C_{1-4})$alkoxy, halogen, cyano, $(C_{1-3})$fluoroalkyl, and $(C_{1-3})$fluoroalkoxy (preferably such phenyl or 5- or 6-membered heteroaryl is unsubstituted phenyl);

and the remaining substituents, if present, are independently selected from the group consisting of:

$(C_{1-4})$alkyl, $(C_{1-4})$alkoxy, halogen, $(C_{1-3})$fluoroalkyl, $(C_{1-3})$fluoroalkoxy; hydroxy-$(C_{1-4})$alkoxy, dihydroxy-$(C_{1-4})$alkoxy, $(C_{3-6})$cycloalkyl-$(C_{1-4})$alkoxy, and $(C_{1-4})$alkoxy-$(C_{1-4})$alkoxy.

In a sub-embodiment, in case said aryl or heteroaryl is mono-cyclic, preferably one of said remaining substituents is attached in the other ortho-position to the point of attachment of R² to the rest of the molecule.

31) A further embodiment relates to compounds according to any one of embodiments 1) to 25), wherein R² represents a group selected from the group consisting of:

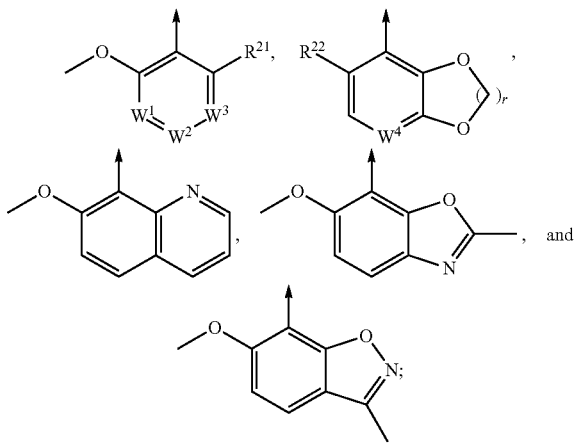

wherein
$W^1$ and $W^3$ represent CH, and $W^2$ represents $CR^{23}$ or N; or one or two of $W^1$ and $W^3$ represent N, and $W^2$ represents CH;
$R^{21}$ represents methyl, $(C_{1-3})$alkoxy, halogen, $(C_{1-2})$fluoroalkoxy, or trifluoromethyl (notably ethoxy or methoxy, especially methoxy);
$R^{22}$ represents hydrogen or methoxy;
$R^{23}$ represents hydrogen, methyl, methoxy, fluoro, or chloro (notably hydrogen); and
$W^4$ represents CH, or N (notably CH);
r represents the integer 1 or 2.

32) A further embodiment relates to compounds according to embodiment 31), wherein R² represents a group selected from the group consisting of:

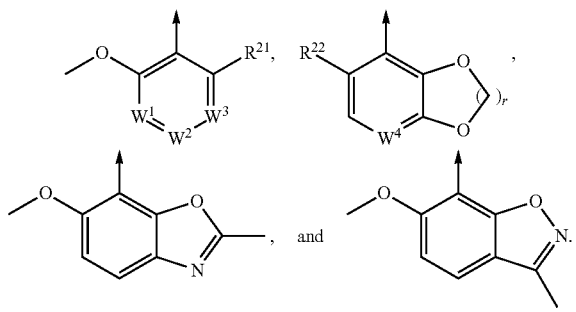

33) A further embodiment relates to compounds according to embodiments 31) or 32); wherein, R² represents

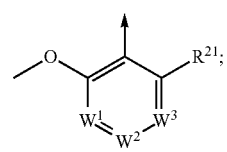

wherein
$W^1$ and $W^3$ represent CH, and $W^2$ represents $CR^{23}$ or N; or one or two of $W^1$ and $W^3$ represent N, and $W^2$ represents CH;
$R^{21}$ represents methyl, $(C_{1-3})$alkoxy, halogen, $(C_{1-2})$fluoroalkoxy, or trifluoromethyl (notably ethoxy or methoxy, especially methoxy); and $R^{23}$ represents hydrogen, methyl, methoxy, fluoro, or chloro (notably hydrogen); and wherein each combination of $W^1$, $W^2$, and $W^3$ (i.e. the particular combinations $W^1/W^2/W^3$=CH/CH/CH; N/CH/CH; CH/CH/N; and N/CH/N) constitutes a particular sub-embodiment.

34) A further embodiment relates to compounds according to any one of embodiments 1) to 25); wherein $R^2$ represents phenyl or 5- or 6-membered heteroaryl, wherein the phenyl or 5- or 6-membered heteroaryl is independently substituted with one, or two substituents, wherein at least one substituent is attached in ortho-position to the point of attachment of $R^2$ to the rest of the molecule; wherein said ortho-substituent is phenyl or 5- or 6-membered heteroaryl, wherein said phenyl or 5- or 6-membered heteroaryl is independently unsubstituted, or mono-substituted, wherein the substituent is independently selected from the group consisting of $(C_{1-4})$alkyl, $(C_{1-4})$alkoxy, halogen, cyano, $(C_{1-3})$fluoroalkyl, and $(C_{1-3})$fluoroalkoxy (preferably such ortho-substituent is unsubstituted phenyl);

and the remaining substituent, if present, is independently selected from the group consisting of methyl, $(C_{1-3})$alkoxy, halogen, $(C_{1-2})$fluoroalkoxy, or trifluoromethyl (notably ethoxy or methoxy, especially methoxy).

35) A further embodiment relates to compounds according to any one of embodiments 1) to 34), wherein $R^3$ represents hydrogen or methyl (especially hydrogen).

36) A particular embodiment of the invention relates to compounds according to embodiment 1), which combine the particular characteristics of embodiments 5), 20), 22) and 32).

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

The relative configuration of stereoisomers is denoted as follows: for example, (3R*,5S*)-3-chloro-5-(2,6-dimethoxyphenyl)-1-(4-(trifluoromethoxy)benzyl)pyrrolidin-2-one, if not explicitly mentioned as racemate, denominates (3R,5S)-3-chloro-5-(2,6-dimethoxyphenyl)-1-(4-(trifluoromethoxy)benzyl)pyrrolidin-2-one, or (3S,5R)-3-chloro-5-(2,6-dimethoxyphenyl)-1-(4-(trifluoromethoxy)benzyl)pyrrolidin-2-one, or any mixture of these two enantiomers.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

In this patent application, an arrow shows the point of attachment of the radical drawn. For example, the radical drawn below

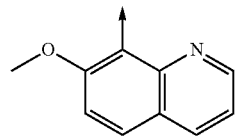

is the 7-methoxy-quinolin-8-yl group.

In some instances, the substituent $R^2$ is attached to the rest of the molecule on an aromatic ring in alpha position to a bridgehead atom. Such possible attachment points are further illustrated in the following examples:

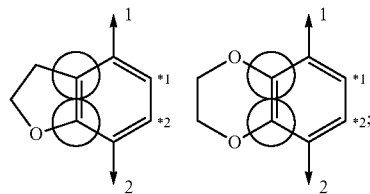

wherein ○ designates a bridgehead atom of the bicyclic ring system; ↑ designates a bond with which in these examples the aryl or heteroaryl group may be attached to the rest of the molecule. In addition, the asterisks * illustrate for the respective point of attachment the corresponding (other) ortho-position.

Where the plural form is used for compounds, salts, pharmaceutical compositions, diseases and the like, this is intended to mean also a single compound, salt, or the like.

Any reference to compounds of formula (I) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The term "halogen" means fluorine, chlorine, or bromine, preferably fluorine or chlorine.

The term "alkyl", used alone or in combination, refers to a saturated straight or branched chain alkyl group containing one to six carbon atoms. The term "$(C_{x-y})$alkyl" (x and y each being an integer), refers to an alkyl group as defined before, containing x to y carbon atoms. For example a $(C_{1-4})$alkyl group contains from one to four carbon atoms. Examples of alkyl groups are methyl, ethyl, propyl, isopropyl, n-butyl, isobutyl, sec.-butyl and tert.-butyl. Preferred are methyl and ethyl. Most preferred is methyl.

The term "cycloalkyl", used alone or in combination, refers to a saturated cyclic alkyl group containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of cycloalkyl groups are cyclopropyl, cyclobutyl, cyclopentyl and cyclohexyl. Preferred is cyclopropyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy. For substituents of the group $R^2$ preferred examples are ethoxy and methoxy, especially methoxy. For substituents of the group $R^1$, especially in the meaning of $Ar^1$ representing a phenyl group, preferred examples are ethoxy and especially isopropoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_{x-y})$fluoroalkyl groups such as trifluoromethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$fluoroalkoxy groups such as trifluoromethoxy and difluoromethoxy. For substituents of the group $R^1$, especially in the meaning of $R^{11}$, preferred examples are trifluoromethoxy, difluoromethoxy, 2-fluoroethoxy, and 2,2,2-trifluoroethoxy (notably trifluoromethoxy, and difluoromethoxy).

The term "aryl", alone or in combination, means notably a phenyl, or a naphthyl group. The aryl group may be unsubstituted or substituted as explicitly defined.

For the particular sub-group of aryl groups wherein "substituents form a non-aromatic 5- or 6-membered ring fused to said aryl, wherein said ring optionally contains one or two heteroatoms independently selected from oxygen and nitrogen" (as used for the substituent $R^2$), or wherein "the aryl is fused to a non-aromatic 5- or 6-membered ring, wherein said ring optionally contains one or two heteroatoms independently selected from oxygen and nitrogen" (as used for the substituent $R^1$) the aryl is preferably phenyl. Examples of such aryl groups fused to a non-aromatic 5- or 6-membered ring are indanyl, tetrahydronaphthyl, 2,3-dihydrobenzofuranyl, chromanyl, chromenyl, benzo[1,3]dioxolyl, 2,3-dihydro-benzo[1,4]dioxinyl, benzo[b][1,4]dioxinyl, 1,2,3,4-tetrahydro-quinolinyl, and 3,4-dihydro-2H-benzo[b][1,4]oxazinyl. The above-mentioned aryl groups are optionally substituted in said non-aromatic 5- or 6-membered ring with one or two substituents independently selected from $(C_{1-3})$alkyl, oxo, and halogen. Particular examples of fragments forming a non-aromatic 5- or 6-membered ring fused to said aryl are selected from the group consisting of —$(CH_2)_n$—, wherein n represents the integer 3 or 4; —$(CH_2)_p$—O—, wherein p represents the integer 1 or 2; —CH═CH—$CH_2$—O—; —O—$(CH_2)_q$—O—, wherein q represents the integer 1 or 2; —O—(C═O)—O—; —O—$(CF_2)$—O—, —O—CH═CH—O—; —$(CH_2)_3$—NH—; —$(CH_2)_3$—N$(CH_3)$—; —O—$(CH_2)_2$—NH—; and —O—$(CH_2)_2$—N$(CH_3)$—. Aryl groups carrying such substituents may be further substituted on the aromatic ring as explicitly defined.

For the substituent $R^1$, examples of aryl groups carrying such substituents forming a non-aromatic 5- or 6-membered ring fused to said aryl are especially benzo[1,3]dioxolyl, and 1,2,3,4-tetrahydro-quinolinyl; which groups are notably unsubstituted, or, in the case of benzo[1,3]dioxolyl unsubstituted or di-substituted with fluoro. Particular examples are 1,2,3,4-tetrahydro-quinolin-6-yl, benzo[1,3]dioxol-5-yl, and 2,2-difluoro-benzo[1,3]dioxol-5-yl.

For the substituent $R^2$, the above mentioned aryl groups carrying such substituents forming a non-aromatic 5- or 6-membered ring fused to said aryl are preferably attached to the rest of the molecule in ortho-position to said fused non-aromatic 5- or 6-membered ring (i.e. they are attached to the rest of the molecule on the aromatic ring in alpha position to a bridgehead atom of such bicyclic mixed aromatic-non-aromatic ring system). Examples are benzo[1,3]dioxolyl (especially attached in alpha position to the bridgehead atom: benzo[1,3]dioxol-4-yl), and 2,3-dihydro-benzo[1,4]dioxinyl (especially attached in alpha position to the bridgehead atom: 2,3-dihydro-benzo[1,4]dioxin-5-yl). In one embodiment; the above mentioned groups as used for $R^2$ are notably unsubstituted.

In a further embodiment, said groups as used for $R^2$ are unsubstituted on said non-aromatic 5- or 6-membered ring and optionally carry a further substituent on the aromatic ring as explicitly defined (notably a $(C_{1-4})$alkoxy substituent); which is preferably in (the other) ortho-position to the point of attachment of $R^2$ to the rest of the molecule. Particular examples of such groups as used for $R^2$ are 5-methoxy-benzo[1,3]dioxol-4-yl, 6-methoxy-2,3-dihydro-benzo[1,4]dioxin-5-yl, and notably benzo[1,3]dioxol-4-yl, and 2,3-dihydro-benzo[1,4]dioxin-5-yl.

For the substituent $R^1$, examples of aryl groups are 1-naphthyl, 2-naphthyl, 6-methoxy-naphthalen-2-yl, 4-chlorophenyl, 3-chlorophenyl, 4-fluorophenyl, 3-chloro-4-fluorophenyl, 4-chloro-2-fluorophenyl, 4-chloro-3-fluorophenyl, 4-methoxyphenyl, 3-methoxyphenyl, 4-ethoxyphenyl, 4-(n-propoxy)phenyl, 4-isopropoxyphenyl, 4-trifluoromethylphenyl, 4-difluoromethoxyphenyl, 3-difluoromethoxyphenyl, 4-trifluoromethyl-sulfanyl-phenyl, 4-(methanesulfonyl)-phenyl, 4-trifluoromethoxyphenyl, 3-trifluoromethoxyphenyl, 3-fluoro-4-trifluoromethoxyphenyl, 3-chloro-4-trifluoromethoxyphenyl, 4-(2,2,2-trifluoroethoxy)phenyl, 4-(2-fluoroethoxy)phenyl, 4-(cyclopropylmethoxy)-phenyl, 4-pyrrolidin-1-yl-phenyl, 3-pyrrolidin-1-yl-phenyl, 3-piperidin-1-yl-phenyl, 3-morpholin-4-yl-phenyl, biphenyl-4-yl, biphenyl-3-yl, biphenyl-2-yl, 4-pyrrol-1-yl-phenyl, 4-pyrazol-1-yl-phenyl, 3-pyrazol-1-yl-phenyl, 3-imidazol-1-yl-phenyl, 3-[1,2,3]triazol-1-yl-phenyl, 3-[1,2,3]triazol-2-yl-phenyl, 3-[1,2,4]triazol-1-yl-phenyl, 3-(5-methyl-[1,2,4]oxadiazol-3-yl)-phenyl, 3-thiazol-5-yl-phenyl, 3-thiazol-4-yl-phenyl, 3-(2-methyl-thiazol-4-yl)-phenyl, 3-thiazol-2-yl-phenyl, 3-(5-methyl-thiazol-2-yl)-phenyl, 3-pyridin-4-yl-phenyl, 3-pyridin-3-yl-phenyl, 3-pyridin-2-yl-phenyl, 2-fluoro-5-pyridin-2-yl-phenyl, 2-fluoro-3-pyridin-2-yl-phenyl, 4-fluoro-3-pyridin-2-yl-phenyl, 3-chloro-5-pyridin-2-yl-phenyl, 2-chloro-5-pyridin-2-yl-phenyl, 3-pyrimidin-2-yl-phenyl, 4-phenoxy-phenyl, 3-phenoxy-phenyl, 2-phenoxy-phenyl, 4-(thiazol-2-yloxy)-phenyl, 1,2,3,4-tetrahydro-quinolin-6-yl, benzo[1,3]dioxol-5-yl, and 2,2-difluoro-benzo[1,3]dioxol-5-yl.

Particular examples of aryl groups as used for the substituent $R^1$ (especially in the particular meaning of the group $Ar^1$) are 1-naphthyl, 2-naphthyl, 6-methoxy-naphthalen-2-yl, 4-chlorophenyl, 4-fluorophenyl, 4-methoxyphenyl, 4-ethoxyphenyl, 4-(n-propoxy)phenyl, 4-isopropoxyphenyl, 4-trifluoromethylphenyl, 4-difluoromethoxyphenyl, 3-difluoromethoxyphenyl, 4-trifluoromethyl-sulfanyl-phenyl, 4-(methanesulfonyl)-phenyl, 4-trifluoromethoxyphenyl, 3-fluoro-4-trifluoromethoxyphenyl, 3-chloro-4-trifluoromethoxyphenyl, 4-(2,2,2-trifluoroethoxy)phenyl, 4-(2-fluoroethoxy)phenyl, 4-(cyclopropyl-methoxy)-phenyl, 4-pyrrolidin-1-yl-phenyl, 3-pyrrolidin-1-yl-phenyl, 3-piperidin-1-yl-phenyl, 3-morpholin-4-yl-phenyl, 4-phenoxy-phenyl, 3-phenoxy-phenyl, 2-phenoxy-phenyl, 4-(thiazol-2-yloxy)-phenyl, 1,2,3,4-tetrahydro-quinolin-6-yl, benzo[1,3]dioxol-5-yl, and 2,2-difluoro-benzo[1,3]dioxol-5-yl. In addition to the above-mentioned groups, further particular examples of aryl groups for the substituent $R^1$ (especially in the particular meaning of the group $Ar^1$) are 3-ethoxyphenyl, 3-isopropoxyphenyl, 3-(2-fluoroethoxy)phenyl, 4-(2-fluoroethoxy)phenyl, 3-chloro-4-difluoromethoxyphenyl, 4-difluoromethoxy-3-methoxyphenyl, 4-methoxy-3-trifluoromethoxyphenyl, 2-methoxy-5-trifluoromethoxyphenyl, 3-(2,2-difluoroethoxy)-phenyl, 4-(2,2-difluoroethoxy)-phenyl, 3-(2,2,2-trifluoroethoxy)-phenyl, 3-(1,1,2,2-tetrafluoroethoxy)-phenyl, and 4-(1,1,2,2-tetrafluoroethoxy)-phenyl. In addition to the above particular examples, further particular examples of aryl groups as used for the substituent $R^1$ (especially in the particular meaning of the group $Ar^3$—X—$Ar^2$—*, wherein $Ar^2$ is a phenyl group) are biphenyl-4-yl, biphenyl-3-yl, biphenyl-2-yl, 4-pyrrol-1-yl-phenyl, 4-pyrazol-1-yl-phenyl, 3-pyrazol-1-yl-phenyl, 3-imidazol-1-yl-phenyl, 3-[1,2,3]triazol-1-yl-phenyl, 3-[1,2,3]triazol-2-yl-phenyl, 3-[1,2,4]triazol-1-yl-phenyl, 3-(5-methyl-[1,2,4]oxadiazol-3-yl)-phenyl, 3-thiazol-5-yl-phenyl, 3-thiazol-4-yl-phenyl, 3-(2-methyl-thiazol-4-yl)-phenyl, 3-thiazol-2-yl-phenyl, 3-(5-methyl-thiazol-2-yl)-phenyl, 3-pyridin-4-yl-phenyl, 3-pyridin-3-yl-phenyl, 3-pyridin-2-yl-phenyl, 2-fluoro-5-pyridin-2-yl-phenyl, 2-fluoro-3-pyridin-2-yl-phenyl, 4-fluoro-3-pyridin-2-yl-phenyl, 3-chloro-5-pyridin-2-yl-phenyl, 2-chloro-5-pyridin-2-yl-phenyl, and 3-pyrimidin-2-yl-phenyl. Preferred are those groups —$Ar^2$— wherein the group $Ar^3$—X— and the rest of the molecule are attached to —$Ar^2$— being (optionally substituted) phenyl in a meta-(1,3-diyl-), or a para-(1,4-diyl-) arrangement.

For the substituent $R^2$, examples of aryl groups are 2-methoxy-naphthalen-1-yl, 2,6-difluorophenyl, 2,6-dichlorophenyl, 2-chloro-6-fluorophenyl, 2,6-difluoro-3-methylphenyl, 2,6-difluoro-4-methoxyphenyl, 2-methoxyphenyl, 2-ethoxyphenyl, 2-fluoro-6-methoxyphenyl, 2-chloro-6-methoxyphenyl, 2-methoxy-6-methylphenyl, 2,6-dimethoxyphenyl, 2,5-dimethoxyphenyl, 4-fluoro-2,6-dimethoxyphenyl, 2-fluoro-4,6-dimethoxyphenyl, 4-chloro-2,6-dimethoxyphenyl, 3-chloro-2,6-dimethoxyphenyl, 2-chloro-4,6-dimethoxyphenyl, 2-ethoxy-6-methoxyphenyl, 2,6-diethoxyphenyl, 2-isopropoxy-6-methoxyphenyl, 3-fluoro-2,6-dimethoxyphenyl, 2,6-dimethoxy-3-methylphenyl, 2,6-dimethoxy-4-methylphenyl, 2-(2-hydroxyethoxy)-6-methoxyphenyl, 2-(cyclopropylmethoxy)-6-methoxyphenyl, 2-(3-hydroxypropoxy)-6-methoxyphenyl, 2-(2,3-dihydroxypropoxy)-6-methoxyphenyl, 2-(2-methoxyethoxy)-6-methoxyphenyl, 2,4,6-trimethoxyphenyl, 2-methoxy-6-trifluoromethylphenyl, 2-trifluoromethylphenyl, 2-fluoro-6-trifluoromethylphenyl, 2-trifluoromethoxyphenyl, 6-methoxy-indan-5-yl, benzo[1,3]dioxol-4-yl, 5-methoxy-benzo[1,3]dioxol-4-yl, 2,3-dihydro-benzo[1,4]dioxin-5-yl, and 6-methoxy-2,3-dihydro-benzo[1,4]dioxin-5-yl. In addition to the above-mentioned groups, further examples of aryl groups for the substituent $R^2$ are 2-ethoxy-6-fluorophenyl, 2-ethoxy-4-fluorophenyl, 2-ethoxy-3-fluorophenyl, 2-chloro-6-ethoxyphenyl, 2-ethoxy-4,6-difluorophenyl, 6-ethoxy-2,3-difluorophenyl, 2-fluoro-(2-hydroxyethoxy)-phenyl, 2-fluoro-6-(2-fluoroethoxy)-phenyl, 2-fluoro-6-isopropoxy-phenyl, 2-fluoro-6-n-propoxy-phenyl, 3,6-difluoro-2-methoxy-phenyl, 3-fluoro-2,6-dimethoxyphenyl, and 4-fluoro-2-methoxyphenyl. In addition to the above-mentioned groups, further examples of aryl groups for the substituent $R^2$ are 2-pyridin-3-yl-phenyl, 2-pyridin-4-yl-phenyl, 2-thiazol-5-yl-phenyl, 2-thiazol-4-yl-phenyl, and biphenyl-2-yl. In a sub-embodiment, particular examples of aryl groups for the substituent $R^2$ are 2,6-difluorophenyl, 2,6-dichlorophenyl, 2-chloro-6-fluorophenyl, 2,6-difluoro-3-methylphenyl, 2,6-difluoro-4-methoxyphenyl, 2-methoxyphenyl, 2-ethoxyphenyl, 2-fluoro-6-methoxyphenyl, 2-chloro-6-methoxyphenyl, 2-methoxy-6-methylphenyl, 2,6-dimethoxyphenyl, 4-fluoro-2,6-dimethoxyphenyl, 4-chloro-2,6-dimethoxyphenyl, 3-chloro-2,6-dimethoxyphenyl, 2-ethoxy-6-methoxyphenyl, 2,6-diethoxyphenyl, 2-isopropoxy-6-methoxyphenyl, 2,6-dimethoxy-4-methylphenyl, 2-(2-hydroxyethoxy)-6-methoxyphenyl, 2-(cyclopropylmethoxy)-6-methoxyphenyl, 2-(3-hydroxypropoxy)-6-methoxyphenyl, 2-(2,3-dihydroxypropoxy)-6-methoxyphenyl, 2-(2-methoxyethoxy)-6-methoxyphenyl, 2,4,6-trimethoxyphenyl, 2-methoxy-6-trifluoromethylphenyl, 2-trifluoromethylphenyl, 2-fluoro-6-trifluoromethylphenyl, 2-trifluoromethoxyphenyl, benzo[1,3]dioxol-4-yl, and 2,3-dihydro-benzo[1,4]dioxin-5-yl. In further sub-embodiment, particular examples of aryl groups for the substituent $R^2$ are 2-methoxy-6-methylphenyl, 2,6-dimethoxyphenyl, 4-fluoro-2,6-dimethoxyphenyl, 2-ethoxy-6-methoxyphenyl, 2,6-diethoxyphenyl, 2-isopropoxy-6-methoxyphenyl, 2,6-dimethoxy-4-methylphenyl, 2-(2-hydroxyethoxy)-6-methoxyphenyl, 2-(cyclopropylmethoxy)-6-methoxyphenyl, 2-(3-hydroxypropoxy)-6-methoxyphenyl, 2-(2-methoxyethoxy)-6-methoxyphenyl, and 2-methoxy-6-trifluoromethyl phenyl.

The term "heteroaryl", if not explicitly stated otherwise, means a 5- to 14-membered monocyclic, bicyclic, or tricyclic aromatic ring containing 1 to a maximum of 4 heteroatoms independently selected from oxygen, nitrogen and sulfur. Examples of such heteroaryl groups are 5-membered monocyclic heteroaryl groups such as furanyl, oxazolyl, isoxazolyl, oxadiazolyl, thienyl, thiazolyl, isothiazolyl, thiadiazolyl, pyrrolyl, imidazolyl, pyrazolyl, and triazolyl; 6-membered monocyclic heteroaryl such as pyridyl, pyrimidyl, pyridazinyl, and pyrazinyl; bicyclic heteroaryl such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl, 1H-pyrrolo[3,2-b]pyridyl, 1H-pyrrolo[2,3-b]pyridyl, 4H-furo[3,2-b]pyrrolyl, pyrrolo[2,1-b]thiazolyl and imidazo[2,1-b]thiazolyl; and tricyclic heteroaryl groups such as dibenzofuranyl, and 9H-carbazolyl.

The heteroaryl group may be unsubstituted or substituted as explicitly defined.

Examples of heteroaryl groups as used for the substituent $R^1$ (especially in the particular meaning of the group $Ar^1$) are 6-membered monocyclic heteroaryl such as pyridyl, pyrimidyl, pyridazinyl, and pyrazinyl; bicyclic heteroaryl such as indolyl, benzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl, 1H-pyrrolo[3,2-b]pyridyl, 1H-pyrrolo[2,3-b]pyridyl, 4H-furo[3,2-b]pyrrolyl, pyrrolo[2,1-b]thiazolyl, and imidazo[2,1-b]thiazolyl; and tricyclic heteroaryl groups such as dibenzofuranyl, and 9H-carbazolyl. In addition to the obove-mentioned groups, a further example of tricyclic heteroaryl groups is dibenzothiophenyl. In a sub-embodiment, examples are pyridyl; bicyclic heteroaryl such as indolyl, benzofuranyl, benzothiophenyl, benzoxazolyl, benzothiazolyl, benzotriazolyl, benzoxadiazolyl, quinolinyl, quinoxalinyl, and imidazo[1,2-a]pyridyl; and tricyclic heteroaryl groups such as dibenzofuranyl, and 9H-carbazolyl. Particular examples of heteroaryl groups as used for the substituent $R^1$ (in the particular meaning of the group $Ar^1$) are 6-membered monocyclic heteroaryl such as 6-difluoromethoxy-pyridin-3-yl, 6-difluoromethoxy-pyridin-2-yl, 5-difluoromethoxy-pyridin-2-yl, 4-difluoromethoxy-pyridin-2-yl, 5-chloro-6-difluoromethoxy-pyridin-3-yl, 6-difluoromethoxy-5-methyl-pyridin-3-yl, 6-(piperidin-1-yl)pyridin-2-yl, 2-(pyrrolidin-1-yl)pyridin-4-yl, bicyclic heteroaryl such as benzo[b]thiophen-2-yl, benzo[b]thiophen-5-yl, benzofuran-2-yl, 1-methyl-1H-benzotriazol-5-yl, 2-methyl-benzoxazol-5-yl, benzo[c][1,2,5]oxadiazol-5-yl, 2-methyl-benzothiazol-6-yl, 2-methyl-benzothiazol-5-yl, benzothiazol-2-yl, imidazo[1,2-a]pyridin-2-yl, 1-methyl-1H-indol-2-yl, 1-methyl-1H-indol-5-yl, quinoxalin-6-yl, quinolin-2-yl, and quinolin-3-yl; and tricyclic heteroaryl groups such as dibenzofuran-2-yl, and 9-methyl-9H-carbazol-3-yl. In addition to the above-mentioned groups, further particular examples of such heteroaryl groups as used for the substituent $R^1$ are bicyclic heteroaryl such as 1H-indol-2-yl, 5-fluoro-1-methyl-1H-indol-2-yl; and tricyclic heteroaryl such as dibenzothiophen-2-yl.

In addition to the above examples, further examples of heteroaryl groups as used for the substituent $R^1$ (especially in the particular meaning of —$Ar^2$— within the group $Ar^3$—X—$Ar^2$—*, wherein —$Ar^2$— is a 5- or 6-membered heteroaryl group) are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, and pyrazinyl. In a sub-embodiment, examples of such groups $R^1$ are isoxazolyl, thienyl, thiazolyl, pyrazolyl, and pyridyl; especially thiazolyl, and pyridyl. Preferred are those groups wherein the group $Ar^3$—X— and the rest of the molecule are attached to —$Ar^2$— in a meta-(1,3-diyl-) or para-(1,4-diyl-) arrangement (for —$Ar^2$— being 6-membered heteroaryl); respectively in a 1,3 diyl-arrangement (for —$Ar^2$— being 5-membered heteroaryl); such as especially thiazol-2,4-diyl (wherein the substituent $Ar^3$ may be attached in either position 2 or 4), pyridin-2,4-diyl (wherein the substituent $Ar^3$ may be attached in either position 2 or 4), and pyridin-2,6-diyl (wherein the substituent $Ar^3$ may be attached in either position 2 or 6).

Examples of 5- or 6-membered heteroaryl groups as used for 5- or 6-membered heteroaryl substituents of the substituent $R^1$ (in the particular meaning of $Ar^3$ within the group $Ar^3$—X—$Ar^2$—*, wherein $Ar^3$ is a 5- or 6-membered heteroaryl group) are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, and pyrazinyl. In a sub-embodiment, examples of $Ar^3$ are oxadiazolyl, thiazolyl, pyrrolyl, imidazolyl, pyrazolyl, triazolyl, pyridyl, and pyrimidyl. Particular examples of 5- or 6-membered heteroaryl groups as used for 5- or 6-membered heteroaryl substituents of the substituent $R^1$ (in the particular meaning of $Ar^3$; as used for example within the group $Ar^3$—X—$Ar^2$—*, wherein $Ar^3$ is a 5- or 6-membered heteroaryl group) are pyrrol-1-yl, pyrazol-1-yl, imidazo-1-yl, thiazol-2-yl, thiazol-4-yl, thiazol-5-yl, 2-methyl-thiazol-4-yl, 5-methyl-thiazol-2-yl, [1,2,3]triazol-2-yl, [1,2,3]triazol-1-yl, [1,2,4]triazol-1-yl, 5-methyl-[1,2,4]oxadiazol-3-yl, pyridin-2-yl, pyridin-3-yl, pyridin-4-yl, and pyrimidin-2-yl. In addition to the above-mentioned groups, a further example of such substituents $Ar^3$ is 4-chloro-thiazol-2-yl.

For the substituent $R^2$ examples of 5- to 10-membered heteroaryl groups are pyridyl, pyrimidyl, pyridazinyl, benzofuranyl, isobenzofuranyl, benzothiophenyl, benzoxazolyl, benzisoxazolyl, benzothiazolyl, benzoisothiazolyl, benzotriazolyl, benzoxadiazolyl, benzothiadiazolyl, quinolinyl, quinazolinyl, quinoxalinyl, pyrazolo[1,5-a]pyridyl, pyrazolo[1,5-a]pyrimidyl, imidazo[1,2-a]pyridyl, 1H-pyrrolo[3,2-b]pyridyl, 1H-pyrrolo[2,3-b]pyridyl, 4H-furo[3,2-b]pyrrolyl, pyrrolo[2,1-b]thiazolyl and imidazo[2,1-b]thiazolyl. For the substituent $R^2$ particular examples of 5- to 10-membered heteroaryl groups are monocyclic heteroaryl groups such as 2,4-dimethoxypyridin-3-yl, 3,5-dimethoxypyridin-4-yl and 4,6-dimethoxypyrimidin-4-yl; and bicyclic heteroaryl groups such as 6-methoxy-benzoxazol-7-yl, 6-methoxy-3-methyl-benzo[d]isoxazol-7-yl, and 6-methoxy-2-methyl-benzoxazol-7-yl. Preferred are pyridyl, pyrimidyl, benzoxazolyl, and benzisoxazolyl groups; especially 3-pyridyl, 4-pyridyl, and 5-pyrimidyl groups. In addition to the above-mentioned groups, a further particular example is 2-ethyl-6-methoxy-benzoxazol-7-yl; another particular example is 2-phenyl-2H-pyrazol-3-yl.

For the particular sub-group of heteroaryl groups wherein "substituents form a non-aromatic 5- or 6-membered ring fused to said heteroaryl, wherein said ring optionally contains one or two heteroatoms independently selected from oxygen and nitrogen" (as used for the substituent $R^2$), or wherein "the heteroaryl is fused to a non-aromatic 5- or 6-membered ring, wherein said ring optionally contains one or two heteroatoms independently selected from oxygen and nitrogen" (as used for the substituent $R^1$) the heteroaryl is preferably 6-membered heteroaryl ring. Examples of such heteroaryl groups fused to a non-aromatic 5- or 6-membered ring are 2,3-dihydro-[1,4]dioxino-pyridinyl groups (such as especially 2,3-dihydro-[1,4]dioxino[2,3-b]pyridinyl or 2,3-dihydro-[1,4]dioxino[2,3-c]pyridinyl), and [1,3]dioxolopyridinyl groups (such as especially [1,3]dioxolo[4,5-b]pyridinyl or [1,3]dioxolo[4,5-c]pyridinyl). The above-mentioned heteroaryl groups are optionally substituted in said non-aromatic 5- or 6-membered ring with one or two substituents independently selected from $(C_{1-3})$alkyl, oxo, and halogen. Particular examples of fragments forming a non-aromatic 5- or 6-membered ring fused to said heteroaryl are selected from the group consisting of —$(CH_2)_n$—, wherein n represents the integer 3 or 4; —$(CH_2)_p$—O—, wherein p represents the integer 1 or 2; —CH=CH—$CH_2$—O—; —O—$(CH_2)_q$—O—, wherein q represents the integer 1 or 2; —O—(C=O)—O—; —O—(CF_2)—O—, —O—CH=CH—O—; —$(CH_2)_3$—NH—; —$(CH_2)_3$—N($CH_3$)—; —O—$(CH_2)_2$—NH—; and —O—$(CH_2)_2$—N($CH_3$)—. Heteroaryl groups carrying such substituents may be further substituted on the aromatic ring as explicitly defined.

The term "fluoroalkyl-thio" refers to an alkyl group as defined before containing one to three carbon atoms in which one or more (and possibly all) hydrogen atoms have been replaced with fluorine, said group being attached to the rest of the molecule via a sulfur atom. The term "$(C_{x-y})$fluoroalkyl-thio" (x and y each being an integer) refers to a fluoroalkyl-thio group as defined before containing x to y carbon atoms.

For example a (C$_{1-3}$)fluoroalkyl-thio group contains from one to three carbon atoms in which one to seven hydrogen atoms have been replaced with fluorine. A representative example of a fluoroalkyl-thio group is trifluoromethyl-sulfanyl (F$_3$C—S—).

The term "(C$_{3-6}$)cycloalkyl-(C$_{1-4}$)alkoxy" refers to a (C$_{1-4}$)alkoxy group as defined before containing one to four carbon atoms in which one hydrogen atom has been replaced with a (C$_{3-6}$)cycloalkyl group as defined before. A representative example of (C$_{3-6}$)cycloalkyl-(C$_{1-4}$)alkoxygroups is cyclopropylmethoxy.

The term "hydroxy-(C$_{1-4}$)alkoxy" refers to an alkoxy group as defined before containing one to four carbon atoms in which one hydrogen atom has been replaced with hydroxy. Representative examples of hydroxy-(C$_{1-4}$)alkoxy groups are 2-hydroxy-ethoxy and 2-hydroxy-propoxy (notably 2-hydroxy-ethoxy).

The term "dihydroxy-(C$_{1-4}$)alkoxy" refers to refers to an alkoxy group as defined before containing one to four carbon atoms in which two hydrogen atoms have been replaced with hydroxy. A representative example of a dihydroxy-(C$_{1-4}$)alkoxy group is 2,3-dihydroxy-propoxy.

The term "(C$_{1-4}$)alkoxy-(C$_{1-4}$)alkoxy" refers to an alkoxy group as defined before containing one to four carbon atoms in which one hydrogen atom has been replaced with a (C$_{1-4}$)alkoxy group as defined before. A representative example of a (C$_{1-4}$)alkoxy-(C$_{1-4}$)alkoxy group is 2-methoxy-ethoxy.

The term "oxo" refers to a substituent O=; preferably being bound to a carbon atom thus forming a carbonyl group; especially in alpha position to a heteroatom such as nitrogen or oxygen, thus forming an amide, respectively an carboxylic acid/ester group.

36) Another embodiment relates to compounds of formula (I) according to embodiment 1) selected from the group consisting of:

6-(2,6-dimethoxyphenyl)-1-((2-methylbenzo[d]thiazol-5-yl)methyl)piperidin-2-one;
6-(2,6-dimethoxyphenyl)-1-(quinolin-6-ylmethyl)piperidin-2-one;
(R)-6-(2,6-dimethoxyphenyl)-1-(quinolin-2-ylmethyl)piperidin-2-one;
(S)-6-(2,6-dimethoxyphenyl)-1-(quinolin-2-ylmethyl)piperidin-2-one;
1-((5-chloro-6-(difluoromethoxy)pyridin-3-yl)methyl)-6-(2,6-dimethoxyphenyl)piperidin-2-one;
6-(2,6-dimethoxyphenyl)-1-((6-(4-fluorophenyl)pyridin-2-yl)methyl)piperidin-2-one;
6-(2,6-dimethoxyphenyl)-1-(3-(pyridin-3-yl)benzyl)piperidin-2-one;
6-(2,6-dimethoxyphenyl)-1-(3-(pyridin-4-yl)benzyl)piperidin-2-one;
6-(2,6-dimethoxyphenyl)-1-(3-(pyridin-2-yl)benzyl)piperidin-2-one;
6-(2,6-dimethoxyphenyl)-1-((6-phenylpyridin-2-yl)methyl)piperidin-2-one;
6-(2,6-dimethoxyphenyl)-1-((2-phenylpyridin-4-yl)methyl)piperidin-2-one;
6-(2,6-dimethoxyphenyl)-1-(3-(piperidin-1-yl)benzyl)piperidin-2-one;
6-(2,6-dimethoxyphenyl)-1-(3-(thiazol-2-yl)benzyl)piperidin-2-one;
6-(2,6-dimethoxyphenyl)-1-(naphthalen-1-ylmethyl)piperidin-2-one;
6-(2,6-dimethoxyphenyl)-1-(3-(2-methylthiazol-4-yl)benzyl)piperidin-2-one;
6-(2,6-dimethoxyphenyl)-1-((5-phenylthiophen-2-yl)methyl)piperidin-2-one;
1-(3-(1H-pyrazol-1-yl)benzyl)-6-(2,6-dimethoxyphenyl)piperidin-2-one;
6-(2,6-dimethoxyphenyl)-1-((4-phenylpyridin-2-yl)methyl)piperidin-2-one;
6-(2,6-dimethoxyphenyl)-1-(3-(pyrrolidin-1-yl)benzyl)piperidin-2-one;
6-(2,6-dimethoxyphenyl)-1-((1-phenyl-1H-pyrazol-4-yl)methyl)piperidin-2-one;
1-(3-(1H-imidazol-1-yl)benzyl)-6-(2,6-dimethoxyphenyl)piperidin-2-one;
6-(2,6-dimethoxyphenyl)-1-((6-(piperidin-1-yl)pyridin-2-yl)methyl)piperidin-2-one;
6-(2,6-dimethoxyphenyl)-1-(3-(pyrimidin-2-yl)benzyl)piperidin-2-one;
1-(dibenzo[b,d]furan-2-ylmethyl)-6-(2,6-dimethoxyphenyl)piperidin-2-one;
6-(2,6-dimethoxyphenyl)-1-((9-methyl-9H-carbazol-3-yl)methyl)piperidin-2-one;
6-(2,6-dimethoxyphenyl)-1-(3-(5-methyl-1,2,4-oxadiazol-3-yl)benzyl)piperidin-2-one;
6-(2,6-dimethoxyphenyl)-1-((2-phenylthiazol-4-yl)methyl)piperidin-2-one;
6-(2,6-dimethoxyphenyl)-1-(2-fluoro-3-(pyridin-2-yl)benzyl)piperidin-2-one;
1-([2,2'-bipyridin]-6-ylmethyl)-6-(2,6-dimethoxyphenyl)piperidin-2-one;
6-(2,6-dimethoxyphenyl)-1-((6-(thiazol-2-yl)pyridin-2-yl)methyl)piperidin-2-one;
6-(2,6-dimethoxyphenyl)-1-(2-fluoro-5-(pyridin-2-yl)benzyl)piperidin-2-one;
6-(2,6-dimethoxyphenyl)-1-(4-fluoro-3-(pyridin-2-yl)benzyl)piperidin-2-one;
6-(2,6-dimethoxyphenyl)-1-(3-(thiazol-5-yl)benzyl)piperidin-2-one;
6-(2,6-dimethoxyphenyl)-1-(3-(5-methylthiazol-2-yl)benzyl)piperidin-2-one;
1-(3-(2H-1,2,3-triazol-2-yl)benzyl)-6-(2,6-dimethoxyphenyl)piperidin-2-one;
6-(2,6-dimethoxyphenyl)-1-(3-(thiazol-4-yl)benzyl)piperidin-2-one;
6-(2,6-dimethoxyphenyl)-1-((2-methylbenzo[d]thiazol-6-yl)methyl)piperidin-2-one;
1-(2-chloro-5-(pyridin-2-yl)benzyl)-6-(2,6-dimethoxyphenyl)piperidin-2-one;
1-(3-chloro-5-(pyridin-2-yl)benzyl)-6-(2,6-dimethoxyphenyl)piperidin-2-one;
1-([2,2'-bipyridin]-4-ylmethyl)-6-(2,6-dimethoxyphenyl)piperidin-2-one;
1-((6-(1H-pyrazol-1-yl)pyridin-2-yl)methyl)-6-(2,6-dimethoxyphenyl)piperidin-2-one;
1-((2-(1H-pyrazol-1-yl)pyridin-4-yl)methyl)-6-(2,6-dimethoxyphenyl)piperidin-2-one;
6-(2,4-dimethoxypyridin-3-yl)-1-(3-(thiazol-2-yl)benzyl)piperidin-2-one;
6-(2,4-dimethoxypyridin-3-yl)-1-(3-(2-methylthiazol-4-yl)benzyl)piperidin-2-one;
6-(2,4-dimethoxypyridin-3-yl)-1-(3-(pyridin-2-yl)benzyl)piperidin-2-one;
6-(2,4-dimethoxypyridin-3-yl)-1-((2-phenylthiazol-4-yl)methyl)piperidin-2-one;
1-(dibenzo[b,d]furan-2-ylmethyl)-6-(2,4-dimethoxypyridin-3-yl)piperidin-2-one;
6-(2,4-dimethoxypyridin-3-yl)-1-(4-fluoro-3-(pyridin-2-yl)benzyl)piperidin-2-one;
1-([1,1'-biphenyl]-3-ylmethyl)-6-(2,4-dimethoxypyridin-3-yl)piperidin-2-one;

6-(3,5-dimethoxypyridin-4-yl)-1-(3-(thiazol-2-yl)benzyl)piperidin-2-one;
6-(3,5-dimethoxypyridin-4-yl)-1-(3-(2-methylthiazol-4-yl)benzyl)piperidin-2-one;
6-(3,5-dimethoxypyridin-4-yl)-1-(3-(pyridin-2-yl)benzyl)piperidin-2-one;
1-(dibenzo[b,d]furan-2-ylmethyl)-6-(3,5-dimethoxypyridin-4-yl)piperidin-2-one;
1-(3-(2H-1,2,3-triazol-2-yl)benzyl)-6-(3,5-dimethoxypyridin-4-yl)piperidin-2-one;
1-([1,1'-biphenyl]-3-ylmethyl)-6-(3,5-dimethoxypyridin-4-yl)piperidin-2-one;
1-((6-(difluoromethoxy)-5-methylpyridin-3-yl)methyl)-6-(2,6-dimethoxyphenyl)piperidin-2-one;
1-([1,1'-biphenyl]-3-ylmethyl)-7-(2,6-dimethoxyphenyl)azepan-2-one;
7-(2,6-dimethoxyphenyl)-1-(4-phenoxybenzyl)azepan-2-one;
7-(2,6-dimethoxyphenyl)-1-(3-phenoxybenzyl)azepan-2-one;
7-(2,6-dimethoxyphenyl)-1-(naphthalen-2-ylmethyl)azepan-2-one;
7-(2,6-dimethoxyphenyl)-1-(naphthalen-1-ylmethyl)azepan-2-one;
1-([1,1'-biphenyl]-4-ylmethyl)-7-(2,6-dimethoxyphenyl)azepan-2-one;
7-(2,6-dimethoxyphenyl)-1-(quinolin-2-ylmethyl)azepan-2-one;
7-(2,6-dimethoxyphenyl)-1-((2-phenyl pyridin-4-yl)methyl)azepan-2-one;
7-(2,6-dimethoxyphenyl)-1-((6-phenylpyridin-2-yl)methyl)azepan-2-one;
7-(2,6-dimethoxyphenyl)-1-(3-(pyrimidin-2-yl)benzyl)azepan-2-one;
7-(2,6-dimethoxyphenyl)-1-(3-(pyridin-2-yl)benzyl)azepan-2-one;
7-(2,6-dimethoxyphenyl)-1-(3-(thiazol-2-yl)benzyl)azepan-2-one;
7-(2,6-dimethoxyphenyl)-1-((9-methyl-9H-carbazol-3-yl)methyl)azepan-2-one;
7-(2,6-dimethoxyphenyl)-1-(3-(pyridin-3-yl)benzyl)azepan-2-one;
7-(2,6-dimethoxyphenyl)-1-(3-(piperidin-1-yl)benzyl)azepan-2-one;
1-((5-chloro-6-(difluoromethoxy)pyridin-3-yl)methyl)-7-(2,6-dimethoxyphenyl)azepan-2-one;
1-(dibenzo[b,d]furan-2-ylmethyl)-7-(2,6-dimethoxyphenyl)azepan-2-one;
7-(2,6-dimethoxyphenyl)-1-(3-(2-methylthiazol-4-yl)benzyl)azepan-2-one;
7-(2,6-dimethoxyphenyl)-1-(3-(pyrrolidin-1-yl)benzyl)azepan-2-one;
7-(2,6-dimethoxyphenyl)-1-((1-phenyl-1H-pyrazol-4-yl)methyl)azepan-2-one;
7-(2,6-dimethoxyphenyl)-1-((2-methylbenzo[d]thiazol-5-yl)methyl)azepan-2-one;
7-(2,6-dimethoxyphenyl)-1-(3-(pyridin-4-yl)benzyl)azepan-2-one;
1-(3-(1H-pyrazol-1-yl)benzyl)-7-(2,6-dimethoxyphenyl)azepan-2-one;
7-(2,6-dimethoxyphenyl)-1-((2-phenylthiazol-4-yl)methyl)azepan-2-one;
7-(2,6-dimethoxyphenyl)-1-(3-(thiazol-5-yl)benzyl)azepan-2-one;
7-(2,6-dimethoxyphenyl)-1-(3-(5-methylthiazol-2-yl)benzyl)azepan-2-one;
1-(3-(2H-1,2,3-triazol-2-yl)benzyl)-7-(2,6-dimethoxyphenyl)azepan-2-one;
7-(2,6-dimethoxyphenyl)-1-(3-(thiazol-4-yl)benzyl)azepan-2-one;
1-((2-(1H-pyrazol-1-yl)pyridin-4-yl)methyl)-7-(2,6-dimethoxyphenyl)azepan-2-one;
1-((6-(1H-pyrazol-1-yl)pyridin-2-yl)methyl)-7-(2,6-dimethoxyphenyl)azepan-2-one;
7-(2,6-dimethoxyphenyl)-1-((2-methylbenzo[d]thiazol-6-yl)methyl)azepan-2-one;
7-(2,6-dimethoxyphenyl)-1-(2-fluoro-3-(pyridin-2-yl)benzyl)azepan-2-one;
7-(2,6-dimethoxyphenyl)-1-(4-fluoro-3-(pyridin-2-yl)benzyl)azepan-2-one;
5-(2,6-dimethoxyphenyl)-1-(quinolin-3-ylmethyl)pyrrolidin-2-one;
5-(2,6-dimethoxyphenyl)-1-(quinolin-2-ylmethyl)pyrrolidin-2-one;
5-(2,6-dimethoxyphenyl)-1-(naphthalen-2-ylmethyl)pyrrolidin-2-one;
1-((5-chloro-6-(difluoromethoxy)pyridin-3-yl)methyl)-5-(2,6-dimethoxyphenyl)pyrrolidin-2-one;
1-([1,1'-biphenyl]-3-ylmethyl)-5-(2,6-dimethoxyphenyl)pyrrolidin-2-one;
1-([1,1'-biphenyl]-4-ylmethyl)-5-(2,6-dimethoxyphenyl)pyrrolidin-2-one;
5-(2,6-dimethoxyphenyl)-1-(3-phenoxybenzyl)pyrrolidin-2-one;
5-(2,6-dimethoxyphenyl)-1-(4-phenoxybenzyl)pyrrolidin-2-one;
5-(2,6-dimethoxyphenyl)-1-(3-(pyridin-2-yl)benzyl)pyrrolidin-2-one;
5-(2,6-dimethoxyphenyl)-1-((2-phenylpyridin-4-yl)methyl)pyrrolidin-2-one;
5-(2,6-dimethoxyphenyl)-1-((6-phenylpyridin-2-yl)methyl)pyrrolidin-2-one;
1-([1,1'-biphenyl]-3-ylmethyl)-5-(2,6-dimethoxyphenyl)-3-methylpyrrolidin-2-one;
5-(2,6-dimethoxyphenyl)-3-methyl-1-(3-(pyrrolidin-1-yl)benzyl)pyrrolidin-2-one;
5-(2,6-dimethoxyphenyl)-1-(3-(thiazol-2-yl)benzyl)pyrrolidin-2-one;
5-(2,6-dimethoxyphenyl)-1-(3-(2-methylthiazol-4-yl)benzyl)pyrrolidin-2-one;
1-(3-(1H-pyrazol-1-yl)benzyl)-5-(2,6-dimethoxyphenyl)pyrrolidin-2-one;
1-(dibenzo[b,d]furan-2-ylmethyl)-5-(2,6-dimethoxyphenyl)pyrrolidin-2-one;
5-(2,6-dimethoxyphenyl)-1-(3-(piperidin-1-yl)benzyl)pyrrolidin-2-one;
5-(2,6-dimethoxyphenyl)-3-methyl-1-(naphthalen-2-ylmethyl)pyrrolidin-2-one;
5-(2,6-dimethoxyphenyl)-3-methyl-1-(3-(thiazol-2-yl)benzyl)pyrrolidin-2-one;
5-(2,6-dimethoxyphenyl)-3-methyl-1-(3-(2-methylthiazol-4-yl)benzyl)pyrrolidin-2-one;
5-(2,6-dimethoxyphenyl)-3-methyl-1-(3-(piperidin-1-yl)benzyl)pyrrolidin-2-one;
1-(3-(1H-pyrazol-1-yl)benzyl)-5-(2,6-dimethoxyphenyl)-3-methylpyrrolidin-2-one;
1-(dibenzo[b,d]furan-2-ylmethyl)-5-(2,6-dimethoxyphenyl)-3-methylpyrrolidin-2-one;
5-(2,6-dimethoxyphenyl)-3-methyl-1-((6-phenylpyridin-2-yl)methyl)pyrrolidin-2-one;
5-(2,6-dimethoxyphenyl)-3-methyl-1-((2-phenylpyridin-4-yl)methyl)pyrrolidin-2-one;

5-(2,6-dimethoxyphenyl)-3-methyl-1-(3-(pyridin-2-yl)benzyl)pyrrolidin-2-one;
5-(2,6-dimethoxyphenyl)-3-methyl-1-(3-(pyridin-3-yl)benzyl)pyrrolidin-2-one;
5-(2,6-dimethoxyphenyl)-3-methyl-1-(3-(pyrimidin-2-yl)benzyl)pyrrolidin-2-one;
5-(2,6-dimethoxyphenyl)-3-methyl-1-(3-(5-methyl-1,2,4-oxadiazol-3-yl)benzyl)pyrrolidin-2-one;
5-(2,6-dimethoxyphenyl)-3-methyl-1-((2-phenylthiazol-4-yl)methyl)pyrrolidin-2-one;
5-(2,6-dimethoxyphenyl)-1-(2-fluoro-3-(pyridin-2-yl)benzyl)-3-methylpyrrolidin-2-one;
5-(2,6-dimethoxyphenyl)-3-methyl-1-(3-(thiazol-5-yl)benzyl)pyrrolidin-2-one;
5-(2,6-dimethoxyphenyl)-3-methyl-1-(3-(5-methylthiazol-2-yl)benzyl)pyrrolidin-2-one;
1-(3-(2H-1,2,3-triazol-2-yl)benzyl)-5-(2,6-dimethoxyphenyl)-3-methylpyrrolidin-2-one;
5-(2,6-dimethoxyphenyl)-3-methyl-1-(3-(thiazol-4-yl)benzyl)pyrrolidin-2-one;
5-(2,6-dimethoxyphenyl)-3-methyl-1-((2-methylbenzo[d]thiazol-6-yl)methyl)pyrrolidin-2-one;
1-(3-chloro-5-(pyridin-2-yl)benzyl)-5-(2,6-dimethoxyphenyl)-3-methylpyrrolidin-2-one;
5-(2,6-dimethoxyphenyl)-1-(4-fluoro-3-(pyridin-2-yl)benzyl)-3-methylpyrrolidin-2-one;
1-((2-(1H-pyrazol-1-yl)pyridin-4-yl)methyl)-5-(2,6-dimethoxyphenyl)-3-methylpyrrolidin-2-one;
1-((6-(1H-pyrazol-1-yl)pyridin-2-yl)methyl)-5-(2,6-dimethoxyphenyl)-3-methylpyrrolidin-2-one;
6-(2,6-dimethoxyphenyl)-1-(4-(trifluoromethoxy)benzyl)piperidin-2-one;
1-(4-chlorobenzyl)-6-(2,6-dimethoxyphenyl)piperidin-2-one;
6-(2,6-dimethoxyphenyl)-1-(3-fluoro-4-(trifluoromethoxy)benzyl)piperidin-2-one;
1-(3-chloro-4-(trifluoromethoxy)benzyl)-6-(2,6-dimethoxyphenyl)piperidin-2-one;
6-(2,6-dimethoxyphenyl)-1-(4-((trifluoromethyl)thio)benzyl)piperidin-2-one;
6-(2,6-dimethoxyphenyl)-1-(4-(trifluoromethyl)benzyl)piperidin-2-one;
6-(2,6-dimethoxyphenyl)-1-(4-phenoxybenzyl)piperidin-2-one;
1-(4-(difluoromethoxy)benzyl)-6-(2,6-dimethoxyphenyl)piperidin-2-one;
6-(4-chloro-2,6-dimethoxyphenyl)-1-(4-(trifluoromethoxy)benzyl)piperidin-2-one;
1-(4-(1H-pyrrol-1-yl)benzyl)-6-(2,6-dimethoxyphenyl)piperidin-2-one;
6-(2,6-dimethoxyphenyl)-1-((6-methoxynaphthalen-2-yl)methyl)piperidin-2-one;
1-(4-(trifluoromethoxy)benzyl)-6-(2,4,6-trimethoxyphenyl)piperidin-2-one;
6-(2,6-dimethoxyphenyl)-1-(3-(trifluoromethoxy)benzyl)piperidin-2-one;
6-(2,6-dimethoxyphenyl)-1-(4-(2-fluoroethoxy)benzyl)piperidin-2-one;
1-((6-(difluoromethoxy)pyridin-3-yl)methyl)-6-(2,6-dimethoxyphenyl)piperidin-2-one;
1-(3-(difluoromethoxy)benzyl)-6-(2,6-dimethoxyphenyl)piperidin-2-one;
6-(2,6-dimethoxyphenyl)-1-(3-phenoxybenzyl)piperidin-2-one;
1-(benzofuran-2-ylmethyl)-6-(2,6-dimethoxyphenyl)piperidin-2-one;
1-((2,2-difluorobenzo[d][1,3]dioxol-5-yl)methyl)-6-(2,6-dimethoxyphenyl)piperidin-2-one;
1-((6-(difluoromethoxy)pyridin-2-yl)methyl)-6-(2,6-dimethoxyphenyl)piperidin-2-one;
6-(2,6-dimethoxyphenyl)-1-(1-(4-(trifluoromethoxy)phenyl)ethyl)piperidin-2-one;
1-(1-(5-chloro-6-(difluoromethoxy)pyridin-3-yl)ethyl)-6-(2,6-dimethoxyphenyl)piperidin-2-one;
1-((5-(difluoromethoxy)pyridin-2-yl)methyl)-6-(2,6-dimethoxyphenyl)piperidin-2-one;
1-([1,1'-biphenyl]-3-ylmethyl)-6-(2,6-dimethoxyphenyl)piperidin-2-one;
6-(2,6-dimethoxyphenyl)-1-(2-phenoxybenzyl)piperidin-2-one;
6-(2,6-dimethoxyphenyl)-1-((6-phenoxypyridin-3-yl)methyl)piperidin-2-one;
7-(2,6-dimethoxyphenyl)-1-(4-(trifluoromethoxy)benzyl)azepan-2-one;
5-(2,6-dimethoxyphenyl)-1-(4-(trifluoromethoxy)benzyl)pyrrolidin-2-one;
1-(3-(difluoromethoxy)benzyl)-5-(2,6-dimethoxyphenyl)-3-methylpyrrolidin-2-one;
5-(2,6-dimethoxyphenyl)-3-methyl-1-(3-(trifluoromethoxy)benzyl)pyrrolidin-2-one;
1-((6-(difluoromethoxy)pyridin-2-yl)methyl)-5-(2,6-dimethoxyphenyl)-3-methylpyrrolidin-2-one;
6-(2,6-dimethoxyphenyl)-1-(4-ethoxybenzyl)piperidin-2-one;
6-(2,6-dimethoxyphenyl)-1-(4-isopropoxybenzyl)piperidin-2-one;
6-(2,6-dimethoxyphenyl)-1-(4-propoxybenzyl)piperidin-2-one;
1-(4-(cyclopropylmethoxy)benzyl)-6-(2,6-dimethoxyphenyl)piperidin-2-one;
6-(2-ethoxy-6-methoxyphenyl)-1-(4-(trifluoromethoxy)benzyl)piperidin-2-one;
6-(2-(2-hydroxyethoxy)-6-methoxyphenyl)-1-(4-(trifluoromethoxy)benzyl)piperidin-2-one;
6-(2,6-dimethoxyphenyl)-3-methyl-1-(4-(trifluoromethoxy)benzyl)piperidin-2-one;
5-(2,6-dimethoxyphenyl)-3,3-dimethyl-1-(4-(trifluoromethoxy)benzyl)pyrrolidin-2-one;
5-(2,6-dimethoxyphenyl)-3-methyl-1-(4-(trifluoromethoxy)benzyl)pyrrolidin-2-one;
6-(2,6-dimethoxyphenyl)-1-((2-(thiazol-2-yl)pyridin-4-yl)methyl)piperidin-2-one;
6-(2-fluoro-6-methoxyphenyl)-1-(4-(trifluoromethoxy)benzyl)piperidin-2-one;
6-(2-chloro-6-methoxyphenyl)-1-(4-(trifluoromethoxy)benzyl)piperidin-2-one;
6-(2-isopropoxy-6-methoxyphenyl)-1-(4-(trifluoromethoxy)benzyl)piperidin-2-one;
6-(4-fluoro-2,6-dimethoxyphenyl)-1-(4-(trifluoromethoxy)benzyl)piperidin-2-one;
6-(2,6-dimethoxy-4-methylphenyl)-1-(4-(trifluoromethoxy)benzyl)piperidin-2-one;
1-([1,1'-biphenyl]-3-ylmethyl)-6-(6-methoxy-3-methylbenzo[d]isoxazol-7-yl)piperidin-2-one;
6-(2,6-dimethoxyphenyl)-1-(naphthalen-2-ylmethyl)piperidin-2-one;
1-([1,1'-biphenyl]-4-ylmethyl)-6-(2,6-dimethoxyphenyl)piperidin-2-one;
6-(2,6-dimethoxyphenyl)-1-(4-(pyrrolidin-1-yl)benzyl)piperidin-2-one;
6-(2,6-dimethoxyphenyl)-1-(4-(2,2,2-trifluoroethoxy)benzyl)piperidin-2-one;

6-(2,6-dimethoxyphenyl)-1-((1-methyl-1H-indol-2-yl)methyl)piperidin-2-one;
6-(2,6-dimethoxyphenyl)-1-((2-methylbenzo[d]oxazol-5-yl)methyl)piperidin-2-one;
1-(benzo[b]thiophen-5-ylmethyl)-6-(2,6-dimethoxyphenyl)piperidin-2-one;
(3S*,5S*)-5-(2,6-dimethoxyphenyl)-3-methoxy-1-(4-(trifluoromethoxy)benzyl)pyrrolidin-2-one;
5-(2,6-dimethoxyphenyl)-3,3-difluoro-1-(4-(trifluoromethoxy)benzyl)pyrrolidin-2-one;
(3R*,5S*)-3-chloro-5-(2,6-dimethoxyphenyl)-1-(4-(trifluoromethoxy)benzyl)pyrrolidin-2-one;
(3R*,5S*)-5-(2,6-dimethoxyphenyl)-3-hydroxy-1-(4-(trifluoromethoxy)benzyl)pyrrolidin-2-one;
(3S*,5S*)-5-(2,6-dimethoxyphenyl)-3-methyl-1-(4-(trifluoromethoxy)benzyl)pyrrolidin-2-one;
(3S*,5S*)-5-(2,6-dimethoxyphenyl)-3-fluoro-1-(4-(trifluoromethoxy)benzyl)pyrrolidin-2-one;
(3S*,5S*)-3-chloro-5-(2,6-dimethoxyphenyl)-1-(4-(trifluoromethoxy)benzyl)pyrrolidin-2-one;
(3R*,5S*)-5-(2,6-dimethoxyphenyl)-3-methyl-1-(4-(trifluoromethoxy)benzyl)pyrrolidin-2-one;
5-(2,6-dimethoxyphenyl)-4-(4-(trifluoromethoxy)benzyl)morpholin-3-one;
7-(3,5-dimethoxypyridin-4-yl)-1-(3-(2-methylthiazol-4-yl)benzyl)azepan-2-one;
1-([1,1'-biphenyl]-3-ylmethyl)-7-(3,5-dimethoxypyridin-4-yl)azepan-2-one;
7-(3,5-dimethoxypyridin-4-yl)-1-((2-phenylthiazol-4-yl)methyl)azepan-2-one;
6-(2,6-dimethoxyphenyl)-1-((2-phenoxythiazol-4-yl)methyl)piperidin-2-one;
6-(3-chloro-2,6-dimethoxyphenyl)-1-(3-(2-methylthiazol-4-yl)benzyl)piperidin-2-one; and
5-(2,6-dimethoxyphenyl)-1-(4-(thiazol-2-yloxy)benzyl)pyrrolidin-2-one.

37) In addition to the compounds listed in embodiment 36), further compounds of formula (I) according to embodiment 1) are selected from the group consisting of:

5-([1,1'-biphenyl]-2-yl)-1-(3-(2-methylthiazol-4-yl)benzyl)pyrrolidin-2-one;
5-([1,1'-biphenyl]-2-yl)-3-methyl-1-(3-(2-methylthiazol-4-yl)benzyl)pyrrolidin-2-one;
5-(2,6-dimethoxyphenyl)-1-(4-((4-methylthiazol-2-yl)oxy)benzyl)pyrrolidin-2-one;
(3R*,5S*)-5-(2-ethoxyphenyl)-3-hydroxy-1-(4-(trifluoromethoxy)benzyl)pyrrolidin-2-one;
(3S*,5S*)-5-(2-ethoxyphenyl)-3-fluoro-1-(4-(trifluoromethoxy)benzyl)pyrrolidin-2-one;
(3S*,5S*)-3-fluoro-6-methoxyphenyl)-1-(4-(trifluoromethoxy)benzyl)pyrrolidin-2-one;
(3S*,5S*)-5-(2-chloro-6-methoxyphenyl)-3-fluoro-1-(4-(trifluoromethoxy)benzyl)pyrrolidin-2-one;
(3S*,5S*)-3-fluoro-5-(4-fluoro-2-methoxyphenyl)-1-(4-(trifluoromethoxy)benzyl)pyrrolidin-2-one;
(3S*,5S*)-3-chloro-5-(2-ethoxyphenyl)-1-(4-(trifluoromethoxy)benzyl)pyrrolidin-2-one;
(3S*,5S*)-3-chloro-5-(2-fluoro-6-methoxyphenyl)-1-(4-(trifluoromethoxy)benzyl)pyrrolidin-2-one;
(3S*,5S*)-3-chloro-5-(2-chloro-6-methoxyphenyl)-1-(4-(trifluoromethoxy)benzyl)pyrrolidin-2-one;
(3S*,5S*)-3-chloro-5-(3-chloro-2,6-dimethoxyphenyl)-1-(4-(trifluoromethoxy)benzyl)pyrrolidin-2-one;
(3S*,5S*)-3-fluoro-5-(2-methoxy-6-methylphenyl)-1-(4-(trifluoromethoxy)benzyl)pyrrolidin-2-one;
(3S*,5S*)-3-chloro-5-(2-methoxy-6-methyl phenyl)-1-(4-(trifluoromethoxy)benzyl)pyrrolidin-2-one;
(3S*,5S*)-3-chloro-5-(3-fluoro-2,6-dimethoxyhenyl)-1-(4-(trifluoromethoxy)benzyl)pyrrolidin-2-one;
(3R*,5S*)-3-chloro-5-(2-ethoxy-6-fluorophenyl)-1-(4-(trifluoromethoxy)benzyl)pyrrolidin-2-one;
(3R*,5S*)-5-(2-ethoxy-6-fluorophenyl)-3-hydroxy-1-(4-(trifluoromethoxy)benzyl)pyrrolidin-2-one;
1-([1,1'-biphenyl]-3-ylmethyl)-5-(2,6-dimethoxyphenyl)-3,3-difluoropyrrolidin-2-one;
1-([1,1'-biphenyl]-3-ylmethyl)-5-(2-ethoxy-6-methoxyphenyl)-3,3-difluoropyrrolidin-2-one;
(3R*,5S*)-5-(6-ethoxy-2,3-difluorophenyl)-3-hydroxy-1-(4-(trifluoromethoxy)benzyl)pyrrolidin-2-one;
(3S*,5S*)-3-chloro-5-(6-ethoxy-2,3-difluorophenyl)-1-(4-(trifluoromethoxy)benzyl)pyrrolidin-2-one;
(3S*,5S*)-5-(6-ethoxy-2,3-difluorophenyl)-3-fluoro-1-(4-(trifluoromethoxy)benzyl)pyrrolidin-2-one;
(3S*,5S*)-5-(2-ethoxy-6-fluorophenyl)-3-fluoro-1-(4-(trifluoromethoxy)benzyl)pyrrolidin-2-one;
(3S*,5S*)-3-chloro-5-(2-ethoxy-6-fluorophenyl)-1-(4-(trifluoromethoxy)benzyl)pyrrolidin-2-one;
5-(2,4-dimethoxypyridin-3-yl)-3-methyl-1-(3-(5-methylthiazol-2-yl)benzyl)pyrrolidin-2-one;
5-(2,4-dimethoxypyridin-3-yl)-3-methyl-1-((2-(p-tolyl)thiazol-4-yl)methyl)pyrrolidin-2-one;
5-(2,6-dimethoxyphenyl)-3-methyl-1-((2-(5-methylthiazol-2-yl)pyridin-4-yl)methyl)pyrrolidin-2-one;
1-(dibenzo[b,d]furan-2-ylmethyl)-5-(2,4-dimethoxypyridin-3-yl)-3-methylpyrrolidin-2-one;
1-(dibenzo[b,d]furan-2-ylmethyl)-5-(2,6-dimethoxyphenyl)-3,3-difluoropyrrolidin-2-one;
1-([1,1'-biphenyl]-3-ylmethyl)-5-(2,4-dimethoxypyridin-3-yl)-3-methylpyrrolidin-2-one;
1-(3-(4-chlorothiazol-2-yl)benzyl)-5-(2,4-dimethoxypyridin-3-yl)-3-methylpyrrolidin-2-one;
5-(2,4-dimethoxypyridin-3-yl)-3-methyl-1-(3-(2-methylthiazol-4-yl)benzyl)pyrrolidin-2-one;
(3R*,5S*)-1-(dibenzo[b,d]furan-2-ylmethyl)-5-(2,6-dimethoxyphenyl)-3-hydroxypyrrolidin-2-one;
5-(2-fluoro-6-methoxyphenyl)-3-methyl-1-((2-(5-methylthiazol-2-yl)pyridin-4-yl)methyl)pyrrolidin-2-one;
1-((2-(1H-pyrazol-1-yl)pyridin-4-yl)methyl)-5-(2-fluoro-6-methoxyphenyl)-3-methylpyrrolidin-2-one;
1-(dibenzo[b,d]furan-2-ylmethyl)-5-(2-fluoro-6-methoxyphenyl)-3-methylpyrrolidin-2-one;
5-(2-fluoro-6-methoxyphenyl)-3-methyl-1-((2-(p-tolyl)thiazol-4-yl)methyl)pyrrolidin-2-one;
5-(2-fluoro-6-methoxyphenyl)-3-methyl-1-(3-(5-methylthiazol-2-yl)benzyl)pyrrolidin-2-one;
1-(3-(4-chlorothiazol-2-yl)benzyl)-5-(2-fluoro-6-methoxyphenyl)-3-methylpyrrolidin-2-one;
5-(2-fluoro-6-methoxyphenyl)-3-methyl-1-((2-(4-methylthiazol-2-yl)pyridin-4-yl)methyl)pyrrolidin-2-one;
(3S*,5S*)-1-(dibenzo[b,d]furan-2-ylmethyl)-5-(2,6-dimethoxyphenyl)-3-fluoropyrrolidin-2-one;
(3R*,5S*)-1-(dibenzo[b,d]furan-2-ylmethyl)-5-(2,6-dimethoxyphenyl)-3-fluoropyrrolidin-2-one;
(3S*,5S*)-3-chloro-1-(dibenzo[b,d]furan-2-ylmethyl)-5-(2,6-dimethoxyphenyl)pyrrolidin-2-one;
5-(2-ethoxy-6-fluorophenyl)-3-methyl-1-(4-(trifluoromethoxy)benzyl)pyrrolidin-2-one;
5-(2-ethoxy-6-fluorophenyl)-3-methyl-1-(3-(trifluoromethoxy)benzyl)pyrrolidin-2-one;
5-(2-ethoxy-6-fluorophenyl)-1-(3-fluoro-4-(trifluoromethoxy)benzyl)-3-methylpyrrolidin-2-one;
1-(4-(difluoromethoxy)benzyl)-5-(2-ethoxy-6-fluorophenyl)-3-methylpyrrolidin-2-one;

1-(3-(difluoromethoxy)benzyl)-5-(2-ethoxy-6-fluorophenyl)-3-methylpyrrolidin-2-one;
1-(3-chloro-4-(difluoromethoxy)benzyl)-5-(2-ethoxy-6-fluorophenyl)-3-methylpyrrolidin-2-one;
5-(2-ethoxy-6-fluorophenyl)-1-(3-ethoxybenzyl)-3-methylpyrrolidin-2-one;
5-(2-ethoxy-6-fluorophenyl)-3-methyl-1-(4-propoxybenzyl)pyrrolidin-2-one;
5-(2-ethoxy-6-fluorophenyl)-3-methyl-1-(quinolin-2-ylmethyl)pyrrolidin-2-one;
5-(2-ethoxy-6-fluorophenyl)-3-methyl-1-((2-(5-methylthiazol-2-yl)pyridin-4-yl)methyl)pyrrolidin-2-one;
1-((2-(1H-pyrazol-1-yl)pyridin-4-yl)methyl)-5-(2-ethoxy-6-fluorophenyl)-3-methylpyrrolidin-2-one;
1-(dibenzo[b,d]furan-2-ylmethyl)-5-(2-ethoxy-6-fluorophenyl)-3-methylpyrrolidin-2-one;
5-(2-ethoxy-6-fluorophenyl)-3-methyl-1-((2-(p-tolyl)thiazol-4-yl)methyl)pyrrolidin-2-one;
5-(2-ethoxy-6-fluorophenyl)-3-methyl-1-(3-(5-methylthiazol-2-yl)benzyl)pyrrolidin-2-one;
1-(3-(4-chlorothiazol-2-yl)benzyl)-5-(2-ethoxy-6-fluorophenyl)-3-methylpyrrolidin-2-one;
5-(2-ethoxy-6-fluorophenyl)-3-methyl-1-((2-(4-methylthiazol-2-yl)pyridin-4-yl)methyl)pyrrolidin-2-one;
5-(2,6-dimethoxyphenyl)-3-methyl-1-((9-methyl-9H-carbazol-3-yl)methyl)pyrrolidin-2-one;
5-(2,6-dimethoxyphenyl)-3-methyl-1-((1-methyl-1H-indol-2-yl)methyl)pyrrolidin-2-one;
5-(2,6-dimethoxyphenyl)-1-((5-fluoro-1-methyl-1H-indol-2-yl)methyl)-3-methylpyrrolidin-2-one;
5-(2,6-dimethoxyphenyl)-3-methyl-1-((1-methyl-1H-indol-5-yl)methyl)pyrrolidin-2-one;
5-(2,6-dimethoxyphenyl)-3-methyl-1-((2-methylbenzo[d]thiazol-5-yl)methyl)pyrrolidin-2-one;
(3R*,5S*)-5-(2-fluoro-6-isopropoxyphenyl)-3-hydroxy-1-(4-(trifluoromethoxy)benzyl)pyrrolidin-2-one;
(3R*,5S*)-1-(dibenzo[b,d]furan-2-ylmethyl)-3-fluoro-5-(2-fluoro-6-methoxyphenyl)pyrrolidin-2-one;
(3R*,5S*)-3-chloro-1-(dibenzo[b,d]furan-2-ylmethyl)-5-(2-fluoro-6-methoxyphenyl)pyrrolidin-2-one;
5-(2,6-dimethoxyphenyl)-3-methyl-1-(4-(1,1,2,2-tetrafluoroethoxy)benzyl)pyrrolidin-2-one;
5-(2,6-dimethoxyphenyl)-1-(3-fluoro-4-(trifluoromethoxy)benzyl)-3-methylpyrrolidin-2-one;
1-(3-chloro-4-(difluoromethoxy)benzyl)-5-(2,6-dimethoxyphenyl)-3-methylpyrrolidin-2-one;
5-(2,6-dimethoxyphenyl)-3-methyl-1-(2-(trifluoromethoxy)benzyl)pyrrolidin-2-one;
(3S*,5S*)-1-(dibenzo[b,d]furan-2-ylmethyl)-3-fluoro-5-(2-fluoro-6-methoxyphenyl)pyrrolidin-2-one;
(3S*,5S*)-3-fluoro-5-(2-fluoro-6-isopropoxyphenyl)-1-(4-(trifluoromethoxy)benzyl)pyrrolidin-2-one;
(3S*,5S*)-3-chloro-1-(dibenzo[b,d]furan-2-ylmethyl)-5-(2-fluoro-6-methoxyphenyl)pyrrolidin-2-one;
(3S*,5S*)-3-chloro-5-(2-fluoro-6-isopropoxyphenyl)-1-(4-(trifluoromethoxy)benzyl)pyrrolidin-2-one;
1-(dibenzo[b,d]furan-2-ylmethyl)-3,3-difluoro-5-(2-fluoro-6-methoxyphenyl)pyrrolidin-2-one;
3,3-difluoro-5-(2-fluoro-6-isopropoxyphenyl)-1-(4-(trifluoromethoxy)benzyl)pyrrolidin-2-one;
(3R*,5S*)-1-(dibenzo[b,d]furan-2-ylmethyl)-5-(2-fluoro-6-methoxyphenyl)-3-hydroxypyrrolidin-2-one;
5-(2-fluoro-6-isopropoxyphenyl)-3-methyl-1-(4-(trifluoromethoxy)benzyl)pyrrolidin-2-one;
5-(2-fluoro-6-(2-fluoroethoxy)phenyl)-3-methyl-1-(4-(trifluoromethoxy)benzyl)pyrrolidin-2-one;
5-(2-fluoro-6-(2-hydroxyethoxy)phenyl)-3-methyl-1-(4-(trifluoromethoxy)benzyl)pyrrolidin-2-one;
5-(2,6-dimethoxyphenyl)-3-methyl-1-(3-(2,2,2-trifluoroethoxy)benzyl)pyrrolidin-2-one;
1-(3-(2,2-difluoroethoxy)benzyl)-5-(2,6-dimethoxyphenyl)-3-methylpyrrolidin-2-one;
5-(2,6-dimethoxyphenyl)-1-(3-isopropoxybenzyl)-3-methylpyrrolidin-2-one;
5-(2,6-dimethoxyphenyl)-3-methyl-1-(3-(1,1,2,2-tetrafluoroethoxy)benzyl)pyrrolidin-2-one;
1-(dibenzo[b,d]thiophen-2-ylmethyl)-5-(2,6-dimethoxyphenyl)-3-methylpyrrolidin-2-one;
(3R*,5S*)-5-(2-chloro-6-ethoxyphenyl)-3-hydroxy-1-(4-(trifluoromethoxy)benzyl)pyrrolidin-2-one;
(3R*,5S*)-5-(2-ethoxy-6-fluorophenyl)-1-(3-fluoro-4-(trifluoromethoxy)benzyl)-3-hydroxypyrrolidin-2-one;
(3R*,5S*)-1-(3-chloro-4-(trifluoromethoxy)benzyl)-5-(2-ethoxy-6-fluorophenyl)-3-hydroxypyrrolidin-2-one;
(3R*,5S*)-5-(2-fluoro-6-methoxyphenyl)-3-hydroxy-1-(3-(trifluoromethoxy)benzyl)pyrrolidin-2-one;
(3R*,5S*)-5-(2-fluoro-6-(2-fluoroethoxy)phenyl)-3-hydroxy-1-(4-(trifluoromethoxy)benzyl)pyrrolidin-2-one;
(3S*,5S*)-5-(2-ethoxy-6-fluorophenyl)-3-fluoro-1-(3-fluoro-4-(trifluoromethoxy)benzyl)pyrrolidin-2-one;
(3S*,5S*)-3-chloro-5-(2-ethoxy-6-fluorophenyl)-1-(3-fluoro-4-(trifluoromethoxy)benzyl)pyrrolidin-2-one;
(3S*,5S*)-5-(2-chloro-6-ethoxyphenyl)-3-fluoro-1-(4-(trifluoromethoxy)benzyl)pyrrolidin-2-one;
(3S*,5S*)-3-chloro-5-(2-chloro-6-ethoxyphenyl)-1-(4-(trifluoromethoxy)benzyl)pyrrolidin-2-one;
(3S*,5S*)-5-(2-ethoxy-4,6-difluorophenyl)-3-fluoro-1-(4-(trifluoromethoxy)benzyl)pyrrolidin-2-one;
(3S*,5S*)-3-chloro-5-(2-ethoxy-4,6-difluorophenyl)-1-(4-(trifluoromethoxy)benzyl)pyrrolidin-2-one;
1-([1,1'-biphenyl]-3-ylmethyl)-6-(6-methoxy-2-methylbenzo[d]oxazol-7-yl)piperidin-2-one;
6-(6-methoxy-2-methylbenzo[d]oxazol-7-yl)-1-(3-(2-methylthiazol-4-yl)benzyl)piperidin-2-one;
6-(2-ethyl-6-methoxybenzo[d]oxazol-7-yl)-1-(3-(2-methylthiazol-4-yl)benzyl)piperidin-2-one;
6-(6-methoxy-2,3-dihydrobenzo[b][1,4]dioxin-5-yl)-1-(3-(2-methylthiazol-4-yl)benzyl)piperidin-2-one;
6-(6-methoxy-2,3-dihydrobenzo[b][1,4]dioxin-5-yl)-1-(3-(5-methylthiazol-2-yl)benzyl)piperidin-2-one;
6-(2-methoxynaphthalen-1-yl)-1-(3-(pyrimidin-2-yl)benzyl)piperidin-2-one;
6-(2-methoxynaphthalen-1-yl)-1-(3-(5-methylthiazol-2-yl)benzyl)piperidin-2-one;
6-(2-methoxynaphthalen-1-yl)-1-(3-phenoxybenzyl)piperidin-2-one;
6-(5-methoxybenzo[d][1,3]dioxol-4-yl)-1-(3-(2-methylthiazol-4-yl)benzyl)piperidin-2-one;
6-(5-methoxybenzo[d][1,3]dioxol-4-yl)-1-(4-(trifluoromethoxy)benzyl)piperidin-2-one;
7-(2-(pyridin-4-yl)phenyl)-1-(3-(thiazol-2-yl)benzyl)azepan-2-one;
1-(3-(thiazol-2-yl)benzyl)-7-(2-(thiazol-5-yl)phenyl)azepan-2-one;
1-(3-(thiazol-2-yl)benzyl)-7-(2-(thiazol-4-yl)phenyl)azepan-2-one;
7-(2-(pyridin-3-yl)phenyl)-1-(3-(thiazol-2-yl)benzyl)azepan-2-one;
7-([1,1'-biphenyl]-2-yl)-1-(3-(thiazol-2-yl)benzyl)azepan-2-one;
6-(6-methoxybenzo[d]oxazol-7-yl)-1-(3-(2-methylthiazol-4-yl)benzyl)piperidin-2-one;
1-([1,1'-biphenyl]-3-ylmethyl)-6-(5-methoxybenzo[d][1,3]dioxol-4-yl)piperidin-2-one;
6-(5-methoxybenzo[d][1,3]dioxol-4-yl)-1-(3-phenoxybenzyl)piperidin-2-one;
6-(5-methoxybenzo[d][1,3]dioxol-4-yl)-1-((2-phenylthiazol-4-yl)methyl)piperidin-2-one;
(3S*,5S*)-3-chloro-5-(2-fluoro-6-methoxyphenyl)-1-(3-(trifluoromethoxy)benzyl)pyrrolidin-2-one;

(3S*,5S*)-1-(3-chloro-4-(trifluoromethoxy)benzyl)-5-(2-ethoxy-6-fluorophenyl)-3-fluoropyrrolidin-2-one;

(3S*,5S*)-3-chloro-1-(3-chloro-4-(trifluoromethoxy)benzyl)-5-(2-ethoxy-6-fluorophenyl)pyrrolidin-2-one; and (3S*,5S*)-3-fluoro-5-(2-fluoro-6-methoxyphenyl)-1-(3-(trifluoromethoxy)benzyl)pyrrolidin-2-one.

The compounds of formula (I) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases, such compounds are likewise suitable for use in the preparation of a medicament for the prevention or treatment of said diseases.

The compounds according to formula (I) are useful for the prevention or treatment of diseases related to the orexin system.

Such diseases related to the orexin system may be selected from the group consisting of all types of sleep disorders, of stress-related syndromes, of addictions (especially psychoactive substance use, abuse, seeking and reinstatement), of cognitive dysfunctions in the healthy population and in psychiatric and neurologic disorders, of eating or drinking disorders.

In a sub-embodiment, such diseases related to the orexin system may be selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders (notably all types of insomnias, especially primary insomnia).

In another sub-embodiment, such diseases related to the orexin system may be selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another sub-embodiment, such diseases related to the orexin system may be selected from the group consisting of eating disorders that comprise metabolic dysfunction; dysregulated appetite control; compulsive obesities; emeto-bulimia or anorexia nervosa.

In another sub-embodiment, such diseases related to the orexin system may be selected from the group consisting of all types of addictions (especially psychoactive substance use, abuse, seeking and reinstatement) that comprise all types of psychological or physical addictions and their related tolerance and dependence components.

Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake.

Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders.

Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance.

Addictions may be defined as addiction to one or more rewarding stimuli, notably to one rewarding stimulus. Such rewarding stimuli may be of either natural or synthetic origin. Psychoactive substance use, abuse, seeking and reinstatement are defined as all types of psychological or physical addictions and their related tolerance and dependence components.

Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

The present invention also relates to the compounds of formula (I) for use in the treatment of the above-mentioned diseases related to the orexin system, in combination with one or more further pharmaceutically active ingredients.

Besides, any characteristics described in this invention for the compounds of formula (I) (whether for the compounds themselves, salts thereof, compositions containing the compounds or salts thereof, uses of the compounds or salts thereof, etc.) apply mutatis mutandis to compounds of formula ($I_{E1}$) and formula ($I_{E2}$).

Preparation of Compounds of Formula (I):

A further aspect of the invention is a process for the preparation of compounds of formula (I). Compounds of formula (I) of the present invention can be prepared according to the general sequence of reactions outlined in the schemes below (schemes 1 to 12), wherein $R^1$, $R^2$, $R^3$, and Y are as defined for formula (I). Other abbreviations used herein are explicitly defined, or are as defined in the experimental section. In some instances the generic groups $R^1$, $R^2$, $R^3$, and Y might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into pharmaceutically acceptable salts thereof in a manner known per se.

All chemical transformations can be performed according to well-known standard methodologies as described in the literature or as described in the procedures below. Starting materials are commercially available or prepared according to procedures known in the literature or as illustrated herein.

In some cases the order of carrying out the mentioned synthetic routes may be varied to facilitate the reaction or to avoid unwanted side-products. The compounds obtained may also be converted into pharmaceutically acceptable salts thereof in a manner known per se.

A general synthetic route allowing the preparation of five-, six-, and seven-membered ring lactam derivatives of formula (I) is presented in scheme 1.

Starting either with esters of 4-oxobutanoic acid, 5-oxopentanoic acid, or 6-oxohexanoic acid derivatives A2, this sequence of reactions will deliver respectively pyrrolidin-2-ones, piperidin-2-ones, or azepan-2-ones. Derivatives A2 in turn may result from the oxidative cleavage ($OsO_4/NaIO_4$) of the corresponding olefin derivatives A1. In the reaction sequence, the formyl group of A2 is condensed with 2-methylpropane-2-sulfinamide (t-Bu-S(O)—$NH_2$/$CuSO_4$/DCM) affording the corresponding imines A3. A subsequent addition of an organometallic reagent $R^2$-M (M represents a metal, for example magnesium or lithium) allows the introduction of the respective $R^2$ substituent giving derivatives A4. These organometallic reagents $R^2$-M may be prepared from the corresponding $R^2$—Hal (Hal represents Br or I) after halogen/metal exchange or from the corresponding $R^2$—H after regioselective proton/metal exchange. Acid-mediated removal of the sulfur-containing auxiliary provides primary amines A5. At this stage, five-membered ring lactams (pyrrolidin-2-ones) can be directly obtained from the corresponding γ amino acid derivatives A5 via reductive amination with carbonyl derivatives $R^1C(O)R^3$. For the preparation of six-, and seven-membered ring lactam derivatives, the corresponding primary amines A5 may be first converted into secondary amines A6 via reductive amination with carbonyl derivatives $R^1C(O)R^3$. A subsequent saponification (aq. aOH/MeOH) followed by lactamization (HATU/DMF) will provide the corresponding piperidin-2-ones or azepan-2-ones. A similar sequence of saponification/lactamization can be used for the conversion of primary amines A5 into the corresponding five-, six-, or seven-membered ring lactams A7 which can be converted into compounds of formula (I) via N-alkylation with electrophiles $R^1CH(X)R^3$ (with X=Cl or Br).

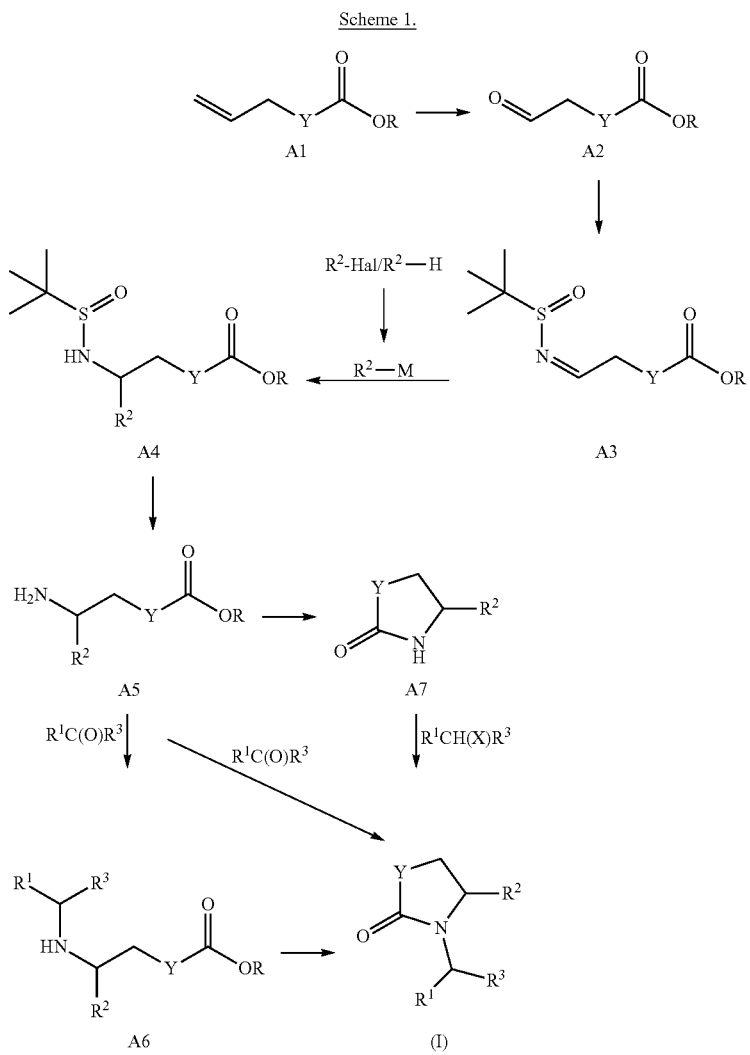

Scheme 1.

Synthetic route allowing the preparation of 5-, 6-, and 7-membered ring lactam derivatives of formula (I); in scheme 1, R represents ($C_{1-2}$)alkyl, Hal represents Br or I, X represents Cl or Br, and M represents a metal (such as for example Li or Mg).

In a variant, the synthetic route presented in scheme 1 is also appropriate for the preparation of compounds of formula (I) possessing additional substituent(s) on the carbon α to the lactam moiety. The preparation of such substituted derivatives is shown in scheme 2.

Scheme 2. Preparation of substituted five-, six-, and seven-membered ring lactam derivatives of formula (I); in scheme 2, R represents $(C_{1\text{-}2})$alkyl, substituents A and B are optional substituents as defined for the group Y, and m represents the interger 1, 2, or 3.

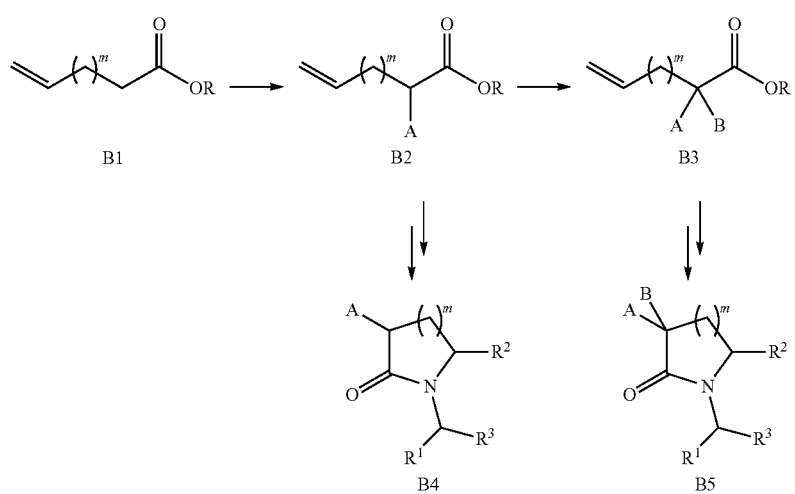

Starting with the commercially available unsaturated esters B1, the corresponding mono- and di-substituted derivatives B2 and B3 can be obtained after deprotonation, and subsequent reaction of the produced enolates with electrophiles. The remaining synthetic steps delivering compounds B4 and B5, which are particular compounds of formula (I), are as described in scheme 1.

In a further variant, compounds of formula (I) can be modified, for example, by manipulation of substituents. These manipulations may include, but are not limited to, reduction, oxidation, organometallic cross-coupling, alkylation, acylation, and hydrolysis reactions which are commonly known to those skilled in the art. For example, the hydroxyl group of phenol derivatives may be alkylated or arylated using well-known standard methodologies.

In a further variant, additional substituent(s) may be regioselectively introduced in compounds of formula (I) on the carbon α to the lactam moiety after regioselective deprotonation, and subsequent reaction with electrophiles, thus introducing the substituent A, and subsequently in a further step the substituent B (scheme 3).

In a further variant, compounds of formula (I) can be further modified by regioselective introduction of substituents. For example, reactions for the selective introduction of substituents may include, but are not limited to, halogenation and nitration.

An alternative synthetic route for the preparation of five-, six-, and seven-membered ring lactam derivatives of formula (I) is presented in scheme 4. In this approach, keto-esters D2 constitute pivotal intermediates, and may be prepared from the corresponding acid chlorides D1 or carboxylic acid anhydrides D3 after reaction with organometallic reagents of after Friedel-Crafts acylation. Compounds of formula (I) can be obtained from keto-esters D2 via reductive amination, and subsequent lactamization. Alternatively compounds of formula (I) may be produced after N-alkylation of lactams D4 which can be obtained from D2 after reductive amination/lactamization.

Lactams D4 can be also accessed from keto-esters D2 after reduction of the corresponding oximes D5, and subsequent lactamization.

Scheme 3. Preparation of substituted five-, six-, and seven-membered ring lactam derivatives via regioselective deprotonation, and subsequent reaction with electrophiles; in scheme 3, substituents A and B are optional substituents as defined for the group Y (especially alkyl or halogen substituents), and m represents the interger 1, 2, or 3.

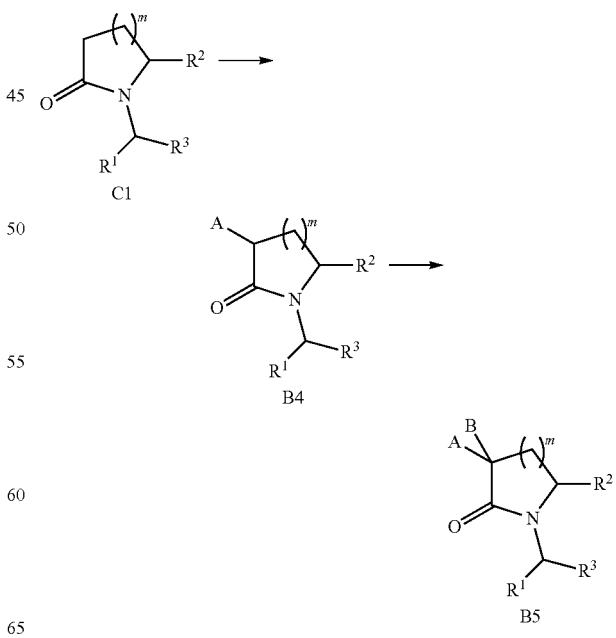

Scheme 4. Preparation of five-, six-, and seven-membered ring lactam derivatives using keto-esters; in scheme 4, R represents $(C_{1-2})$alkyl, and X represents Cl, Br, or I.

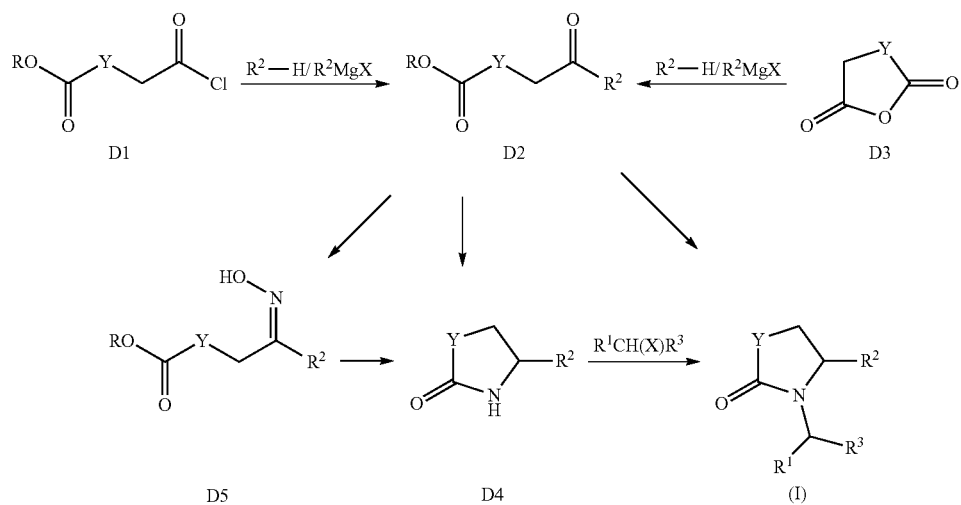

A particular preparation of substituted piperidin-2-ones is described in scheme 5. This approach is based on olefin ring closing methathesis, and starts with the condensation of aldehydes E1 with 2-methylpropane-2-sulfinamide (t-Bu-S(O)NH$_2$/Ti(OEt)$_4$), affording imines E2. A subsequent addition of allylmagnesium bromide gives compounds E3 which can be converted into the corresponding primary amines E4 under acidic conditions. At this stage, a reductive amination between E4 and carbonyl derivatives R$^1$C(O)R$^3$ may deliver secondary amines E5. Acylation of E5 with acryloyl chloride affords E6, which can then be converted into the corresponding dihydro-pyridones E7 via olefin ring closing methathesis. A final hydrogenation of E7 delivers substituted piperidin-2-ones E8. Alternatively E8 may also result from the N-alkylation of lactams E9 which can be obtained from primary amines E4 after acylation with acryloyl chloride, olefin ring closing methathesis, and hydrogenation.

Scheme 5. Preparation of substituted piperidin-2-ones based on olefin ring closing methathesis; in scheme 5, X represents Cl or Br.

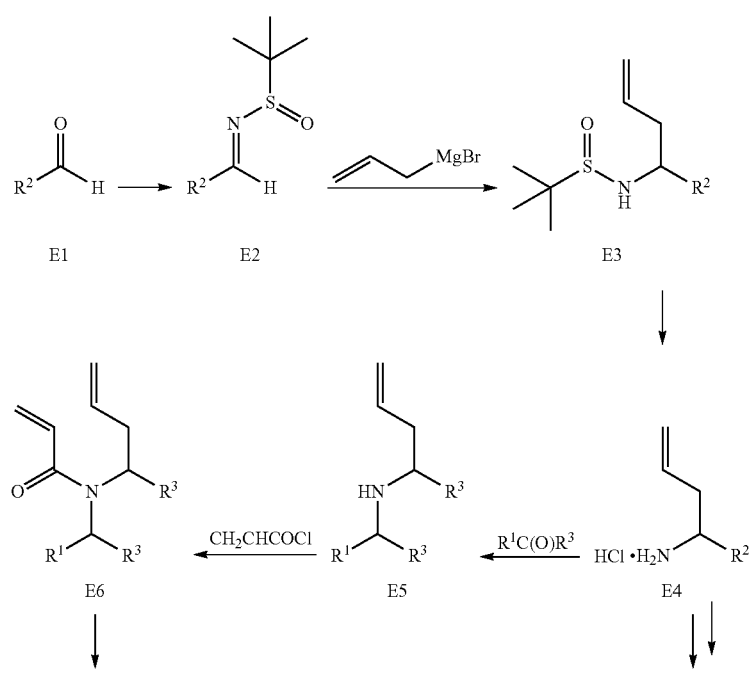

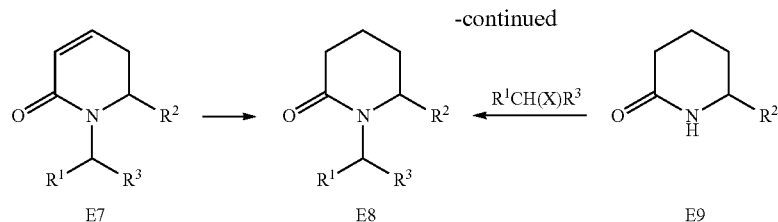

Scheme 6. Variation of the preparation of substituted piperidin-2-ones based on olefin ring closing methathesis.

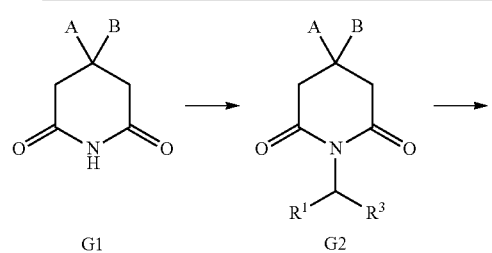

In the variant, presented in scheme 6, substituents connected to the nitrogen of the lactam moiety are introduced at the stage of the imine formation. Thus, imines F2 are obtained after condensation of aldehydes F1 with primary amines $R^1CH(NH_2)R^3$. The target piperidin-2-ones F6 can be obtained after subsequent addition of allylmagnesium bromide, acylation with acryloyl chloride, olefin ring closing methathesis, and a final hydrogenation.

Scheme 7. Preparation of substituted piperidin-2-ones based on a Suzuki cross-coupling reaction between vinyl phosphates and boronic acids; in scheme 7, substituents A and B are as defined for the group Y.

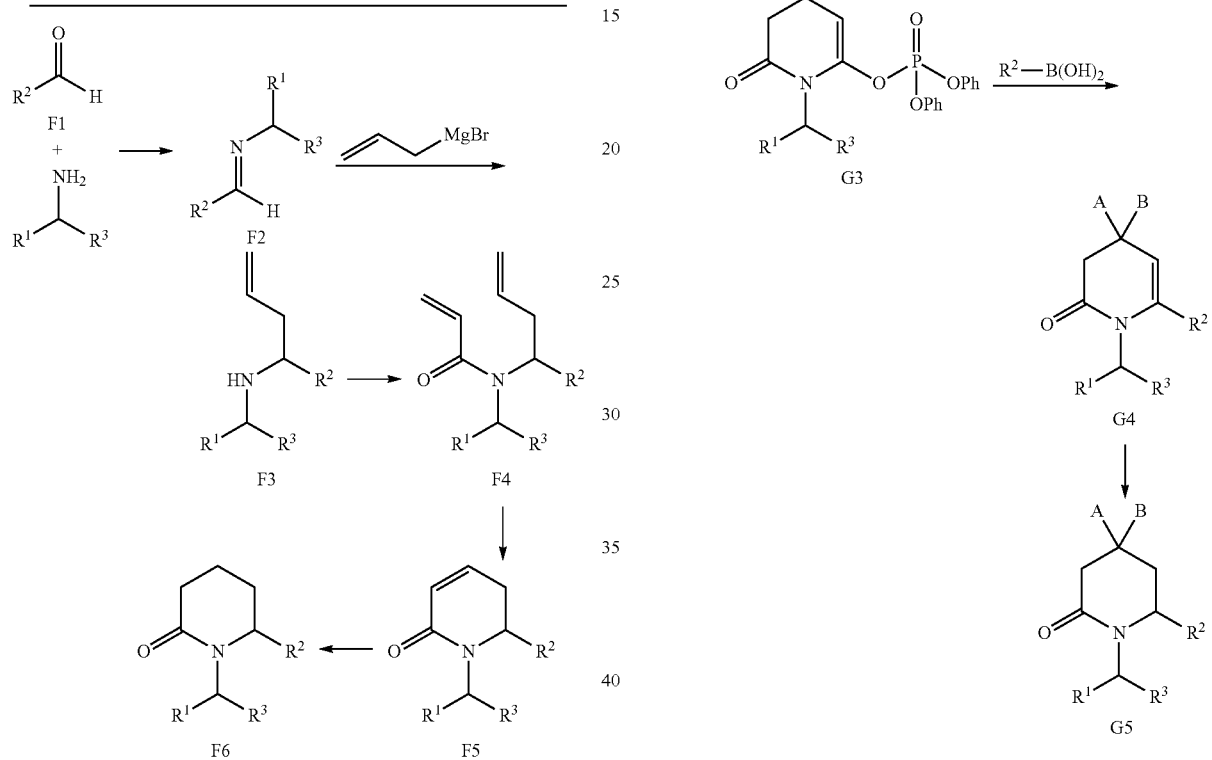

Another specific preparation of substituted piperidin-2-ones based on a Suzuki cross-coupling reaction between vinyl phosphates G3 and boronic acids is described in scheme 7. Starting materials for this sequence of reactions are commercially available piperidine-2,6-dione derivatives G1 which may be N-alkylated with electrophiles $R^1C(X)R^3$ (with X representing Cl or Br) affording G2, which in turn can be converted into the corresponding vinyl phosphates G3 after regioselective deprotonation, and subsequent treatment with diphenyl phosphorochloridate $(PhO)_2P(O)Cl$. Dihydro-pyridones G4 may be obtained via Suzuki cross-coupling reaction between vinyl phosphates G3 and boronic acids. Target piperidin-2-ones G5 can be obtained after a final hydrogenation of G4.

Specific preparations of substituted pyrrolidin-2- are described in scheme 8. Substituted pyrrolidin-2-ones H4 can be obtained after one-pot reaction between primary amines H1, aldehydes H2, and diethyl oxalacetate sodium salt H3 (scheme 8). A subsequent decarboxylation of H4 using Krapcho's reaction conditions ($NaCl/DMSO/H_2O$) delivered pyrrolidine-2,3-diones H5 which can be selectively reduced ($NaBH_4/EtOH$) to the corresponding cis 3-hydroxy-pyrrolidin-2-ones H6. The hydroxyl moiety in H6 may allow additional derivatizations like O-alkylation (H6 to H7) or halogenation (H6 to H8). Pyrrolidine-2,3-diones H5 can be also further derivatized via Wittig olefination, and subsequent hydrogenation affording cis derivatives H9 (scheme 8).

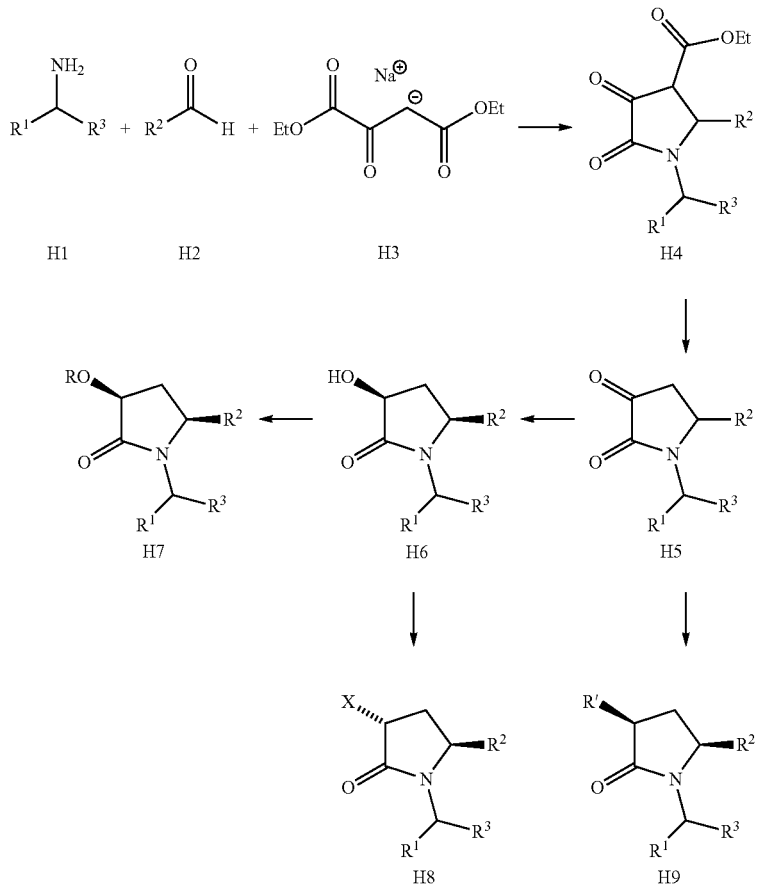

Scheme 8. Synthesis of substituted pyrrolidin-2-ones; in scheme 8, R represents $(C_{1-3})$alkyl, R' represents $(C_{1-3})$alkyl, and X represents halogen.

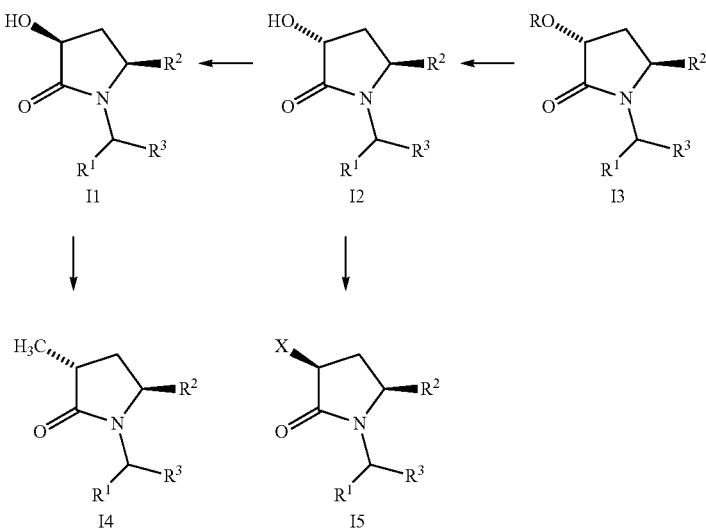

Scheme 9. Synthesis of substituted pyrrolidin-2-ones; in scheme 9, R represents $(C_{1-3})$alkyl, and X represents halogen.

Additional preparations of substituted pyrrolidin-2-ones are described in scheme 9. Inversion of configuration via Mitsunobu reaction allowed the conversion of cis 3-hydroxy-pyrrolidin-2-ones I1 into the corresponding trans 3-hydroxy-pyrrolidin-2-ones I2 which can be O-alkylated (I2 to I3) or halogenated (I2 to I5). Trans 3-methyl-pyrrolidin-2-ones I4 may be obtained from cis 3-hydroxy-pyrrolidin-2-ones I1 after treatment of the corresponding tosylate with Me$_2$CuLi.

A synthetic route allowing the preparation of substituted piperazin-2-ones is presented in scheme 10. In the sequence of reactions, the formyl group of ethyl 2-oxoacetate J1 is condensed with 2-methylpropane-2-sulfinamide (t-Bu-S(O)NH$_2$/DCM/molecular sieves) affording imines J2. A subsequent addition of an organometallic reagent R$^2$-M (M represents a metal, R$^2$-M is for example an organomagnesium or organolithium reagent) allows the introduction of the desired R$^2$ substituents giving derivatives J3. These organometallic reagents R$^2$-M may be prepared from the corresponding R$^2$—Hal (Hal represents Br or I) after halogen/metal exchange or from the corresponding R$^2$—H after regioselective proton/metal exchange. Acid-mediated removal of the sulfur-containing auxiliary, and subsequent reductive amination with carbonyl derivatives R$^1$C(O)R$^3$ provides secondary amines J4. At this stage, acylation of J4 (2-(Boc-amino)acetic acid/HATU/DIPEA/DMF) delivers J5, and subsequent acidic removal of the Boc protecting group afforded substituted piperazine-2,5-diones J6. Boc protection of the lactam moiety (Boc$_2$O/DMAP/MeCN), and its subsequent selective reduction (NaBH$_4$/MeOH; then NaBH$_3$CN/AcOH) provided J8. Acidic removal of the Boc group delivers the corresponding secondary amines which can be further derivatized by N-alkylation giving J9.

A variant allowing the preparation of substituted morpholin-3-ones from secondary amines J4 is presented in scheme 11. The ester moiety of J4 can be reduced (LiAlH$_4$/THF) to the corresponding primary alcohol derivatives K5 which may be converted into K6 after acylation with 2-chloroacetyl chloride. In a final step, K6 can be cyclized (NaH/DMF) to the target morpholin-3-ones K7.

Scheme 11. Synthetic route for the preparation of morpholin-3-ones.

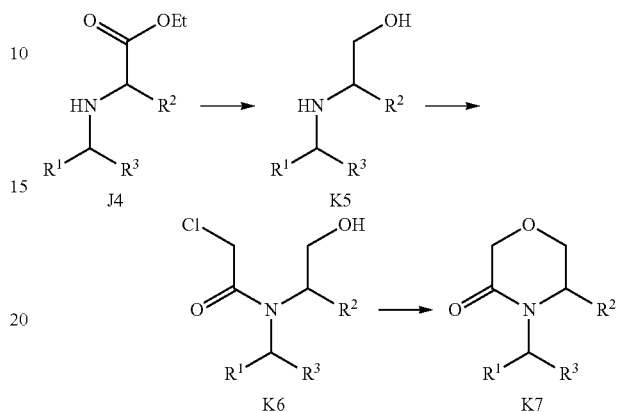

Carbonyl derivatives R$^2$CHO and R$^1$C(O)R$^3$, halides R$^1$CH(X)R$^3$ (with X representing Cl or Br), and amines R$^1$CH(NH$_2$)R$^3$ are commercially available, well known in the art, or readily available from commercially available precursors. Some particular methods of preparations are described in scheme 12. Aldehydes (L2/L6) may be obtained from the corresponding carboxylic acid derivatives (carboxylic acids or esters L1/L4) via reduction, for example reduction to the corresponding alcohols, and subsequent oxidation to the target aldehydes.

Scheme 10. Synthetic route for the preparation of substituted piperazin-2-ones; in scheme 10, R represents (C$_{1-3}$)alkyl.

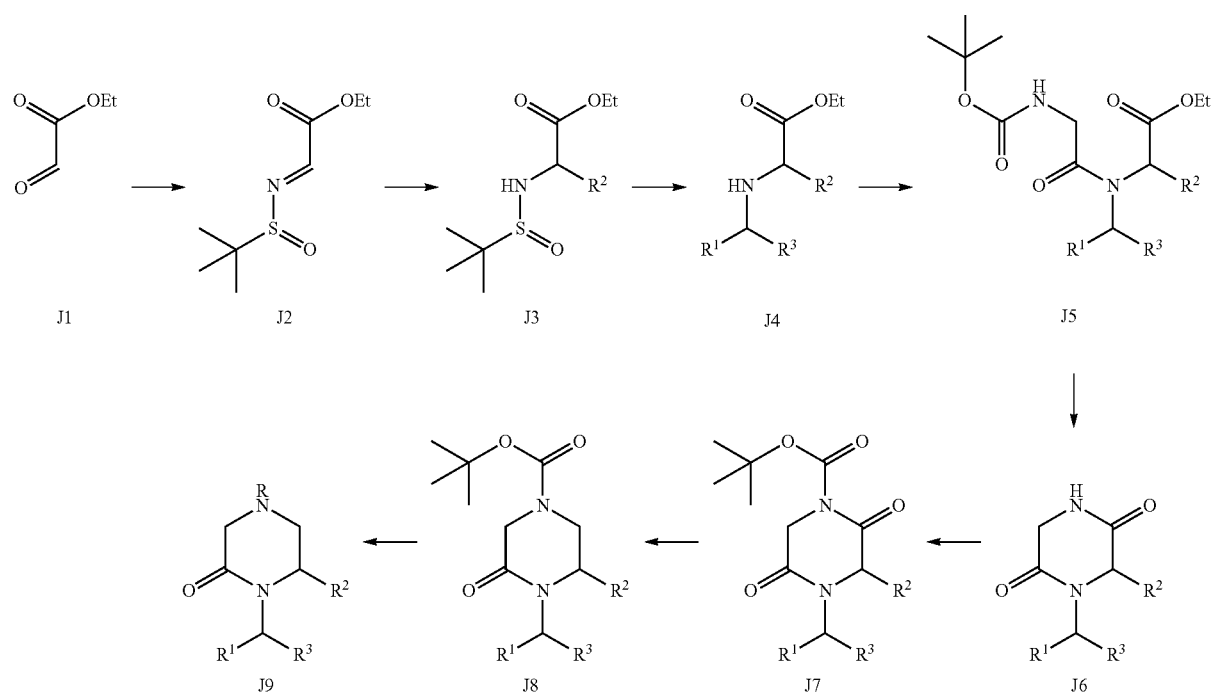

Scheme 12. Preparation of carbonyl derivatives ($R^2CHO$, $R^1C(O)R^3$), halides $R^1CH(X)R^3$, and amines $R^1CH(NH_2)R^3$; in scheme 12, Hal represents Br or I, X represents Cl or Br, and R represents H or ($C_{1-2}$)alkyl.

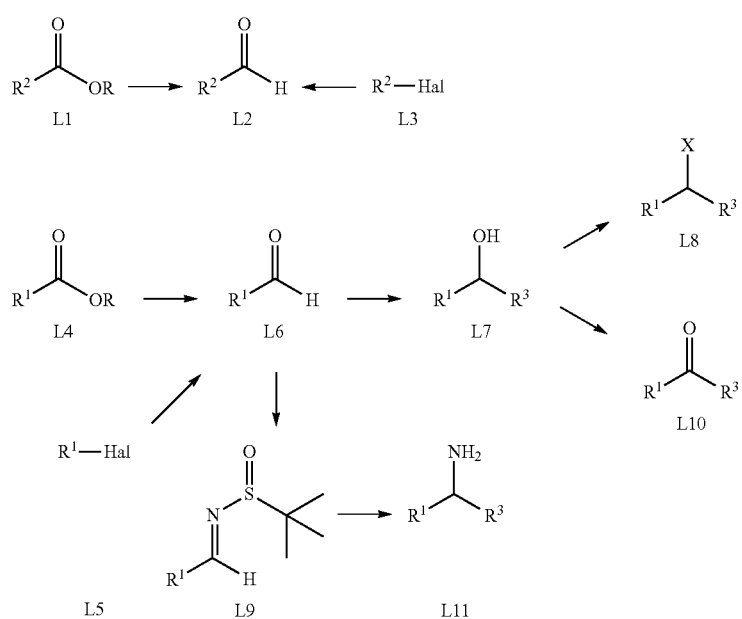

Alternatively these aldehydes (L2/L6) may be also produced from the corresponding aromatic or heteroaromatic halides (L3/L5; X represents Br or I) using a sequence of metallation, followed by formylation (with DMF or piperidine-1-carbaldehyde). Additional alternative methods for the formylation of aromatic or heteroaromatic compounds are well known in the art, e.g. the Vilsmeier-Haackformylation ($POCl_3$/DMF). Treatment of aldehydes L6 with organometallic reagents (for example organomagnesium or organolithium reagents) may deliver the secondary alcohols L7 (with $R^3$ representing methyl or ethyl) which can be oxidized to the ketones L10 or halogenated ($CX_4$/$PPh_3$/DCM, with X representing Cl or Br) affording halides L8 ($R^3$ representing methyl or ethyl). Halides L8 (with $R^3$ representing H) may be directly obtained from the carboxylic acid derivatives L4 after reduction to the alcohols, and subsequent halogenation ($CX_4$/$PPh_3$/DCM, with X representing Cl or Br). Amines L11 can be prepared from the aldehydes L6 after formation of the corresponding imines L9 (t-Bu-S(O)$NH_2$/Ti(OEt)$_4$), and subsequent reduction ($NaBH_4$, for $R^3$ representing H) or treatment with organometallic reagents (for $R^3$ representing methyl or ethyl).

Whenever the compounds of formula (I) are obtained in the form of mixtures of enantiomers, the enantiomers can be separated using methods known to the one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in presence or absence of an amine such as $NEt_3$, diethylamine) and eluent B (hexane), at a flow rate of 0.8 to 150 mL/min.

EXPERIMENTAL SECTION

Abbrevations

As Used Herein and in the Description Above

Ac acetyl
AcOEt ethyl acetate
AcOH acetic acid
anh. anhydrous
aq. aqueous
atm atmosphere
$BH_3$.THF borane-tetrahydrofuran complex
Boc tert-butoxycarbonyl
$Boc_2O$ di-tert-butyl dicarbonate
Bu butyl such as t-Bu=tert-butyl=tertiary butyl
n-BuLi n-butyllithium
DAST (diethylamino)sulfur trifluoride
DCE 1,2-dichloroethane
DCM dichloromethane
DEA diethylamine
DEAD diethyl azodicarboxylate
Deoxo-Fluor bis(2-methoxyethyl)aminosulfur trifluoride
DIBAH diisobutylaluminum hydride
DIPEA N-ethyldiisopropylamine
DMAP 4-(dimethylamino)pyridine
DMF N,N-dimethylformamide
DMSO dimethyl sulfoxide
ELSD Evaporative Light-Scattering Detection
equiv. equivalent
Et ethyl
$Et_2O$ diethylether
EtOH ethanol
FA formic acid
FC flash chromatography (on silica gel)
FLIPR Fluorescent imaging plate reader
$FSO_2CF_2CO_2H$ 2,2-difluoro-2-(fluorosulfonyl)acetic acid h hour(s)
HATU O-(7-azabenzotriazol-1-yl)-N,N,N',N'-tetramethyluronium hexafluorophosphate
$^1$H-NMR nuclear magnetic resonance of the proton
HPLC High Performance Liquid Chromatography
HV High Vacuum
LC-MS Liquid Chromatography-Mass Spectroscopy
LHMDS lithium bis(trimethylsilyl)amide
M mol/l
MeCN acetonitrile
Me$_2$CuLi lithium dimethylcuprate
MeOH methanol
MHz megahertz
μl microliter
min. minute(s)
Ms methanesulfonyl
MS Mass Spectroscopy
NaBH(OAc)$_3$ sodium triacetoxyborohydride
NCS N-chlorosuccinimide
NEt$_3$ triethylamine
NMP N-methyl-2-pyrrolidinone
PBS phosphate buffered saline
Pd(C) palladium on activated charcoal
Pd$_2$(dba)$_3$ tris(dibenzylideneacetone)dipalladium(0)
PdCl$_2$(dbpf) [1,1'-bis(di-tert-butylphosphino)ferrocene]palladium(II) dichloride
PdCl$_2$(PPh$_3$)$_2$ bis(triphenylphosphine)palladium(II) dichloride
Pd(PPh$_3$)$_4$ tetrakis(triphenylphosphine)palladium(0)
Ph phenyl
PPh$_3$ triphenylphosphine
p-TsOH para-toluenesulfonic acid monohydrate
rt room temperature
sat. saturated
Selectfluor 1-chloromethyl-4-fluoro-1,4-diazoniabicyclo[2.2.2]octane bis(tetrafluoroborate)
TFA trifluoroacetic acid
THF tetrahydrofurane
Ti(OEt)$_4$ titanium(IV) ethoxide
TLC Thin Layer Chromatography
t$_R$ retention time
Ts toluenesulfonyl
UV ultra violet
Vis visible
W Watt
wt. % weight %
Xantphos 4,5-bis(diphenylphosphino)-9,9-dimethylxanthene I. Chemistry The following examples illustrate the preparation of biologically active compounds of the invention but do not at all limit the scope thereof.

All temperatures are stated in ° C.

The commercially available starting materials were used as received without further purification. Unless otherwise specified, all reactions were carried out in oven-dried glassware under an atmosphere of nitrogen.

Compounds are purified by column chromatography on silica gel or by preparative HPLC.

Compounds described in the invention are characterized by LC-MS data (retention time t$_R$ is given in min.; molecular weight obtained from the mass spectrum is given in g/mol) using the conditions listed below.

LC-MS with Acidic Conditions (Conditions A)

Apparatus: Agilent 1100 series with mass spectroscopy detection (MS: Finnigan single quadrupole). Column: Waters XBridge C18 (2.5 μm, 4.6×30 mm). Conditions: MeCN [eluent A]; water+0.04% TFA [eluent B]. Gradient: 95% B→5% B over 1.5 min. (flow: 4.5 ml/min.). Detection: UV/Vis+MS.

LC-MS with Acidic Conditions (Conditions B)

Apparatus: Agilent 1100 series with mass spectroscopy detection (MS: Finnigan single quadrupole). Column: Zorbax SB-aq (3.5 μm, 4.6×50 mm) from Agilent Technologies. Conditions: MeCN [eluent A]; water+0.04% TFA [eluent B]. Gradient: 95% B→5% B over 1.5 min. (flow: 4.5 ml/min.). Detection: UV/Vis+MS.

LC-MS with Basic Conditions (Conditions C)

Apparatus: Agilent 1100 series with mass spectroscopy detection (MS: Finnigan single quadrupole). Column: Waters XBridge C18 (5 μm, 4.6×50 mm). Conditions: MeCN [eluent A]; 13 mmol/l NH$_3$ in water [eluent B]. Gradient: 95% B→5% B over 1.5 min. (flow: 4.5 ml/min.). Detection: UV/Vis+MS.

LC-MS with Acidic Conditions (Conditions D)

Column: Zorbax SB-aq (5 μm, 4.6×50 mm) from Agilent Technologies. Conditions: MeCN [eluent A]; water+0.04% TFA [eluent B]. Gradient: 95% B→5% B over 1.5 min. (flow: 4.5 ml/min.). Detection: UV/Vis+MS.

LC-MS with Acidic Conditions (Conditions E)

Column: Zorbax SB-aq (1.8 μm, 4.6×20 mm) from Agilent Technologies. Conditions: MeCN [eluent A]; water+0.04% TFA [eluent B]. Gradient: 95% B→5% B over 1.5 min. (flow: 4.5 ml/min.). Detection: UV/Vis+MS.

LC-MS with Acidic Conditions (Conditions F)

Column: Zorbax SB-aq (1.8 μm, 4.6×30 mm) from Agilent Technologies. Conditions: MeCN [eluent A]; water+0.04% TFA [eluent B]. Gradient: 95% B→5% B over 1.5 min. (flow: 4.5 ml/min.). Detection: UV/Vis+MS.

LC-MS with Acidic Conditions (Conditions G)

Column: Waters XBridge C18 (5 μm, 4.6×50 mm). Conditions: MeCN [eluent A]; water+0.04% TFA [eluent B]. Gradient: 95% B→5% B over 1.5 min. (flow: 4.5 ml/min.). Detection: UV/Vis+MS.

LC-MS with Acidic Conditions (Conditions H)

Column: Ascentis RP-Amide (2.7 μm, 3×30 mm). Conditions: MeCN [eluent A]; water+0.05% FA+2% MeCN [eluent B]. Gradient: 95% B→5% B over 2.4 min. (flow: 3 ml/min.). Detection: UV/Vis+MS.

LC-MS with Basic Conditions (Conditions I)

Column: Ascentis Express C18 (2.7 μm, 2.1×30 mm). Conditions: MeCN [eluent A]; water+0.05% NH$_4$OH+2% MeCN [eluent B]. Gradient: 95% B→5% B over 2.0 min. (flow: 1.8 ml/min.). Detection: UV/Vis+MS.

Preparative HPLC for Purification of Compounds

Column: Waters XBridge (5 μm, 75×30 mm). Conditions: MeCN [eluent A]; water+0.5% NH$_4$OH (25% aq.) [eluent B]; Gradient: 90% B→0% B over 6.5 min. (flow: 75 ml/min.). Detection: UV+ELSD.

Chiral Preparative HPLC for Separation of Enantiomers

Column: Chiralpak AD-H 250×4.6 ID, 5 μm. Conditions: heptane+0.05% DEA [eluent A]; EtOH+0.05% DEA [eluent B]. Composition: 50% A and 50% B (flow: 0.8 ml/min).

A. Preparation of Intermediates

A.1 Preparation of Aldehydes and Ketones

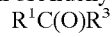

4-fluoro-2,6-dimethoxybenzaldehyde

A cooled (−5° C.) mixture of commercially available 1-fluoro-3,5-dimethoxybenzene (500 mg; 3.20 mmol; 1.0 equiv.) and DMF (4.680 g; 64.03 mmol; 20.0 equiv.) was treated dropwise with POCl$_3$ (2.454 g; 16.01 mmol; 5.0 equiv.). This mixture was further stirred at rt for 1.5 h, and was then heated to 60° C. for 3 h. After cooling to rt, ice-water (50 ml) and a solution of 2.5 M aq. NaOH (24 ml) were successively added. After extractions with AcOEt (3×30 ml), the mixed organic layers were dried over anh. $MgSO_4$, filtered, and concentrated to dryness under reduced pressure. Purification by FC (heptane/AcOEt=1/1) afforded 4-fluoro-2,6-dimethoxybenzaldehyde as a yellow solid. LC-MS (conditions A): $t_R$=0.50 min.; $[M+H]^+$: 185.10 g/mol. According to $^1$H-NMR (CDCl3; 400 MHz), this product also contained 19% of the regioisomer 2-fluoro-4,6-dimethoxybenzaldehyde. This minor regioisomer could be advantageously removed after further chemical transformations of the isomeric mixture.

2-phenoxythiazole-4-carbaldehyde

A mixture of commercially available methyl 2-bromothiazole-4-carboxylate (1.000 g; 4.50 mmol) and sodium phenoxide (627 mg; 5.40 mmol) in anh. DMSO (20 ml) was heated to 80° C., under nitrogen, for 17 h. A second addition of sodium phenoxide (314 mg; 2.70 mmol) was performed, and the resulting mixture was further heated at 80° C. for 1 h. After cooling to rt, water (50 ml), brine (10 ml), and toluene (20 ml) were added. The separated aq. layer was further extracted with toluene (2×20 ml). The mixed organic layers were washed with brine, dried over anh. $MgSO_4$, filtered, and concentrated to dryness under reduced pressure. Purification by FC (DCM/MeOH=50/1) afforded methyl 2-phenoxythiazole-4-carboxylate as a yellow oil. LC-MS (conditions A): $t_R$=0.73 min.; $[M+H]^+$: 236.06 g/mol.

A solution of methyl 2-phenoxythiazole-4-carboxylate (265 mg; 1.12 mmol) in anh. EtOH (6 ml) was treated at rt with $NaBH_4$ (213 mg; 5.64 mmol), and the resulting mixture was stirred at rt, under nitrogen, for 63 h. After concentration to dryness under reduced pressure, water was added, and the resulting mixture was extracted with DCM. The organic layer was dried over anh. $MgSO_4$, filtered, and concentrated to dryness under reduced pressure. Purification by FC (DCM/MeOH=30/1) afforded (2-phenoxythiazol-4-yl)methanol as a colorless oil. LC-MS (conditions A): $t_R$=0.58 min.; $[M+H]^+$: 208.06 g/mol.

A solution of (2-phenoxythiazol-4-yl)methanol (251 mg; 1.21 mmol) in anh. DCE (12 ml) was treated with $MnO_2$ (843 mg; 9.69 mmol), and the resulting mixture was stirred at reflux, under nitrogen, for 1 h. After cooling to rt, the mixture was filtered over a pad of celite, and the separated solids were washed with DCM. The filtrate was then concentrated to dryness under reduced pressure affording 2-phenoxythiazole-4-carbaldehyde as a pale yellow oil. LC-MS (conditions A): $t_R$=0.65 min.; $[M+H]^+$: 206.04 g/mol.

5-phenylnicotinaldehyde

A mixture of commercially available 5-bromonicotinaldehyde (5.070 g; 26.43 mmol), phenylboronic acid (4.934 g; 39.65 mmol), and $Pd(PPh_3)_4$ (1.527 g; 1.32 mmol) in toluene (65 ml) and aq. 2 M $Na_2CO_3$ (59 ml) was heated to reflux, under nitrogen, for 2.5 h. After cooling to rt, water and AcOEt were added. The separated aq. layer was further extracted with AcOEt. The mixed organic layers were washed with brine, dried over anh. $MgSO_4$, filtered, and concentrated to dryness under reduced pressure. Purification by FC (heptane/AcOEt=1/1) afforded 5-phenylnicotinaldehyde as a yellow oil. LC-MS (conditions A): $t_R$=0.61 min.; $[M+H]^+$: 184.48 g/mol.

2-phenylisonicotinaldehyde

A mixture of commercially available 2-bromoisonicotinaldehyde (3.000 g; 16.12 mmol), phenylboronic acid (3.009 g; 24.19 mmol), and $Pd(PPh_3)_4$ (931 mg; 0.80 mmol) in toluene (40 ml) and aq. 2 M $Na_2CO_3$ (34 ml) was heated to reflux, under nitrogen, for 4 h. After cooling to rt, water and AcOEt were added. The separated aq. layer was further extracted with AcOEt. The mixed organic layers were washed with brine, dried over anh. $MgSO_4$, filtered, and concentrated to dryness under reduced pressure. Purification by FC (heptane/AcOEt=7/3) afforded 2-phenylisonicotinaldehyde as a yellow oil. LC-MS (conditions A): $t_R$=0.39 min.; $[M+H]^+$: 184.47 g/mol.

6-phenylpicolinaldehyde

A mixture of commercially available 6-bromopicolinaldehyde (3.000 g; 16.12 mmol), phenylboronic acid (3.009 g; 24.19 mmol), and $Pd(PPh_3)_4$ (931 mg; 0.80 mmol) in toluene (40 ml) and aq. 2 M $Na_2CO_3$ (34 ml) was heated to reflux, under nitrogen, for 4 h. After cooling to rt, water and AcOEt were added. The separated aq. layer was further extracted with AcOEt. The mixed organic layers were washed with brine, dried over anh. $MgSO_4$, filtered, and concentrated to dryness under reduced pressure. Purification by FC (heptane/AcOEt=7/3) afforded 6-phenylpicolinaldehyde as a pale yellow oil. LC-MS (conditions A): $t_R$=0.77 min.; $[M+H]^+$: 184.17 g/mol.

4-fluoro-3-(pyridin-2-yl)benzaldehyde

A mixture of commercially available 2-bromopyridine (250 mg; 1.58 mmol), 2-fluoro-5-formylphenylboronic acid (265 mg; 1.58 mmol), and $Pd(PPh_3)_4$ (91 mg; 0.08 mmol) in toluene (1 ml), EtOH (1 ml), and aq. 2 M $Na_2CO_3$ (1.5 ml) was heated to 80° C., under nitrogen, for 17 h. After cooling to rt, water and AcOEt were added. The separated aq. layer was further extracted with AcOEt. The mixed organic layers were washed with brine, dried over anh. $MgSO_4$, filtered, and concentrated to dryness under reduced pressure. Purification by FC (heptane/AcOEt=7/3) afforded 4-fluoro-3-(pyridin-2-yl)benzaldehyde as a slightly yellow oil. LC-MS (conditions A): $t_R$=0.51 min.; $[M+H]^+$: 202.05 g/mol.

2-fluoro-5-(pyridin-2-yl)benzaldehyde

A mixture of commercially available 2-bromopyridine (300 mg; 1.89 mmol), 4-fluoro-3-formylphenylboronic acid (318 mg; 1.89 mmol), $Cs_2CO_3$ (1.546 g; 4.74 mmol), Xantphos (82 mg; 0.14 mmol), and $Pd_2(dba)_3$ (43 mg; 0.04 mmol) in dioxane (4.5 ml) was heated to 80° C., under nitrogen, for 17 h. After cooling to rt, the mixture was filtered over celite, and the separated solids were washed with AcOEt. The filtrate was then washed with water, and the separated aq. layer was further extracted with AcOEt. The mixed organic layers were washed with brine, dried over anh. $MgSO_4$, filtered, and concentrated to dryness under reduced pressure. Purification by FC (heptane/AcOEt=7/3) afforded 2-fluoro-5-(pyridin-2-yl)benzaldehyde as a colorless solid. LC-MS (conditions A): $t_R$=0.46 min.; $[M+H]^+$: 202.02 g/mol.

2-fluoro-3-(pyridin-2-yl)benzaldehyde

A mixture of commercially available 2-bromopyridine (200 mg; 1.26 mmol), (2-fluoro-3-formylphenyl)boronic acid (212 mg; 1.26 mmol), $K_2CO_3$ (699 mg; 5.06 mmol), and PdCl$_2$(dbpf) (11 mg; 0.017 mmol) in MeCN (5 ml) and water (5 ml) was heated to 80° C., under nitrogen, for 2 h. After cooling to rt, MeCN was removed under reduced pressure, and the aq. layer was extracted with AcOEt (2×). The mixed organic layers were washed with brine, dried over anh. MgSO$_4$, filtered, and concentrated to dryness under reduced pressure. Purification by FC (toluene/AcOEt=8/2) afforded 2-fluoro-3-(pyridin-2-yl)benzaldehyde as a yellow solid. LC-MS (conditions C): t$_R$=0.78 min.; [M+H]$^+$: 202.20 g/mol.

2-chloro-5-(pyridin-2-yl)benzaldehyde

A mixture of commercially available 2-bromopyridine (294 mg; 1.86 mmol), 4-chloro-3-(methoxycarbonyl)phenylboronic acid (400 mg; 1.86 mmol), K$_2$CO$_3$ (515 mg; 3.73 mmol), and PdCl$_2$(PPh$_3$)$_2$ (130 mg; 0.18 mmol) in THF (4 ml) and water (4 ml) was stirred at rt, under nitrogen, for 20 h. Water and AcOEt were added. The separated aq. layer was further extracted with AcOEt. The mixed organic layers were washed with brine, dried over anh. MgSO$_4$, filtered, and concentrated to dryness under reduced pressure. Purification by FC (heptane/AcOEt=7/3) afforded methyl 2-chloro-5-(pyridin-2-yl)benzoate as a colorless solid. LC-MS (conditions A): t$_R$=0.65 min.; [M+H]$^+$: 248.02 g/mol.

A cooled (−10° C.) suspension of LiAlH$_4$ (37 mg; 0.97 mmol) in anh. THF (1.5 ml) was treated with a solution of methyl 2-chloro-5-(pyridin-2-yl)benzoate (220 mg; 0.88 mmol) in anh. THF (1 ml). The mixture was further stirred at −10° C. for 20 min. Water (37 µl), 15% aq. NaOH (37 µl), and water (110 µl) were then successively added, and the resulting mixture was further stirred at rt for 1 h. Filtration, concentration to dryness under reduced pressure, and additional drying under HV afforded (2-chloro-5-(pyridin-2-yl)phenyl)methanol as a colorless solid. LC-MS (conditions A): t$_R$=0.42 min.; [M+H]$^+$: 219.94 g/mol.

A solution of (2-chloro-5-(pyridin-2-yl)phenyl)methanol (129 mg; 0.72 mmol) in anh. THF (7 ml) was treated with MnO$_2$ (975 mg; 11.22 mmol), and the resulting mixture was stirred at rt, under nitrogen, for 6.5 h. The resulting reaction mixture was then filtered over celite, and the separated solids were washed with THF. The filtrate was concentrated to dryness under reduced pressure giving 2-chloro-5-(pyridin-2-yl)benzaldehyde as a yellow oil. LC-MS (conditions A): t$_R$=0.43 min.; no ionisation.

3-chloro-5-(pyridin-2-yl)benzaldehyde

A mixture of commercially available 2-bromopyridine (294 mg; 1.86 mmol), 3-chloro-5-(methoxycarbonyl)phenylboronic acid (400 mg; 1.86 mmol), K$_2$CO$_3$ (515 mg; 3.73 mmol), and PdCl$_2$(PPh$_3$)$_2$ (130 mg; 0.18 mmol) in THF (4 ml) and water (4 ml) was stirred at rt, under nitrogen, for 17 h. Water and AcOEt were added. The separated aq. layer was further extracted with AcOEt. The mixed organic layers were washed with brine, dried over anh. MgSO$_4$, filtered, and concentrated to dryness under reduced pressure. Purification by FC (DCM/MeOH=15/1) afforded methyl 3-chloro-5-(pyridin-2-yl)benzoate as a colorless solid. LC-MS (conditions A): t$_R$=0.79 min.; [M+H]$^+$: 247.95 g/mol.

A cooled (−10° C.) suspension of LiAlH$_4$ (50 mg; 1.34 mmol) in anh. THF (2 ml) was treated with a solution of methyl 3-chloro-5-(pyridin-2-yl)benzoate (302 mg; 1.21 mmol) in anh. THF (1 ml). The mixture was further stirred at −10° C. for 20 min. Water (50 µl), 15% aq. NaOH (50 µl), and water (0.15 ml) were then successively added, and the resulting mixture was further stirred at rt for 1 h. Filtration, concentration to dryness under reduced pressure, and additional drying under HV afforded (3-chloro-5-(pyridin-2-yl)phenyl)methanol as a yellow oil. LC-MS (conditions A): t$_R$=0.48 min.; [M+H]$^+$: 220.08 g/mol.

A solution of (3-chloro-5-(pyridin-2-yl)phenyl)methanol (116 mg; 0.64 mmol) in anh. THF (6 ml) was treated with MnO$_2$ (877 mg; 10.09 mmol), and the resulting mixture was stirred at rt, under nitrogen, for 6.5 h. The resulting reaction mixture was then filtered over celite, and the separated solids were washed with THF. The filtrate was concentrated to dryness under reduced pressure giving 3-chloro-5-(pyridin-2-yl)benzaldehyde as a yellow oil. LC-MS (conditions A): t$_R$=0.43 min.; no ionisation.

3-(thiazol-4-yl)benzaldehyde

A mixture of commercially available ethyl 3-iodobenzoate (650 mg; 2.35 mmol), 4-(tributylstannyl)thiazole (894 mg; 2.39 mmol), and PdCl$_2$(PPh$_3$)$_2$ (165 mg; 0.23 mmol) in anh. THF (20 ml) was heated to 75° C., under nitrogen, for 17 h. Water and AcOEt were added. The separated aq. layer was further extracted with AcOEt. The mixed organic layers were washed with brine, dried over anh. MgSO$_4$, filtered, and concentrated to dryness under reduced pressure. Purification by FC (heptane/AcOEt=1/1) afforded ethyl 3-(thiazol-4-yl)benzoate as a yellow oil. LC-MS (conditions A): t$_R$=0.78 min.; [M+H]$^+$: 233.94 g/mol.

A cooled (−78° C.) solution of ethyl 3-(thiazol-4-yl)benzoate (501 mg; 2.14 mmol) in anh. toluene (7 ml) was treated with a solution of 1 M DIBAH in toluene (6.44 ml; 6.44 mmol), and the resulting mixture was further stirred at −78° C., under nitrogen, for 5 min., and then at 0° C. for 30 min. The mixture was then treated successively with water (35 ml), 1 M aq. NaOH (11 ml), and aq. sat. NaHCO$_3$ (30 ml). The separated aq. layer was further extracted with AcOEt (2×50 ml). The mixed organic layers were then dried over anh. MgSO$_4$, filtered, and concentrated to dryness under reduced pressure. Purification by FC (DCM/MeOH=20/1) afforded (3-(thiazol-4-yl)phenyl)methanol as a pale yellow oil. LC-MS (conditions A): t$_R$=0.50 min.; [M+H]$^+$: 192.04 g/mol.

A solution of (3-(thiazol-4-yl)phenyl)methanol (333 mg; 1.74 mmol) in anh. DCM (17 ml) was treated with MnO$_2$ (2.276 g; 26.18 mmol), and the resulting mixture was stirred at rt, under nitrogen, for 1 h 45. The resulting reaction mixture was then filtered over celite, and the separated solids were washed with DCM. The filtrate was concentrated to dryness under reduced pressure giving 3-(thiazol-4-yl)benzaldehyde as a pale yellow solid. LC-MS (conditions A): t$_R$=0.62 min.; [M+H]$^+$: 190.13 g/mol.

3-(thiazol-5-yl)benzaldehyde

A mixture of commercially available ethyl 3-iodobenzoate (1.000 g; 3.62 mmol), 5-(tributylstannyl)thiazole (1.355 g; 3.62 mmol), and PdCl$_2$(PPh$_3$)$_2$ (254 mg; 0.36 mmol) in anh. THF (20 ml) was heated to 75° C., under nitrogen, for 18 h. After cooling to rt, water and AcOEt were added. The separated aq. layer was further extracted with AcOEt. The mixed organic layers were washed with brine, dried over anh. MgSO$_4$, filtered, and concentrated to dryness under reduced pressure. Purification by FC (heptane/AcOEt=1/1) afforded ethyl 3-(thiazol-5-yl)benzoate as a pale yellow solid. LC-MS (conditions A): t$_R$=0.75 min.; [M+H]$^+$: 233.94 g/mol.

A cooled (−78° C.) solution of ethyl 3-(thiazol-5-yl)benzoate (553 mg; 2.37 mmol) in anh. toluene (8 ml) was treated with a solution of 1 M DIBAH in toluene (7.12 ml; 7.12 mmol), and the resulting mixture was further stirred at −78° C., under nitrogen, for 5 min., and then at 0° C. for 30 min.

The mixture was then treated successively with water (35 ml), 1 M aq. NaOH (11 ml), and aq. sat. NaHCO$_3$ (30 ml). The separated aq. layer was further extracted with Et$_2$O (2×100 ml). The mixed organic layers were then dried over anh. MgSO$_4$, filtered, and concentrated to dryness under reduced pressure. Purification by FC (DCM/MeOH=20/1) afforded (3-(thiazol-5-yl)phenyl)methanol as an orange oil. LC-MS (conditions A): $t_R$=0.49 min.; [M+H]$^+$: 192.10 g/mol.

A solution of (3-(thiazol-5-yl)phenyl)methanol (162 mg; 0.84 mmol) in anh. DCM (6 ml) was treated with MnO$_2$ (1.104 g; 12.70 mmol), and the resulting mixture was stirred at rt, under nitrogen, for 3 h. The resulting reaction mixture was then filtered over celite, and the separated solids were washed with DCM. The filtrate was concentrated to dryness under reduced pressure giving 3-(thiazol-5-yl)benzaldehyde as an orange solid. LC-MS (conditions A): $t_R$=0.58 min.; [M+H]$^+$: 190.02 g/mol.

3-(5-methylthiazol-2-yl)benzaldehyde

A mixture of commercially available ethyl 3-iodobenzoate (485 mg; 1.75 mmol), 5-methyl-2-(tributylstannyl)thiazole (685 mg; 1.76 mmol), and PdCl$_2$(PPh$_3$)$_2$ (123 mg; 0.17 mmol) in anh. THF (10 ml) was heated to 75° C., under nitrogen, for 18 h. In order to complete this reaction, the resulting reaction mixture was then heated to 85° C. for 8 h. After cooling to rt, water and AcOEt were added. The separated aq. layer was further extracted with AcOEt. The mixed organic layers were washed with brine, dried over anh. MgSO$_4$, filtered, and concentrated to dryness under reduced pressure. Purification by FC (heptane/AcOEt=1/1) afforded ethyl 3-(5-methylthiazol-2-yl)benzoate as an orange oil. LC-MS (conditions A): $t_R$=0.88 min.; [M+H]$^+$: 247.98 g/mol.

A cooled (−78° C.) solution of ethyl 3-(5-methylthiazol-2-yl)benzoate (388 mg; 1.57 mmol) in anh. toluene (4 ml) was treated with a solution of 1 M DIBAH in toluene (4.71 ml; 4.71 mmol), and the resulting mixture was further stirred at −78° C., under nitrogen, for 5 min., and then at 0° C. for 30 min. The obtained mixture was then treated successively with water (35 ml), 1 M aq. NaOH (11 ml), and aq. sat. NaHCO$_3$ (30 ml). The separated aq. layer was further extracted with Et$_2$O (2×100 ml). The mixed organic layers were then dried over anh. MgSO$_4$, filtered, and concentrated to dryness under reduced pressure. Purification by FC (DCM/MeOH=20/1) afforded (3-(5-methylthiazol-2-yl)phenyl)methanol as a pale yellow oil. LC-MS (conditions A): $t_R$=0.58 min.; [M+H]$^+$: 206.01 g/mol.

A solution of (3-(5-methylthiazol-2-yl)phenyl)methanol (210 mg; 1.02 mmol) in anh. DCM (8 ml) was treated with MnO$_2$ (1.334 g; 15.34 mmol), and the resulting mixture was stirred at rt, under nitrogen, for 1.5 h. The resulting reaction mixture was then filtered over celite, and the separated solids were washed with DCM. The filtrate was concentrated to dryness under reduced pressure giving 3-(5-methylthiazol-2-yl)benzaldehyde as a colorless solid. LC-MS (conditions A): $t_R$=0.72 min.; [M+H]$^+$: 203.99 g/mol.

6-(thiazol-2-yl)picolinaldehyde

A mixture of commercially available methyl 6-bromopicolinate (300 mg; 1.38 mmol), 2-(tributylstannyl)thiazole (623 mg; 1.66 mmol), and PdCl$_2$(PPh$_3$)$_2$ (97 mg; 0.13 mmol) in anh. THF (8 ml) was heated to 75° C., under nitrogen, for 18 h. After cooling to rt, water and AcOEt were added. The separated aq. layer was further extracted with AcOEt. The mixed organic layers were washed with brine, dried over anh. MgSO$_4$, filtered, and concentrated to dryness under reduced pressure. Purification by FC (heptane/AcOEt=1/1) afforded methyl 6-(thiazol-2-yl)picolinate as a pale yellow solid. LC-MS (conditions A): $t_R$=0.60 min.; [M+H]$^+$: 220.95 g/mol.

A solution of methyl 6-(thiazol-2-yl)picolinate (230 mg; 1.04 mmol) in anh. EtOH (3 ml) was treated with NaBH$_4$ (197 mg; 5.22 mmol), and the resulting mixture was stirred at rt, under nitrogen, for 17 h. After concentration to dryness under reduced pressure, the resulting residue was treated with water, and extracted with DCM. The organic layer was then dried over anh. MgSO$_4$, filtered, and concentrated to dryness under reduced pressure. Purification by FC (DCM/MeOH=25/1) afforded (6-(thiazol-2-yl)pyridin-2-yl)methanol as an orange solid. LC-MS (conditions A): $t_R$=0.45 min.; [M+H]$^+$: 193.05 g/mol.

A solution of (6-(thiazol-2-yl)pyridin-2-yl)methanol (171 mg; 0.89 mmol) in anh. DCM (6 ml) was treated with MnO$_2$ (1.164 g; 13.38 mmol), and the resulting mixture was stirred at rt, under nitrogen, for 2 h. The resulting reaction mixture was then filtered over celite, and the separated solids were washed with DCM. The filtrate was concentrated to dryness under reduced pressure giving 6-(thiazol-2-yl)picolinaldehyde as a yellow solid. LC-MS (conditions A): $t_R$=0.62 min.; [M+H]$^+$: 191.08 g/mol.

[2,2'-bipyridine]-4-carbaldehyde

A mixture of commercially available methyl 2-chloroisonicotinate (300 mg; 1.74 mmol), 2-(trimethylstannyl)pyridine (422 mg; 1.74 mmol), and PdCl$_2$(PPh$_3$)$_2$ (122 mg; 0.17 mmol) in anh. meta-xylene (7 ml) was heated to 75° C., under nitrogen, for 18 h. After cooling to rt, water and AcOEt were added. The separated aq. layer was further extracted with AcOEt. The mixed organic layers were washed with brine, dried over anh. MgSO$_4$, filtered, and concentrated to dryness under reduced pressure. Purification by FC (DCM/MeOH=15/1) afforded methyl[2,2'-bipyridine]-4-carboxylate as a yellow solid. LC-MS (conditions A): $t_R$=0.46 min.; [M+H]$^+$: 215.15 g/mol.

A cooled (−10° C.) suspension of LiAlH$_4$ (40 mg; 1.05 mmol) in anh. THF (3 ml) was treated with a solution of methyl[2,2'-bipyridine]-4-carboxylate (205 mg; 0.95 mmol) in anh. THF (2 ml). The mixture was further stirred at −10° C. for 5 min., and then at rt for 20 min. Water (40 µl), 15% aq. NaOH (40 µl), and water (0.12 ml) were then successively added, and the resulting mixture was further stirred at rt for 1 h. Filtration, concentration to dryness under reduced pressure, and additional drying under HV afforded [2,2'-bipyridin]-4-ylmethanol as a colorless solid. LC-MS (conditions A): $t_R$=0.25 min.; [M+H]$^+$: 187.14 g/mol.

A solution of [2,2'-bipyridin]-4-ylmethanol (120 mg; 0.64 mmol) in anh. THF (5 ml) was treated with MnO$_2$ (873 mg; 10.05 mmol), and the resulting mixture was stirred at rt, under nitrogen, for 6.5 h. The resulting reaction mixture was then filtered over celite, and the separated solids were washed with THF. The filtrate was concentrated to dryness under reduced pressure giving [2,2'-bipyridine]-4-carbaldehyde as a colorless solid. LC-MS (conditions A): $t_R$=0.30 min.; [M+H]$^+$: 185.17 g/mol.

4-phenylpicolinaldehyde

A cooled (−78° C.) solution of commercially available 2-bromo-4-phenylpyridine (500 mg; 2.13 mmol) in anh. THF (9 ml) was treated dropwise with a solution of 1.6 M n-BuLi in hexanes (1.33 ml; 2.13 mmol), and the resulting mixture was further stirred at −78° C., under nitrogen, for 1 h. Commercially available piperidine-1-carbaldehyde (483 mg; 4.27 mmol) was added dropwise to the cooled (−78° C.) reaction mixture, and stirring was continued at −78° C. for 15 min., and then at 0° C. for 1 h. Aq. sat. NH$_4$Cl (25 ml) and AcOEt (50 ml) were added, and the separated organic layer was further washed with brine (20 ml), dried over anh. MgSO$_4$, filtered, and concentrated to dryness under reduced pressure. Purification by FC (toluene/AcOEt=7/3) afforded 4-phenylpicolinaldehyde as a yellow solid. LC-MS (conditions A): t$_R$=0.43 min.; [M+H]$^+$: 184.48 g/mol.

[2,2'-bipyridine]-6-carbaldehyde

A cooled (−78° C.) solution of commercially available 6-bromo-2,2'-bipyridine (600 mg; 2.55 mmol) in anh. THF (10 ml) was treated dropwise with a solution of 1.6 M n-BuLi in hexanes (1.60 ml; 2.56 mmol), and the resulting mixture was further stirred at −78° C., under nitrogen, for 30 min. Piperidine-1-carbaldehyde (577 mg; 5.10 mmol) was added dropwise to the cooled (−78° C.) reaction mixture, and stirring was continued at −78° C. for 30 min. Aq. sat. NH$_4$Cl (25 ml) and AcOEt (50 ml) were added, and the separated organic layer was further washed with brine (20 ml), dried over anh. MgSO$_4$, filtered, and concentrated to dryness under reduced pressure. Purification by FC (toluene/AcOEt=8/2) afforded [2,2'-bipyridine]-6-carbaldehyde as a dark-purple solid. LC-MS (conditions C): t$_R$=0.75 min.; [M+H]$^+$: 185.24 g/mol.

2-methylbenzo[d]thiazole-6-carbaldehyde

A cooled (−10° C.) suspension of LiAlH$_4$ (188 mg; 4.97 mmol) in anh. THF (30 ml) was treated with a solution of commercially available ethyl 2-methylbenzo[d]thiazole-6-carboxylate (1.000 g; 4.51 mmol) in anh. THF (20 ml). The mixture was further stirred at −10° C. for 20 min. Water (0.19 ml), 15% aq. NaOH (0.19 ml), and water (0.57 ml) were then successively added, and the resulting mixture was further stirred at rt for 1 h. Filtration, concentration to dryness under reduced pressure, and additional drying under HV afforded (2-methylbenzo[d]thiazol-6-yl)methanol as a yellow oil. LC-MS (conditions A): t$_R$=0.45 min.; [M+H]$^+$: 180.16 g/mol.

A solution of (2-methylbenzo[d]thiazol-6-yl)methanol (300 mg; 1.67 mmol) in anh. THF (15 ml) was treated with MnO$_2$ (2.269 g; 26.11 mmol), and the resulting mixture was stirred at rt, under nitrogen, for 6.5 h. The resulting reaction mixture was then filtered over celite, and the separated solids were washed with THF. The filtrate was concentrated to dryness under reduced pressure giving 2-methylbenzo[d]thiazole-6-carbaldehyde as a yellow solid. LC-MS (conditions A): t$_R$=0.56 min.; [M+H]$^+$: 178.15 g/mol.

2-methylbenzo[d]thiazole-5-carbaldehyde

A solution of commercially available 2-methylbenzo[d]thiazole-5-carboxylic acid (1.500 g; 7.76 mmol) in anh. DMF (35 ml) was treated with Cs$_2$CO$_3$ (3.161 g; 9.70 mmol), and the heterogeneous mixture was further stirred at rt, under nitrogen, for 15 min. The mixture was then cooled to 0° C., and CH$_3$I (1.652 g; 11.64 mmol) was added dropwise. The resulting mixture was further stirred at 0° C. for 10 min., and then at rt for 16 h. Water and AcOEt were added to the reaction mixture. The separated organic layer was further washed with water and brine, dried over anh. MgSO$_4$, filtered, and concentrated to dryness under reduced pressure affording methyl 2-methylbenzo[d]thiazole-5-carboxylate as a brown solid. LC-MS (conditions A): t$_R$=0.67 min.; [M+H]$^+$: 208.16 g/mol.

A cooled (−10° C.) suspension of LiAlH$_4$ (207 mg; 5.47 mmol) in anh. THF (40 ml) was treated with a solution of methyl 2-methylbenzo[d]thiazole-5-carboxylate (1.032 g; 4.97 mmol) in anh. THF (20 ml). The mixture was further stirred at −10° C. for 20 min. Water (0.20 ml), 15% aq. NaOH (0.20 ml), and water (0.60 ml) were then successively added, and the resulting mixture was further stirred at rt for 1 h. Filtration, concentration to dryness under reduced pressure, and additional drying under HV afforded (2-methylbenzo[d]thiazol-5-yl)methanol as a yellow oil. LC-MS (conditions A): t$_R$=0.48 min.; [M+H]$^+$: 180.19 g/mol.

A solution of (2-methylbenzo[d]thiazol-5-yl)methanol (400 mg; 2.23 mmol) in anh. THF (20 ml) was treated with MnO$_2$ (3.026 g; 34.81 mmol), and the resulting mixture was stirred at rt, under nitrogen, for 6.5 h. The resulting reaction mixture was then filtered over celite, and the separated solids were washed with THF. The filtrate was concentrated to dryness under reduced pressure giving 2-methylbenzo[d]thiazole-5-carbaldehyde as a yellow solid. LC-MS (conditions B): t$_R$=0.70 min.; [M+H]$^+$: 178.03 g/mol.

3-(2H-1,2,3-triazol-2-yl)benzaldehyde

In a sealed tube, a mixture of commercially available 3-iodobenzoic acid (2.000 g; 8.06 mmol), 1H-1,2,3-triazole (1.113 g; 16.12 mmol), trans-N,N'-dimethylcyclohexane-1,2-diamine (236 mg; 1.61 mmol), Cs$_2$CO$_3$ (5.362 g; 16.12 mmol), and CuI (76 mg; 0.40 mmol) in anh. DMF (10 ml) was heated to 120° C. for 16 h. After cooling to rt, water was added, and the mixture was extracted with AcOEt. The separated aq. layer was acidified with aq. 1 M HCl, and extracted with AcOEt (3×). The mixed organic layers were dried over anh. MgSO$_4$, filtered, and concentrated to dryness under reduced pressure. Purification by FC (DCM/MeOH/AcOH=20/1/0.1) afforded the two pure isomers:

3-(2H-1,2,3-triazol-2-yl)benzoic acid (major isomer) as an off-white solid. LC-MS (conditions A): t$_R$=0.57 min.; no ionisation.

3-(1H-1,2,3-triazol-1-yl)benzoic acid (minor isomer) as a colorless solid. LC-MS (conditions A): t$_R$=0.42 min.; [M+H]$^+$: 190.05 g/mol.

A cooled (0° C.) solution of the major isomer 3-(2H-1,2,3-triazol-2-yl)benzoic acid (500 mg; 2.64 mmol) in anh. THF (7 ml) was treated dropwise with a BH$_3$.THF (1.0 M in THF; 6.60 ml; 6.60 mmol), and this mixture was stirred at 0° C., under nitrogen, for 1 h, and then at rt for 1.5 h. The resulting reaction mixture was then cooled to 0° C., and treated successively with MeOH (10 ml) and water (10 ml). The organic solvents were removed under reduced pressure, and the resulting aq. layer was extracted with DCM (3×10 ml). The mixed organic layers were washed with brine, dried over anh. MgSO$_4$, filtered, and concentrated to dryness under reduced pressure. Purification by FC (DCM/MeOH=20/1) afforded (3-(2H-1,2,3-triazol-2-yl)phenyl)methanol as a colorless oil. LC-MS (conditions A): t$_R$=0.51 min.; no ionisation.

A solution of (3-(2H-1,2,3-triazol-2-yl)phenyl)methanol (425 mg; 2.42 mmol) in anh. DCM (24 ml) was treated with MnO$_2$ (3.165 g; 36.41 mmol), and the resulting mixture was stirred at rt, under nitrogen, for 1.5 h. The resulting reaction mixture was then filtered over celite, and the separated solids were washed with DCM. The filtrate was concentrated to dryness under reduced pressure giving 3-(2H-1,2,3-triazol-2-yl)benzaldehyde as a pale yellow solid. LC-MS (conditions A): t$_R$=0.63 min.; no ionisation.

3-(1H-1,2,3-triazol-1-yl)benzaldehyde

In a sealed tube, a mixture of 3-iodobenzoic acid (2.000 g; 8.06 mmol), 1H-1,2,3-triazole (1.113 g; 16.12 mmol), trans- N,N'-dimethylcyclohexane-1,2-diamine (236 mg; 1.61 mmol), $Cs_2CO_3$ (5.362 g; 16.12 mmol), and CuI (76 mg; 0.40 mmol) in anh. DMF (10 ml) was heated to 120° C. for 16 h. After cooling to rt, water was added, and the mixture was extracted with AcOEt. The separated aq. layer was acidified with aq. 1 M HCl, and extracted with AcOEt (3×). The mixed organic layers were dried over anh. $MgSO_4$, filtered, and concentrated to dryness under reduced pressure. Purification by FC (DCM/MeOH/AcOH=20/1/0.1) afforded the two pure isomers:

3-(2H-1,2,3-triazol-2-yl)benzoic acid (major isomer) as an off-white solid. LC-MS (conditions A): $t_R$=0.57 min.; no ionisation.

3-(1H-1,2,3-triazol-1-yl)benzoic acid (minor isomer) as a colorless solid. LC-MS (conditions A): $t_R$=0.42 min.; $[M+H]^+$: 190.05 g/mol.

A cooled (0° C.) solution of the minor isomer 3-(1H-1,2,3-triazol-1-yl)benzoic acid (210 mg; 1.11 mmol) in anh. THF (3 ml) was treated dropwise with a $BH_3$.THF (1.0 M in THF; 2.77 ml; 2.77 mmol), and this mixture was stirred at 0° C., under nitrogen, for 1 h, and then at rt for 17 h. The resulting reaction mixture was then cooled to 0° C., and treated successively with MeOH (10 ml) and water (10 ml). The organic solvents were removed under reduced pressure, and the resulting aq. layer was extracted with DCM (3×10 ml). The mixed organic layers were washed with brine, dried over anh. $MgSO_4$, filtered, and concentrated to dryness under reduced pressure. Purification by FC (DCM/MeOH=20/1) afforded (3-(1H-1,2,3-triazol-1-yl)phenyl)methanol as a pale yellow solid. LC-MS (conditions A): $t_R$=0.38 min.; $[M+H]^+$: 176.18 g/mol.

A solution of (3-(1H-1,2,3-triazol-1-yl)phenyl)methanol (55 mg; 0.31 mmol) in anh. DCM (1 ml) was treated with $MnO_2$ (411 mg; 4.73 mmol), and the resulting mixture was stirred at rt, under nitrogen, for 2 h. The resulting reaction mixture was then filtered over celite, and the separated solids were washed with DCM. The filtrate was concentrated to dryness under reduced pressure giving 3-(1H-1,2,3-triazol-1-yl)benzaldehyde as a colorless solid. LC-MS (conditions A): $t_R$=0.45 min.; $[M+H]^+$: 174.09 g/mol.

2-(1H-pyrazol-1-yl)isonicotinaldehyde

A mixture of commercially available methyl 2-bromoisonicotinate (500 mg; 2.31 mmol), 1H-pyrazole (157 mg; 2.31 mmol), trans-N,N'-dimethylcyclohexane-1,2-diamine (67 mg; 0.46 mmol), $K_2CO_3$ (685 mg; 4.86 mmol), and CuI (22 mg; 0.11 mmol) in anh. toluene (8 ml) was heated at reflux for 16 h. After cooling to rt, water was added, and the mixture was extracted with AcOEt. The mixed organic layers were dried over anh. $MgSO_4$, filtered, and concentrated to dryness under reduced pressure. Purification by FC (DCM/MeOH=20/1) afforded methyl 2-(1H-pyrazol-1-yl)isonicotinate as an off-white solid. LC-MS (conditions A): $t_R$=0.67 min.; $[M+H]^+$: 204.04 g/mol.

A solution of methyl 2-(1H-pyrazol-1-yl)isonicotinate (399 mg; 1.96 mmol) in anh. EtOH (8 ml) was treated with $NaBH_4$ (371 mg; 9.83 mmol), and the resulting mixture was stirred at rt, under nitrogen, for 17 h. After concentration to dryness under reduced pressure, the resulting residue was treated with water, and extracted with DCM. The organic layer was then dried over anh. $MgSO_4$, filtered, and concentrated to dryness under reduced pressure. Purification by FC (DCM/MeOH=25/1) afforded (2-(1H-pyrazol-1-yl)pyridin-4-yl)methanol as a colorless solid. LC-MS (conditions A): $t_R$=0.44 min.; $[M+H]^+$: 176.10 g/mol.

A solution of (2-(1H-pyrazol-1-yl)pyridin-4-yl)methanol (217 mg; 1.23 mmol) in anh. DCE (4 ml) was treated with $MnO_2$ (861 mg; 9.91 mmol), and the resulting mixture was stirred at reflux, under nitrogen, for 1.5 h. After cooling to rt, the resulting reaction mixture was filtered over celite, and the separated solids were washed with DCM. The filtrate was concentrated to dryness under reduced pressure giving 2-(1H-pyrazol-1-yl)isonicotinaldehyde as a colorless solid. LC-MS (conditions C): $t_R$=0.70 min.; $[M+H]^+$: 173.76 g/mol.

6-(1H-pyrazol-1-yl)picolinaldehyde

A mixture of commercially available methyl 6-bromopicolinate (1.000 g; 4.62 mmol), 1H-pyrazole (315 mg; 4.62 mmol), trans-N,N'-dimethylcyclohexane-1,2-diamine (135 mg; 0.92 mmol), $K_2CO_3$ (1.370 g; 9.72 mmol), and CuI (44 mg; 0.23 mmol) in anh. toluene (15 ml) was heated at reflux for 17 h. After cooling to rt, water was added, and the mixture was extracted with AcOEt. The mixed organic layers were dried over anh. $MgSO_4$, filtered, and concentrated to dryness under reduced pressure. Purification by FC (DCM/MeOH=20/1) afforded methyl 6-(1H-pyrazol-1-yl)picolinate as a colorless solid. LC-MS (conditions A): $t_R$=0.59 min.; $[M+H]^+$: 204.04 g/mol.

A solution of methyl 6-(1H-pyrazol-1-yl)picolinate (476 mg; 2.34 mmol) in anh. EtOH (10 ml) was treated with $NaBH_4$ (443 mg; 11.71 mmol), and the resulting mixture was stirred at rt, under nitrogen, for 16 h. After concentration to dryness under reduced pressure, the resulting residue was treated with water, and extracted with DCM. The organic layer was then dried over anh. $MgSO_4$, filtered, and concentrated to dryness under reduced pressure. Purification by FC (DCM/MeOH=20/1) afforded (6-(1H-pyrazol-1-yl)pyridin-2-yl)methanol as a colorless oil. LC-MS (conditions A): $t_R$=0.45 min.; $[M+H]^+$: 176.11 g/mol.

A solution of (6-(1H-pyrazol-1-yl)pyridin-2-yl)methanol (295 mg; 1.68 mmol) in anh. DCE (6 ml) was treated with $MnO_2$ (1.174 g; 13.51 mmol), and the resulting mixture was stirred at reflux, under nitrogen, for 2 h. After cooling to rt, the resulting reaction mixture was filtered over celite, and the separated solids were washed with DCM. The filtrate was concentrated to dryness under reduced pressure giving 6-(1H-pyrazol-1-yl)picolinaldehyde as an off-white solid. LC-MS (conditions C): $t_R$=0.74 min.; $[M+H]^+$: 173.88 g/mol.

2,6-diethoxybenzaldehyde

A solution of commercially available (2,6-diethoxyphenyl)methanol (500 mg; 2.47 mmol) in anh. $CHCl_3$ (10 ml) was treated with $MnO_2$ (3.342 g; 34.60 mmol), and the resulting mixture was heated to 50° C., under nitrogen, for 20 h. After cooling to rt, the resulting reaction mixture was filtered over celite, and the separated solids were washed with DCM. The filtrate was concentrated to dryness under reduced pressure giving 2,6-diethoxybenzaldehyde as a colorless solid. LC-MS (conditions D): $t_R$=0.89 min.; $[M+H]^+$: 194.99 g/mol.

6-methoxy-3-methylbenzo[d]isoxazole-7-carbaldehyde

To a solution of commercially available 3-methylbenzo[d]isoxazol-6-ol (1.125 g; 7.54 mmol) in acetic acid (22.5 ml) was added hexamethylenetetramine (4.500 g; 32.09 mmol), and the resulting mixture was heated over a steam-bath for 6 h. The resulting hot mixture was then treated with 6 M aq. HCl (20 ml), and the heating was continued for 30 min. The solid obtained on dilution of the reaction mixture was filtered, and recrystallised from aq. MeOH to give the desired 6-hydroxy- 3-methylbenzo[d]isoxazole-7-carbaldehyde as a yellow solid. LC-MS (conditions D): $t_R$=0.79 min.; [M+H]$^+$: 177.98 g/mol.

A mixture of 6-hydroxy-3-methylbenzo[d]isoxazole-7-carbaldehyde (437 mg; 2.46 mmol) and K$_2$CO$_3$ (409 mg; 2.96 mmol) in anh. acetone (21 ml) was treated with dimethyl sulfate (373 mg; 2.96 mmol), and the resulting mixture was heated to 60° C., under nitrogen, for 1.5 h. After cooling to rt, the resulting reaction mixture was filtered, and the filtrate was concentrated to dryness under reduced pressure. DCM was added, and the mixture was washed successively with 1 M aq. NH$_4$OH, water, and brine. The organic layer was dried over anh. MgSO$_4$, filtered, and concentrated to dryness under reduced pressure to give 6-methoxy-3-methylbenzo[d]isoxazole-7-carbaldehyde as an orange solid. LC-MS (conditions A): $t_R$=0.53 min.; [M+H]$^+$: 192.12 g/mol.

5-chloro-6-(difluoromethoxy)nicotinaldehyde

A mixture of commercially available 5-chloro-6-oxo-1,6-dihydropyridine-3-carboxylic acid (4.000 g; 23.04 mmol) and concentrated H$_2$SO$_4$ (0.3 ml) in anh. MeOH (52 ml) was refluxed, under nitrogen, for 19 h. MeOH was removed under reduced pressure, and the residue was basified by addition of a solution of 10% aq. NaHCO$_3$. The mixture was then extracted with DCM (5×), and the mixed organic layers were dried over anh. MgSO$_4$, filtered, and concentrated to dryness under reduced pressure affording methyl 5-chloro-6-oxo-1,6-dihydropyridine-3-carboxylate as a pale yellow solid. LC-MS (conditions D): $t_R$=0.61 min.; [M+H]$^+$: 187.93 g/mol.

A mixture of methyl 5-chloro-6-oxo-1,6-dihydropyridine-3-carboxylate (3.810 g; 20.31 mmol) in anh. MeCN (400 ml) was treated portionwise with NaH (60% dispersion in mineral oil; 2.193 g; 54.84 mmol), and stirring at rt, under nitrogen, was continued for 20 min. FSO$_2$CF$_2$CO$_2$H (6.149 g; 34.52 mmol) was then added dropwise, and the resulting heterogeneous mixture was further stirred at rt, under nitrogen, for 45 min. Water (10 ml) was slowly added, and MeCN was removed under reduced pressure. Water (150 ml) and AcOEt (150 ml) were added, and the separated aq. layer was further extracted with AcOEt (3×100 ml). The mixed organic layers were dried over anh. MgSO$_4$, filtered, and concentrated to dryness under reduced pressure. Purification by FC (DCM) afforded methyl 5-chloro-6-(difluoromethoxy)nicotinate as an off-white solid. LC-MS (conditions A): $t_R$=0.81 min.; no ionisation.

A cooled (−78° C.) solution of methyl 5-chloro-6-(difluoromethoxy)nicotinate (4.080 g; 17.17 mmol) in anh. toluene (110 ml) was treated dropwise with a solution of 1 M DIBAH in toluene (60.30 ml; 60.30 mmol), and the resulting mixture was further stirred at −78° C., under nitrogen, for 5 min., and then at 0° C. for 3 h. The obtained mixture was treated successively with water (55 ml), 1 M aq. NaOH (11 ml), and aq. sat. NaHCO$_3$ (100 ml). The separated aq. layer was further extracted with Et$_2$O (2×100 ml). The mixed organic layers were then dried over anh. MgSO$_4$, filtered, and concentrated to dryness under reduced pressure affording (5-chloro-6-(difluoromethoxy)pyridin-3-yl)methanol as an orange oil. LC-MS (conditions A): $t_R$=0.62 min.; [M+H]$^+$: 210.25 g/mol.

A solution of (5-chloro-6-(difluoromethoxy)pyridin-3-yl)methanol (1.000 g; 4.77 mmol) in anh. DCM (40 ml) was treated with MnO$_2$ (6.222 g; 71.57 mmol), and the resulting mixture was stirred at rt, under nitrogen, for 3 h. The resulting reaction mixture was then filtered over celite, and the separated solids were washed with DCM. The filtrate was concentrated to dryness under reduced pressure giving 5-chloro-6-(difluoromethoxy)nicotinaldehyde as a yellow oil. LC-MS (conditions A): $t_R$=0.72 min.; no ionisation.

4-(2-fluoroethoxy)benzaldehyde

A mixture of commercially available 4-hydroxybenzaldehyde (2.000 g; 16.40 mmol), 1-fluoro-2-iodoethane (2.849 g; 16.40 mmol), and K$_2$CO$_3$ (4.527 g; 32.80 mmol) in anh. DMF (30 ml) was heated to 70° C., under nitrogen, for 2.5 h. After cooling to rt, the reaction mixture was filtered over a pad of celite. Et$_2$O was added and the organic layer was washed with water, dried over anh. MgSO$_4$, filtered, and concentrated to dryness under reduced pressure affording 4-(2-fluoroethoxy)benzaldehyde as a yellow oil. LC-MS (conditions A): $t_R$=0.58 min.; no ionisation.

3-(2-fluoroethoxy)benzaldehyde

A mixture of commercially available 3-hydroxybenzaldehyde (2.000 g; 16.40 mmol), 1-fluoro-2-iodoethane (3.849 g; 22.10 mmol), and K$_2$CO$_3$ (4.527 g; 32.80 mmol) in anh. DMF (30 ml) was heated to 70° C., under nitrogen, for 3 h. After cooling to rt, the reaction mixture was filtered over a pad of celite. Et$_2$O was added and the organic layer was washed with water, dried over anh. MgSO$_4$, filtered, and concentrated to dryness under reduced pressure affording 3-(2-fluoroethoxy)benzaldehyde as a green oil. LC-MS (conditions A): $t_R$=0.62 min.; no ionisation.

3,6-difluoro-2-methoxybenzaldehyde

A mixture of commercially available 3,6-difluoro-2-hydroxybenzaldehyde (2.450 g; 15.50 mmol), iodomethane (2.199 g; 15.50 mmol), and K$_2$CO$_3$ (2.570 g; 18.60 mmol) in anh. DMF (50 ml) was heated to 80° C., under nitrogen, for 4 h. Et$_2$O was added and the organic layer was washed with water, dried over anh. MgSO$_4$, filtered, and concentrated to dryness under reduced pressure affording 3,6-difluoro-2-methoxybenzaldehyde as a colorless solid. LC-MS (conditions A): $t_R$=0.62 min.; no ionisation.

3-isopropoxybenzaldehyde

A mixture of commercially available 3-hydroxybenzaldehyde (3.000 g; 24.60 mmol), 2-iodopropane (12.528 g; 73.70 mmol), K$_2$CO$_3$ (6.790 g; 49.10 mmol), and Cs$_2$CO$_3$ (1.601 g; 4.91 mmol) in anh. DMF (60 ml) was stirred at rt, under nitrogen, for 17 h. Et$_2$O was added and the organic layer was washed with water, dried over anh. MgSO$_4$, filtered, and concentrated to dryness under reduced pressure affording 3-isopropoxybenzaldehyde as a yellow oil. LC-MS (conditions A): $t_R$=0.76 min.; [M+H]$^+$: 165.24 g/mol.

2-fluoro-6-isopropoxybenzaldehyde

A mixture of commercially available 2-fluoro-6-hydroxybenzaldehyde (3.000 g; 21.40 mmol), 2-iodopropane (10.919 g; 64.20 mmol), K$_2$CO$_3$ (5.918 g; 42.80 mmol), and Cs$_2$CO$_3$ (1.395 g; 4.28 mmol) in anh. DMF (63 ml) was stirred at rt, under nitrogen, for 16 h. Et$_2$O was added and the organic layer was washed with water, dried over anh. MgSO$_4$, filtered, and concentrated to dryness under reduced pressure affording 2-fluoro-6-isopropoxybenzaldehyde as a yellow oil. LC-MS (conditions A): $t_R$=0.74 min.; [M+H]$^+$: 183.15 g/mol.

6-ethoxy-2,3-difluorobenzaldehyde

A mixture of commercially available 2,3-difluoro-6-hydroxybenzaldehyde (3.000 g; 21.40 mmol), iodoethane (6.679 g; 42.80 mmol), and K$_2$CO$_3$ (3.551 g; 25.70 mmol) in anh. DMF (60 ml) was heated to 80° C., under nitrogen, for 1.5 h. Et$_2$O was added and the organic layer was washed with water, dried over anh. MgSO$_4$, filtered, and concentrated to dryness under reduced pressure affording 6-ethoxy-2,3-difluorobenzaldehyde as a yellow solid. LC-MS (conditions A): t$_R$=0.72 min.; no ionisation.

2-ethoxy-4-fluorobenzaldehyde

A mixture of commercially available 4-fluoro-2-hydroxybenzaldehyde (2.500 g; 17.80 mmol), iodoethane (5.566 g; 35.70 mmol), and K$_2$CO$_3$ (2.959 g; 21.40 mmol) in anh. DMF (50 ml) was heated to 80° C., under nitrogen, for 2 h.

Et$_2$O was added and the organic layer was washed with water, dried over anh. MgSO$_4$, filtered, and concentrated to dryness under reduced pressure affording 2-ethoxy-4-fluorobenzaldehyde as a yellow solid. LC-MS (conditions A): t$_R$=0.73 min.; [M+H]$^+$: 169.16 g/mol.

2-ethoxy-6-fluorobenzaldehyde

A mixture of commercially available 2-fluoro-6-hydroxybenzaldehyde (2.500 g; 17.80 mmol), iodoethane (5.566 g; 35.70 mmol), and K$_2$CO$_3$ (2.959 g; 21.40 mmol) in anh. DMF (50 ml) was heated to 80° C., under nitrogen, for 2 h. Et$_2$O was added and the organic layer was washed with water, dried over anh. MgSO$_4$, filtered, and concentrated to dryness under reduced pressure affording 2-ethoxy-6-fluorobenzaldehyde as a yellow solid. LC-MS (conditions A): t$_R$=0.66 min.; [M+H]$^+$: 169.14 g/mol.

2-chloro-6-ethoxybenzaldehyde

A mixture of commercially available 2-chloro-6-hydroxybenzaldehyde (2.000 g; 12.80 mmol), iodoethane (3.985 g; 25.50 mmol), and K$_2$CO$_3$ (2.119 g; 15.30 mmol) in anh. DMF (35 ml) was heated to 80° C., under nitrogen, for 1 h. Et$_2$O was added and the organic layer was washed with water, dried over anh. MgSO$_4$, filtered, and concentrated to dryness under reduced pressure affording 2-chloro-6-ethoxybenzaldehyde as a yellow solid. LC-MS (conditions A): t$_R$=0.75 min.; [M+H]$^+$: 185.39 g/mol.

2-ethoxy-3-fluorobenzaldehyde

A mixture of commercially available 3-fluoro-2-hydroxybenzaldehyde (5.000 g; 35.70 mmol), iodoethane (11.131 g; 71.40 mmol), and K$_2$CO$_3$ (5.918 g; 42.80 mmol) in anh. DMF (100 ml) was heated to 80° C., under nitrogen, for 3 h. Et$_2$O was added and the organic layer was washed with water, dried over anh. MgSO$_4$, filtered, and concentrated to dryness under reduced pressure affording 2-ethoxy-3-fluorobenzaldehyde as a yellow oil. LC-MS (conditions A): t$_R$=0.74 min.; no ionisation.

2-ethoxy-4,6-difluorobenzaldehyde

A mixture of commercially available 3,5-difluorophenol (3.000 g; 23.10 mmol), anh. magnesium chloride MgCl$_2$ (6.587 g; 69.20 mmol), and NEt$_3$ (8.04 ml; 57.70 mmol) in anh. MeCN (100 ml) was stirred at rt, under nitrogen, for 20 min. Paraformaldehyde (3.459 g; 115.00 mmol) was then added, and the resulting mixture was heated to 80° C., under nitrogen, for 1.5 h. After cooling to rt, aq. 1N HCl (80 ml) was added, and the aq. layer was extracted with AcOEt. The mixed organic layers were dried over anh. MgSO$_4$, filtered, and concentrated to dryness under reduced pressure affording 2,4-difluoro-6-hydroxybenzaldehyde as a yellow oil. LC-MS (conditions A): t$_R$=0.67 min.; no ionisation.

A mixture of 2,4-difluoro-6-hydroxybenzaldehyde (4.340 g; 27.50 mmol), iodoethane (8.562 g; 54.90 mmol), and K$_2$CO$_3$ (4.553 g; 32.90 mmol) in anh. DMF (75 ml) was heated to 80° C., under nitrogen, for 45 min. Et$_2$O and water were added, and the organic layer was further washed with brine, dried over anh. MgSO$_4$, filtered, and concentrated to dryness under reduced pressure affording 2-ethoxy-4,6-difluorobenzaldehyde as an orange solid. LC-MS (conditions A): t$_R$=0.70 min.; [M+H]$^+$: 187.39 g/mol.

3-(2,2,2-trifluoroethoxy)benzaldehyde

A mixture of commercially available 3-hydroxybenzaldehyde (2.000 g; 16.40 mmol), 2,2,2-trifluoroethyl trifluoromethanesulfonate (4.561 g; 19.70 mmol), and Cs$_2$CO$_3$ (8.004 g; 24.60 mmol) in anh. DMF (30 ml) was stirred at rt, under nitrogen, for 1 h. Water and AcOEt were added and the organic layer was washed with water, dried over anh. MgSO$_4$, filtered, and concentrated to dryness under reduced pressure affording 3-(2,2,2-trifluoroethoxy)benzaldehyde as a colorless oil. LC-MS (conditions A): t$_R$=0.75 min.; no ionisation.

4-(2,2,2-trifluoroethoxy)benzaldehyde

A mixture of commercially available 4-hydroxybenzaldehyde (2.000 g; 16.40 mmol), 2,2,2-trifluoroethyl trifluoromethanesulfonate (4.561 g; 19.70 mmol), and Cs$_2$CO$_3$ (8.004 g; 24.60 mmol) in anh. DMF (30 ml) was stirred at rt, under nitrogen, for 1 h. Water and AcOEt were added and the organic layer was washed with water, dried over anh. MgSO$_4$, filtered, and concentrated to dryness under reduced pressure affording 4-(2,2,2-trifluoroethoxy)benzaldehyde as a yellow oil. LC-MS (conditions A): t$_R$=0.72 min.; no ionisation.

3-(2,2-difluoroethoxy)benzaldehyde

A mixture of commercially available 3-hydroxybenzaldehyde (2.000 g; 16.40 mmol), 2,2-difluoroethyl trifluoromethanesulfonate (3.506 g; 16.40 mmol), and Cs$_2$CO$_3$ (8.004 g; 24.60 mmol) in anh. DMF (30 ml) was stirred at rt, under nitrogen, for 17 h. Water and AcOEt were added and the organic layer was washed with water, dried over anh. MgSO$_4$, filtered, and concentrated to dryness under reduced pressure affording 3-(2,2-difluoroethoxy)benzaldehyde as a yellow oil. LC-MS (conditions A): t$_R$=0.67 min.; no ionisation.

4-(2,2-difluoroethoxy)benzaldehyde

A mixture of commercially available 4-hydroxybenzaldehyde (2.000 g; 16.40 mmol), 2,2-difluoroethyl trifluoromethanesulfonate (3.506 g; 16.40 mmol), and Cs$_2$CO$_3$ (8.004 g; 24.60 mmol) in anh. DMF (30 ml) was stirred at rt, under nitrogen, for 18 h. Water and AcOEt were added and the organic layer was washed with water, dried over anh. MgSO$_4$, filtered, and concentrated to dryness under reduced pressure affording 4-(2,2-difluoroethoxy)benzaldehyde as an orange oil. LC-MS (conditions A): t$_R$=0.65 min.; no ionisation.

3-chloro-2,6-dimethoxybenzaldehyde

A solution of commercially available 2,6-dimethoxybenzaldehyde (3.000 g; 18.10 mmol) in DCM (12 ml) was treated dropwise with a solution of sulfuryl dichloride SO$_2$Cl$_2$ (2.437 g; 18.10 mmol) in DCM (9 ml), and the resulting mixture was heated to 50° C., under nitrogen, for 30 min. After cooling to rt, water was added and the separated aq. layer was further extracted with DCM. The mixed organic layers were washed with brine, dried over anh. MgSO$_4$, filtered, and concentrated to dryness under reduced pressure. Purification by FC (heptane/AcOEt=3/1) afforded 3-chloro-2,6-dimethoxybenzaldehyde as a colorless solid. LC-MS (conditions A): $t_R$=0.67 min.; [M+H]$^+$: 201.03 g/mol.

3-fluoro-2,6-dimethoxybenzaldehyde

Commercially available 2,6-dimethoxybenzaldehyde (3.500 g; 21.10 mmol) was added to a suspension of Selectfluor (8.208 g; 23.20 mmol) in MeCN (35 ml), and the resulting mixture was stirred at rt, under nitrogen, for 16 h. Water and Et$_2$O were added and the aq. layer was further extracted with Et$_2$O. The mixed organic layers were dried over anh. MgSO$_4$, filtered, and concentrated to dryness under reduced pressure. Purification by FC (heptane/AcOEt=4/1) afforded 3-fluoro-2,6-dimethoxybenzaldehyde as a yellow oil. LC-MS (conditions A): $t_R$=0.60 min.; [M+H]$^+$: 185.10 g/mol.

2-methoxy-6-methylbenzaldehyde

A mixture of commercially available 1-methoxy-2,3-dimethylbenzene (10.000 g; 73.40 mmol), copper(II) sulfate pentahydrate CuSO$_4$.5H$_2$O (18.334 g; 73.40 mmol), and potassium peroxodisulfate K$_2$S$_2$O$_8$ (59.547 g; 220.00 mmol) in MeCN (250 ml) and water (250 ml) was heated at reflux, under nitrogen, for 30 min. After cooling to rt, DCM was added and the aq. layer was further extracted with DCM. The mixed organic layers were dried over anh. MgSO$_4$, filtered, and concentrated to dryness under reduced pressure. Purification by FC (heptane/AcOEt=9/1) afforded 2-methoxy-6-methylbenzaldehyde as a yellow oil. LC-MS (conditions A): $t_R$=0.70 min.; no ionisation.

dibenzo[b,d]thiophene-2-carbaldehyde

A cooled (0° C.) suspension of commercially available 2-bromodibenzo[b,d]thiophene (500 mg; 1.90 mmol) in anh. Et$_2$O (5 ml), under nitrogen, was treated dropwise with a solution of 1.6 M n-BuLi in hexanes (1.26 ml; 2.01 mmol). The resulting suspension was further stirred at 0° C. for 30 min. Anh. DMF (0.156 ml; 2.03 mmol) was then added, and the mixture was stirred at rt for 20 min. Aq. sat. NH$_4$Cl and Et$_2$O were successively added, and the aq. layer was further extracted with Et$_2$O. The mixed organic layers were washed with water, dried over anh. MgSO$_4$, filtered, and concentrated to dryness under reduced pressure. Purification by FC (DCM) afforded dibenzo[b,d]thiophene-2-carbaldehyde as an off-white solid. LC-MS (conditions A): $t_R$=0.87 min.; no ionisation.

6-methoxy-2,3-dihydrobenzo[b][1,4]dioxine-5-carbaldehyde

A mixture of 2,3-dihydrobenzo[b][1,4]dioxin-6-ol (2.600 g; 17.10 mmol), and K$_2$CO$_3$ (2.598 g; 18.80 mmol) in anh. acetone (40 ml) was stirred at rt, under nitrogen, for 1 h. Iodomethane (13.340 g; 94.00 mmol) was then added, and the resulting mixture was heated at reflux, under nitrogen, for 2 h. After cooling to rt, the reaction mixture was filtered over a pad of celite, and the filtrate was concentrated to dryness under reduced pressure. Et$_2$O and water were added, and the organic layer was further washed with brine, dried over anh. MgSO$_4$, filtered, and concentrated to dryness under reduced pressure affording 6-methoxy-2,3-dihydrobenzo[b][1,4]dioxine as a yellow oil. LC-MS (conditions A): $t_R$=0.65 min.; [M+H]$^+$: 167.11 g/mol.

A cooled (−20° C.) mixture of 6-methoxy-2,3-dihydrobenzo[b][1,4]dioxine (2.119 g; 12.80 mmol), and N1,N1,N2,N2-tetramethylethane-1,2-diamine (2.28 ml; 15.30 mmol) in anh. THF (100 ml), under nitrogen, was treated dropwise with a solution of 1.6 M n-BuLi in hexanes (8.00 ml; 12.80 mmol). The resulting mixture was further stirred at −20° C. for 1 h. Anh. DMF (5.0 ml; 64.57 mmol) was then added, and the mixture was stirred at rt for 20 min. Aq. sat. NH$_4$Cl and Et$_2$O were successively added, and the aq. layer was further extracted with Et$_2$O. The mixed organic layers were washed with water, dried over anh. MgSO$_4$, filtered, and concentrated to dryness under reduced pressure. Purification by FC (heptane/AcOEt=1/1) afforded 6-methoxy-2,3-dihydrobenzo[b][1,4]dioxine-5-carbaldehyde as a yellow oil. LC-MS (conditions A): $t_R$=0.52 min.; [M+H]$^+$: 195.19 g/mol.

5-methoxybenzo[d][1,3]dioxole-4-carbaldehyde

A mixture of benzo[d][1,3]dioxol-5-ol (5.000 g; 36.20 mmol), and K$_2$CO$_3$ (5.503 g; 39.80 mmol) in anh. acetone (100 ml) was stirred at rt, under nitrogen, for 1 h. Iodomethane (28.258 g; 199.00 mmol) was then added, and the resulting mixture was heated at reflux, under nitrogen, for 20 h. After cooling to rt, the reaction mixture was filtered over a pad of celite, and the filtrate was concentrated to dryness under reduced pressure. Et$_2$O and water were added, and the organic layer was further washed with brine, dried over anh. MgSO$_4$, filtered, and concentrated to dryness under reduced pressure affording 5-methoxybenzo[d][1,3]dioxole as a yellow oil. LC-MS (conditions A): $t_R$=0.66 min.; no ionisation.

A cooled (−20° C.) mixture of 5-methoxybenzo[d][1,3]dioxole (4.560 g; 30.00 mmol), and N1,N1,N2,N2-tetramethylethane-1,2-diamine (5.36 ml; 36.00 mmol) in anh. THF (300 ml), under nitrogen, was treated dropwise with a solution of 1.6 M n-BuLi in hexanes (18.75 ml; 30.00 mmol). The resulting mixture was further stirred at −20° C. for 1 h. Anh. DMF (12.0 ml; 154.98 mmol) was then added, and the mixture was stirred at rt for 20 min. Aq. sat. NH$_4$Cl and Et$_2$O were successively added, and the aq. layer was further extracted with Et$_2$O. The mixed organic layers were washed with water, dried over anh. MgSO$_4$, filtered, and concentrated to dryness under reduced pressure. Purification by FC (heptane/AcOEt=1/1) afforded 5-methoxybenzo[d][1,3]dioxole-4-carbaldehyde as a yellow oil. LC-MS (conditions A): $t_R$=0.55 min.; [M+H]$^+$: 181.09 g/mol.

2-ethoxy-6-methoxybenzaldehyde

A mixture of commercially available 2-fluoro-6-methoxybenzaldehyde (3.372 g; 21.90 mmol) and sodium hydroxide NaOH (10.208 g; 255.00 mmol) in EtOH (525 ml) was heated to 55° C. for 1 h. After cooling to rt, the reaction mixture was concentrated under reduced pressure. Water and DCM were added, and the aq. layer was further extracted with DCM. The mixed organic layers were dried over anh. MgSO$_4$, filtered, and concentrated to dryness under reduced pressure affording 2-ethoxy-6-methoxybenzaldehyde as a yellow oil. LC-MS (conditions A): $t_R$=0.61 min.; [M+H]$^+$: 181.13 g/mol.

3-(4-chlorothiazol-2-yl)benzaldehyde

A mixture of commercially available 2,4-dichlorothiazole (800 mg; 5.19 mmol), (3-formylphenyl)boronic acid (833 mg; 5.56 mmol), potassium phosphate tribasic K$_3$PO$_4$ (3.308 g; 15.60 mmol), Xantphos (75 mg; 0.13 mmol), and Pd(OAc)$_2$ (29 mg; 0.13 mmol) in anh. THF (26 ml) was heated to 60° C., under nitrogen, for 3 h. After cooling to rt, the mixture was filtered over celite, and the separated solids were washed with DCM. Concentration to dryness under reduced pressure, and subsequent purification by FC (DCM) afforded 3-(4-chlorothiazol-2-yl)benzaldehyde as a colorless solid. LC-MS (conditions A): t$_R$=0.77 min.; [M+H]$^+$: 224.03 g/mol.

2-(4-methylthiazol-2-yl)isonicotinaldehyde

A mixture of commercially available methyl 2-bromoisonicotinate (2.750 g; 12.70 mmol), 4-methyl-2-(tributylstannyl)thiazole (4.942 g; 12.70 mmol), copper iodide CuI (242 mg; 1.27 mmol), and Pd(PPh$_3$)$_4$ (1.471 g; 1.27 mmol) in anh. DMF (55 ml) was heated to 90° C., under nitrogen, for 18 h. After cooling to rt, the reaction mixture was filtered over a pad of celite, and the separated solids were washed with AcOEt. The organic layer was washed with water and brine, dried over anh. MgSO$_4$, filtered, and concentrated to dryness under reduced pressure. Purification by FC (heptane/AcOEt=7/3) afforded methyl 2-(4-methylthiazol-2-yl)isonicotinate as a yellow solid. LC-MS (conditions A): t$_R$=0.74 min.; [M+H]$^+$: 234.94 g/mol.

A solution of methyl 2-(4-methylthiazol-2-yl)isonicotinate (2.400 g; 10.20 mmol) in anh. MeOH (50 ml) was treated with NaBH$_4$ (775 mg; 20.50 mmol), and the resulting mixture was stirred at rt, under nitrogen, for 17 h. After concentration to dryness under reduced pressure, the resulting residue was treated with water, and extracted with DCM. The organic layer was then dried over anh. MgSO$_4$, filtered, and concentrated to dryness under reduced pressure. Purification by FC (DCM/MeOH=20/1) afforded (2-(4-methylthiazol-2-yl)pyridin-4-yl)methanol as a yellow solid. LC-MS (conditions A): t$_R$=0.47 min.; [M+H]$^+$: 207.05 g/mol.

A solution of (2-(4-methylthiazol-2-yl)pyridin-4-yl)methanol (750 mg; 3.64 mmol) in anh. DCE (40 ml) was treated with MnO$_2$ (1.581 g; 18.20 mmol), and the resulting mixture was heated at reflux, under nitrogen, for 1.5 h. After cooling to rt, the resulting reaction mixture was filtered over celite, and the separated solids were washed with DCM. The filtrate was concentrated to dryness under reduced pressure giving 2-(4-methylthiazol-2-yl)isonicotinaldehyde as an off-white solid. LC-MS (conditions A): t$_R$=0.64 min.; [M+H]$^+$: 205.04 g/mol.

2-(5-methylthiazol-2-yl)isonicotinaldehyde

A mixture of commercially available methyl 2-bromoisonicotinate (2.750 g; 12.70 mmol), 5-methyl-2-(tributylstannyl)thiazole (4.942 g; 12.70 mmol), copper iodide CuI (242 mg; 1.27 mmol), and Pd(PPh$_3$)$_4$ (1.471 g; 1.27 mmol) in anh. DMF (55 ml) was heated to 90° C., under nitrogen, for 18 h. After cooling to rt, the reaction mixture was filtered over a pad of celite, and the separated solids were washed with AcOEt. The organic layer was washed with water and brine, dried over anh. MgSO$_4$, filtered, and concentrated to dryness under reduced pressure. Purification by FC (heptane/AcOEt=7/3) afforded methyl 2-(5-methylthiazol-2-yl)isonicotinate as an orange solid. LC-MS (conditions A): t$_R$=0.74 min.; [M+H]$^+$: 235.10 g/mol.

A solution of methyl 2-(5-methylthiazol-2-yl)isonicotinate (2.390 g; 10.20 mmol) in anh. MeOH (50 ml) was treated with NaBH$_4$ (772 mg; 20.40 mmol), and the resulting mixture was stirred at rt, under nitrogen, for 24 h. After concentration to dryness under reduced pressure, the resulting residue was treated with water, and extracted with DCM. The organic layer was then dried over anh. MgSO$_4$, filtered, and concentrated to dryness under reduced pressure. Purification by FC (DCM/MeOH=20/1) afforded (2-(5-methylthiazol-2-yl)pyridin-4-yl)methanol as an off-white solid. LC-MS (conditions A): t$_R$=0.48 min.; [M+H]$^+$: 207.05 g/mol.

A solution of (2-(5-methylthiazol-2-yl)pyridin-4-yl)methanol (1.910 g; 9.26 mmol) in anh. DCE (80 ml) was treated with MnO$_2$ (4.025 g; 46.30 mmol), and the resulting mixture was heated at reflux, under nitrogen, for 1.5 h. After cooling to rt, the resulting reaction mixture was filtered over celite, and the separated solids were washed with DCM. The filtrate was concentrated to dryness under reduced pressure giving 2-(5-methylthiazol-2-yl)isonicotinaldehyde as an off-white solid. LC-MS (conditions A): t$_R$=0.65 min.; [M+H]$^+$: 205.35 g/mol.

A.2 Preparation of Electrophiles R$^1$CH(X)R$^3$ (X Representing Cl or Br)

5-(bromomethyl)-2-(difluoromethoxy)pyridine

A mixture of commercially available methyl 6-hydroxynicotinate (3.000 g; 19.59 mmol) in anh. MeCN (320 ml) was treated portionwise with NaH (60% dispersion in mineral oil; 2.115 g; 52.89 mmol), and stirring at rt, under nitrogen, was continued for 20 min. FSO$_2$CF$_2$CO$_2$H (5.931 g; 33.30 mmol) was then added dropwise, and the resulting heterogeneous mixture was further stirred at rt, under nitrogen, for 30 min. Water (10 ml) was slowly added, and acetonitrile was removed under reduced pressure. Water (150 ml) and AcOEt (150 ml) were added, and the separated aq. layer was further extracted with AcOEt (2×100 ml). The mixed organic layers were washed with brine (100 ml), dried over anh. MgSO$_4$, filtered, and concentrated to dryness under reduced pressure. Purification by FC (DCM) afforded methyl 6-(difluoromethoxy)nicotinate as a beige solid. LC-MS (conditions D): t$_R$=0.93 min.; no ionisation.

A cooled (−78° C.) solution of methyl 6-(difluoromethoxy)nicotinate (4.700 g; 23.13 mmol) in anh. toluene (130 ml) was treated dropwise with a solution of 1 M DIBAH in toluene (69.40 ml; 69.40 mmol), and the resulting mixture was further stirred at −78° C., under nitrogen, for 5 min., and then at 0° C. for 1.5 h. The obtained mixture was then treated successively with water (55 ml), 1 M aq. NaOH (12 ml), and aq. sat. NaHCO$_3$ (100 ml). The separated aq. layer was further extracted with Et$_2$O (2×100 ml). The mixed organic layers were then dried over anh. MgSO$_4$, filtered, and concentrated to dryness under reduced pressure affording (6-(difluoromethoxy)pyridin-3-yl)methanol as a yellow oil (3.758 g; 93%). LC-MS (conditions D): t$_R$=0.71 min.; no ionisation.

A solution of (6-(difluoromethoxy)pyridin-3-yl)methanol (246 mg; 1.41 mmol) in anh. DCM (10 ml) was treated at rt with CBr$_4$ (467 mg; 1.41 mmol), and with triphenylphosphine (369 mg; 1.41 mmol). The resulting mixture was further stirred at rt, under nitrogen, for 15 h. Concentration to dryness under reduced pressure, and subsequent purification by FC (DCM) afforded 5-(bromomethyl)-2-(difluoromethoxy)pyridine as an orange oil which was directly used for the next reaction.

4-(bromomethyl)-2-(difluoromethoxy)pyridine

A mixture of commercially available methyl 2-oxo-1,2-dihydropyridine-4-carboxylate (4.000 g; 26.12 mmol) in anh. MeCN (300 ml) was treated portionwise with NaH (60% dispersion in mineral oil; 2.821 g; 70.52 mmol), and stirring at rt, under nitrogen, was continued for 30 min. FSO$_2$CF$_2$CO$_2$H (7.908 g; 44.40 mmol) was then added dropwise, and the resulting heterogeneous mixture was further stirred at rt, under nitrogen, for 30 min. Water (15 ml) was slowly added, and acetonitrile was removed under reduced pressure. Water (150 ml) and AcOEt (150 ml) were added, and the separated aq. layer was further extracted with AcOEt (2×100 ml). The mixed organic layers were washed with brine (200 ml), dried over anh. MgSO$_4$, filtered, and concentrated to dryness under reduced pressure. Purification by FC (DCM) afforded methyl 2-(difluoromethoxy)isonicotinate as a yellow oil. LC-MS (conditions A): $t_R$=0.72 min.; [M+H]$^+$: 204.30 g/mol.

A cooled (−78° C.) solution of methyl 2-(difluoromethoxy)isonicotinate (2.690 g; 13.24 mmol) in anh. toluene (60 ml) was treated dropwise with a solution of 1 M DIBAH in toluene (40.00 ml; 40.00 mmol), and the resulting mixture was further stirred at −78° C., under nitrogen, for 5 min., and then at 0° C. for 1.5 h. The obtained mixture was treated successively with water (55 ml), 1 M aq. NaOH (12 ml), and aq. sat. NaHCO$_3$ (100 ml). The separated aq. layer was further extracted with Et$_2$O (2×100 ml). The mixed organic layers were then dried over anh. MgSO$_4$, filtered, and concentrated to dryness under reduced pressure affording (2-(difluoromethoxy)pyridin-4-yl)methanol as a yellow oil. LC-MS (conditions A): $t_R$=0.49 min.; [M+H]$^+$: 176.37 g/mol.

A solution of (2-(difluoromethoxy)pyridin-4-yl)methanol (250 mg; 1.42 mmol) in anh. DCM (12 ml) was treated at rt with CBr$_4$ (473 mg; 1.42 mmol), and with PPh$_3$ (374 mg; 1.42 mmol). The resulting mixture was further stirred at rt, under nitrogen, for 1 h. Concentration to dryness under reduced pressure, and subsequent purification by FC (DCM) afforded 4-(bromomethyl)-2-(difluoromethoxy)pyridine as a yellow oil which was directly used for the next reaction. LC-MS (conditions A): $t_R$=0.78 min.

2-(bromomethyl)-6-(difluoromethoxy)pyridine

A mixture of commercially available 6-oxo-1,6-dihydropyridine-2-carboxylic acid (4.000 g; 28.75 mmol) and concentrated H$_2$SO$_4$ (3.5 ml) in anh. MeOH (65 ml) was refluxed, under nitrogen, for 22 h. MeOH was removed under reduced pressure, and the residue was basified by addition of a solution of 10% aq. NaHCO$_3$. The mixture was then extracted with DCM (3×), and the mixed organic layers were dried over anh. MgSO$_4$, filtered, and concentrated to dryness under reduced pressure affording methyl 6-oxo-1,6-dihydropyridine-2-carboxylate as a beige solid. LC-MS (conditions D): $t_R$=0.54 min.; no ionisation.

A mixture of methyl 6-oxo-1,6-dihydropyridine-2-carboxylate (3.074 g; 20.07 mmol) in anh. MeCN (310 ml) was treated portionwise with NaH (60% dispersion in mineral oil; 2.167 g; 54.19 mmol), and stirring at rt, under nitrogen, was continued for 30 min. FSO$_2$CF$_2$CO$_2$H (6.077 g; 34.12 mmol) was then added dropwise, and the resulting heterogeneous mixture was further stirred at rt, under nitrogen, for 30 min. Water (25 ml) was slowly added, and MeCN was removed under reduced pressure. Water (150 ml) and AcOEt (150 ml) were added, and the separated aq. layer was further extracted with AcOEt (2×100 ml). The mixed organic layers were washed with brine (100 ml), dried over anh. MgSO$_4$, filtered, and concentrated to dryness under reduced pressure. Purification by FC (DCM) afforded methyl 6-(difluoromethoxy)picolinate as a yellow solid. LC-MS (conditions D): $t_R$=0.89 min.; no ionisation.

A cooled (−78° C.) solution of methyl 6-(difluoromethoxy)picolinate (4.310 g; 21.21 mmol) in anh. toluene (120 ml) was treated dropwise with a solution of 1 M DIBAH in toluene (63.60 ml; 63.60 mmol), and the resulting mixture was further stirred at −78° C., under nitrogen, for 5 min., and then at 0° C. for 1.5 h. The obtained mixture was treated successively with water (55 ml), 1 M aq. NaOH (12 ml), and aq. sat. NaHCO$_3$ (100 ml). The separated aq. layer was further extracted with Et$_2$O (2×100 ml). The mixed organic layers were then dried over anh. MgSO$_4$, filtered, and concentrated to dryness under reduced pressure affording (6-(difluoromethoxy)pyridin-2-yl)methanol as a yellow oil (3.310 g; 89%). LC-MS (conditions D): $t_R$=0.76 min.; no ionisation.

A solution of (6-(difluoromethoxy)pyridin-2-yl)methanol (250 mg; 1.42 mmol) in anh. DCM (12 ml) was treated at rt with CBr$_4$ (473 mg; 1.42 mmol), and with PPh$_3$ (374 mg; 1.42 mmol). The resulting mixture was further stirred at rt, under nitrogen, for 1 h. Concentration to dryness under reduced pressure, and subsequent purification by FC (DCM) afforded 2-(bromomethyl)-6-(difluoromethoxy)pyridine as a yellow oil which was directly used for the next reaction. LC-MS (conditions D): $t_R$=0.95 min.; [M+H]$^+$: 237.82 g/mol.

2-(bromomethyl)-4-(difluoromethoxy)pyridine

A mixture of commercially available 4-hydroxypicolinic acid (3.000 g; 21.56 mmol) and concentrated H$_2$SO$_4$ (0.6 ml) in anh. MeOH (40 ml) was refluxed, under nitrogen, for 22 h. MeOH was removed under reduced pressure, and the residue was basified by addition of a solution of 10% aq. NaHCO$_3$. The mixture was then extracted with DCM (3×), and the mixed organic layers were dried over anh. MgSO$_4$, filtered, and concentrated to dryness under reduced pressure affording methyl 4-hydroxypicolinate as a beige solid. LC-MS (conditions A): $t_R$=0.18 min.; [M+H]$^+$: 154.11 g/mol.

A mixture of methyl 4-hydroxypicolinate (2.000 g; 13.06 mmol), commercially available sodium chlorofluoroacetate (2.986 g; 19.59 mmol), and K$_2$CO$_3$ (1.805 g; 13.06 mmol) in anh. DMF (40 ml) was heated to 90° C., under nitrogen, for 24 h. AcOEt (100 ml) was added, and the mixture was filtered over a pad of celite.

Water was slowly added, and the separated aq. layer was further extracted with AcOEt (3×). The mixed organic layers were washed with brine, dried over anh. MgSO$_4$, filtered, and concentrated to dryness under reduced pressure. Purification by FC (heptane/AcOEt=1/1) afforded methyl 4-(difluoromethoxy)picolinate as a yellow oil. LC-MS (conditions A): $t_R$=0.52 min.; [M+H]$^+$: 204.34 g/mol.

A cooled (−78° C.) solution of methyl 4-(difluoromethoxy)picolinate (600 mg; 2.95 mmol) in anh. toluene (12 ml) was treated dropwise with a solution of 1 M DIBAH in toluene (8.90 ml; 8.90 mmol), and the resulting mixture was further stirred at −78° C., under nitrogen, for 5 min., and then at 0° C. for 3 h. The obtained mixture was treated successively with water (50 ml), 1 M aq. NaOH (10 ml), and aq. sat. NaHCO$_3$ (100 ml). The separated aq. layer was further extracted with Et$_2$O (2×100 ml). The mixed organic layers were then dried over anh. MgSO$_4$, filtered, and concentrated to dryness under reduced pressure. Purification by FC (heptane/AcOEt=1/1) afforded (4-(difluoromethoxy)pyridin-2-yl)methanol as a yellow solid. LC-MS (conditions A): $t_R$=0.20 min.; [M+H]$^+$: 176.17 g/mol.

A solution of (4-(difluoromethoxy)pyridin-2-yl)methanol (250 mg; 1.42 mmol) in anh. DCM (12 ml) was treated at rt with CBr$_4$ (473 mg; 1.42 mmol), and with PPh$_3$ (374 mg; 1.42 mmol). The resulting mixture was further stirred at rt, under nitrogen, for 1 h. Concentration to dryness under reduced pressure, and subsequent purification by FC (DCM) afforded 2-(bromomethyl)-4-(difluoromethoxy)pyridine as a yellow oil which was directly used for the next reaction. LC-MS (conditions A): $t_R$=0.56 min.; [M+H]$^+$: 237.92 g/mol.

1-(1-bromoethyl)-4-(trifluoromethoxy)benzene

A cooled (0° C.) solution of 4-(trifluoromethoxy)benzaldehyde (3.000 g; 15.78 mmol) in anh. THF (50 ml) was treated dropwise with a solution of methylmagnesium bromide (3 M in Et$_2$O; 6.30 ml; 18.90 mmol), and the resulting mixture was stirred at rt, under nitrogen, for 4 h. The resulting reaction mixture was cooled to 0° C., and aq. sat. NH$_4$Cl (30 ml) was added dropwise. The separated aq. layer was further extracted with AcOEt (3×20 ml), and the mixed organic layers were dried over anh. MgSO$_4$, filtered, and concentrated to dryness under reduced pressure. Purification by FC (DCM/MeOH=40/1) afforded 1-(4-(trifluoromethoxy)phenyl)ethanol as a colorless oil. LC-MS (conditions D): $t_R$=0.88 min.; no ionisation.

A solution of 1-(4-(trifluoromethoxy)phenyl)ethanol (150 mg; 0.72 mmol) in anh. DCM (5 ml) was treated at rt with CBr$_4$ (241 mg; 0.72 mmol), and with PPh$_3$ (190 mg; 0.72 mmol). The resulting mixture was further stirred at rt, under nitrogen, for 16 h. Concentration to dryness under reduced pressure, and subsequent purification by FC (DCM) afforded 1-(1-bromoethyl)-4-(trifluoromethoxy)benzene as a colorless oil which was directly used for the next reaction.

1-(1-bromopropyl)-4-(trifluoromethoxy)benzene

A cooled (0° C.) solution of 4-(trifluoromethoxy)benzaldehyde (5.000 g; 26.29 mmol) in anh. THF (50 ml) was treated dropwise with a solution of ethylmagnesium bromide (3 M in Et$_2$O; 10.50 ml; 31.50 mmol), and the resulting mixture was stirred at rt, under nitrogen, for 17 h. The resulting reaction mixture was cooled to 0° C., and aq. sat. NH$_4$Cl (30 ml) was added dropwise. The separated aq. layer was further extracted with AcOEt (3×20 ml), and the mixed organic layers were dried over anh. MgSO$_4$, filtered, and concentrated to dryness under reduced pressure. Purification by FC (DCM/MeOH=60/1) afforded 1-(4-(trifluoromethoxy)phenyl)propan-1-ol as a colorless oil. LC-MS (conditions A): $t_R$=0.79 min.; no ionisation.

A solution of 1-(4-(trifluoromethoxy)phenyl)propan-1-ol (300 mg; 1.36 mmol) in anh. DCM (10 ml) was treated at rt with CBr$_4$ (451 mg; 1.36 mmol), and with PPh$_3$ (357 mg; 1.36 mmol). The resulting mixture was further stirred at rt, under nitrogen, for 17 h. Concentration to dryness under reduced pressure, and subsequent purification by FC (DCM) afforded 1-(1-bromopropyl)-4-(trifluoromethoxy)benzene as a slightly yellow oil which was directly used for the next reaction. LC-MS (conditions A): $t_R$=1.01 min.; no ionisation.

2-(bromomethyl)benzo[b]thiophene

A solution of commercially available benzo[b]thiophen-2-ylmethanol (123 mg; 0.73 mmol) in anh. DCM (5 ml) was treated at rt with CBr$_4$ (242 mg; 0.73 mmol), and with PPh$_3$ (191 mg; 0.73 mmol). The resulting mixture was further stirred at rt, under nitrogen, for 17 h. Concentration to dryness under reduced pressure, and subsequent purification by FC (DCM) afforded 2-(bromomethyl)benzo[b]thiophene as a yellow/orange oil which was directly used for the next reaction.

2-(bromomethyl)benzofuran

A cooled (0° C.) solution of commercially available benzofuran-2-carbaldehyde (1.000 g; 6.84 mmol) in anh. methanol (37 ml) was treated portionwise with NaBH$_4$ (1.294 g; 34.21 mmol), and the resulting mixture was stirred at 0° C., under nitrogen, for 1 h 45. After concentration to dryness under reduced pressure, the resulting residue was treated with water (30 ml), and extracted with DCM (2×100 ml). The mixed organic layers were washed with brine, dried over anh. MgSO$_4$, filtered, concentrated to dryness under reduced pressure, and the residue was further dried under HV affording benzofuran-2-ylmethanol as a slightly yellow oil. LC-MS (conditions D): $t_R$=0.78 min.; no ionisation.

A solution of benzofuran-2-ylmethanol (120 mg; 0.81 mmol) in anh. DCM (5 ml) was treated at rt with CBr$_4$ (268 mg; 0.81 mmol), and with PPh$_3$ (212 mg; 0.81 mmol). The resulting mixture was further stirred at rt, under nitrogen, for 17 h. Concentration to dryness under reduced pressure, and subsequent purification by FC (DCM) afforded 2-(bromomethyl)benzofuran as a yellow oil (128 mg; 75%) which was directly used for the next reaction.

5-(bromomethyl)-2,2-difluorobenzo[d][1,3]dioxole

A cooled (0° C.) solution of commercially available 2,2-difluorobenzo[d][1,3]dioxole-5-carbaldehyde (1.500 g; 8.06 mmol) in anh. MeOH (60 ml) was treated portionwise with NaBH$_4$ (1.524 g; 40.29 mmol), and the resulting mixture was stirred at 0° C., under nitrogen, for 1 h. After concentration to dryness under reduced pressure, the resulting residue was treated with water (30 ml), and extracted with DCM (2×100 ml). The mixed organic layers were washed with brine, dried over anh. MgSO$_4$, filtered, concentrated to dryness under reduced pressure, and the residue was further dried under HV affording (2,2-difluorobenzo[d][1,3]dioxol-5-yl)methanol as a colorless oil. LC-MS (conditions D): $t_R$=0.85 min.; no ionisation.

A solution of (2,2-difluorobenzo[d][1,3]dioxol-5-yl)methanol (120 mg; 0.63 mmol) in anh. DCM (5 ml) was treated at rt with CBr$_4$ (211 mg; 0.63 mmol), and with PPh$_3$ (167 mg; 0.63 mmol). The resulting mixture was further stirred at rt, under nitrogen, for 17 h. Concentration to dryness under reduced pressure, and subsequent purification by FC (DCM) afforded 5-(bromomethyl)-2,2-difluorobenzo[d][1,3]dioxole as a pale yellow oil which was directly used for the next reaction.

5-(bromomethyl)-2-phenoxypyridine

A solution of commercially available (6-phenoxypyridin-3-yl)methanol (150 mg; 0.74 mmol) in anh. DCM (6 ml) was treated at rt with CBr$_4$ (247 mg; 0.74 mmol), and with PPh$_3$ (195 mg; 0.74 mmol). The resulting mixture was further stirred at rt, under nitrogen, for 15 h. Concentration to dryness under reduced pressure, and subsequent purification by FC (DCM) afforded 5-(bromomethyl)-2-phenoxypyridine as a pale yellow oil which was directly used for the next reaction. LC-MS (conditions A): $t_R$=0.84 min.; [M+H]$^+$: 263.98 g/mol.

1-(bromomethyl)-4-(2-fluoroethoxy)benzene

A mixture of commercially available ethyl 4-hydroxybenzoate (2.500 g; 15.04 mmol), K$_2$CO$_3$ (4.158 g; 30.08 mmol), and 1-fluoro-2-iodoethane (2.617 g; 15.04 mmol) in anh. DMF (30 ml) was heated to 70° C., under nitrogen, for 2.5 h. After cooling to rt, Et$_2$O (100 ml) and water (50 ml) were added. The separated organic layer was further washed with water (2×50 ml), dried over anh. MgSO$_4$, filtered, concentrated to dryness under reduced pressure, and the residue was further dried under HV affording ethyl 4-(2-fluoroethoxy) benzoate as a colorless solid. LC-MS (conditions D): $t_R$=0.96 min.; no ionisation.

A cooled (−78° C.) solution of ethyl 4-(2-fluoroethoxy) benzoate (3.062 g; 14.42 mmol) in anh. toluene (100 ml) was treated dropwise with a solution of 1 M DIBAH in toluene (43.00 ml; 43.00 mmol), and the resulting mixture was further stirred at −78° C., under nitrogen, for 5 min., at 0° C. for 1 h, and then at rt for 17 h. The obtained mixture was cooled to 0° C., treated successively with water (5 ml), 1 M aq. NaOH (10 ml), and aq. sat. NaHCO$_3$ (50 ml).

The separated aq. layer was further extracted with Et$_2$O (3×50 ml). The mixed organic layers were then dried over anh. MgSO$_4$, filtered, and concentrated to dryness under reduced pressure affording (4-(2-fluoroethoxy)phenyl) methanol as a pale yellow oil. LC-MS (conditions F): $t_R$=0.47 min.; no ionisation.

A solution of (4-(2-fluoroethoxy)phenyl)methanol (117 mg; 0.68 mmol) in anh. DCM (5 ml) was treated at rt with CBr$_4$ (228 mg; 0.68 mmol), and with PPh$_3$ (180 mg; 0.68 mmol). The resulting mixture was further stirred at rt, under nitrogen, for 1 h. Concentration to dryness under reduced pressure, and subsequent purification by FC (DCM) afforded 1-(bromomethyl)-4-(2-fluoroethoxy)benzene as a slightly yellow oil which was directly used for the next reaction.

2-(chloromethyl)-6-methoxynaphthalene

A solution of commercially available 6-methoxy-2-naphthaldehyde (200 mg; 1.07 mmol) in MeOH (5 ml) was treated portionwise at rt with NaBH$_4$ (50 mg; 1.31 mmol), and the resulting mixture was further stirred at rt, under nitrogen, for 1 h. 2 M aq. HCl was added, and the organic solvent was removed under reduced pressure. AcOEt and water were added, and the separated organic layer was dried over anh. MgSO$_4$, filtered, and concentrated to dryness under reduced pressure affording (6-methoxynaphthalen-2-yl)methanol as a colorless solid. LC-MS (conditions E): $t_R$=0.55 min.; no ionisation.

A cooled (0° C.) mixture of (6-methoxynaphthalen-2-yl) methanol (90 mg; 0.48 mmol) in anh. DCM (2 ml) was treated dropwise with SOCl$_2$ (89 mg; 0.75 mmol), and the resulting mixture was stirred at rt, under nitrogen, for 17 h. The volatiles were removed under reduced pressure, and the solid residue was triturated with Et$_2$O. Filtration afforded 2-(chloromethyl)-6-methoxynaphthalene which was directly used for the next reaction. LC-MS (conditions E): $t_R$=0.75 min.; no ionisation.

A.3 Preparation of Building Blocks

A.3.1 Preparation of Imines methyl 5-((tert-butylsulfinyl)imino)pentanoate

A colorless solution of commercially available methyl hex-5-enoate (5.000 g; 39.01 mmol) in dioxane (290 ml) and water (95 ml) was treated successively with 2,6-lutidine (8.360 g; 78.02 mmol), a solution of osmium tetroxide (2.5 wt. % in 2-methylpropan-2-ol; 0.50 ml), and NaIO$_4$ (33.375 g; 156.04 mmol). The resulting beige heterogeneous reaction mixture was further stirred at rt, under nitrogen, for 16 h. The resulting milky heterogeneous mixture was treated with water (100 ml) and DCM (500 ml). The layers were separated, and the aq. layer was further extracted with DCM (200 ml/150 ml). The mixed slightly yellow organic layers were then washed with brine (200 ml), dried over anh. MgSO$_4$, filtered, and concentrated to dryness under reduced pressure to give crude methyl 5-oxopentanoate as a green oil which was directly used for the next step without additional purification.

A yellow solution of methyl 5-oxopentanoate (39.01 mmol) in DCM (80 ml) was treated with commercially available 2-methylpropane-2-sulfinamide (4.728 g; 39.01 mmol) and with anh. CuSO$_4$ (12.452 g; 78.02 mmol).

The resulting grey/slightly green heterogeneous mixture was further stirred at rt, under nitrogen, for 90 h. The resulting mixture was then filtered over a short pad of celite, and the separated solids were further washed with DCM. The obtained yellow filtrate was concentrated to dryness under reduced pressure. Purification by FC (DCM/MeOH=25/1) afforded methyl 5-((tert-butylsulfinyl)imino)-pentanoate as a yellow oil. LC-MS (conditions B): $t_R$=0.71 min.; [M+H]$^+$: 234.00 g/mol.

ethyl 6-((tert-butylsulfinyl)imino)hexanoate

A colorless solution of commercially available ethyl hept-6-enoate (7.000 g; 44.80 mmol) in dioxane (330 ml) and water (110 ml) was treated successively with 2,6-lutidine (9.603 g; 89.61 mmol), a solution of osmium tetroxide (2.5 wt. % in 2-methylpropan-2-ol; 0.56 ml), and NaIO$_4$ (38.335 g; 179.23 mmol). The resulting beige heterogeneous reaction mixture was further stirred at rt, under nitrogen, for 13.5 h. The resulting milky mixture was treated with water (100 ml) and DCM (500 ml). The layers were separated, and the aq. layer was further extracted with DCM (200 ml/150 ml). The mixed slightly yellow organic layers were then washed with brine (200 ml), dried over anh. MgSO$_4$, filtered, and concentrated to dryness under reduced pressure to give crude ethyl 6-oxohexanoate as a dark-yellow/brown oil which was directly used for the next step without additional purification.

A yellow solution of ethyl 6-oxohexanoate (44.80 mmol) in DCM (92 ml) was treated with 2-methylpropane-2-sulfinamide (5.431 g; 44.80 mmol) and with anh. CuSO$_4$ (14.302 g; 89.61 mmol). The resulting beige heterogeneous mixture was further stirred at rt, under nitrogen, for 24 h. The resulting heterogeneous mixture was then filtered over a short pad of celite, and the separated solids were further washed with DCM. The obtained orange filtrate was concentrated to dryness under reduced pressure. Purification by FC (DCM/ MeOH=25/1) afforded ethyl 6-((tert-butylsulfinyl)imino) hexanoate as a yellow/orange oil. LC-MS (conditions B): $t_R$=0.81 min.; [M+H]$^+$: 262.07 g/mol.

methyl 6-((tert-butylsulfinyl)imino)hexanoate

Methyl 6-((tert-butylsulfinyl)imino)hexanoate was prepared from methyl hept-6-enoate according to the procedure described for ethyl 6-((tert-butylsulfinyl)imino)hexanoate. Purification by FC (DCM/MeOH=25/1) afforded methyl 6-((tert-butylsulfinyl)imino)hexanoate as a yellow oil. LC-MS (conditions D): $t_R$=0.87 min.; [M+H]$^+$: 248.17 g/mol.

methyl 4-((tert-butylsulfinyl)imino)butanoate

A solution of commercially available methyl 4-oxobutanoate (4.454 g; 38.36 mmol) in DCM (90 ml) was treated with 2-methylpropane-2-sulfinamide (4.650 g; 38.36 mmol) and with anh. CuSO$_4$ (12.246 g; 76.73 mmol). The resulting heterogeneous mixture was further stirred at rt, under nitrogen, for 12 h. The resulting grey mixture was then filtered over a short pad of celite, and the separated solids were further washed with DCM. The obtained orange filtrate was concentrated to dryness under reduced pressure. Purification by FC (DCM/MeOH=25/1) afforded methyl 4-((tert-butylsulfinyl) imino)-butanoate as a yellow oil. LC-MS (conditions A): $t_R$=0.56 min.; [M+H]$^+$: 220.40 g/mol.

ethyl 4-((tert-butylsulfinyl)imino)-2-methylbutanoate

A colorless solution of ethyl 2-methylpent-4-enoate (5.000 g; 35.16 mmol) in dioxane (260 ml) and water (85 ml) was treated successively with 2,6-lutidine (7.536 g; 70.32 mmol), a solution of osmium tetroxide (2.5 wt. % in 2-methylpropan-2-ol; 0.45 ml), and NaIO$_4$ (30.083 g; 140.65 mmol). The resulting beige heterogeneous reaction mixture was further stirred at rt, under nitrogen, for 20.5 h. The resulting milky mixture was treated with water (100 ml) and DCM (500 ml). The layers were separated, and the aq. layer was further extracted with DCM (200 ml/150 ml). The mixed slightly yellow organic layers were then washed with brine (200 ml), dried over anh. MgSO$_4$, filtered, and concentrated to dryness under reduced pressure to give crude ethyl 2-methyl-4-oxobutanoate as a dark-yellow/slightly brown oil which was directly used for the next step without additional purification.

A yellow solution of ethyl 2-methyl-4-oxobutanoate (35.16 mmol) in DCM (72 ml) was treated with 2-methylpropane-2-sulfinamide (4.261 g; 35.16 mmol) and with anh. CuSO$_4$ (11.223 g; 70.32 mmol). The resulting beige heterogeneous mixture was further stirred at rt, under nitrogen, for 24 h. The resulting heterogeneous mixture was then filtered over a short pad of celite, and the separated solids were further washed with DCM. The obtained yellow filtrate was concentrated to dryness under reduced pressure. Purification by FC (DCM/MeOH=25/1) afforded ethyl 4-((tert-butylsulfinyl) imino)-2-methylbutanoate as a yellow oil. LC-MS (conditions B): $t_R$=0.78 min.; [M+H]$^+$: 248.38 g/mol.

A.3.2 Preparation of Acyclic Amino-Ester Derivatives, Acyclic Keto-Ester Derivatives, and Preparation of Lactam Derivatives methyl 5-amino-5-(2,6-dimethoxyphenyl)pentanoate A cooled (−78° C.) yellow solution of commercially available 2-iodo-1,3-dimethoxybenzene (9.930 g; 37.60 mmol) in anh. THF (170 ml), under nitrogen, was treated dropwise with a solution of 1.6 M n-BuLi in hexanes (23.5 ml; 37.60 mmol). The resulting slightly yellow solution was further stirred at −78° C. for 15 min. A yellow solution of methyl 5-((tert-butylsulfinyl)imino)pentanoate (5.850 g; 25.07 mmol) in anh. THF (12 ml) was then added dropwise to the cooled reaction mixture, and stirring at −78° C. was continued for 45 min. The resulting yellow reaction mixture was treated successively with aq. sat. NH$_4$Cl (80 ml), Et$_2$O (250 ml) and water (75 ml). The separated yellow organic layer was then washed with brine (75 ml), dried over anh. MgSO$_4$, filtered, and concentrated to dryness under reduced pressure. Purification by FC (DCM/MeOH=25/1) afforded methyl 5-(2,6-dimethoxyphenyl)-5-(1,1-dimethylethylsulfinamido)pentanoate as a yellow oil. LC-MS (conditions B): $t_R$=0.85 min.; [M+H]$^+$: 372.34 g/mol.

A cooled (0° C.) slightly yellow solution of methyl 5-(2,6-dimethoxyphenyl)-5-(1,1-dimethylethylsulfinamido)pentanoate (5.560 g; 14.96 mmol) in MeOH (115 ml) was treated dropwise with a solution of 4 M HCl in 1,4-dioxane (7.5 ml; 30.00 mmol). The resulting yellow mixture was further stirred at 0° C., under nitrogen, for 10 min., and then at rt for 1 h. The obtained yellow solution was then concentrated to dryness under reduced pressure and the yellow oily residue was further dried under HV to give the chlorhydrate salt of methyl 5-amino-5-(2,6-dimethoxyphenyl)pentanoate as a yellow oil. LC-MS (conditions B): $t_R$=0.73 min.; [M+H]$^+$: 268.01 g/mol.

6-(2,6-dimethoxyphenyl)piperidin-2-one

A yellow solution of the chlorhydrate salt of methyl 5-amino-5-(2,6-dimethoxyphenyl)pentanoate (14.96 mmol) in THF (92 ml) was treated with a solution of aq. sat. NaHCO$_3$ (23.5 ml). The resulting heterogeneous mixture was further stirred at rt, under nitrogen, for 327 h. This reaction mixture was then treated with a solution of aq. sat. NaHCO$_3$ (25 ml), water (50 ml), and AcOEt (200 ml). The layers were separated and the slightly yellow aq. layer was further extracted with AcOEt (50 ml). The mixed yellow organic layers were then dried over anh. MgSO$_4$, filtered, and concentrated to dryness under reduced pressure. Purification by FC (DCM/MeOH=20/1) afforded 6-(2,6-dimethoxyphenyl)-piperidin-2-one as a beige solid. LC-MS (conditions B): $t_R$=0.83 min.; [M+H]$^+$: 236.49 g/mol.

methyl 6-amino-6-(2,6-dimethoxyphenyl)hexanoate

A cooled (−78° C.) yellow solution of 2-iodo-1,3-dimethoxybenzene (6.337 g; 24.00 mmol) in anh. THF (130 ml), under nitrogen, was treated dropwise with a solution of 1.6 M n-BuLi in hexanes (15.0 ml; 24.00 mmol). The resulting yellow solution was further stirred at −78° C. for 15 min. A yellow solution of ethyl 6-((tert-butylsulfinyl)imino)hexanoate (5.018 g; 19.20 mmol) in anh. THF (12 ml) was then added dropwise to the cooled reaction mixture, and stirring at −78° C. was continued for 50 min. The resulting orange reaction mixture was treated successively with aq. sat. NH$_4$Cl (65 ml), Et$_2$O (200 ml) and water (60 ml). The separated yellow organic layer was then washed with brine (60 ml), dried over anh. MgSO$_4$, filtered, and concentrated to dryness under reduced pressure. Purification by FC (DCM/MeOH=25/1) afforded ethyl 6-(2,6-dimethoxyphenyl)-6-(1,1-dimethylethylsulfinamido)hexanoate as a yellow oil. LC-MS (conditions B): $t_R$=0.91 min.; [M+H]$^+$: 400.05 g/mol.

A cooled (0° C.) yellow solution of ethyl 6-(2,6-dimethoxyphenyl)-6-(1,1-dimethylethylsulfinamido)hexanoate (5.360 g; 13.41 mmol) in MeOH (100 ml) was treated dropwise with a solution of 4 M HCl in 1,4-dioxane (6.7 ml; 26.80 mmol). The resulting yellow mixture was further stirred at 0° C., under nitrogen, for 10 min., and then at rt for 1 h50. The obtained yellow solution was then concentrated to dryness under reduced pressure and the yellow oily residue was further dried under HV to give the chlorhydrate salt of methyl 6-amino-6-(2,6-dimethoxyphenyl)hexanoate as a yellow oil. LC-MS (conditions B): $t_R$=0.62 min.; [M+H]$^+$: 282.10 g/mol.

7-(2,6-dimethoxyphenyl)azepan-2-one 7-(2,6-dimethoxyphenyl)azepan-2-one was obtained from methyl 6-amino-6-(2,6-dimethoxyphenyl)hexanoate after saponification and lactamization according to the general procedure 1 (GP1) described below in the section B.1.1. Subsequent purification by FC (DCM/MeOH=50/1) afforded 7-(2,6-dimethoxyphenyl)azepan-2-one as a beige solid. LC-MS (conditions A): $t_R$=0.66 min.; [M+H]$^+$: 250.27 g/mol.

methyl 4-amino-4-(2,6-dimethoxyphenyl)butanoate

A cooled (−78° C.) yellow solution of 2-iodo-1,3-dimethoxybenzene (13.798 g; 52.25 mmol) in anh. THF (200 ml), under nitrogen, was treated dropwise with a solution of 1.6 M n-BuLi in hexanes (32.66 ml; 52.25 mmol). The resulting slightly yellow solution was further stirred at −78° C. for 15 min. A yellow solution of methyl 4-((tert-butylsulfinyl)imino)butanoate (7.640 g; 34.83 mmol) in anh. THF (50 ml) was then added dropwise to the cooled reaction mixture, and stirring at −78° C. was continued for 45 min. The resulting yellow reaction mixture was treated successively with aq. sat. $NH_4Cl$ (20 ml), $Et_2O$ (250 ml) and water (75 ml). The separated yellow organic layer was then washed with brine (75 ml), dried over anh. $MgSO_4$, filtered, and concentrated to dryness under reduced pressure. Purification by FC (DCM/MeOH=30/1) afforded methyl 4-(2,6-dimethoxyphenyl)-4-(1,1-dimethylethylsulfinamido)butanoate as a yellow oil. LC-MS (conditions A): $t_R$=0.73 min.; [M+H]$^+$: 358.34 g/mol.

A cooled (0° C.) solution of methyl 4-(2,6-dimethoxyphenyl)-4-(1,1-dimethylethylsulfinamido)butanoate (7.750 g; 21.68 mmol) in MeOH (70 ml) was treated dropwise with a solution of 4 M HCl in 1,4-dioxane (10.9 ml; 43.60 mmol). The resulting yellow mixture was further stirred at 0° C., under nitrogen, for 10 min., and then at rt for 1 h. The reaction mixture was then concentrated to dryness under reduced pressure and the yellow oily residue was further dried under HV to give the chlorhydrate salt of methyl 4-amino-4-(2,6-dimethoxyphenyl)butanoate as a dark-yellow/brown oil. LC-MS (conditions A): $t_R$=0.45 min.; [M+H]$^+$: 254.40 g/mol.

5-(2,6-dimethoxyphenyl)pyrrolidin-2-one 5-(2,6-Dimethoxyphenyl)pyrrolidin-2-one was obtained from methyl 4-amino-4-(2,6-dimethoxyphenyl)butanoate after saponification and lactamization according to the general procedure 1 (GP1) described below in the section B.1.1. Subsequent purification by FC (DCM/MeOH=20/1) afforded 5-(2,6-dimethoxyphenyl)pyrrolidin-2-one. LC-MS (conditions E): $t_R$=0.50 min.; [M+H]$^+$: 222.24 g/mol.

ethyl 4-amino-4-(2,6-dimethoxyphenyl)-2-methylbutanoate

A cooled (−78° C.) yellow solution of 2-iodo-1,3-dimethoxybenzene (8.553 g; 32.39 mmol) in anh. THF (175 ml), under nitrogen, was treated dropwise with a solution of 1.6 M n-BuLi in hexanes (20.25 ml; 32.40 mmol). The resulting slightly yellow solution was further stirred at −78° C. for 15 min. A yellow solution of ethyl 4-((tert-butylsulfinyl)imino)-2-methylbutanoate (6.410 g; 25.91 mmol) in anh. THF (15 ml) was then added dropwise to the cooled reaction mixture, and stirring at −78° C. was continued for 30 min. The resulting yellow reaction mixture was treated successively with aq. sat. $NH_4Cl$ (80 ml), $Et_2O$ (250 ml) and water (75 ml). The separated yellow organic layer was then washed with brine (75 ml), dried over anh. $MgSO_4$, filtered, and concentrated to dryness under reduced pressure. Purification by FC (DCM/MeOH=25/1) afforded ethyl 4-(2,6-dimethoxyphenyl)-4-(1,1-dimethylethylsulfinamido)-2-methylbutanoate as an orange oil. LC-MS (conditions B): $t_R$=0.88 min. and [M+H]$^+$: 386.15 g/mol; $t_R$=0.89 min. and [M+H]$^+$: 386.14 g/mol (mixture of diastereoisomers).

A cooled (0° C.) orange solution of ethyl 4-(2,6-dimethoxyphenyl)-4-(1,1-dimethylethylsulfinamido)-2-methylbutanoate (9.210 g; 23.89 mmol) in MeOH (100 ml) was treated dropwise with a solution of 4 M HCl in 1,4-dioxane (11.95 ml; 47.80 mmol). The resulting orange mixture was further stirred at 0° C., under nitrogen, for 10 min., and then at rt for 3 h. The reaction mixture was then concentrated to dryness under reduced pressure and the oily residue was further dried under HV to give the chlorhydrate salt of ethyl 4-amino-4-(2,6-dimethoxyphenyl)-2-methylbutanoate as an orange oil. LC-MS (conditions B): $t_R$=0.62 min. and [M+H]$^+$: 282.42 g/mol; $t_R$=0.64 min. and [M+H]$^+$: 282.42 g/mol (mixture of diastereoisomers). Due to transesterification, a reduced amount of methyl 4-amino-4-(2,6-dimethoxyphenyl)-2-methylbutanoate was also detected: $t_R$=0.57 min. and [M+H]$^+$: 268.40 g/mol.

5-(2,6-dimethoxyphenyl)-3-methylpyrrolidin-2-one 5-(2,6-Dimethoxyphenyl)-3-methylpyrrolidin-2-one was prepared from ethyl 4-amino-4-(2,6-dimethoxyphenyl)-2-methylbutanoate according to the procedure described for 6-(2,6-dimethoxyphenyl)piperidin-2-one. Subsequent purification by FC (DCM/MeOH=20/1) afforded 5-(2,6-dimethoxyphenyl)-3-methylpyrrolidin-2-one as a light orange solid. LC-MS (conditions D): $t_R$=0.84 min.; [M+H]$^+$: 236.43 g/mol.

methyl 5-amino-5-(2,4-dimethoxypyridin-3-yl)pentanoate

A cooled (−78° C.) yellow solution of commercially available 3-bromo-2,4-dimethoxypyridine (1.490 g; 6.83 mmol) in anh. THF (42 ml), under nitrogen, was treated dropwise with a solution of 1.6 M n-BuLi in hexanes (4.3 ml; 6.88 mmol). The resulting orange solution was further stirred at −78° C. for 10 min. A yellow solution of methyl 5-((tert-butylsulfinyl)imino)pentanoate (1.450 g; 6.21 mmol) in anh. THF (5 ml) was then added to the cooled reaction mixture, and stirring at −78° C. was continued for 65 min. The resulting orange reaction mixture was treated successively with aq. sat. $NH_4Cl$ (22 ml), $Et_2O$ (75 ml) and water (20 ml). The separated orange organic layer was then washed with brine (30 ml), dried over anh. $MgSO_4$, filtered, and concentrated to dryness under reduced pressure. Purification by FC (DCM/MeOH=30/1) afforded methyl 5-(2,4-dimethoxypyridin-3-yl)-5-(1,1-dimethylethylsulfinamido)pentanoate as a yellow oil. LC-MS (conditions B): $t_R$=0.75 min.; [M+H]$^+$: 372.82 g/mol.

A cooled (0° C.) yellow solution of methyl 5-(2,4-dimethoxypyridin-3-yl)-5-(1,1-dimethylethylsulfinamido)pentanoate (653 mg; 1.75 mmol) in MeOH (14 ml) was treated dropwise with a solution of 4 M HCl in 1,4-dioxane (0.90 ml; 3.60 mmol). The resulting yellow mixture was further stirred at 0° C., under nitrogen, for 10 min., and at rt for 1 h. The reaction mixture was then concentrated to dryness under reduced pressure and the yellow oily residue was further dried under HV to give the chlorhydrate salt of methyl 5-amino-5-(2,4-dimethoxypyridin-3-yl)pentanoate as a beige solid. LC-MS (conditions B): $t_R$=0.51 min.; [M+H]$^+$: 269.03 g/mol.

methyl 5-amino-5-(3,5-dimethoxypyridin-4-yl)pentanoate

A cooled (−78° C.) slightly yellow solution of diisopropylamine (1.946 g; 19.23 mmol) in anh. THF (85 ml), under nitrogen, was treated dropwise with a solution of 1.6 M n-BuLi in hexanes (12.0 ml; 19.23 mmol). The resulting slightly yellow solution was further stirred at −78° C. for 20 min. A slightly yellow solution of 3,5-dimethoxypyridine (2.433 g; 17.48 mmol) in anh. THF (7 ml) was then added dropwise. The resulting yellow heterogeneous mixture was further stirred at −78° C. for 30 min. A yellow solution of methyl 5-((tert-butylsulfinyl)imino)pentanoate (4.080 g; 17.48 mmol) in anh. THF (8 ml) was then added to the cooled reaction mixture, and stirring at −78° C. was continued for 90 min. The resulting orange reaction mixture was treated successively with aq. sat. NH$_4$Cl (29 ml), Et$_2$O (100 ml) and water (25 ml). The separated yellow organic layer was then washed with brine (30 ml), dried over anh. MgSO$_4$, filtered, and concentrated to dryness under reduced pressure. Purification by FC (DCM/MeOH=20/1) afforded methyl 5-(3,5-dimethoxypyridin-4-yl)-5-(1,1-dimethylethylsulfinamido) pentanoate as a yellow oil. LC-MS (conditions B): $t_R$=0.59 min.; [M+H]$^+$: 373.00 g/mol.

A cooled (0° C.) yellow solution of methyl 5-(3,5-dimethoxypyridin-4-yl)-5-(1,1-dimethylethylsulfinamido) pentanoate (780 mg; 2.09 mmol) in MeOH (16 ml) was treated dropwise with a solution of 4 M HCl in 1,4-dioxane (1.05 ml; 4.20 mmol). The resulting yellow mixture was further stirred at 0° C., under nitrogen, for 10 min., and then at rt for 1 h. The reaction mixture was then concentrated to dryness under reduced pressure and the yellow oily residue was further dried under HV to give the chlorhydrate salt of methyl 5-amino-5-(3,5-dimethoxypyridin-4-yl)pentanoate as a beige solid. LC-MS (conditions B): $t_R$=0.43 min.; [M+H]$^+$: 269.02 g/mol.

methyl 6-amino-6-(3,5-dimethoxypyridin-4-yl)hexanoate

A cooled (−78° C.) solution of commercially available 4-bromo-3,5-dimethoxypyridine (4.998 g; 22.92 mmol) in anh. THF (90 ml), under nitrogen, was treated dropwise with a solution of 1.6 M n-BuLi in hexanes (14.30 ml; 22.88 mmol). The resulting solution was further stirred at −78° C. for 10 min. A solution of methyl 6-((tert-butylsulfinyl)imino) hexanoate (3.780 g; 15.28 mmol) in anh. THF (10 ml) was then added to the cooled reaction mixture, and stirring at −78° C. was continued for 60 min. The resulting reaction mixture was treated successively with aq. sat. NH$_4$Cl (80 ml), Et$_2$O (250 ml) and water (75 ml). The separated organic layer was then washed with brine (75 ml), dried over anh. MgSO$_4$, filtered, and concentrated to dryness under reduced pressure. Purification by FC (DCM/MeOH=25/1) afforded methyl 6-(3,5-dimethoxypyridin-4-yl)-6-(1,1-dimethylethylsulfinamido)hexanoate as a yellow oil. LC-MS (conditions A): $t_R$=0.49 min.; [M+H]$^+$: 387.11 g/mol.

A cooled (0° C.) yellow solution of methyl 6-(3,5-dimethoxypyridin-4-yl)-6-(1,1-dimethylethylsulfinamido) hexanoate (506 mg; 1.30 mmol) in MeOH (9 ml) was treated dropwise with a solution of 4 M HCl in 1,4-dioxane (0.65 ml; 2.60 mmol). The resulting yellow mixture was further stirred at 0° C., under nitrogen, for 10 min., and then at rt for 1 h. The reaction mixture was then concentrated to dryness under reduced pressure and the yellow oily residue was further dried under HV to give the chlorhydrate salt of methyl 6-amino-6-(3,5-dimethoxypyridin-4-yl)hexanoate as a brown solid. LC-MS (conditions A): $t_R$=0.36 min.; [M+H]$^+$: 284.25 g/mol.

methyl 5-amino-5-(4,6-dimethoxypyrimidin-5-yl)pentanoate

A solution of commercially available 5-bromo-4,6-dichloropyrimidine (500 mg; 2.19 mmol) and sodium hydroxide NaOH (219 mg; 5.48 mmol) in MeOH (20 ml) was heated at reflux, under nitrogen, for 4 h. After cooling to rt, the resulting reaction mixture was concentrated to dryness under reduced pressure affording 5-bromo-4,6-dimethoxypyrimidine as a colorless solid. LC-MS (conditions A): $t_R$=0.69 min.; [M+H]$^+$: 220.79 g/mol.

A cooled (−78° C.) solution of 5-bromo-4,6-dimethoxypyrimidine (473 mg; 2.15 mmol) in anh. THF (5 ml), under nitrogen, was treated dropwise with a solution of 1.6 M n-BuLi in hexanes (1.50 ml; 2.40 mmol). The resulting solution was further stirred at −78° C. for 10 min. A solution of methyl 5-((tert-butylsulfinyl)imino)pentanoate (503 mg; 2.15 mmol) in anh. THF (2 ml) was then added to the cooled reaction mixture, and stirring at −78° C. was continued for 60 min. The resulting reaction mixture was treated successively with aq. sat. NH$_4$Cl (15 ml), Et$_2$O (30 ml) and water (15 ml). The separated organic layer was then washed with brine (15 ml), dried over anh. MgSO$_4$, filtered, and concentrated to dryness under reduced pressure. Purification by FC (DCM/MeOH=25/1) afforded methyl 5-(4,6-dimethoxypyrimidin-5-yl)-5-(1,1-dimethylethylsulfinamido)pentanoate as a yellow solid. LC-MS (conditions A): $t_R$=0.66 min.; [M+H]$^+$: 374.06 g/mol.

A cooled (0° C.) slightly yellow solution of methyl 5-(4,6-dimethoxypyrimidin-5-yl)-5-(1,1-dimethylethylsulfinamido)pentanoate (178 mg; 0.47 mmol) in MeOH (4 ml) was treated dropwise with a solution of 4 M HCl in 1,4-dioxane (0.24 ml; 0.96 mmol). The resulting yellow mixture was further stirred at 0° C., under nitrogen, for 10 min., and then at rt for 5 h. The reaction mixture was then concentrated to dryness under reduced pressure and the yellow oily residue was further dried under HV to give methyl 5-amino-5-(4,6-dimethoxypyrimidin-5-yl)pentanoate HCl salt as a yellow solid. LC-MS (conditions A): $t_R$=0.41 min.; [M+H]$^+$: 270.10 g/mol.

methyl 5-amino-5-(2,3-dihydrobenzo[b][1,4]dioxin-5-yl)pentanoate

A cooled (−78° C.) solution of commercially available 5-bromo-2,3-dihydrobenzo[b][1,4]dioxine (500 mg; 2.32 mmol) in anh. THF (5 ml), under nitrogen, was treated dropwise with a solution of 1.6 M n-BuLi in hexanes. The resulting solution was further stirred at −78° C. for 10 min. A solution of methyl 5-((tert-butylsulfinyl)imino)pentanoate (542 mg; 2.32 mmol) in anh. THF (2 ml) was added to the cooled reaction mixture, and stirring at −78° C. was continued for 10 min., and then at −20° C. for 2 h. The resulting reaction mixture was treated successively with aq. sat. NH$_4$Cl (15 ml), Et$_2$O (30 ml) and water (15 ml). The separated organic layer was then washed with brine (15 ml), dried over anh. MgSO$_4$, filtered, and concentrated to dryness under reduced pressure. Purification by FC (DCM/MeOH=20/1) afforded methyl 5-(2,3-dihydrobenzo[b][1,4]dioxin-5-yl)-5-(1,1-dimethylethylsulfinamido)-pentanoate as a yellow oil. LC-MS (conditions A): $t_R$=0.73 min.; [M+H]$^+$: 369.73 g/mol.

A cooled (0° C.) slightly yellow solution of methyl 5-(2,3-dihydrobenzo[b][1,4]dioxin-5-yl)-5-(1,1-dimethylethylsulfinamido)pentanoate (160 mg; 0.43 mmol) in MeOH (2 ml) was treated dropwise with a solution of 4 M HCl in 1,4-dioxane (0.22 ml; 0.88 mmol). The resulting yellow mixture was further stirred at 0° C., under nitrogen, for 10 min., and then at rt for 1 h. The reaction mixture was then concentrated to dryness under reduced pressure and the yellow oily residue was further dried under HV to give the chlorhydrate salt of methyl 5-amino-5-(2,3-dihydrobenzo[b][1,4]dioxin-5-yl) pentanoate as a yellow solid. LC-MS (conditions A): $t_R$=0.47 min.; [M+H]$^+$: 266.11 g/mol.

methyl 5-([1,1'-biphenyl]-2-yl)-5-aminopentanoate

A cooled (−78° C.) solution of commercially available 2-iodo-1,1'-biphenyl (617 mg; 2.20 mmol) in anh. THF (5 ml), under nitrogen, was treated dropwise with a solution of 1.6 M n-BuLi in hexanes (1.50 ml; 2.40 mmol). The resulting solution was further stirred at −78° C. for 10 min. A solution of methyl 5-((tert-butylsulfinyl)imino)pentanoate (514 mg; 2.20 mmol) in anh. THF (2 ml) was added to the cooled reaction mixture, and stirring at −78° C. was continued for 10 min., and then at −20° C. for 2 h. The resulting reaction mixture was treated successively with aq. sat. $NH_4Cl$ (15 ml), $Et_2O$ (30 ml) and water (15 ml). The separated organic layer was then washed with brine (15 ml), dried over anh. $MgSO_4$, filtered, and concentrated to dryness under reduced pressure. Purification by FC (heptane/AcOEt=7/3) afforded methyl 5-([1,1'-biphenyl]-2-yl)-5-(1,1-dimethylethylsulfinamido)pentanoate as a yellow oil. LC-MS (conditions A): $t_R$=0.85 min.; [M+H]$^+$: 387.83 g/mol.

A cooled (0° C.) slightly yellow solution of methyl 5-([1,1'-biphenyl]-2-yl)-5-(1,1-dimethylethylsulfinamido)pentanoate (270 mg; 0.69 mmol) in MeOH (4 ml) was treated dropwise with a solution of 4 M HCl in 1,4-dioxane (0.35 ml; 1.40 mmol). The resulting yellow mixture was further stirred at 0° C., under nitrogen, for 10 min., and then at rt for 1 h. The reaction mixture was then concentrated to dryness under reduced pressure and the colorless solid residue was further dried under HV to give the chlorhydrate salt of methyl 5-([1,1'-biphenyl]-2-yl)-5-aminopentanoate as a colorless solid. LC-MS (conditions A): $t_R$=0.57 min.; [M+H]$^+$: 284.13 g/mol.

methyl 4-([1,1'-biphenyl]-2-yl)-4-aminobutanoate

A cooled (−78° C.) solution of commercially available 2-iodo-1,1'-biphenyl (1.916 g; 6.84 mmol) in anh. THF (62 ml), under nitrogen, was treated dropwise with a solution of 1.6 M n-BuLi in hexanes (4.27 ml; 6.84 mmol). The resulting solution was further stirred at −78° C. for 10 min. A solution of methyl 4-((tert-butylsulfinyl)imino)butanoate (1.500 g; 6.84 mmol) in anh. THF (8 ml) was added to the cooled reaction mixture, and stirring was continued from −78° C. to 0° C. over 1 h. The resulting reaction mixture was treated successively with aq. sat. $NH_4Cl$ (80 ml), $Et_2O$ (250 ml) and water (75 ml). The separated organic layer was then washed with brine (75 ml), dried over anh. $MgSO_4$, filtered, and concentrated to dryness under reduced pressure. Purification by FC (DCM/MeOH=25/1) afforded methyl 4-([1,1'-biphenyl]-2-yl)-4-(1,1-dimethylethylsulfinamido)butanoate. LC-MS (conditions A): $t_R$=0.85 min.; [M+H]$^+$: 374.12 g/mol.

A cooled (0° C.) slightly yellow solution of methyl 4-([1,1'-biphenyl]-2-yl)-4-(1,1-dimethylethylsulfinamido)butanoate (330 mg; 0.88 mmol) in MeOH (4 ml) was treated dropwise with a solution of 4 M HCl in 1,4-dioxane (0.44 ml; 1.77 mmol). The resulting yellow mixture was further stirred at 0° C., under nitrogen, for 10 min., and then at rt for 1 h. The reaction mixture was then concentrated to dryness under reduced pressure and the oily residue was further dried under HV to give the chlorhydrate salt of methyl 4-([1,1'-biphenyl]-2-yl)-4-aminobutanoate. LC-MS (conditions A): $t_R$=0.56 min.; [M+H]$^+$: 270.06 g/mol.

ethyl 4-([1,1'-biphenyl]-2-yl)-4-amino-2-methylbutanoate

A cooled (−78° C.) solution of commercially available 2-iodo-1,1'-biphenyl (680 mg; 2.43 mmol) in anh. THF (20 ml), under nitrogen, was treated dropwise with a solution of 1.6 M n-BuLi in hexanes (1.52 ml; 2.43 mmol). The resulting solution was further stirred at −78° C. for 10 min. A solution of ethyl 4-((tert-butylsulfinyl)imino)-2-methylbutanoate (600 mg; 2.43 mmol) in anh. THF (5 ml) was added to the cooled reaction mixture, and stirring was continued from −78° C. to 0° C. over 1 h. The resulting reaction mixture was treated successively with aq. sat. $NH_4Cl$ (80 ml), $Et_2O$ (250 ml) and water (75 ml). The separated organic layer was then washed with brine (75 ml), dried over anh. $MgSO_4$, filtered, and concentrated to dryness under reduced pressure. Purification by FC (DCM/MeOH=25/1) afforded ethyl 4-([1,1'-biphenyl]-2-yl)-4-(1,1-dimethylethylsulfinamido)-2-methylbutanoate as a mixture of stereoisomers. LC-MS (conditions A): $t_R$=0.93 min.; [M+H]$^+$: 401.79 g/mol and $t_R$=0.94 min.; [M+H]$^+$: 401.80 g/mol.

A cooled (0° C.) slightly yellow solution of ethyl 4-([1,1'-biphenyl]-2-yl)-4-(1,1-dimethylethylsulfinamido)-2-methylbutanoate (220 mg; 0.54 mmol) in MeOH (3 ml) was treated dropwise with a solution of 4 M HCl in 1,4-dioxane (0.27 ml; 1.08 mmol). The resulting yellow mixture was further stirred at 0° C., under nitrogen, for 10 min., and then at rt for 1 h. The reaction mixture was then concentrated to dryness under reduced pressure and the oily residue was further dried under HV to give the chlorhydrate salt of ethyl 4-([1,1'-biphenyl]-2-yl)-4-amino-2-methylbutanoate. LC-MS (conditions A): $t_R$=0.63 min.; [M+H]$^+$: 298.22 g/mol.

ethyl 4-amino-4-(2-ethoxy-6-fluorophenyl)-2-methylbutanoate

A mixture of commercially available 2-bromo-3-fluorophenol (5.000 g; 26.20 mmol), iodoethane (8.166 g; 52.40 mmol), and $K_2CO_3$ (4.342 g; 31.40 mmol) in anh. DMF (100 ml) was heated to 80° C., under nitrogen, for 1.5 h. $Et_2O$ was added and the organic layer was washed with water, dried over anh. $MgSO_4$, filtered, and concentrated to dryness under reduced pressure affording 2-bromo-1-ethoxy-3-fluorobenzene as a yellow oil. LC-MS (conditions A): $t_R$=0.88 min.; no ionisation.

A cooled (−78° C.) solution of 2-bromo-1-ethoxy-3-fluorobenzene (3.520 g; 16.10 mmol) in anh. THF (60 ml), under nitrogen, was treated dropwise with a solution of 1.6 M n-BuLi in hexanes (10.05 ml; 16.10 mmol). The resulting solution was further stirred at −78° C. for 5 min. A solution of ethyl 4-((tert-butylsulfinyl)imino)-2-methylbutanoate (2.650 g; 10.70 mmol) in anh. THF (20 ml) was then added dropwise to the cooled reaction mixture, and stirring at −78° C. was continued for 30 min. The resulting reaction mixture was treated successively with aq. sat. $NH_4Cl$ (75 ml), $Et_2O$ (250 ml) and water (75 ml). The separated organic layer was then washed with brine (75 ml), dried over anh. $MgSO_4$, filtered, and concentrated to dryness under reduced pressure. Purification by FC (DCM/MeOH=30/1) afforded ethyl 4-(1,1-dimethylethylsulfinamido)-4-(2-ethoxy-6-fluorophenyl)-2-methylbutanoate as a yellow oil. LC-MS (conditions A): $t_R$=0.85 min. and [M+H]$^+$: 388.35 g/mol; $t_R$=0.88 min. and [M+H]$^+$: 388.37 g/mol (mixture of diastereoisomers).

A cooled (0° C.) solution of ethyl 4-(1,1-dimethylethylsulfinamido)-4-(2-ethoxy-6-fluorophenyl)-2-methylbutanoate (1.550 g; 4.00 mmol) in EtOH (20 ml) was treated dropwise with a solution of 4 M HCl in 1,4-dioxane (2.0 ml; 8.00 mmol). The resulting mixture was further stirred at 0° C., under nitrogen, for 10 min., and then at rt for 30 min. The reaction mixture was then concentrated to dryness under reduced pressure and the oily residue was further dried under HV to give the chlorhydrate salt of ethyl 4-amino-4-(2-ethoxy-6-fluorophenyl)-2-methylbutanoate. LC-MS (conditions A): $t_R$=0.55 min. and [M+H]$^+$: 284.07 g/mol; $t_R$=0.57 min. and [M+H]$^+$: 284.07 g/mol (mixture of diastereoisomers).

ethyl 4-amino-4-(2-fluoro-6-methoxyphenyl)-2-methylbutanoate

A cooled (−78° C.) solution of commercially available 2-bromo-1-fluoro-3-methoxybenzene (2.642 g; 12.90 mmol) in anh. THF (60 ml), under nitrogen, was treated dropwise with a solution of 1.6 M n-BuLi in hexanes (8.05 ml; 12.90 mmol). The resulting solution was further stirred at −78° C. for 5 min. A solution of ethyl 4-((tert-butylsulfinyl)imino)-2-methylbutanoate (2.550 g; 10.30 mmol) in anh. THF (20 ml) was then added dropwise to the cooled reaction mixture, and stirring at −78° C. was continued for 45 min. The resulting reaction mixture was treated successively with aq. sat. $NH_4Cl$ (75 ml), $Et_2O$ (250 ml) and water (75 ml). The separated organic layer was then washed with brine (75 ml), dried over anh. $MgSO_4$, filtered, and concentrated to dryness under reduced pressure. Purification by FC (DCM/MeOH=30/1) afforded ethyl 4-(1,1-dimethylethylsulfinamido)-4-(2-fluoro-6-methoxyphenyl)-2-methylbutanoate as a yellow oil. LC-MS (conditions A): $t_R$=0.81 min. and [M+H]$^+$: 374.02 g/mol; $t_R$=0.83 min. and [M+H]$^+$: 374.34 g/mol (mixture of diastereoisomers).

A cooled (0° C.) solution of ethyl 4-(1,1-dimethylethylsulfinamido)-4-(2-fluoro-6-methoxyphenyl)-2-methylbutanoate (1.060 g; 2.84 mmol) in EtOH (15 ml) was treated dropwise with a solution of 4 M HCl in 1,4-dioxane (1.5 ml; 6.00 mmol). The resulting mixture was further stirred at 0° C., under nitrogen, for 10 min., and then at rt for 30 min. The reaction mixture was then concentrated to dryness under reduced pressure and the oily residue was further dried under HV to give the chlorhydrate salt of ethyl 4-amino-4-(2-fluoro-6-methoxyphenyl)-2-methylbutanoate. LC-MS (conditions A): $t_R$=0.50 min. and [M+H]$^+$: 270.33 g/mol.

methyl 4-amino-4-(2,4-dimethoxypyridin-3-yl)-2-methylbutanoate

A cooled (−78° C.) solution of commercially available 3-bromo-2,4-dimethoxypyridine (1.390 g; 5.74 mmol) in anh. THF (70 ml), under nitrogen, was treated dropwise with a solution of 1.6 M n-BuLi in hexanes (3.60 ml; 5.74 mmol). The resulting solution was further stirred at −78° C. for 15 min. A solution of ethyl 4-((tert-butylsulfinyl)imino)-2-methylbutanoate (1.290 g; 5.22 mmol) in anh. THF (5 ml) was then added to the cooled reaction mixture, and stirring at −78° C. was continued for 30 min. The resulting reaction mixture was treated successively with aq. sat. $NH_4Cl$ (35 ml), $Et_2O$ (75 ml) and water (20 ml). The separated organic layer was then washed with brine (30 ml), dried over anh. $MgSO_4$, filtered, and concentrated to dryness under reduced pressure. Purification by FC (DCM/MeOH=30/1) afforded ethyl 4-(2,4-dimethoxypyridin-3-yl)-4-(1,1-dimethylethylsulfinamido)-2-methylbutanoate as a yellow oil. LC-MS (conditions B): $t_R$=0.78 min. and [M+H]$^+$: 386.68 g/mol; $t_R$=0.80 min. and [M+H]$^+$: 386.76 g/mol (mixture of diastereoisomers).

A cooled (0° C.) solution of ethyl 4-(2,4-dimethoxypyridin-3-yl)-4-(1,1-dimethylethylsulfinamido)-2-methylbutanoate (0.709 g; 1.83 mmol) in MeOH (15 ml) was treated dropwise with a solution of 4 M HCl in 1,4-dioxane (0.92 ml; 3.67 mmol). The resulting mixture was further stirred at 0° C., under nitrogen, for 10 min., and then at rt for 30 min. The reaction mixture was then concentrated to dryness under reduced pressure and the oily residue was further dried under HV to give the chlorhydrate salt of methyl 4-amino-4-(2,4-dimethoxypyridin-3-yl)-2-methylbutanoate. LC-MS (conditions B): $t_R$=0.45 min. and [M+H]$^+$: 269.33 g/mol; $t_R$=0.47 min. and [M+H]$^+$: 269.33 g/mol (mixture of diastereoisomers).

methyl 5-amino-5-(2-methoxynaphthalen-1-yl)pentanoate

A cooled (−78° C.) solution of commercially available 1-bromo-2-methoxynaphthalene (0.839 g; 2.14 mmol) in anh. THF (20 ml), under nitrogen, was treated dropwise with a solution of 1.6 M n-BuLi in hexanes (1.35 ml; 2.16 mmol). The resulting solution was further stirred at −78° C. for 10 min. A solution of methyl 5-((tert-butylsulfinyl)imino)pentanoate (0.500 g; 2.14 mmol) in anh. THF (2 ml) was then added to the cooled reaction mixture, and stirring at −78° C. was continued for 30 min. The resulting reaction mixture was treated successively with aq. sat. $NH_4Cl$ (35 ml), $Et_2O$ (75 ml) and water (20 ml). The separated organic layer was then washed with brine (30 ml), dried over anh. $MgSO_4$, filtered, and concentrated to dryness under reduced pressure. Purification by FC (DCM/MeOH=15/1) afforded methyl 5-(1,1-dimethylethylsulfinamido)-5-(2-methoxynaphthalen-1-yl)pentanoate as a yellow oil. LC-MS (conditions A): $t_R$=0.83 min. and [M+H]$^+$: 391.93 g/mol.

A cooled (0° C.) solution of methyl 5-(1,1-dimethylethylsulfinamido)-5-(2-methoxynaphthalen-1-yl)pentanoate (0.268 g; 0.68 mmol) in MeOH (5 ml) was treated dropwise with a solution of 4 M HCl in 1,4-dioxane (0.35 ml; 1.40 mmol). The resulting mixture was further stirred at 0° C., under nitrogen, for 10 min., and then at rt for 1 h. The reaction mixture was then concentrated to dryness under reduced pressure and the oily residue was further dried under HV to give the chlorhydrate salt of methyl 5-amino-5-(2-methoxynaphthalen-1-yl)pentanoate. LC-MS (conditions A): $t_R$=0.55 min. and [M+H]$^+$: 288.16 g/mol.

6-(2-hydroxy-6-methoxyphenyl)-1-(4-(trifluoromethoxy)benzyl)piperidin-2-one

A mixture of commercially available 2-hydroxy-6-methoxybenzaldehyde (1.000 g; 6.57 mmol), benzyl bromide (2.867 g; 16.43 mmol), and $K_2CO_3$ (2.960 g; 21.42 mmol) in anh. acetone (33 ml) was refluxed, under nitrogen, for 5.5 h. After cooling to rt, volatiles were removed under reduced pressure, and the residue was dissolved in water and AcOEt. The separated aq. layer was further extracted with AcOEt (2×), and the mixed organic layers were washed with brine, dried dried over anh. $MgSO_4$, filtered, and concentrated to dryness under reduced pressure. Purification by FC (heptane/AcOEt=8/2) afforded 2-(benzyloxy)-6-methoxybenzaldehyde. LC-MS (conditions E): $t_R$=0.68 min.; [M+H]$^+$: 243.27 g/mol.

6-(2-(Benzyloxy)-6-methoxyphenyl)-1-(4-(trifluoromethoxy)benzyl)-5,6-dihydropyridin-2(1H)-one was then prepared using 2-(benzyloxy)-6-methoxybenzaldehyde according to general procedure 5 (GP5) that is described in section B.3.1. 6-(2-(Benzyloxy)-6-methoxyphenyl)-1-(4-(trifluoromethoxy)benzyl)-5,6-dihydropyridin-2(1H)-one was obtained as a brown oil after purification by FC (heptane/AcOEt=8/2 to 1/1). LC-MS (conditions E): $t_R$=0.88 min.; [M+H]$^+$: 484.27 g/mol.

A mixture of 6-(2-(benzyloxy)-6-methoxyphenyl)-1-(4-(trifluoromethoxy)benzyl)-5,6-dihydropyridin-2(1H)-one (313 mg; 0.64 mmol), and 10% Pd(C) (300 mg) in anh. EtOH (20 ml) was stirred at rt, under hydrogen atmosphere (1 atm), for 17 h. Filtration over a pad of celite, concentration to dryness under reduced pressure, and additional drying under HV afforded 6-(2-hydroxy-6-methoxyphenyl)-1-(4-(trifluoromethoxy)benzyl)piperidin-2-one as a grey solid. LC-MS (conditions E): $t_R$=0.73 min.; [M+H]$^+$: 396.24 g/mol.

6-(2,6-dimethoxyphenyl)-1-(4-hydroxybenzyl)piperidin-2-one

A mixture of 6-(2,6-dimethoxyphenyl)piperidin-2-one (110 mg; 0.46 mmol) in anh. DMF (2 ml) was treated at rt with NaH (60% dispersion in mineral oil; 118 mg; 2.95 mmol), and with commercially available 1-(benzyloxy)-4-(chloromethyl)benzene (130 mg; 0.56 mmol). The resulting mixture was then heated to 60° C., under nitrogen, for 1 h. After cooling to rt, aq. sat. NaHCO$_3$ was added, and this mixture was extracted with AcOEt (2×). The mixed organic layers were washed with brine, dried over anh. MgSO$_4$, filtered, and concentrated to dryness under reduced pressure. Purification by FC (AcOEt) afforded 1-(4-(benzyloxy)benzyl)-6-(2,6-dimethoxyphenyl)piperidin-2-one as a yellow oil. LC-MS (conditions E): $t_R$=0.82 min.; [M+H]$^+$: 432.24 g/mol.

A mixture of 1-(4-(benzyloxy)benzyl)-6-(2,6-dimethoxyphenyl)piperidin-2-one (74 mg; 0.17 mmol), and 10% Pd(C) (35 mg) in anh. EtOH (3 ml) was stirred at rt, under hydrogen atmosphere (1 atm), for 15 h. Filtration over a pad of celite, concentration to dryness under reduced pressure, and additional drying under HV afforded 6-(2,6-dimethoxyphenyl)-1-(4-hydroxybenzyl)piperidin-2-one as a yellow oil. LC-MS (conditions E): $t_R$=0.62 min.; [M+H]$^+$: 342.20 g/mol.

5-(2-ethoxyphenyl)pyrrolidin-2-one

Synthesized from methyl 4-((tert-butylsulfinyl)imino)butanoate and commercially available 1-ethoxy-2-iodobenzene according to the procedures described for the preparations of methyl 4-amino-4-(2,6-dimethoxyphenyl)butanoate and 5-(2,6-dimethoxyphenyl)pyrrolidin-2-one. The target product 5-(2-ethoxyphenyl)pyrrolidin-2-one was obtained as a colorless solid after purification by FC (heptane/AcOEt=7/3 to 3/7). LC-MS (conditions D): $t_R$=0.81 min.; [M+H]$^+$: 205.99 g/mol.

6-(4-chloro-2,6-dimethoxyphenyl)piperidin-2-one

A mixture of commercially available 1-chloro-3,5-dimethoxybenzene (1.243 g; 6.98 mmol), P$_2$O$_5$ (991 mg; 6.98 mmol), and methanesulfonic acid (5.659 g; 58.89 mmol) was treated with commercially available (S)-6-oxopiperidine-2-carboxylic acid (1.000 g; 6.98 mmol), and the resulting mixture was heated to 100° C. for 30 min. After cooling to rt, water was added, and the resulting solution was extracted with DCM. The mixed organic layers were dried over anh. MgSO$_4$, filtered, and concentrated to dryness under reduced pressure. Purification by preparative HPLC afforded 6-(4-chloro-2,6-dimethoxyphenyl)piperidin-2-one as a colorless solid. LC-MS (conditions E): $t_R$=0.61 min.; [M+H]$^+$: 270.26 g/mol.

6-(2,6-dimethoxyphenyl)-4-methylpiperidin-2-one

A cooled (−10° C.) solution of commercially available 2-iodo-1,3-dimethoxybenzene (2.000 g; 7.57 mmol) in anh. THF (30 ml) was treated dropwise with a solution of 2 M isopropylmagnesium chloride in THF (5.10 ml; 10.20 mmol), and the mixture was further stirred at −10° C., under nitrogen, for 15 min. This mixture was then added dropwise to a cooled (−40° C.) solution of commercially available 4-methyldihydro-2H-pyran-2,6(3H)-dione (970 mg; 7.57 mmol) and CuI (360 mg; 1.89 mmol) in anh. THF (20 ml). Stirring was continued at −40° C. for 20 min., and 2 M aq. HCl (11.5 ml) was then added dropwise. Et$_2$O (100 ml), and aq. sat. NH$_4$Cl (30 ml) were added, and the separated organic layer was dried over anh. MgSO$_4$, filtered, and concentrated to dryness under reduced pressure. Anh. DMF (20 ml), and Cs$_2$CO$_3$ (3.165 g; 9.71 mmol) were successively added, and stirring at rt was continued for 15 min. After cooling to 0° C., iodomethane (1.655 g; 11.66 mmol) was added dropwise, and the resulting mixture was further stirred at 0° C. for 10 min., and then at rt for 1.5 h. AcOEt (100 ml) and water (100 ml) were added, and the separated organic layer was further washed with brine (25 ml), dried over anh. MgSO$_4$, filtered, and concentrated to dryness under reduced pressure. Purification by FC (DCM/MeOH=20/1) afforded methyl 5-(2,6-dimethoxyphenyl)-3-methyl-5-oxopentanoate as a yellow oil. LC-MS (conditions D): $t_R$=0.97 min.; [M+H]$^+$: 281.29 g/mol.

A sealed tube containing a mixture of methyl 5-(2,6-dimethoxyphenyl)-3-methyl-5-oxopentanoate (200 mg; 0.71 mmol), ammonium acetate (549 mg; 7.13 mmol), and NaBH$_3$CN (47 mg; 0.71 mmol) in anh. MeOH (3 ml) was heated to 80° C. for 48 h. After cooling to rt, 2 M aq. HCl (6 ml) was added, and the volatiles were removed under reduced pressure. The resulting aq. layer was extracted with DCM (3×20 ml), and the mixed organic layers were dried over anh. MgSO$_4$, filtered, and concentrated to dryness under reduced pressure. Purification by FC (DCM/MeOH=25/1) afforded 6-(2,6-dimethoxyphenyl)-4-methylpiperidin-2-one as a colorless oil. LC-MS (conditions D): $t_R$=0.89 min.; [M+H]$^+$: 250.35 g/mol.

6-(2,6-dimethoxyphenyl)-4,4-dimethylpiperidin-2-one

A cooled (−10° C.) solution of commercially available 2-iodo-1,3-dimethoxybenzene (2.000 g; 7.57 mmol) in anh. THF (30 ml) was treated dropwise with a solution of 2 M isopropylmagnesium chloride in THF (5.10 ml; 10.20 mmol), and the mixture was further stirred at −10° C., under nitrogen, for 15 min. This mixture was then added dropwise to a cooled (−40° C.) solution of commercially available 4,4-dimethyldihydro-2H-pyran-2,6(3H)-dione (1.184 g; 8.33 mmol) and CuI (360 mg; 1.89 mmol) in anh. THF (20 ml). Stirring was continued at −40° C. for 20 min., and 2 M aq. HCl (11.5 ml) was then added dropwise. Et$_2$O (100 ml), and aq. sat. NH$_4$Cl (30 ml) were added, and the separated organic layer was dried over anh. MgSO$_4$, filtered, and concentrated to dryness under reduced pressure. Anh. DMF (20 ml), and Cs$_2$CO$_3$ (3.080 g; 9.45 mmol) were successively added, and stirring at rt was continued for 15 min. After cooling to 0° C., iodomethane (1.610 g; 11.34 mmol) was added dropwise, and the resulting mixture was further stirred at 0° C. for 10 min., and then at rt for 1.5 h. AcOEt (100 ml) and water (100 ml) were added, and the separated organic layer was further washed with brine (25 ml), dried over anh. MgSO$_4$, filtered, and concentrated to dryness under reduced pressure. Purification by FC (DCM/MeOH=20/1) afforded methyl 5-(2,6-dimethoxyphenyl)-3,3-dimethyl-5-oxopentanoate as a yellow oil. LC-MS (conditions D): $t_R$=1.01 min.; [M+H]$^+$: 295.39 g/mol.

A sealed tube containing a mixture of methyl 5-(2,6-dimethoxyphenyl)-3,3-dimethyl-5-oxopentanoate (474 mg; 1.61 mmol), ammonium acetate (1.241 g; 16.10 mmol), and NaBH$_3$CN (106 mg; 1.61 mmol) in anh. MeOH (8 ml) was heated to 80° C. for 48 h. After cooling to rt, 2 M aq. HCl (7.5 ml) was added, and the volatiles were removed under reduced pressure. The resulting aq. layer was extracted with DCM (3×20 ml), and the mixed organic layers were dried over anh. MgSO$_4$, filtered, and concentrated to dryness under reduced pressure. Purification by FC (DCM/MeOH=25/1) afforded 6-(2,6-dimethoxyphenyl)-4,4-dimethylpiperidin-2-one as a yellow solid. LC-MS (conditions D): $t_R$=0.91 min.; [M+H]$^+$: 264.22 g/mol.

methyl 4-oxo-4-(2,4,6-trimethoxyphenyl)butanoate

A cooled (0° C.) suspension of AlCl$_3$ (2.036 g; 15.27 mmol) in anh. DCE (10 ml) was treated with commercially available 1,3,5-trimethoxybenzene (1.675 g; 9.96 mmol), and stirring at 0° C., under nitrogen, was continued for 10 min. Commercially available methyl 4-chloro-4-oxobutanoate (1.000 g; 6.64 mmol) was then added, and the mixture was stirred at rt for 24 h. The resulting reaction mixture was poured onto crushed ice (30 g), and DCM (20 ml) was added. The separated aq. layer was further extracted with DCM (3×10 ml). The mixed organic layers were washed successively with water (15 ml) and brine (2×15 ml), dried over anh. MgSO$_4$, filtered, and concentrated to dryness under reduced pressure affording methyl 4-oxo-4-(2,4,6-trimethoxyphenyl)butanoate as a colorless oil. LC-MS (conditions D): $t_R$=0.88 min.; [M+H]$^+$: 283.02 g/mol.

methyl 5-oxo-5-(2,4,6-trimethoxyphenyl)pentanoate

A cooled (0° C.) suspension of aluminum chloride (9.316 g; 69.87 mmol) in anh. DCE (50 ml) was treated with commercially available 1,3,5-trimethoxybenzene (7.664 g; 45.56 mmol), and stirring at 0° C., under nitrogen, was continued for 10 min. Commercially available methyl 5-chloro-5-oxopentanoate (5.000 g; 30.37 mmol) was then added, and the mixture was stirred at rt for 26 h. The resulting reaction mixture was poured onto crushed ice (150 g), and DCM (100 ml) was added. The separated aq. layer was further extracted with DCM (3×50 ml). The mixed organic layers were washed successively with water (75 ml) and brine (2×75 ml), dried over anh. MgSO$_4$, filtered, and concentrated to dryness under reduced pressure. Purification by FC (heptane/AcOEt=10/1 to AcOEt) afforded methyl 5-oxo-5-(2,4,6-trimethoxyphenyl)pentanoate as a yellow oil. LC-MS (conditions D): $t_R$=0.94 min.; [M+H]$^+$: 297.13 g/mol.

6-(2,4,6-trimethoxyphenyl)piperidin-2-one

A sealed tube containing a mixture of methyl 5-oxo-5-(2,4,6-trimethoxyphenyl)pentanoate (200 mg; 0.67 mmol), ammonium acetate (520 mg; 6.75 mmol), and NaBH$_3$CN (44 mg; 0.67 mmol) in anh. MeOH (3 ml) was heated to 75° C. for 18 h. After cooling to rt, 2 M aq. HCl was added, and the volatiles were removed under reduced pressure. The aq. solution was extracted with DCM (3×20 ml), and the mixed organic layers were dried over anh. MgSO$_4$, filtered, and concentrated to dryness under reduced pressure. Purification by FC (DCM/MeOH=25/1) afforded 6-(2,4,6-trimethoxyphenyl)piperidin-2-one as a colorless solid. LC-MS (conditions D): $t_R$=0.86 min.; [M+H]$^+$: 266.84 g/mol.

A.4 Preparation of Amines R$^1$CH(NH$_2$)R$^3$ (2-methylbenzo[d]oxazol-5-yl)methanamine A mixture of commercially available 2,5-dimethylbenzo[d]oxazole (1.000 g; 6.79 mmol), N-bromosuccinimide (1.209 g; 6.79 mmol), and commercially available dibenzoyl peroxide (11 mg; 0.046 mmol) in anh. CCl$_4$ (10 ml) was refluxed, under nitrogen, for 17 h. After cooling to rt, the reaction mixture was filtered, and the filtrate was concentrated to dryness under reduced pressure. Purification by FC (heptane/AcOEt=9/1) afforded 5-(bromomethyl)-2-methylbenzo[d]oxazole as a yellow solid. LC-MS (conditions E): $t_R$=0.61 min.; [M+H]$^+$: 226.12 g/mol.

A solution of 5-(bromomethyl)-2-methylbenzo[d]oxazole (400 mg; 1.76 mmol) in anh. DMF (2 ml) was treated portionwise with phthalimide potassium salt (327 mg; 1.76 mmol), and the resulting mixture was stirred at rt, under nitrogen, for 18 h. Water was added, and the resulting precipitate was collected by filtration, and washed with water. Drying under HV afforded 2-((2-methylbenzo[d]oxazol-5-yl)methyl)isoindoline-1,3-dione as a brown solid. LC-MS (conditions E): $t_R$=0.66 min.; [M+H]$^+$: 293.15 g/mol.

A mixture of 2-((2-methylbenzo[d]oxazol-5-yl)methyl)isoindoline-1,3-dione (200 mg; 0.68 mmol), and hydrazine monohydrate (715 mg; 21.89 mmol) in EtOH (30 ml) was refluxed, under nitrogen, for 4 h. After cooling to rt, the mixture was filtered, and the filtrate was concentrated to dryness under reduced pressure affording (2-methylbenzo[d]oxazol-5-yl)methanamine as an orange oil. LC-MS (conditions D): $t_R$=0.50 min.; [M+H]$^+$: 163.07 g/mol.

dibenzo[b,d]furan-2-ylmethanamine

A mixture of commercially available dibenzo[b,d]furan-2-carbaldehyde (1.992 g; 10.20 mmol), titanium(IV) ethoxide Ti(OEt)$_4$ (3.98 ml; 19.00 mmol), and 2-methylpropane-2-sulfinamide (1.150 g; 9.49 mmol) in anh. THF (18 ml) was stirred at rt, under nitrogen, for 4 h. AcOEt and brine were added, and the organic layer was further washed with brine, dried over anh. MgSO$_4$, filtered, and concentrated to dryness under reduced pressure. Purification by FC (DCM) afforded N-(dibenzo[b,d]furan-2-ylmethylene)-2-methylpropane-2-sulfinamide as a pale yellow solid. LC-MS (conditions A): $t_R$=0.96 min.; [M+H]$^+$: 300.33 g/mol.

A solution of N-(dibenzo[b,d]furan-2-ylmethylene)-2-methylpropane-2-sulfinamide (2.260 g; 7.55 mmol) in anh. MeOH (27 ml) and anh. DCM (57 ml) was treated with NaBH$_4$ (343 mg; 9.06 mmol), and the resulting mixture was stirred at rt, under nitrogen, for 10 min. Water and DCM were added, and the organic layer was then dried over anh. MgSO$_4$, filtered, and concentrated to dryness under reduced pressure affording N-(dibenzo[b,d]furan-2-ylmethyl)-2-methylpropane-2-sulfinamide as a yellow solid. LC-MS (conditions A): $t_R$=0.82 min.; [M+H]$^+$: 302.01 g/mol.

A cooled (0° C.) solution of N-(dibenzo[b,d]furan-2-ylmethyl)-2-methylpropane-2-sulfinamide (2.280 g; 7.55 mmol) in MeOH (24 ml) was treated dropwise with a solution of 4 M HCl in 1,4-dioxane (4.0 ml; 16.00 mmol). The resulting mixture was further stirred at 0° C., under nitrogen, for 10 min., and then at rt for 1 h. The reaction mixture was concentrated to dryness under reduced pressure. DCM, water, and Na$_2$CO$_3$ (5.50 g) were added, and the organic layer was then dried over anh. MgSO$_4$, filtered, and concentrated to dryness under reduced pressure affording dibenzo[b,d]furan-2-ylmethanamine as a yellow solid. LC-MS (conditions A): $t_R$=0.51 min.; no ionisation.

B. Methods and General Procedures for the Preparation of Example Compounds

B.1 Methods for the Preparation of Example Compounds Via Reductive Amination/Saponification/Lactamization or Via One-Pot Reductive Amination I Lactamization

B.1.1 First General Procedure (GP1) for the Preparation of Example Compounds Via Reductive Amination/Saponification/Lactamization The sequence of reactions is described in scheme 1. The following general procedure (GP1) describes the reaction between an amine derivative A5 and a carbonyl derivative $R^1C(O)R^3$ in order to produce lactam derivatives corresponding to compounds of formula (I) after 3 steps.

6-(2,6-dimethoxyphenyl)-1-(quinolin-3-ylmethyl) piperidin-2-one (Example Compound 1)

Step 1: Reductive Amination

A solution of the chlorhydrate salt of methyl 5-amino-5-(2,6-dimethoxyphenyl)pentanoate (1.177 g; 3.87 mmol; 1.0 equiv.) in anh. DCE (24 ml) was treated successively with DIPEA (1.35 ml; 7.75 mmol; 2.0 equiv.), quinoline-3-carbaldehyde (609 mg; 3.87 mmol; 1.0 equiv.), and $NaBH(OAc)_3$ (1.150 g; 5.42 mmol; 1.4 equiv.). The resulting beige heterogeneous mixture was further stirred at rt, under nitrogen, for 2 h 45 min. DCM (50 ml) and a solution of aq. sat. $NaHCO_3$ (35 ml) were then added. The organic layer was further washed with a solution of aq. sat. $NaHCO_3$ (35 ml) and with brine (35 ml). The resulting yellow organic layer was then dried over anh. $MgSO_4$, filtered, and concentrated to dryness under reduced pressure. Purification by FC (DCM/MeOH=10/1) afforded methyl 5-(2,6-dimethoxyphenyl)-5-((quinolin-3-ylmethyl)amino)-pentanoate as a yellow oil. LC-MS (conditions B): $t_R$=0.66 min.; $[M+H]^+$: 409.35 g/mol.

Step 2: Saponification

A yellow solution of methyl 5-(2,6-dimethoxyphenyl)-5-((quinolin-3-ylmethyl)amino)-pentanoate (1.320 g; 3.23 mmol; 1.0 equiv.) in MeOH (15 ml) was treated at rt with a solution of 1 M aq. NaOH (6.5 ml; 6.5 mmol; 2.0 equiv.). The resulting solution was further stirred at rt for 1 h45. Concentration to dryness under reduced pressure, and subsequent drying under HV afforded 5-(2,6-dimethoxyphenyl)-5-((quinolin-3-ylmethyl)amino)pentanoic acid as a beige solid. LC-MS (conditions B): $t_R$=0.59 min.; $[M+H]^+$: 395.36 g/mol.

Step 3: Lactamization

A yellow solution of 5-(2,6-dimethoxyphenyl)-5-((quinolin-3-ylmethyl)amino)pentanoic acid (1.074 g; 2.72 mmol; 1.0 equiv.) in anh. DMF (50 ml) was treated successively with HATU (1.294 g; 3.40 mmol; 1.25 equiv.) and with DIPEA (0.59 ml; 3.40 mmol; 1.25 equiv.). The resulting orange solution was stirred at rt, under nitrogen, for 2 h45. Water (100 ml) and $Et_2O$ (100 ml) were then added, and the separated aq. layer was further extracted with $Et_2O$ (3×100 ml). The mixed organic layers were washed with water (15 ml) and with brine (15 ml), dried over anh. $MgSO_4$, filtered, and concentrated to dryness under reduced pressure. Purification by FC (DCM/MeOH=20/1) afforded 6-(2,6-dimethoxyphenyl)-1-(quinolin-3-ylmethyl)piperidin-2-one as a beige solid. LC-MS (conditions B): $t_R$=0.68 min.; $[M+H]^+$: 377.36 g/mol.

B.1.2 Second General Procedure (GP2) for the Preparation of Example Compounds (pyrrolidin-2-pnes) Via One-Pot Reductive Amination/Lactamization The sequence of reactions is described in scheme 1. The following general procedure (GP2) describes the reaction between an amine derivative A5 and a carbonyl derivative $R^1C(O)R^3$ in order to produce pyrrolidin-2-ones corresponding to compounds of formula (I). Pyrrolidin-2-ones could be obtained directly under the typical reaction conditions of reductive amination. A subsequent saponification/lactamization procedure can be avoided in the case of five-membered ring derivatives.

5-(2,6-dimethoxyphenyl)-1-(3-(2-methylthiazol-4-yl) benzyl)pyrrolidin-2-one (Example Compound 125)

One-Pot Reductive Amination/Lactamization for the Preparation of pyrrolidin-2-ones A solution of the chlorhydrate salt of methyl 4-amino-4-(2,6-dimethoxyphenyl)butanoate (100 mg; 0.34 mmol; 1.0 equiv.) in anh. DCE (1.5 ml) was treated successively with DIPEA (0.12 ml; 0.69 mmol; 2.0 equiv.), 3-(2-methylthiazol-4-yl)benzaldehyde (70 mg; 0.34 mmol; 1.0 equiv.), and $NaBH(OAc)_3$ (102 mg; 0.48 mmol; 1.4 equiv.). The resulting mixture was further stirred at rt, under nitrogen, for 72 h. DCM (50 ml) and a solution of aq. sat. $NaHCO_3$ (35 ml) were then added. The organic layer was further washed with a solution of aq. sat. $NaHCO_3$ (35 ml) and with brine (35 ml). The resulting organic layer was then dried over anh. $MgSO_4$, filtered, and concentrated to dryness under reduced pressure. Purification by preparative HPLC afforded 5-(2,6-dimethoxyphenyl)-1-(3-(2-methylthiazol-4-yl)benzyl)pyrrolidin-2-one as a beige solid. LC-MS (conditions A): $t_R$=0.81 min.; $[M+H]^+$: 409.15 g/mol.

B.1.3 Third General Procedure (GP3) for the Preparation of Example Compounds Via Reductive Amination/Lactamization The sequence of reactions is described in scheme 4. The following general procedure (GP3) describes the reaction between a keto-ester D2 and an amine in order to produce lactam derivatives of formula (I).

1-(4-(trifluoromethoxy)benzyl)-5-(2,4,6-trimethoxyphenyl)pyrrolidin-2-one (Example Compound 108)

A mixture of methyl 4-oxo-4-(2,4,6-trimethoxyphenyl)butanoate (200 mg; 0.70 mmol; 1.0 equiv.), (4-(trifluoromethoxy)phenyl)methanamine (677 mg; 3.54 mmol; 5.0 equiv.), acetic acid (472 mg; 7.86 mmol; 11.1 equiv.), and $NaBH_3CN$ (93 mg; 1.41 mmol; 2.0 equiv.) in anh. THF (1.5 ml), and anh. MeOH (1.5 ml) was refluxed, under nitrogen, for 24 h. After cooling to rt, 15% aq. NaOH was added, and the organic solvents were removed under reduced pressure. The residue was extracted with DCM, and the mixed organic layers were washed with brine, dried over anh. $MgSO_4$, filtered, and concentrated to dryness under reduced pressure. Purification by FC (DCM/MeOH=50/1) afforded 1-(4-(trifluoromethoxy)benzyl)-5-(2,4,6-trimethoxyphenyl)pyrrolidin-2-one as a colorless oil. LC-MS (conditions D): $t_R$=1.08 min.; [M+H]$^+$: 425.72 g/mol.

B.2 Methods for the Preparation of Example Compounds Via N-Alkylation of Lactam Derivatives with Electrophiles The sequence of reactions is described in schemes 1, 4, and 5. The following general procedure (GP4) describes the reaction between a lactam derivative A7 and an electrophile R$^1$C(X)R$^3$ (X represents Cl or Br) in order to produce lactam derivatives corresponding to compounds of formula (I).

B.2.1 General Procedure (GP4) for the Preparation of Example Compounds Via N-Alkylation of Lactam Derivatives with Electrophiles 1-([1,1'-biphenyl]-3-ylmethyl)-6-(2,6-dimethoxyphenyl)piperidin-2-one (Example Compound 189)

A solution of 6-(2,6-dimethoxyphenyl)piperidin-2-one (70 mg; 0.29 mmol; 1.0 equiv.) in anh. DMF (3 ml) was treated at rt with NaH (60% dispersion in mineral oil; 71 mg; 1.78 mmol; 6.0 equiv.), and 3-(bromomethyl)-1,1'-biphenyl (110 mg; 0.44 mmol; 1.5 equiv.). The resulting mixture was then heated to 60° C., under nitrogen, for 1 h. The reaction mixture was allowed to cool to rt, and a solution of aq. sat. NaHCO3 (10 ml) was added. After extractions with AcOEt (2×20 ml), the mixed organic layers were further washed with brine (10 ml), dried over anh. MgSO$_4$, filtered, and concentrated to dryness under reduced pressure. Purification by preparative HPLC afforded 1-([1,1'-biphenyl]-3-ylmethyl)-6-(2,6-dimethoxyphenyl)piperidin-2-one as a colorless oil. LC-MS (conditions A): $t_R$=0.95 min.; [M+H]$^+$: 402.16 g/mol.

B.3 Methods for the Preparation of Example Compounds Via Olefin Ring-Closing Methathesis

B.3.1 General Procedure (GP5) for the Preparation of Example Compounds Via Olefin Ring-Closing Methathesis The sequence of reactions is described in scheme 5. The following general procedure (GP5) describes the conversion of an aldehyde derivative E1 into lactam derivatives E8 corresponding to compounds of formula (I).

1-([1,1'-biphenyl]-3-ylmethyl)-6-(4-fluoro-2,6-dimethoxyphenyl)piperidin-2-one (Example Compound 234)

Step 1: Imine Formation

A solution of the aldehyde derivative 4-fluoro-2,6-dimethoxybenzaldehyde (558 mg; 3.03 mmol; 1.0 equiv.) and 2-methylpropane-2-sulfinamide (379 mg; 3.03 mmol; 1.0 equiv.) in anh. THF (12 ml) was treated with Ti(OEt)$_4$ (1.457 g; 6.06 mmol; 2.0 equiv.), and the resulting mixture was heated to 75° C., under nitrogen, for 2 h. After cooling to rt, a solution of aq. sat. NaHCO$_3$ (25 ml) and DCM (50 ml) were successively added. After filtration over celite and additional washing of the separated solids with DCM, the layers of the obtained filtrate were separated. The organic layer was then washed with brine, dried over anh. MgSO$_4$, filtered, and concentrated to dryness under reduced pressure. Purification by FC (heptane/AcOEt=1/1) afforded pure N-(4-fluoro-2,6-dimethoxybenzylidene)-2-methylpropane-2-sulfinamide as a colorless solid. LC-MS (conditions A): $t_R$=0.79 min.; [M+H]$^+$: 288.11 g/mol.

Step 2: Reaction of the Imine with Allylmagnesium Bromide

A cooled (−50° C.) solution of the imine derivative N-(4-fluoro-2,6-dimethoxybenzylidene)-2-methylpropane-2-sulfinamide (549 mg; 1.91 mmol; 1.0 equiv.) in anh. THF (5 ml) was treated dropwise with a solution of 1 M allylmagnesium bromide in Et$_2$O (9.6 ml; 9.6 mmol; 5.0 equiv.). The resulting yellow solution was further stirred at −50° C., under nitrogen, for 15 min., and then at 0° C. for 15 min. After successive addition of a solution of aq. sat. NH$_4$Cl and water, the resulting mixture was extracted with Et$_2$O (3×). The mixed organic layers were dried over anh. MgSO$_4$, filtered, and concentrated to dryness under reduced pressure. Purification by FC (heptane/AcOEt=1/1) afforded N-(1-(4-fluoro-2,6-dimethoxyphenyl)but-3-en-1-yl)-2-methylpropane-2-sulfinamide as a colorless oil. LC-MS (conditions A): $t_R$=0.80 min. and [M+H]$^+$: 330.03 g/mol; $t_R$=0.87 min. and [M+H]$^+$: 330.03 g/mol (mixture of diastereoisomers).

Step 3: Deprotection of the Primary Amine

A cooled (0° C.) slightly yellow solution of N-(1-(4-fluoro-2,6-dimethoxyphenyl)but-3-en-1-yl)-2-methylpropane-2-sulfinamide (630 mg; 1.91 mmol; 1.0 equiv.) in anh. MeOH (10 ml) was treated dropwise with a solution of 4 M HCl in 1,4-dioxane (0.96 ml; 3.84 mmol; 2.0 equiv.). The resulting mixture was further stirred at 0° C., under nitrogen, for 20 min., and then at rt for 20 min. Subsequent concentration to dryness under reduced pressure, and additional drying under HV delivered the chlorhydrate salt of 1-(4-fluoro-2,6-dimethoxyphenyl)but-3-en-1-amine as a pale yellow oil. LC-MS (conditions A): $t_R$=0.50 min.; no ionisation.

Step 4: Reductive Amination

A solution of the chlorhydrate salt of the amine derivative 1-(4-fluoro-2,6-dimethoxyphenyl)but-3-en-1-amine (200 mg; 0.76 mmol; 1.0 equiv.) in anh. DCE (4 ml) was treated successively with DIPEA (198 mg; 1.52 mmol; 2.0 equiv.), the aldehyde derivative [1,1'-biphenyl]-3-carbaldehyde (139 mg; 0.76 mmol; 1.0 equiv.), and NaBH(OAc)$_3$ (238 mg; 1.07 mmol; 1.4 equiv.). The resulting yellow mixture was further stirred at rt, under nitrogen, for 16 h. DCM (75 ml) and a solution of aq. sat. NaHCO$_3$ (100 ml) were then added. The organic layer was further washed with a solution of aq. sat. NaHCO$_3$ (35 ml) and with brine (35 ml). The resulting yellow organic layer was then dried over anh. MgSO$_4$, filtered, and concentrated to dryness under reduced pressure. Purification by FC (DCM/MeOH/25% aq. NH$_4$OH=40/1/0.1) afforded N-([1,1'-biphenyl]-3-ylmethyl)-1-(4-fluoro-2,6-dimethoxyphenyl)but-3-en-1-amine as a pale yellow oil. LC-MS (conditions A): $t_R$=0.76 min.; [M+H]$^+$: 392.14 g/mol.

Step 5: Acylation of the Secondary Amine with Acryloyl Chloride

A cooled (0° C.) yellow solution of the secondary amine derivative N-([1,1'-biphenyl]-3-ylmethyl)-1-(4-fluoro-2,6-dimethoxyphenyl)but-3-en-1-amine (148 mg; 0.37 mmol; 1.0 equiv.) in anh. DCM (3 ml) was treated successively with NEt$_3$ (58 mg; 0.57 mmol; 1.5 equiv.), DMAP (3.5 mg; 0.03 mmol; 0.075 equiv.), and acryloyl chloride (50 mg; 0.53 mmol; 1.4 equiv.). The resulting solution was stirred at rt, under nitrogen, for 1 h. The reaction mixture was then treated with a solution of aq. sat. NaHCO₃ (10 ml), and extracted with DCM (3×20 ml). The mixed organic layers were washed with brine (50 ml), dried over anh. MgSO₄, filtered, and concentrated to dryness under reduced pressure. Purification by FC (DCM/MeOH=50/1) afforded N-([1,1'-biphenyl]-3-ylmethyl)-N-(1-(4-fluoro-2,6-dimethoxyphenyl)but-3-en-1-yl) acrylamide as a pale yellow oil. LC-MS (conditions A): $t_R$=1.00 min.; [M+H]⁺: 446.17 g/mol.

Step 6: Olefin Ring Closing Methathesis

A yellow solution of N-([1,1'-biphenyl]-3-ylmethyl)-N-(1-(4-fluoro-2,6-dimethoxyphenyl)but-3-en-1-yl)acrylamide (152 mg; 0.34 mmol; 1.0 equiv.) in anh. DCM (17 ml) was treated with titanium(IV) isopropoxide (0.20 ml; 0.68 mmol; 2.0 equiv.), and the mixture was heated to 50° C., under nitrogen, for 1 h. Benzylidene-bis(tricyclohexylphosphine) dichlororuthenium (11.3 mg; 0.04 equiv.) was then added, and the resulting mixture was further heated at reflux for 20 h. Subsequent concentration to dryness under reduced pressure, and purification by FC (DCM/MeOH=50/1) afforded 1-([1,1'-biphenyl]-3-ylmethyl)-6-(4-fluoro-2,6-dimethoxyphenyl)-5,6-dihydropyridin-2(1H)-one as a pale yellow foam. LC-MS (conditions A): $t_R$=0.94 min.; [M+H]⁺: 417.76 g/mol.

Step 7: hydrogenation of the dihydropyridinone derivative

A mixture of 1-([1,1'-biphenyl]-3-ylmethyl)-6-(4-fluoro-2,6-dimethoxyphenyl)-5,6-dihydropyridin-2(1H)-one (130 mg; 0.31 mmol; 1.0 equiv.), 10% Pd(C) (13 mg; 10% in mass) in anh. AcOEt (2 ml) was stirred at rt, under hydrogen atmosphere (1 atm), for 1 h. Filtration over a pad of celite, concentration to dryness under reduced pressure, and subsequent purification by preparative HPLC afforded 1-([1,1'-biphenyl]-3-ylmethyl)-6-(4-fluoro-2,6-dimethoxyphenyl)piperidin-2-one as a yellow solid. LC-MS (conditions A): $t_R$=0.94 min.; [M+H]⁺: 419.92 g/mol.

Reaction Conditions for the Hydrogenation of Sensitive Dihydropyridinone Derivatives:

The following reaction conditions are used in the case of sensitive substrates (e.g. derivatives containing chloro-substituted aromatic or heteroaromatic rings).

A mixture of dihydropyridinone derivative (1.0 mmol; 1.0 equiv.), zinc bromide (0.2 equiv.), 10% Pd(C) (10% in mass) in anh. AcOEt (6 ml) was stirred at rt, under hydrogen atmosphere (1 atm), for 17 h. Filtration over a pad of celite, concentration to dryness under reduced pressure, and subsequent purification by preparative HPLC afforded the target lactam derivative.

B.3.2 General Procedure 6 (GP6) for the Preparation of Example Compounds Via Olefin Ring-Closing Methathesis The sequence of reactions is described in scheme 6. The following general procedure (GP6) describes the conversion of an aldehyde derivative F1 into lactam derivatives F6 of formula (I). Imines F2 are obtained after condensation of aldehydes F1 with primary amines R¹CH(NH₂)R³. The target piperidin-2-ones F6 can be obtained after subsequent addition of allylmagnesium bromide, acylation with acryloyl chloride, olefin ring closing methathesis, and a final hydrogenation.

Step 1: Imine Formation

A mixture of the respective aldehyde derivative (1 mmol), amine derivative (1 mmol), and 4 Å molecular sieves (200 mg) in anh. THF (4 ml) was stirred at rt, under nitrogen, for 2 days (conversion monitored by LC-MS using the above described basic conditions C).

Step 2: Reaction of the Imine with Allylmagnesium Bromide

The previous cooled (0° C.) batches of imines (1.0 equiv.) in THF are treated dropwise with a solution of 1 M allylmagnesium bromide in Et₂O (1.1 equiv.). The resulting mixtures were then stirred at rt, under nitrogen, for 2 h. After successive addition of a solution of aq. sat. NH₄Cl and water, the resulting mixtures were extracted with Et₂O (3×). The mixed organic layers were dried over anh. MgSO₄, filtered, and concentrated to dryness under reduced pressure. Purification by FC (heptane/AcOEt=1/1) afforded the target secondary amines.

The remaining steps (acylation of the secondary amine with acryloyl chloride, olefin ring closing methathesis, and hydrogenation of the dihydropyridinone derivative) are as described for the general procedure 5 (GP5) in the section B.3.1.

B.4 General Procedure for the O-Alkylation of Phenol Derivatives

The following general procedure (GP7) describes the reaction of a phenol derivative with an electrophile in order to produce lactam derivatives of formula (I).

B.4.1 General Procedure 7 (GP7) for the O-Alkylation of Phenol Derivatives

A cooled (0° C.) mixture of phenol derivative (50 mg; 1.0 equiv.) and Cs₂CO₃ (1.3 equiv.) in anh. DMF (1 ml) was treated dropwise with a solution of the halogenated electrophile (bromo- or chloro-derivative; 3.0 equiv.) in anh. DMF (0.25 ml). The resulting mixture was further stirred at 0° C., under nitrogen, for 5 min., and was then heated to 90° C. for 3 h. After cooling to rt, the reaction mixture was filtered, and the filtrate was directly purified by preparative HPLC.

B.5 General Procedure for the C-Alkylation of Lactam Derivatives

The sequence of reactions is described in scheme 3. The following general procedure (GP8) describes the regioselective deprotonation of a lactam derivative C1 or C2, and the subsequent reaction with an electrophile in order to produce lactam derivatives C2 or C3 corresponding to compounds of formula (I).

B.5.1 General Procedure 8 (GP8) for the C-Alkylation of Lactam Derivatives

A cooled (−78° C.) solution of lactam derivative (100 mg; 1.0 equiv.) in anh. THF (2 ml) was treated dropwise with a solution of 1 M LHMDS in THF (3.0 equiv.). The resulting mixture was further stirred at −78° C., under nitrogen, for 15 min., and was treated dropwise with a solution of the appropriate electrophile (5.0 equiv.) in anh. THF (0.25 ml). The obtained mixture was then allowed to warm-up to rt over 30 min. In case of unsatisfying conversion, the reaction mixture was again cooled to −78° C., and treated successively with a solution of 1 M LHMDS in THF (3.0 equiv.), and with a solution of the appropriate electrophile (5.0 equiv.) in anh. THF (0.25 ml). The reaction mixture was allowed to warm-up to rt, and was finally quenched by dropwise addition of aq. sat. NH$_4$Cl (1 ml). Water was added, and the resulting mixture was extracted with AcOEt (3×). The mixed organic layers were dried over anh. MgSO$_4$, filtered, and concentrated to dryness under reduced pressure. Purification by preparative HPLC afforded the target compound.

B.6 General Procedure for the Preparation of Lactam Derivatives Via Suzuki Cross-Coupling Reaction Between Vinyl Phosphates and Boronic Acids The sequence of reactions is described in scheme 7. The following general procedure (GP9) describes the conversion of a piperidine-2,6-dione derivative G1 into lactam derivatives G5 of formula (I).

B.6.1 General Procedure 9 (GP9)

6-(2-ethoxyphenyl)-1-(4-(trifluoromethoxy)benzyl) piperidin-2-one (Example Compound 251)

Step 1: N-Alkylation of Piperidine-2,6-Dione Derivatives with Electrophiles 1-(4-(trifluoromethoxy)benzyl)piperidine-2,6-dione A cooled (0° C.) mixture of commercially available piperidine-2,6-dione (400 mg; 3.46 mmol; 1.0 equiv.) and KOH (213 mg; 3.81 mmol; 1.1 equiv.) in anh. DMF (3.5 ml) was stirred, under nitrogen, for 30 min., and was then treated with a solution of commercially available 1-(bromomethyl)-4-(trifluoromethoxy)benzene (956 mg; 3.63 mmol; 1.05 equiv.) in anh. DMF (1 ml). The resulting mixture was further stirred at rt, under nitrogen, for 3 days. Water was added, and the mixture was extracted with Et$_2$O (3×). The mixed organic layers were washed successively with 2 M aq. NaOH, aq. sat. NH$_4$Cl, and brine, dried over anh. MgSO$_4$, filtered, and concentrated to dryness under reduced pressure affording 1-(4-(trifluoromethoxy)benzyl)piperidine-2,6-dione as a colorless oil. LC-MS (conditions E): $t_R$=0.67 min.; no ionisation.

Step 2: Formation of Vinyl Phosphate Derivatives 6-oxo-1-(4-(trifluoromethoxy)benzyl)-1,4,5,6-tetrahydropyridin-2-yl diphenyl phosphate A cooled (0° C.) solution of 1 M LHMDS in THF (1.25 ml; 1.25 mmol; 1.2 equiv.) in anh. THF (2 ml) was treated dropwise with a solution of 1-(4-(trifluoromethoxy)benzyl)piperidine-2,6-dione (300 mg; 1.04 mmol; 1.0 equiv.) in anh. THF (2 ml), and the resulting mixture was stirred at rt, under nitrogen, for 1 h. The obtained mixture was cooled to −78° C., and treated with a solution of diphenyl phosphorochloridate (343 mg; 1.25 mmol; 1.2 equiv.) in anh. THF (1 ml). Stirring was continued at −78° C. for 10 min., and at rt for 1.5 h. A solution of 10% aq. NaOH (25 ml) was added, and the obtained mixture was extracted with Et$_2$O (3×). The mixed organic layers were dried over anh. K$_2$CO$_3$, filtered, and concentrated to dryness under reduced pressure affording 6-oxo-1-(4-(trifluoromethoxy)benzyl)-1,4,5,6-tetrahydropyridin-2-yl diphenyl phosphate as a yellow oil which was directly used for the next reaction. LC-MS (conditions E): $t_R$=0.84 min.; [M+H]$^+$: 520.19 g/mol.

Step 3: Suzuki Cross-Coupling Reaction Between Vinyl Phosphate Derivatives and Boronic Acids 6-(2-ethoxyphenyl)-1-(4-(trifluoromethoxy)benzyl)-3,4-dihydropyridin-2(1H)-one A mixture of 6-oxo-1-(4-(trifluoromethoxy)benzyl)-1,4,5,6-tetrahydropyridin-2-yl diphenyl phosphate (140 mg; 0.13 mmol; 1.0 equiv.), (2-ethoxyphenyl)boronic acid (34 mg; 0.20 mmol; 1.5 equiv.), PdCl$_2$(PPh$_3$)$_2$ (5 mg; 0.007 mmol; 0.05 equiv.), Na$_2$CO$_3$ (188 mg; 1.78 mmol; 13.2 equiv.) in THF (2 ml) and water (0.9 ml) was heated to 40° C., under nitrogen, for 1.5 h. After cooling to rt, water was added, and the mixture was extracted with Et$_2$O (3×). The mixed organic layers were dried over anh. K$_2$CO$_3$, filtered, and concentrated to dryness under reduced pressure. Purification by preparative HPLC afforded 6-(2-ethoxyphenyl)-1-(4-(trifluoromethoxy)benzyl)-3,4-dihydropyridin-2(1H)-one. LC-MS (conditions E): $t_R$=0.83 min.; [M+H]$^+$: 392.2 g/mol.

Step 4: Hydrogenation of dihydropyridin-2-one Derivatives 6-(2-ethoxyphenyl)-1-(4-(trifluoromethoxy)benzyl) piperidin-2-one A mixture of 6-(2-ethoxyphenyl)-1-(4-(trifluoromethoxy)benzyl)-3,4-dihydropyridin-2(1H)-one (11 mg; 0.028 mmol) and PtO$_2$ (10 mg) in anh. EtOH (1 ml), under hydrogen (60 bars), was heated to 50° C. for 17 h. After cooling to rt, the mixture was filtered over celite, and the filtrate was concentrated to dryness under reduced pressure affording 6-(2-ethoxyphenyl)-1-(4-(trifluoromethoxy)benzyl)piperidin-2-one. LC-MS (conditions E): $t_R$=0.82 min.; [M+H]$^+$: 394.22 g/mol.

B.7 General Procedures for the Specific Preparation of Substituted pyrrolidin-2-one Derivatives The sequence of reactions is described in schemes 8 and 9.

B.7.1.1 General Procedure 10A (GP10A) for the Preparation of pyrrolidine-2,3-dione Derivatives 5-(2,6-dimethoxyphenyl)-1-(4-(trifluoromethoxy) benzyl)pyrrolidine-2,3-dione A solution of commercially available (4-(trifluoromethoxy)phenyl)methanamine (11.858 g; 60.17 mmol) and commercially available 2,6-dimethoxybenzaldehyde (10.000 g; 60.17 mmol) in anh. EtOH (160 ml) was treated with diethyl oxalacetate sodium salt (13.312 g; 60.17 mmol). The resulting mixture was then refluxed, under nitrogen, for 8 h. After cooling to rt, the reaction mixture was concentrated to dryness under reduced pressure. DCM was added and the resulting heterogeneous mixture was washed with 1 M aq. HCl (2×), and with brine. The separated organic layer was then dried over anh. MgSO$_4$, filtered, and concentrated to dryness under reduced pressure. Purification by FC (DCM to DCM/MeOH=30/1) afforded ethyl 2-(2,6-dimethoxyphenyl)-4,5-dioxo-1-(4-(trifluoromethoxy)benzyl)pyrrolidine-3-carboxylate as an orange oil. LC-MS (conditions A): $t_R$=0.89 min.; [M+H]$^+$: 481.92 g/mol.

A mixture of ethyl 2-(2,6-dimethoxyphenyl)-4,5-dioxo-1-(4-(trifluoromethoxy)-benzyl)pyrrolidine-3-carboxylate (11.400 g; 23.68 mmol) and NaCl (2.767 g; 47.36 mmol) in DMSO (111 ml) and water (37 ml) was refluxed, under nitrogen, for 3 h. After cooling to rt, water (150 ml) was added, and the mixture was extracted with AcOEt (3×150 ml). The mixed organic layers were washed with brine (50 ml), dried over anh. MgSO$_4$, filtered, and concentrated to dryness under reduced pressure. Addition of Et$_2$O and trituration allowed the precipitation of the product. Subsequent filtration, and drying of the obtained solid under HV afforded 5-(2,6-dimethoxyphenyl)-1-(4-(trifluoromethoxy)benzyl)pyrrolidine-2,3-dione as a pink solid. LC-MS (conditions A): $t_R$=0.85 min.; [M+H]$^+$: 410.15 g/mol.

B.7.1.2 General Procedure 10A2 (GP100A2) for the Preparation of pyrrolidine-2,3-dione Derivatives 5-(2-fluoro-6-methoxyphenyl)-1-(4-(trifluoromethoxy)benzyl)pyrrolidine-2,3-dione A solution of commercially available (4-(trifluoromethoxy)phenyl)methanamine (2.557 g; 13.00 mmol), anh. copper(II) sulfate (3.107 g; 19.50 mmol) and commercially available 2-fluoro-6-methoxybenzaldehyde (2.000 g; 13.00 mmol) in anh. ethyl acetate (30 ml) was treated with diethyl oxalacetate sodium salt (3.444 g; 15.60 mmol).

The resulting heterogeneous mixture was then refluxed, under nitrogen, for 3 h. After cooling to rt, the reaction mixture was concentrated to dryness under reduced pressure. DCM (100 ml) was added and the resulting mixture was washed with 1 M aq. HCl (35 ml), with brine (35 ml), and with a solution of ammonium hydroxide (25% NH$_3$ in H$_2$O; 2×200 ml). The resulting organic layer was dried over anh. MgSO$_4$, filtered, and concentrated to dryness under reduced pressure. Purification by FC (DCM/MeOH=30/1) afforded ethyl 2-(2-fluoro-6-methoxyphenyl)-4,5-dioxo-1-(4-(trifluoromethoxy)benzyl)pyrrolidine-3-carboxylate as a beige solid. LC-MS (conditions A): $t_R$=0.89 min.; [M+H]$^+$: 470.12 g/mol.

A solution of ethyl 2-(2-fluoro-6-methoxyphenyl)-4,5-dioxo-1-(4-(trifluoromethoxy)benzyl)pyrrolidine-3-carboxylate (2.937 g; 6.26 mmol) in dioxane (13 ml) was treated with 25% hydrochloric acid (13 ml). The resulting mixture was then refluxed, under nitrogen, for 11 h. After cooling to rt, DCM and aq. sat. NaHCO$_3$ were added. The separated aqueous layer was further extracted with DCM. The mixed organic layers were washed with brine, dried over anh. MgSO$_4$, filtered, and concentrated to dryness under reduced pressure affording 5-(2-fluoro-6-methoxyphenyl)-1-(4-(trifluoromethoxy)benzyl)pyrrolidine-2,3-dione which was used for the next step without additional purification. LC-MS (conditions A): $t_R$=0.85 min.; [M+H]$^+$: 397.99 g/mol.

B.7.2 General Procedure 10B (GP10B) for the Preparation of 3-hydroxypyrrolidin-2-one Derivatives Via Selective Reduction of pyrrolidine-2,3-dione Derivatives rac-(3S*,5S*)-5-(2,6-dimethoxyphenyl)-3-hydroxy-1-(4-(trifluoromethoxy)benzyl)pyrrolidin-2-one (Example Compound 253)

A solution of 5-(2,6-dimethoxyphenyl)-1-(4-(trifluoromethoxy)benzyl)pyrrolidine-2,3-dione (1.514 g; 3.69 mmol) in anh. EtOH (20 ml) was treated with NaBH$_4$ (700 mg; 18.49 mmol), and the mixture was stirred at rt, under nitrogen, for 2 h. After concentration to dryness under reduced pressure, the resulting residue was treated with 1 M aq. HCl and with water. After extractions with DCM, the mixed organic layers were dried over anh. MgSO$_4$, filtered, and concentrated to dryness under reduced pressure affording rac-(3S*,5S*)-5-(2,6-dimethoxyphenyl)-3-hydroxy-1-(4-(trifluoromethoxy)benzyl)pyrrolidin-2-one as a colorless foam. LC-MS (conditions A): $t_R$=0.81 min.; [M+H]$^+$: 412.27 g/mol.

B.7.3 General Procedure 10C (GP10C) for the O-Alkylation of 3-hydroxypyrrolidin-2-one Derivatives rac-(3S*,5S*)-5-(2,6-dimethoxyphenyl)-3-methoxy-1-(4-(trifluoromethoxy)benzyl)pyrrolidin-2-one (Example Compound 254)

A cooled (0° C.) solution of rac-(3S*,5S*)-5-(2,6-dimethoxyphenyl)-3-hydroxy-1-(4-(trifluoromethoxy)benzyl)pyrrolidin-2-one (53 mg; 0.12 mmol) in anh. THF (3 ml) was treated with NaH (60% dispersion in mineral oil; 6 mg; 0.14 mmol). Stirring was continued at 0° C., under nitrogen, for 5 min., and then at rt for 20 min. The mixture was again cooled to 0° C., and a solution of CH$_3$I (20 mg; 0.14 mmol) in anh. THF (1 ml) was added. The obtained mixture was further stirred at 0° C. for 5 min., and then at rt for 17 h. Water and AcOEt were added, and the separated aq. layer was further extracted with AcOEt. The mixed organic layers were dried over anh. MgSO$_4$, filtered, and concentrated to dryness under reduced pressure. Purification by FC (DCM/MeOH=30/1) afforded rac-(3S*,5S*)-5-(2,6-dimethoxyphenyl)-3-methoxy-1-(4-(trifluoromethoxy)benzyl)pyrrolidin-2-one as a yellow oil. LC-MS (conditions A): $t_R$=0.88 min.; [M+H]$^+$: 426.19 g/mol.

B.7.4 General Procedure 10D (GP10D) for the Conversion of 3-hydroxypyrrolidin-2-one derivatives into 3-chloropyrrolidin-2-one Derivatives rac-(3R*,5S*)-3-chloro-5-(2,6-dimethoxyphenyl)-1-(4-(trifluoromethoxy)benzyl)pyrrolidin-2-one (Example Compound 257)

A solution of rac-(3S*,5S*)-5-(2,6-dimethoxyphenyl)-3-hydroxy-1-(4-(trifluoromethoxy)-benzyl)pyrrolidin-2-one (200 mg; 0.48 mmol) in dioxane (1 ml) was treated at rt successively with SOCl$_2$ (69 mg; 0.58 mmol) and pyridine (46 mg; 0.58 mmol). The resulting mixture was then heated to 80° C. for 3 h. After cooling to rt, the mixture was concentrated under reduced pressure before water and AcOEt were added. The separated organic layer was washed with brine, dried over anh. MgSO$_4$, filtered, and concentrated to dryness under reduced pressure. Purification by FC (DCM/MeOH=50/1) afforded rac-(3R*,5S*)-3-chloro-5-(2,6-dimethoxyphenyl)-1-(4-(trifluoromethoxy)benzyl)pyrrolidin-2-one as a pale yellow solid. LC-MS (conditions A): $t_R$=0.95 min.; [M+H]$^+$: 430.20 g/mol.

B.7.5 General procedure 10E (GP10E) for the conversion of 3-hydroxypyrrolidin-2-one derivatives into 3-methylpyrrolidin-2-one derivatives rac-(3R*,5S*)-5-(2,6-dimethoxyphenyl)-3-methyl-1-(4-(trifluoromethoxy)benzyl)pyrrolidin-2-one (Example Compound 264)

A mixture of rac-(3S*,5S*)-5-(2,6-dimethoxyphenyl)-3-hydroxy-1-(4-(trifluoromethoxy)benzyl)-pyrrolidin-2-one (100 mg; 0.24 mmol), commercially available 4-methylbenzene-1-sulfonyl chloride (51 mg; 0.26 mmol), NEt$_3$ (28 mg; 0.28 mmol), and DMAP (32 mg; 0.26 mmol) in anh. DCM (2 ml) was stirred at rt, under nitrogen, for 4 h. Water was added, and the mixture was extracted with DCM. The mixed organic layers were dried over anh. MgSO$_4$, filtered, and concentrated to dryness under reduced pressure affording the tosylates rac-(3S,5S)-5-(2,6-dimethoxyphenyl)-2-oxo-1-(4-(trifluoromethoxy)benzyl)pyrrolidin-3-yl 4-methylbenzenesulfonate.

A cooled (0° C.) mixture of copper(I) iodide CuI (277 mg; 1.45 mmol) in anh. THF (1.5 ml) was treated dropwise with a solution of methyllithium-lithium bromide complex (1.5 M in Et$_2$O; 1.94 ml; 2.91 mmol). This mixture was then cooled to −78° C., and treated with a solution of the prepared tosylates rac-(3S,5S)-5-(2,6-dimethoxyphenyl)-2-oxo-1-(4-(trifluoromethoxy)benzyl)pyrrolidin-3-yl 4-methylbenzenesulfonate (0.24 mmol) in anh. THF (0.5 ml). The resulting mixture was then stirred at −20° C., under nitrogen, for 1 h, and then at rt for 17 h. Aq. sat. NH$_4$Cl and AcOEt were added, and the organic layer was washed with 25% aq. NH$_4$OH, dried over anh. MgSO$_4$, filtered, and concentrated to dryness under reduced pressure. Purification by FC (DCM/MeOH=30/1) afforded rac-(3R*,5S*)-5-(2,6-dimethoxyphenyl)-3-methyl-1-(4-(trifluoromethoxy)benzyl)pyrrolidin-2-one as a colorless oil. LC-MS (conditions A): $t_R$=0.94 min.; [M+H]$^+$: 410.32 g/mol.

B.7.6 General Procedure 10F (GP100F) for the Inversion of Configuration of 3-hydroxypyrrolidin-2-one Derivatives Via Mitsunobu Reaction rac-(3R*,5S*)-5-(2,6-dimethoxyphenyl)-3-hydroxy-1-(4-(trifluoromethoxy)benzyl)pyrrolidin-2-one (Example Compound 258)

A cooled (0° C.) mixture of rac-(3S*,5S*)-5-(2,6-dimethoxyphenyl)-3-hydroxy-1-(4-(trifluoromethoxy)benzyl)pyrrolidin-2-one (1.260 g; 3.06 mmol), 4-nitrobenzoic acid (1.023 g; 6.12 mmol), and PPh$_3$ (1.767 g; 6.73 mmol) in anh. THF (50 ml) was treated dropwise with a solution of DEAD (1.173 g; 6.73 mmol) in anh. THF (10 ml). The resulting mixture was further stirred at 0° C., under nitrogen, for 5 min., and then at rt for 4 h. Concentration to dryness under reduced pressure, and subsequent purification by FC (toluene/AcOEt=5/1) afforded rac-(3R*,5S*)-5-(2,6-dimethoxyphenyl)-2-oxo-1-(4-(trifluoromethoxy)-benzyl)-pyrrolidin-3-yl 4-nitrobenzoate as a colorless solid. LC-MS (conditions A): $t_R$=1.02 min.; [M+H]$^+$: 561.17 g/mol.

A mixture of rac-(3R*,5S*)-5-(2,6-dimethoxyphenyl)-2-oxo-1-(4-(trifluoromethoxy)-benzyl)pyrrolidin-3-yl 4-nitrobenzoate (1.600 g; 2.85 mmol), and K$_2$CO$_3$ (789 mg; 5.70 mmol) in anh. MeOH (50 ml) was stirred at rt, under nitrogen, for 30 min. Water was added, and the resulting mixture was extracted with Et$_2$O. The mixed organic layers were dried over anh. MgSO$_4$, filtered, and concentrated to dryness under reduced pressure.

Purification by FC (AcOEt) afforded rac-(3R*,5S*)-5-(2,6-dimethoxyphenyl)-3-hydroxy-1-(4-(trifluoromethoxy)-benzyl)-pyrrolidin-2-one as a colorless solid. LC-MS (conditions A): $t_R$=0.80 min.; [M+H]$^+$: 412.10 g/mol.

B.7.7 General Procedure 10G (GP10G) for the Fluorination of Pyrrolidine-2,3-dione Derivatives 5-(2,6-dimethoxyphenyl)-3,3-difluoro-1-(4-(trifluoromethoxy)benzyl)pyrrolidin-2-one (Example Compound 256)

A cooled (0° C.) mixture of 5-(2,6-dimethoxyphenyl)-1-(4-(trifluoromethoxy)benzyl)pyrrolidine-2,3-dione (100 mg; 0.24 mmol) in anh. DCM (1 ml) was treated dropwise with Deoxo-Fluor (162 mg; 0.73 mmol). The resulting mixture was allowed to warm-up to rt, and was then heated to 40° C. for 17 h. Aq. sat. NaHCO$_3$ (10 ml) was added, and the mixture was extracted with DCM (3×10 ml). The mixed organic layers were dried over anh. MgSO$_4$, filtered, and concentrated to dryness under reduced pressure. Subsequent purification by preparative HPLC afforded 5-(2,6-dimethoxyphenyl)-3,3-difluoro-1-(4-(trifluoromethoxy)benzyl)pyrrolidin-2-one as a brown oil. LC-MS (conditions A): $t_R$=0.96 min.; [M+H]$^+$: 432.22 g/mol.

B.7.8 General Procedure 10H (GP10H) for the Conversion of pyrrolidine-2,3-dione Derivatives into 3-alkylpyrrolidin-2-one Derivatives Via Wittig Olefination and Subsequent Hydrogenation rac-(3S*,5S*)-5-(2,6-dimethoxyphenyl)-3-methyl-1-(4-(trifluoromethoxy)benzyl)pyrrolidin-2-one (Example Compound 259)

A cooled (−78° C.) mixture of methyltriphenylphosphonium bromide (754 mg; 2.11 mmol) in anh. THF (6 ml) was treated dropwise with a solution of n-BuLi (1.6 M in hexanes; 1.32 ml; 2.11 mmol). Stirring was then continued at rt, under nitrogen, for 30 min. The resulting mixture was then cooled to 0° C., and treated with a solution of 5-(2,6-dimethoxyphenyl)-1-(4-(trifluoromethoxy)-benzyl)pyrrolidine-2,3-dione (800 mg; 1.95 mmol) in anh. THF (4 ml). Stirring was continued at 0° C. for 25 min., and at 60° C. for 1 h. After cooling to rt, aq. sat. NH$_4$Cl (25 ml) was added, and this mixture was extracted with AcOEt (3×50 ml). The mixed organic layers were dried over anh. MgSO$_4$, filtered, and concentrated to dryness under reduced pressure. Purification by FC (DCM/MeOH=30/1) afforded rac-(S*)-5-(2,6-dimethoxyphenyl)-3-methylene-1-(4-(trifluoromethoxy)benzyl)pyrrolidin-2-one as a colorless oil. LC-MS (conditions A): $t_R$=0.93 min.; [M+H]$^+$: 408.29 g/mol.

A mixture of rac-(S*)-5-(2,6-dimethoxyphenyl)-3-methylene-1-(4-(trifluoromethoxy)-benzyl)pyrrolidin-2-one (310 mg; 0.76 mmol), and 10% Pd(C) (62 mg; 20% in mass) in anh. MeOH (3 ml) was stirred at rt, under hydrogen atmosphere (1 atm), for 60 h. Filtration over a pad of celite, concentration to dryness under reduced pressure, and subsequent purification by FC (DCM/MeOH=30/1) afforded rac-(3S*,5S*)-5-(2,6-dimethoxyphenyl)-3-methyl-1-(4-(trifluoromethoxy)-benzyl)pyrrolidin-2-one as an orange oil. LC-MS (conditions A): $t_R$=0.94 min.; [M+H]$^+$: 410.27 g/mol.

B.7.9 General Procedure 10I (GP10I) for the Fluorination of 3-hydroxypyrrolidin-2-one derivatives rac-(3S*,5S*)-5-(2,6-dimethoxyphenyl)-3-fluoro-1-(4-(trifluoromethoxy)benzyl)pyrrolidin-2-one (Example Compound 260)

A cooled (−78° C.) mixture of DAST (117 mg; 0.72 mmol) in anh. DCM (0.5 ml) was treated dropwise with a solution of rac-(3R*,5S*)-5-(2,6-dimethoxyphenyl)-3-hydroxy-1-(4-(trifluoromethoxy)benzyl)-pyrrolidin-2-one (100 mg; 0.24 mmol) in anh. DCM (0.5 ml). The resulting mixture was further stirred at −78° C., under nitrogen, for 1 h, at 0° C. for 30 min., and finally at rt for 1 h. Aq. sat. NaHCO$_3$ was added, and the resulting mixture was extracted with DCM. The mixed organic layers were dried over anh. MgSO$_4$, filtered, and concentrated to dryness under reduced pressure. Purification by preparative HPLC afforded rac-(3S*,5S*)-5-(2,6-dimethoxyphenyl)-3-fluoro-1-(4-(trifluoromethoxy)benzyl)pyrrolidin-2-one as a colorless solid. LC-MS (conditions A): t$_R$=0.90 min.; [M+H]$^+$: 414.12 g/mol.

B.8 General Procedures (GP11A, GP11B, and GP11C) for the Preparation of Substituted piperazin-2-one Derivatives The sequence of reactions is described in scheme 10.

6-(2,6-dimethoxyphenyl)-1-(4-(trifluoromethoxy)benzyl)piperazin-2-one (Example Compound 267)

Steps 1 to 3: Preparation of the Substituted Amino Acid (General Procedure 11A)

A mixture of ethyl 2-oxoacetate (50% solution in toluene; 4.066 g; 20.00 mmol), 2-methylpropane-2-sulfinamide (2.424 g; 20.00 mmol), and 4 angstrom molecular sieves (60 g) in anh. DCM (250 ml) was stirred at rt, under nitrogen, for 65 h. The reaction mixture was then filtered over celite, and the separated solids were washed with AcOEt (3×200 ml). The filtrate was then dried over anh. MgSO$_4$, filtered, and concentrated to dryness under reduced pressure affording ethyl 2-((tert-butylsulfinyl)imino)acetate as a yellow oil.

A cooled (−78° C.) solution of 2-iodo-1,3-dimethoxybenzene (4.119 g; 15.13 mmol) in anh. THF (40 ml) was treated dropwise with a solution of 1.6 M n-BuLi in hexanes (10.40 ml; 16.64 mmol), and the resulting mixture was stirred at −78° C., under nitrogen, for 10 min. A solution of ethyl 2-((tert-butylsulfinyl)imino)acetate (3.106 g; 15.13 mmol) in anh. THF (20 ml) was added dropwise, and stirring at −78° C. was then continued for 25 min. The reaction mixture was treated with aq. sat. NH$_4$Cl (30 ml), water (40 ml), and Et$_2$O (60 ml). The separated aq. layer was extracted with Et$_2$O (2×50 ml), and the mixed organic layers were washed with brine (40 ml), dried over anh. MgSO$_4$, filtered, and concentrated to dryness under reduced pressure. Purification by FC (DCM/MeOH=20/1) afforded ethyl 2-(2,6-dimethoxyphenyl)-2-(1,1-dimethylethylsulfinamido)acetate as a yellow oil. LC-MS (conditions D): t$_R$=0.91 min.; [M+H]$^+$: 344.45 g/mol.

A cooled (0° C.) solution of ethyl 2-(2,6-dimethoxyphenyl)-2-(1,1-dimethylethylsulfinamido)-acetate (4.215 g; 12.27 mmol) in anh. MeOH (120 ml) was treated dropwise with a solution of 4 M HCl in dioxane (6.30 ml; 25.20 mmol). The resulting heterogeneous mixture was further stirred at 0° C., under nitrogen, for 10 min., and then at rt for 1 h. Concentration to dryness under reduced pressure afforded the chlorhydrate salt of ethyl 2-amino-2-(2,6-dimethoxyphenyl)acetate as a yellow oil. LC-MS (conditions D): t$_R$=0.66 min.; [M+H]$^+$: 240.40 g/mol.

Steps 4 to 6: Preparation of the Substituted piperazine-2,5-dione (General Procedure 11B)

A mixture of the chlorhydrate salt of ethyl 2-amino-2-(2,6-dimethoxyphenyl)acetate (8.43 mmol), commercially available 4-(trifluoromethoxy)benzaldehyde (1.603 g; 8.43 mmol), DIPEA (2.179 g; 16.86 mmol), NaBH(OAc)$_3$ (2.633 g; 11.80 mmol), and acetic acid (506 mg; 8.43 mmol) in anh. DCE (9 ml) was stirred at rt, under nitrogen, for 16 h. 1 M aq. NaOH (17 ml) was added, and the separated aq. layer was further extracted with DCM (3×50 ml). The mixed organic layers were then dried over anh. MgSO$_4$, filtered, and concentrated to dryness under reduced pressure. Purification by FC (DCM/MeOH=25/1) afforded ethyl 2-(2,6-dimethoxyphenyl)-2-((4-(trifluoromethoxy)benzyl)amino)acetate. LC-MS (conditions D): t$_R$=0.92 min.; [M+H]$^+$: 414.05 g/mol.

A mixture of ethyl 2-(2,6-dimethoxyphenyl)-2-((4-(trifluoromethoxy)benzyl)-amino)acetate (1.121 g; 2.71 mmol), 2-(tert-butoxycarbonylamino)acetic acid (1.187 g; 6.77 mmol), DIPEA (1.752 g; 13.55 mmol), and HATU (2.577 g; 6.77 mmol) in anh. DMF (20 ml) was stirred at rt, under nitrogen, for 18 h. Et$_2$O (20 ml) and water (20 ml) were then added to the reaction mixture, and the separated aq. layer was further extracted with Et$_2$O (3×50 ml). The mixed organic layers were washed with brine (50 ml), dried over anh. MgSO$_4$, filtered, and concentrated to dryness under reduced pressure. Purification by FC (DCM/MeOH=50/1) afforded ethyl 2-(2-((tert-butoxycarbonyl)amino)-N-(4-(trifluoromethoxy)benzyl)acetamido)-2-(2,6-dimethoxyphenyl)acetate as a yellow oil. LC-MS (conditions D): t$_R$=1.12 min.; [M+H]$^+$: 571.78 g/mol.

A cooled (0° C.) solution of ethyl 2-(2-((tert-butoxycarbonyl)amino)-N-(4-(trifluoromethoxy)-benzyl)acetamido)-2-(2,6-dimethoxyphenyl)acetate (900 mg; 1.57 mmol) in anh. DCM (18 ml) was treated dropwise with 4 M HCl in dioxane (6.00 ml; 24.00 mmol), and the resulting mixture was further stirred at rt, under nitrogen, for 2.5 h. The reaction mixture was concentrated to dryness under reduced pressure, the resulting residue was treated with aq. sat. NaHCO$_3$ (7.5 ml) and AcOEt (7.5 ml), and stirring at rt was then continued for 17 h. The separated aq. layer was extracted with AcOEt (20 ml), and the mixed organic layers were washed with brine, dried over anh. MgSO$_4$, filtered, and concentrated to dryness under reduced pressure affording 6-(2,6-dimethoxyphenyl)-1-(4-(trifluoromethoxy)benzyl)-piperazine-2,5-dione as a slightly orange solid. LC-MS (conditions D): t$_R$=0.94 min.; [M+H]$^+$: 424.88 g/mol.

Steps 7 to 9: Conversion of the Substituted piperazine-2,5-dione into the Substituted piperazin-2-one (General Procedure 11C)

A mixture of 6-(2,6-dimethoxyphenyl)-1-(4-(trifluoromethoxy)benzyl)piperazine-2,5-dione (634 mg; 1.49 mmol), Boc$_2$O (366 mg; 1.64 mmol), DMAP (36 mg; 0.29 mmol) in anh. MeCN (10 ml) was stirred at rt, under nitrogen, for 3 h. AcOEt (100 ml) was added, and the mixture was successively washed with 0.5 M aq. HCl (40 ml), aq. sat. NaHCO$_3$ (40 ml), and brine (40 ml). The organic layer was dried over anh. MgSO$_4$, filtered, and concentrated to dryness under reduced pressure affording tert-butyl 3-(2,6-dimethoxyphenyl)-2,5-dioxo-4-(4-(trifluoromethoxy)benzyl)-piperazine-1-carboxylate as a slightly yellow oil (768 mg; 98%). LC-MS (conditions D): t$_R$=1.09 min.; [M+H]$^+$: 524.89 g/mol.

A cooled (0° C.) solution of tert-butyl 3-(2,6-dimethoxyphenyl)-2,5-dioxo-4-(4-(trifluoromethoxy)benzyl)piperazine-1-carboxylate (718 mg; 1.36 mmol) in anh. MeOH (15 ml) was treated with NaBH$_4$ (221 mg; 5.47 mmol), and stirring at 0° C., under nitrogen, was continued for 30 min. After concentration to dryness under reduced pressure, the residue was dissolved in AcOEt, and washed successively with 1 M aq. HCl and brine. The separated aq. layer was further extracted with AcOEt (3×10 ml), and the mixed organic layers were dried over anh. MgSO$_4$, filtered, and concentrated to dryness under reduced pressure. Acetic acid (20 ml) was added, and the cooled (0° C.) mixture was then treated portionwise with NaBH$_3$CN (516 mg; 8.21 mmol). The resulting mixture was further stirred at rt, under nitrogen, for 1 h. DCM and aq. sat. Na$_2$CO$_3$ were then added, and the separated aq. layer was further extracted with DCM. The mixed organic layers were then dried over anh. MgSO$_4$, filtered, and concentrated to dryness under reduced pressure. Purification by FC (DCM/MeOH=25/1) afforded tert-butyl 3-(2,6-dimethoxyphenyl)-5-oxo-4-(4-(trifluoromethoxy)benzyl)piperazine-1-carboxylate as an orange oil. LC-MS (conditions D): t$_R$=1.12 min.; [M+H]$^+$: 511.01 g/mol.

A cooled (0° C.) solution of tert-butyl 3-(2,6-dimethoxyphenyl)-5-oxo-4-(4-(trifluoromethoxy)-benzyl)piperazine-1-carboxylate (540 mg; 1.05 mmol) in anh. DCM (10 ml) was treated dropwise with 4 M HCl in dioxane (4.00 ml; 16.00 mmol), and the resulting mixture was further stirred at rt, under nitrogen, for 16 h. The reaction mixture was concentrated to dryness under reduced pressure, the resulting residue was dissolved in DCM, and washed successively with 1 M aq. NaOH, aq. sat. NaHCO$_3$, and brine. The organic layer was dried over anh. MgSO$_4$, filtered, and concentrated to dryness under reduced pressure. Purification by FC (DCM/MeOH=10/1) afforded 6-(2,6-dimethoxyphenyl)-1-(4-(trifluoromethoxy)benzyl)piperazin-2-one as an orange oil. LC-MS (conditions D): t$_R$=0.85 min.; [M+H]$^+$: 411.13 g/mol.

B.9 General Procedure 12 (GP12) for the Preparation of Substituted morpholin-3-one Derivatives The sequence of reactions is described in scheme 11.

5-(2,6-dimethoxyphenyl)-4-(4-(trifluoromethoxy)benzyl)morpholin-3-one (Example Compound 266)

Steps 1 to 3: Preparation of the Substituted Amino Acid

A mixture of ethyl 2-oxoacetate (50% solution in toluene; 4.066 g; 20.00 mmol), 2-methylpropane-2-sulfinamide (2.424 g; 20.00 mmol), and 4 angstrom molecular sieves (60 g) in anh. DCM (250 ml) was stirred at rt, under nitrogen, for 65 h. The reaction mixture was then filtered over celite, and the separated solids were washed with AcOEt (3×200 ml). The filtrate was then dried over anh. MgSO$_4$, filtered, and concentrated to dryness under reduced pressure affording ethyl 2-((tert-butylsulfinyl)imino)acetate as a yellow oil.

A cooled (−78° C.) solution of 2-iodo-1,3-dimethoxybenzene (4.119 g; 15.13 mmol) in anh. THF (40 ml) was treated dropwise with a solution of 1.6 M n-BuLi in hexanes (10.40 ml; 16.64 mmol), and the resulting mixture was stirred at −78° C., under nitrogen, for 10 min. A solution of ethyl 2-((tert-butylsulfinyl)imino)acetate (3.106 g; 15.13 mmol) in anh. THF (20 ml) was added dropwise, and stirring at −78° C. was then continued for 25 min. The reaction mixture was treated with aq. sat. NH$_4$Cl (30 ml), water (40 ml), and Et$_2$O (60 ml). The separated aq. layer was extracted with Et$_2$O (2×50 ml), and the mixed organic layers were washed with brine (40 ml), dried over anh. MgSO$_4$, filtered, and concentrated to dryness under reduced pressure. Purification by FC (DCM/MeOH=20/1) afforded ethyl 2-(2,6-dimethoxyphenyl)-2-(1,1-dimethylethylsulfinamido)acetate as a yellow oil. LC-MS (conditions D): t$_R$=0.91 min.; [M+H]$^+$: 344.45 g/mol.

A cooled (0° C.) solution of ethyl 2-(2,6-dimethoxyphenyl)-2-(1,1-dimethylethylsulfinamido) acetate (4.215 g; 12.27 mmol) in anh. MeOH (120 ml) was treated dropwise with a solution of 4 M HCl in dioxane (6.30 ml; 25.20 mmol). The resulting heterogeneous mixture was further stirred at 0° C., under nitrogen, for 10 min., and then at rt for 1 h. Concentration to dryness under reduced pressure afforded the chlorhydrate salt of ethyl 2-amino-2-(2,6-dimethoxyphenyl)acetate as a yellow oil. LC-MS (conditions D): t$_R$=0.66 min.; [M+H]$^+$: 240.40 g/mol.

Steps 4 to 7: Preparation of the Substituted morpholin-3-one Derivative

A mixture of the chlorhydrate salt of ethyl 2-amino-2-(2,6-dimethoxyphenyl)acetate (8.43 mmol), 4-(trifluoromethoxy)benzaldehyde (1.603 g; 8.43 mmol), DIPEA (2.179 g; 16.86 mmol), NaBH(OAc)$_3$ (2.633 g; 11.80 mmol), and acetic acid (506 mg; 8.43 mmol) in anh. DCE (9 ml) was stirred at rt, under nitrogen, for 16 h. 1 M aq. NaOH (17 ml) was added, and the separated aq. layer was further extracted with DCM (3×50 ml). The mixed organic layers were then dried over anh. MgSO$_4$, filtered, and concentrated to dryness under reduced pressure. Purification by FC (DCM/MeOH=25/1) afforded ethyl 2-(2,6-dimethoxyphenyl)-2-((4-(trifluoromethoxy)benzyl)amino)acetate. LC-MS (conditions D): t$_R$=0.92 min.; [M+H]$^+$: 414.05 g/mol.

A cooled (0° C.) mixture of LiAlH$_4$ (6 mg; 0.15 mmol) in anh. THF (1 ml) was treated dropwise with a solution of ethyl 2-(2,6-dimethoxyphenyl)-2-((4-(trifluoromethoxy)benzyl)amino)acetate (65 mg; 0.15 mmol) in anh. THF (1 ml). The resulting mixture was further stirred at rt, under nitrogen, for 1 h. Water (6 µl), 15% aq. NaOH (6 µl), and water (18 µl) were then successively added, and the heterogeneous mixture was filtered. The filtrate was concentrated to dryness under reduced pressure, and the oily residue was further dried under HV affording 2-(2,6-dimethoxyphenyl)-2-((4-(trifluoromethoxy)benzyl)-amino)ethanol as a yellow oil. LC-MS (conditions E): t$_R$=0.59 min.; [M+H]$^+$: 372.10 g/mol.

A cooled (−10° C.) mixture of 2-(2,6-dimethoxyphenyl)-2-((4-(trifluoromethoxy)benzyl)-amino)ethanol (32 mg; 0.08 mmol) and NaOH (7 mg; 0.17 mmol) in DCM (1 ml) and water (0.5 ml) was treated with 2-chloroacetyl chloride (12 mg; 0.10 mmol). The resulting mixture was further stirred at −10° C., under nitrogen, for 15 min. Water and DCM were added, and the separated aq. layer was further extracted with DCM. The mixed organic layers were washed with brine, dried over anh. MgSO$_4$, filtered, and concentrated to dryness under reduced pressure affording 2-chloro-N-(1-(2,6-dimethoxyphenyl)-2-hydroxyethyl)-N-(4-(trifluoromethoxy)benzyl)-acetamide as a yellow oil. LC-MS (conditions E): t$_R$=0.75 min.; [M+H]$^+$: 447.98 g/mol.

A cooled (−25° C.) mixture of NaH (60% dispersion in mineral oil; 1 mg; 0.025 mmol) in anh. DMF (1 ml) was treated with a solution of 2-chloro-N-(1-(2,6-dimethoxyphenyl)-2-hydroxyethyl)-N-(4-(trifluoromethoxy)benzyl)acetamide (10 mg; 0.022 mmol) in anh. DMF (1 ml). The resulting mixture was further stirred at rt, under nitrogen, for 30 min. The mixture was then filtered, and the obtained filtrate was directly purified by preparative HPLC affording 5-(2,6-dimethoxyphenyl)-4-(4-(trifluoromethoxy)benzyl)-morpholin-3-one as a yellow oil. LC-MS (conditions E): t$_R$=0.79 min.; [M+H]$^+$: 412.06 g/mol.

C. Synthesis of Example Compounds

If not explicitly stated otherwise, all example compounds have been synthesized in racemic form.

Example 1

6-(2,6-dimethoxyphenyl)-1-(quinolin-3-ylmethyl)piperidin-2-one

Prepared according to the described general procedure 1 (GP1) by reaction of methyl 5-amino-5-(2,6-dimethoxyphenyl)pentanoate with commercially available quinoline-3-carbaldehyde. Subsequent purification by preparative HPLC afforded the target compound. LC-MS (conditions B): $t_R$=0.68 min.; [M+H]$^+$: 377.36 g/mol.

Example 2

6-(2,6-dimethoxyphenyl)-1-((2-methylbenzo[d]thiazol-5-yl)methyl)piperidin-2-one

Prepared according to the described general procedure 1 (GP1) by reaction of methyl 5-amino-5-(2,6-dimethoxyphenyl)pentanoate with 2-methylbenzo[d]thiazole-5-carbaldehyde. Subsequent purification by preparative HPLC afforded the target compound. LC-MS (conditions A): $t_R$=0.78 min.; [M+H]$^+$: 397.01 g/mol.

Example 3

6-(2,6-dimethoxyphenyl)-1-(quinolin-6-ylmethyl)piperidin-2-one

Prepared according to the described general procedure 1 (GP1) by reaction of methyl 5-amino-5-(2,6-dimethoxyphenyl)pentanoate with commercially available quinoline-6-carbaldehyde. Subsequent purification by preparative HPLC afforded the target compound. LC-MS (conditions A): $t_R$=0.56 min.; [M+H]$^+$: 377.15 g/mol.

Example 4

6-(2,6-dimethoxyphenyl)-1-(quinolin-2-ylmethyl)piperidin-2-one

Prepared according to the described general procedure 1 (GP1) by reaction of methyl 5-amino-5-(2,6-dimethoxyphenyl)pentanoate with commercially available quinoline-2-carbaldehyde. Subsequent purification by preparative HPLC afforded the target compound. LC-MS (conditions A): $t_R$=0.59 min.; [M+H]$^+$: 377.18 g/mol.

The two enantiomers were then separated by HPLC using a chiral column (see conditions described above):!
(R)-6-(2,6-dimethoxyphenyl)-1-(quinolin-2-ylmethyl)piperidin-2-one and
(S)-6-(2,6-dimethoxyphenyl)-1-(quinolin-2-ylmethyl)piperidin-2-one

Example 4a

Enantiomer 1 retention time 5.66 min.

Example 4b

Enantiomer 2 retention time 7.79 min.

Example 5

1-((5-chloro-6-(difluoromethoxy)pyridin-3-yl)methyl)-6-(2,6-dimethoxyphenyl)piperidin-2-one Prepared according to the described general procedure 1 (GP1) by reaction of methyl 5-amino-5-(2,6-dimethoxyphenyl)pentanoate with 5-chloro-6-(difluoromethoxy)-nicotinaldehyde. Subsequent purification by preparative HPLC afforded the target compound. LC-MS (conditions A): $t_R$=0.88 min.; [M+H]$^+$: 427.28 g/mol.

Example 6

6-(2,6-dimethoxyphenyl)-1-((6-(4-fluorophenyl)pyridin-2-yl)methyl)piperidin-2-one Prepared according to the described general procedure 1 (GP1) by reaction of methyl 5-amino-5-(2,6-dimethoxyphenyl)pentanoate with commercially available 6-(4-fluorophenyl)picolinaldehyde. Subsequent purification by preparative HPLC afforded the target compound. LC-MS (conditions A): $t_R$=0.77 min.; [M+H]$^+$: 421.35 g/mol.

Example 7

6-(2,6-dimethoxyphenyl)-1-(3-(pyridin-3-yl)benzyl)piperidin-2-one

Prepared according to the described general procedure 1 (GP1) by reaction of methyl 5-amino-5-(2,6-dimethoxyphenyl)pentanoate with commercially available 3-(pyridin-3-yl)benzaldehyde. Subsequent purification by preparative HPLC afforded the target compound. LC-MS (conditions A): $t_R$=0.60 min.; [M+H]$^+$: 403.35 g/mol.

Example 8

6-(2,6-dimethoxyphenyl)-1-((5-phenylpyridin-3-yl)methyl)piperidin-2-one

Prepared according to the described general procedure 1 (GP1) by reaction of methyl 5-amino-5-(2,6-dimethoxyphenyl)pentanoate with 5-phenylnicotinaldehyde. Subsequent purification by preparative HPLC afforded the target compound. LC-MS (conditions A): $t_R$=0.64 min.; [M+H]$^+$: 403.36 g/mol.

Example 9

6-(2,6-dimethoxyphenyl)-1-(3-(pyridin-4-yl)benzyl)piperidin-2-one

Prepared according to the described general procedure 1 (GP1) by reaction of methyl 5-amino-5-(2,6-dimethoxyphenyl)pentanoate with commercially available 3-(pyridin-4-yl)benzaldehyde. Subsequent purification by preparative HPLC afforded the target compound. LC-MS (conditions A): $t_R$=0.59 min.; [M+H]$^+$: 403.35 g/mol.

Example 10

6-(2,6-dimethoxyphenyl)-1-(3-(pyridin-2-yl)benzyl)piperidin-2-one

Prepared according to the described general procedure 1 (GP1) by reaction of methyl 5-amino-5-(2,6-dimethoxyphenyl)pentanoate with commercially available 3-(pyridin-2-yl) benzaldehyde. Subsequent purification by preparative HPLC afforded the target compound. LC-MS (conditions A): $t_R$=0.62 min.; [M+H]$^+$: 403.37 g/mol.

Example 11

6-(2,6-dimethoxyphenyl)-1-((6-phenylpyridin-2-yl) methyl)piperidin-2-one

Prepared according to the described general procedure 1 (GP1) by reaction of methyl 5-amino-5-(2,6-dimethoxyphenyl)pentanoate with 6-phenylpicolinaldehyde. Subsequent purification by preparative HPLC afforded the target compound. LC-MS (conditions A): $t_R$=0.72 min.; [M+H]$^+$: 403.01 g/mol.

Example 12

6-(2,6-dimethoxyphenyl)-1-((2-phenylpyridin-4-yl) methyl)piperidin-2-one

Prepared according to the described general procedure 1 (GP1) by reaction of methyl 5-amino-5-(2,6-dimethoxyphenyl)pentanoate with 2-phenylisonicotinaldehyde. Subsequent purification by preparative HPLC afforded the target compound. LC-MS (conditions A): $t_R$=0.63 min.; [M+H]$^+$: 403.13 g/mol.

Example 13

6-(2,6-dimethoxyphenyl)-1-(3-(piperidin-1-yl)benzyl)piperidin-2-one

Prepared according to the described general procedure 1 (GP1) by reaction of methyl 5-amino-5-(2,6-dimethoxyphenyl)pentanoate with commercially available 3-(piperidin-1-yl)benzaldehyde. Subsequent purification by preparative HPLC afforded the target compound. LC-MS (conditions A): $t_R$=0.61 min.; [M+H]$^+$: 409.25 g/mol.

Example 14

6-(2,6-dimethoxyphenyl)-1-(3-(thiazol-2-yl)benzyl) piperidin-2-one

Prepared according to the described general procedure 1 (GP1) by reaction of methyl 5-amino-5-(2,6-dimethoxyphenyl)pentanoate with commercially available 3-(thiazol-2-yl) benzaldehyde. Subsequent purification by preparative HPLC afforded the target compound. LC-MS (conditions A): $t_R$=0.82 min.; [M+H]$^+$: 409.14 g/mol.

Example 15

6-(2,6-dimethoxyphenyl)-1-(naphthalen-1-ylmethyl) piperidin-2-one

Prepared according to the described general procedure 1 (GP1) by reaction of methyl 5-amino-5-(2,6-dimethoxyphenyl)pentanoate with commercially available 1-naphthaldehyde. Subsequent purification by preparative HPLC afforded the target compound. LC-MS (conditions A): $t_R$=0.90 min.; [M+H]$^+$: 376.17 g/mol.

Example 16

6-(2,6-dimethoxyphenyl)-1-(3-(2-methylthiazol-4-yl) benzyl)piperidin-2-one

Prepared according to the described general procedure 1 (GP1) by reaction of methyl 5-amino-5-(2,6-dimethoxyphenyl)pentanoate with commercially available 3-(2-methylthiazol-4-yl)benzaldehyde. Subsequent purification by preparative HPLC afforded the target compound. LC-MS (conditions A): $t_R$=0.85 min.; [M+H]$^+$: 423.01 g/mol.

Example 17

6-(2,6-dimethoxyphenyl)-1-(3-morpholinobenzyl) piperidin-2-one

Prepared according to the described general procedure 1 (GP1) by reaction of methyl 5-amino-5-(2,6-dimethoxyphenyl)pentanoate with commercially available 3-morpholinobenzaldehyde. Subsequent purification by preparative HPLC afforded the target compound. LC-MS (conditions A): $t_R$=0.72 min.; [M+H]$^+$: 411.21 g/mol.

Example 18

6-(2,6-dimethoxyphenyl)-1-((5-phenylthiophen-2-yl) methyl)piperidin-2-one

Prepared according to the described general procedure 1 (GP1) by reaction of methyl 5-amino-5-(2,6-dimethoxyphenyl)pentanoate with commercially available 5-phenylthiophene-2-carbaldehyde. Subsequent purification by preparative HPLC afforded the target compound. LC-MS (conditions A): $t_R$=0.95 min.; [M+H]$^+$: 408.32 g/mol.

Example 19

1-(3-(1H-pyrazol-1-yl)benzyl)-6-(2,6-dimethoxyphenyl)piperidin-2-one

Prepared according to the described general procedure 1 (GP1) by reaction of methyl 5-amino-5-(2,6-dimethoxyphenyl)pentanoate with commercially available 3-(1H-pyrazol-1-yl)benzaldehyde. Subsequent purification by preparative HPLC afforded the target compound. LC-MS (conditions A): $t_R$=0.80 min.; [M+H]$^+$: 392.16 g/mol.

Example 20

6-(2,6-dimethoxyphenyl)-1-(quinoxalin-6-ylmethyl) piperidin-2-one

Prepared according to the described general procedure 1 (GP1) by reaction of methyl 5-amino-5-(2,6-dimethoxyphenyl)pentanoate with commercially available quinoxaline-6-carbaldehyde. Subsequent purification by preparative HPLC

Example 21

6-(2,6-dimethoxyphenyl)-1-((2-phenylthiazol-5-yl)methyl)piperidin-2-one

Prepared according to the described general procedure 1 (GP1) by reaction of methyl 5-amino-5-(2,6-dimethoxyphenyl)pentanoate with commercially available 2-phenylthiazole-5-carbaldehyde. Subsequent purification by preparative HPLC afforded the target compound. LC-MS (conditions A): $t_R$=0.85 min.; [M+H]$^+$: 409.16 g/mol.

Example 22

6-(2,6-dimethoxyphenyl)-1-((4-phenylpyridin-2-yl)methyl)piperidin-2-one

Prepared according to the described general procedure 1 (GP1) by reaction of methyl 5-amino-5-(2,6-dimethoxyphenyl)pentanoate with 4-phenylpicolinaldehyde. Subsequent purification by preparative HPLC afforded the target compound. LC-MS (conditions A): $t_R$=0.65 min.; [M+H]$^+$: 403.16 g/mol.

Example 23

1-(3-(1H-1,2,4-triazol-1-yl)benzyl)-6-(2,6-dimethoxyphenyl)piperidin-2-one

Prepared according to the described general procedure 1 (GP1) by reaction of methyl 5-amino-5-(2,6-dimethoxyphenyl)pentanoate with commercially available 3-(1H-1,2,4-triazol-1-yl)benzaldehyde. Subsequent purification by preparative HPLC afforded the target compound. LC-MS (conditions A): $t_R$=0.70 min.; [M+H]$^+$: 393.15 g/mol.

Example 24

6-(2,6-dimethoxyphenyl)-1-(3-(pyrrolidin-1-yl)benzyl)piperidin-2-one

Prepared according to the described general procedure 1 (GP1) by reaction of methyl 5-amino-5-(2,6-dimethoxyphenyl)pentanoate with commercially available 3-(pyrrolidin-1-yl)benzaldehyde. Subsequent purification by preparative HPLC afforded the target compound. LC-MS (conditions A): $t_R$=0.78 min.; [M+H]$^+$: 395.18 g/mol.

Example 25

6-(2,6-dimethoxyphenyl)-1-((5-phenylisoxazol-3-yl)methyl)piperidin-2-one

Prepared according to the described general procedure 1 (GP1) by reaction of methyl 5-amino-5-(2,6-dimethoxyphenyl)pentanoate with commercially available 5-phenylisoxazole-3-carbaldehyde. Subsequent purification by preparative HPLC afforded the target compound. LC-MS (conditions A): $t_R$=0.85 min.; [M+H]$^+$: 393.12 g/mol.

Example 26

6-(2,6-dimethoxyphenyl)-1-((1-phenyl-1H-pyrazol-4-yl)methyl)piperidin-2-one

Prepared according to the described general procedure 1 (GP1) by reaction of methyl 5-amino-5-(2,6-dimethoxyphenyl)pentanoate with commercially available 1-phenyl-1H-pyrazole-4-carbaldehyde. Subsequent purification by preparative HPLC afforded the target compound. LC-MS (conditions A): $t_R$=0.80 min.; [M+H]$^+$: 392.36 g/mol.

Example 27

1-(3-(1H-imidazol-1-yl)benzyl)-6-(2,6-dimethoxyphenyl)piperidin-2-one

Prepared according to the described general procedure 1 (GP1) by reaction of methyl 5-amino-5-(2,6-dimethoxyphenyl)pentanoate with commercially available 3-(1H-imidazol-1-yl)benzaldehyde. Subsequent purification by preparative HPLC afforded the target compound. LC-MS (conditions A): $t_R$=0.57 min.; [M+H]$^+$: 392.38 g/mol.

Example 28

6-(2,6-dimethoxyphenyl)-1-((6-(piperidin-1-yl)pyridin-2-yl)methyl)piperidin-2-one Prepared according to the described general procedure 1 (GP1) by reaction of methyl 5-amino-5-(2,6-dimethoxyphenyl)pentanoate with commercially available 6-(piperidin-1-yl)picolinaldehyde. Subsequent purification by preparative HPLC afforded the target compound. LC-MS (conditions A): $t_R$=0.65 min.; [M+H]$^+$: 410.42 g/mol.

Example 29

6-(2,6-dimethoxyphenyl)-1-(3-(pyrimidin-2-yl)benzyl)piperidin-2-one

Prepared according to the described general procedure 1 (GP1) by reaction of methyl 5-amino-5-(2,6-dimethoxyphenyl)pentanoate with commercially available 3-(pyrimidin-2-yl)benzaldehyde. Subsequent purification by preparative HPLC afforded the target compound. LC-MS (conditions A): $t_R$=0.78 min.; [M+H]$^+$: 404.37 g/mol.

Example 30

1-(dibenzo[b,d]furan-2-ylmethyl)-6-(2,6-dimethoxyphenyl)piperidin-2-one

Prepared according to the described general procedure 1 (GP1) by reaction of methyl 5-amino-5-(2,6-dimethoxyphenyl)pentanoate with commercially available dibenzo[b,d]furan-2-carbaldehyde. Subsequent purification by preparative HPLC afforded the target compound. LC-MS (conditions A): $t_R$=0.95 min.; [M+H]$^+$: 416.22 g/mol.

Example 31

1-(benzo[d]thiazol-2-ylmethyl)-6-(2,6-dimethoxyphenyl)piperidin-2-one

Prepared according to the described general procedure 1 (GP1) by reaction of methyl 5-amino-5-(2,6-dimethoxyphenyl)pentanoate with commercially available benzo[d]thiazole-2-carbaldehyde. Subsequent purification by preparative

--- afforded the target compound. LC-MS (conditions A): $t_R$=0.68 min.; [M+H]$^+$: 378.17 g/mol.

HPLC afforded the target compound. LC-MS (conditions A): $t_R$=0.82 min.; [M+H]$^+$: 383.14 g/mol.

Example 32

6-(2,6-dimethoxyphenyl)-1-((9-methyl-9H-carbazol-3-yl)methyl)piperidin-2-one

Prepared according to the described general procedure 1 (GP1) by reaction of methyl 5-amino-5-(2,6-dimethoxyphenyl)pentanoate with commercially available 9-methyl-9H-carbazole-3-carbaldehyde. Subsequent purification by preparative HPLC afforded the target compound. LC-MS (conditions A): $t_R$=0.94 min.; [M+H]$^+$: 429.28 g/mol.

Example 33

6-(2,6-dimethoxyphenyl)-1-(3-(5-methyl-1,2,4-oxadiazol-3-yl)benzyl)piperidin-2-one Prepared according to the described general procedure 1 (GP1) by reaction of methyl 5-amino-5-(2,6-dimethoxyphenyl)pentanoate with commercially available 3-(5-methyl-1,2,4-oxadiazol-3-yl)benzaldehyde. Subsequent purification by preparative HPLC afforded the target compound. LC-MS (conditions A): $t_R$=0.81 min.; [M+H]$^+$: 408.04 g/mol.

Example 34

6-(2,6-dimethoxyphenyl)-1-((2-(pyrrolidin-1-yl)pyridin-4-yl)methyl)piperidin-2-one Prepared according to the described general procedure 1 (GP1) by reaction of methyl 5-amino-5-(2,6-dimethoxyphenyl)pentanoate with commercially available 2-(pyrrolidin-1-yl)isonicotinaldehyde. Subsequent purification by preparative HPLC afforded the target compound. LC-MS (conditions A): $t_R$=0.58 min.; [M+H]$^+$: 396.07 g/mol.

Example 35

6-(2,6-dimethoxyphenyl)-1-((2-phenylthiazol-4-yl)methyl)piperidin-2-one

Prepared according to the described general procedure 1 (GP1) by reaction of methyl 5-amino-5-(2,6-dimethoxyphenyl)pentanoate with commercially available 2-phenylthiazole-4-carbaldehyde. Subsequent purification by preparative HPLC afforded the target compound. LC-MS (conditions A): $t_R$=0.87 min.; [M+H]$^+$: 408.99 g/mol.

Example 36

1-((2-bromopyridin-4-yl)methyl)-6-(2,6-dimethoxyphenyl)piperidin-2-one

Prepared according to the described general procedure 1 (GP1) by reaction of methyl 5-amino-5-(2,6-dimethoxyphenyl)pentanoate with commercially available 2-bromoisonicotinaldehyde. Subsequent purification by preparative HPLC afforded the target compound. LC-MS (conditions A): $t_R$=0.75 min.; [M+H]$^+$: 404.91 g/mol.

Example 37

6-(2,6-dimethoxyphenyl)-1-(2-fluoro-3-(pyridin-2-yl)benzyl)piperidin-2-one

Prepared according to the described general procedure 1 (GP1) by reaction of methyl 5-amino-5-(2,6-dimethoxyphenyl)pentanoate with 2-fluoro-3-(pyridin-2-yl)benzaldehyde. Subsequent purification by preparative HPLC afforded the target compound. LC-MS (conditions A): $t_R$=0.65 min.; [M+H]$^+$: 421.00 g/mol.

Example 38

1-([2,2'-bipyridin]-6-ylmethyl)-6-(2,6-dimethoxyphenyl)piperidin-2-one

Prepared according to the described general procedure 1 (GP1) by reaction of methyl 5-amino-5-(2,6-dimethoxyphenyl)pentanoate with [2,2'-bipyridine]-6-carbaldehyde. Subsequent purification by preparative HPLC afforded the target compound. LC-MS (conditions A): $t_R$=0.58 min.; [M+H]$^+$: 403.99 g/mol.

Example 39

6-(2,6-dimethoxyphenyl)-1-((6-(thiazol-2-yl)pyridin-2-yl)methyl)piperidin-2-one

Prepared according to the described general procedure 1 (GP1) by reaction of methyl 5-amino-5-(2,6-dimethoxyphenyl)pentanoate with 6-(thiazol-2-yl)picolinaldehyde. Subsequent purification by preparative HPLC afforded the target compound. LC-MS (conditions A): $t_R$=0.77 min.; [M+H]$^+$: 409.94 g/mol.

Example 40

6-(2,6-dimethoxyphenyl)-1-(2-fluoro-5-(pyridin-2-yl)benzyl)piperidin-2-one

Prepared according to the described general procedure 1 (GP1) by reaction of methyl 5-amino-5-(2,6-dimethoxyphenyl)pentanoate with 2-fluoro-5-(pyridin-2-yl)benzaldehyde. Subsequent purification by preparative HPLC afforded the target compound. LC-MS (conditions A): $t_R$=0.66 min.; [M+H]$^+$: 420.83 g/mol.

Example 41

6-(2,6-dimethoxyphenyl)-1-(4-fluoro-3-(pyridin-2-yl)benzyl)piperidin-2-one

Prepared according to the described general procedure 1 (GP1) by reaction of methyl 5-amino-5-(2,6-dimethoxyphenyl)pentanoate with 4-fluoro-3-(pyridin-2-yl)benzaldehyde. Subsequent purification by preparative HPLC afforded the target compound. LC-MS (conditions A): $t_R$=0.68 min.; [M+H]$^+$: 420.97 g/mol.

Example 42

6-(2,6-dimethoxyphenyl)-1-(3-(thiazol-5-yl)benzyl)piperidin-2-one

Prepared according to the described general procedure 1 (GP1) by reaction of methyl 5-amino-5-(2,6-dimethoxyphenyl)pentanoate with 3-(thiazol-5-yl)benzaldehyde. Subsequent purification by preparative HPLC afforded the target compound. LC-MS (conditions A): $t_R$=0.78 min.; [M+H]$^+$: 409.08 g/mol.

Example 43

6-(2,6-dimethoxyphenyl)-1-(3-(5-methylthiazol-2-yl)benzyl)piperidin-2-one

Prepared according to the described general procedure 1 (GP1) by reaction of methyl 5-amino-5-(2,6-dimethoxyphenyl)pentanoate with 3-(5-methylthiazol-2-yl)benzaldehyde. Subsequent purification by preparative HPLC afforded the target compound. LC-MS (conditions A): $t_R$=0.87 min.; [M+H]$^+$: 423.11 g/mol.

Example 44

1-(3-(2H-1,2,3-triazol-2-yl)benzyl)-6-(2,6-dimethoxyphenyl)piperidin-2-one

Prepared according to the described general procedure 1 (GP1) by reaction of methyl 5-amino-5-(2,6-dimethoxyphenyl)pentanoate with 3-(2H-1,2,3-triazol-2-yl)benzaldehyde. Subsequent purification by preparative HPLC afforded the target compound. LC-MS (conditions A): $t_R$=0.83 min.; [M+H]$^+$: 393.13 g/mol.

Example 45

6-(2,6-dimethoxyphenyl)-1-(3-(thiazol-4-yl)benzyl)piperidin-2-one

Prepared according to the described general procedure 1 (GP1) by reaction of methyl 5-amino-5-(2,6-dimethoxyphenyl)pentanoate with 3-(thiazol-4-yl)benzaldehyde. Subsequent purification by preparative HPLC afforded the target compound. LC-MS (conditions A): $t_R$=0.81 min.; [M+H]$^+$: 409.07 g/mol.

Example 46

1-(3-(1H-1,2,3-triazol-1-yl)benzyl)-6-(2,6-dimethoxyphenyl)piperidin-2-one

Prepared according to the described general procedure 1 (GP1) by reaction of methyl 5-amino-5-(2,6-dimethoxyphenyl)pentanoate with 3-(1H-1,2,3-triazol-1-yl)benzaldehyde. Subsequent purification by preparative HPLC afforded the target compound. LC-MS (conditions A): $t_R$=0.71 min.; [M+H]$^+$: 393.08 g/mol.

Example 47

6-(2,6-dimethoxyphenyl)-1-((2-methylbenzo[d]thiazol-6-yl)methyl)piperidin-2-one

Prepared according to the described general procedure 1 (GP1) by reaction of methyl 5-amino-5-(2,6-dimethoxyphenyl)pentanoate with 2-methylbenzo[d]thiazole-6-carbaldehyde. Subsequent purification by preparative HPLC afforded the target compound. LC-MS (conditions A): $t_R$=0.77 min.; [M+H]$^+$: 397.01 g/mol.

Example 48

1-(2-chloro-5-(pyridin-2-yl)benzyl)-6-(2,6-dimethoxyphenyl)piperidin-2-one

Prepared according to the described general procedure 1 (GP1) by reaction of methyl 5-amino-5-(2,6-dimethoxyphenyl)pentanoate with 2-chloro-5-(pyridin-2-yl)benzaldehyde. Subsequent purification by preparative HPLC afforded the target compound. LC-MS (conditions A): $t_R$=0.74 min.; [M+H]$^+$: 437.10 g/mol.

Example 49

1-(3-chloro-5-(pyridin-2-yl)benzyl)-6-(2,6-dimethoxyphenyl)piperidin-2-one

Prepared according to the described general procedure 1 (GP1) by reaction of methyl 5-amino-5-(2,6-dimethoxyphenyl)pentanoate with 3-chloro-5-(pyridin-2-yl)benzaldehyde. Subsequent purification by preparative HPLC afforded the target compound. LC-MS (conditions A): $t_R$=0.80 min.; [M+H]$^+$: 437.10 g/mol.

Example 50

1-([2,2'-bipyridin]-4-ylmethyl)-6-(2,6-dimethoxyphenyl)piperidin-2-one

Prepared according to the described general procedure 1 (GP1) by reaction of methyl 5-amino-5-(2,6-dimethoxyphenyl)pentanoate with [2,2'-bipyridine]-4-carbaldehyde. Subsequent purification by preparative HPLC afforded the target compound. LC-MS (conditions A): $t_R$=0.59 min.; [M+H]$^+$: 403.97 g/mol.

Example 51

1-((6-(1H-pyrazol-1-yl)pyridin-2-yl)methyl)-6-(2,6-dimethoxyphenyl)piperidin-2-one Prepared according to the described general procedure 1 (GP1) by reaction of methyl 5-amino-5-(2,6-dimethoxyphenyl)pentanoate with 6-(1H-pyrazol-1-yl)picolinaldehyde. Subsequent purification by preparative HPLC afforded the target compound. LC-MS (conditions A): $t_R$=0.79 min.; [M+H]$^+$: 392.97 g/mol.

Example 52

1-((2-(1H-pyrazol-1-yl)pyridin-4-yl)methyl)-6-(2,6-dimethoxyphenyl)piperidin-2-one Prepared according to the described general procedure 1 (GP1) by reaction of methyl 5-amino-5-(2,6-dimethoxyphenyl)pentanoate with 2-(1H-pyrazol-1-yl)isonicotinaldehyde.

Subsequent purification by preparative HPLC afforded the target compound. LC-MS (conditions A): $t_R$=0.78 min.; [M+H]$^+$: 393.12 g/mol.

Example 53

6-(2,4-dimethoxypyridin-3-yl)-1-(3-(thiazol-2-yl)benzyl)piperidin-2-one

Prepared according to the described general procedure 1 (GP1) by reaction of methyl 5-amino-5-(2,4-dimethoxypyridin-3-yl)pentanoate with commercially available 3-(thiazol-2-yl)benzaldehyde. Subsequent purification by preparative HPLC afforded the target compound. LC-MS (conditions A): $t_R$=0.68 min.; [M+H]$^+$: 409.86 g/mol.

Example 54

6-(2,4-dimethoxypyridin-3-yl)-1-(3-(2-methylthiazol-4-yl)benzyl)piperidin-2-one

Prepared according to the described general procedure 1 (GP1) by reaction of methyl 5-amino-5-(2,4-dimethoxypyridin-3-yl)pentanoate with commercially available 3-(2-methylthiazol-4-yl)benzaldehyde. Subsequent purification by preparative HPLC afforded the target compound. LC-MS (conditions A): $t_R$=0.71 min.; [M+H]$^+$: 423.95 g/mol.

Example 55

6-(2,4-dimethoxypyridin-3-yl)-1-(3-(pyridin-2-yl)benzyl)piperidin-2-one

Prepared according to the described general procedure 1 (GP1) by reaction of methyl 5-amino-5-(2,4-dimethoxypyridin-3-yl)pentanoate with commercially available 3-(pyridin-2-yl)benzaldehyde. Subsequent purification by preparative HPLC afforded the target compound. LC-MS (conditions A): $t_R$=0.52 min.; [M+H]$^+$: 403.81 g/mol.

Example 56

6-(2,4-dimethoxypyridin-3-yl)-1-((2-phenylthiazol-4-yl)methyl)piperidin-2-one

Prepared according to the described general procedure 1 (GP1) by reaction of methyl 5-amino-5-(2,4-dimethoxypyridin-3-yl)pentanoate with commercially available 2-phenylthiazole-4-carbaldehyde. Subsequent purification by preparative HPLC afforded the target compound. LC-MS (conditions A): $t_R$=0.74 min.; [M+H]$^+$: 409.83 g/mol.

Example 57

1-(dibenzo[b,d]furan-2-ylmethyl)-6-(2,4-dimethoxypyridin-3-yl)piperidin-2-one

Prepared according to the described general procedure 1 (GP1) by reaction of methyl 5-amino-5-(2,4-dimethoxypyridin-3-yl)pentanoate with commercially available dibenzo[b,d]furan-2-carbaldehyde. Subsequent purification by preparative HPLC afforded the target compound. LC-MS (conditions A): $t_R$=0.83 min.; [M+H]$^+$: 416.86 g/mol.

Example 58

6-(2,4-dimethoxypyridin-3-yl)-1-((2-methylbenzo[d]thiazol-6-yl)methyl)piperidin-2-one Prepared according to the described general procedure 1 (GP1) by reaction of methyl 5-amino-5-(2,4-dimethoxypyridin-3-yl)pentanoate with 2-methylbenzo[d]thiazole-6-carbaldehyde. Subsequent purification by preparative HPLC afforded the target compound. LC-MS (conditions A): $t_R$=0.63 min.; [M+H]$^+$: 397.76 g/mol.

Example 59

6-(2,4-dimethoxypyridin-3-yl)-1-(4-fluoro-3-(pyridin-2-yl)benzyl)piperidin-2-one Prepared according to the described general procedure 1 (GP1) by reaction of methyl 5-amino-5-(2,4-dimethoxypyridin-3-yl)pentanoate with 4-fluoro-3-(pyridin-2-yl)benzaldehyde. Subsequent purification by preparative HPLC afforded the target compound. LC-MS (conditions A): $t_R$=0.58 min.; [M+H]$^+$: 421.83 g/mol.

Example 60

1-([1,1'-biphenyl]-3-ylmethyl)-6-(2,4-dimethoxypyridin-3-yl)piperidin-2-one

Prepared according to the described general procedure 1 (GP1) by reaction of methyl 5-amino-5-(2,4-dimethoxypyridin-3-yl)pentanoate with commercially available [1,1'-biphenyl]-3-carbaldehyde. Subsequent purification by preparative HPLC the target compound. LC-MS (conditions A): $t_R$=0.83 min.; [M+H]$^+$: 403.34 g/mol.

Example 61

6-(3,5-dimethoxypyridin-4-yl)-1-(3-(thiazol-2-yl)benzyl)piperidin-2-one

Prepared according to the described general procedure 1 (GP1) by reaction of methyl 5-amino-5-(3,5-dimethoxypyridin-4-yl)pentanoate with commercially available 3-(thiazol-2-yl)benzaldehyde. Subsequent purification by preparative HPLC afforded the target compound. LC-MS (conditions A): $t_R$=0.52 min.; [M+H]$^+$: 409.72 g/mol.

Example 62

6-(3,5-dimethoxypyridin-4-yl)-1-(3-(2-methylthiazol-4-yl)benzyl)piperidin-2-one

Prepared according to the described general procedure 1 (GP1) by reaction of methyl 5-amino-5-(3,5-dimethoxypyridin-4-yl)pentanoate with commercially available 3-(2-methylthiazol-4-yl)benzaldehyde. Subsequent purification by preparative HPLC afforded the target compound. LC-MS (conditions A): $t_R$=0.54 min.; [M+H]$^+$: 423.76 g/mol.

Example 63

6-(3,5-dimethoxypyridin-4-yl)-1-(3-(pyridin-2-yl)benzyl)piperidin-2-one

Prepared according to the described general procedure 1 (GP1) by reaction of methyl 5-amino-5-(3,5-dimethoxypyridin-4-yl)pentanoate with commercially available 3-(pyridin-2-yl)benzaldehyde. Subsequent purification by preparative HPLC afforded the target compound. LC-MS (conditions A): $t_R$=0.42 min.; [M+H]$^+$: 403.73 g/mol.

Example 64

6-(3,5-dimethoxypyridin-4-yl)-1-((2-phenylthiazol-4-yl)methyl)piperidin-2-one

Prepared according to the described general procedure 1 (GP1) by reaction of methyl 5-amino-5-(3,5-dimethoxypyridin-4-yl)pentanoate with commercially available 2-phenylthiazole-4-carbaldehyde. Subsequent purification by preparative HPLC afforded the target compound. LC-MS (conditions A): $t_R$=0.56 min.; [M+H]$^+$: 409.95 g/mol.

Example 65

1-(dibenzo[b,d]furan-2-ylmethyl)-6-(3,5-dimethoxypyridin-4-yl)piperidin-2-one

Prepared according to the described general procedure 1 (GP1) by reaction of methyl 5-amino-5-(3,5-dimethoxypyridin-4-yl)pentanoate with commercially available dibenzo[b,d]furan-2-carbaldehyde. Subsequent purification by preparative HPLC afforded the target compound. LC-MS (conditions A): $t_R$=0.64 min.; [M+H]$^+$: 416.86 g/mol.

Example 66

1-((6-(1H-pyrazol-1-yl)pyridin-2-yl)methyl)-6-(3,5-dimethoxypyridin-4-yl)piperidin-2-one Prepared according to the described general procedure 1 (GP1) by reaction of methyl 5-amino-5-(3,5-dimethoxypyridin-4-yl)pentanoate with 6-(1H-pyrazol-1-yl)picolinaldehyde. Subsequent purification by preparative HPLC afforded the target compound. LC-MS (conditions A): $t_R$=0.49 min.; [M+H]$^+$: 393.79 g/mol.

Example 67

1-(3-(2H-1,2,3-triazol-2-yl)benzyl)-6-(3,5-dimethoxypyridin-4-yl)piperidin-2-one Prepared according to the described general procedure 1 (GP1) by reaction of methyl 5-amino-5-(3,5-dimethoxypyridin-4-yl)pentanoate with 3-(2H-1,2,3-triazol-2-yl)benzaldehyde. Subsequent purification by preparative HPLC afforded the target compound. LC-MS (conditions A): $t_R$=0.52 min.; [M+H]$^+$: 393.71 g/mol.

Example 68

1-([1,1'-biphenyl]-3-ylmethyl)-6-(3,5-dimethoxypyridin-4-yl)piperidin-2-one

Prepared according to the described general procedure 1 (GP1) by reaction of methyl 5-amino-5-(3,5-dimethoxypyridin-4-yl)pentanoate with commercially available [1,1'-biphenyl]-3-carbaldehyde. Subsequent purification by preparative HPLC afforded the target compound. LC-MS (conditions A): $t_R$=0.64 min.; [M+H]$^+$: 402.69 g/mol.

Example 69

1-((6-(difluoromethoxy)-5-methylpyridin-3-yl)methyl)-6-(2,6-dimethoxyphenyl)piperidin-2-one Prepared according to the described general procedure 1 (GP1) by reaction of methyl 5-amino-5-(2,6-dimethoxyphenyl)pentanoate with 6-(difluoromethoxy)-5-methylnicotinaldehyde. Subsequent purification by preparative HPLC afforded the target compound. LC-MS (conditions A): $t_R$=0.86 min.; [M+H]$^+$: 406.88 g/mol.

Example 70

1-((5-cyclopropyl-6-(difluoromethoxy)pyridin-3-yl)methyl)-6-(2,6-dimethoxyphenyl)piperidin-2-one Prepared according to the described general procedure 1 (GP1) by reaction of methyl 5-amino-5-(2,6-dimethoxyphenyl)pentanoate with 5-cyclopropyl-6-(difluoromethoxy)nicotinaldehyde. Subsequent purification by preparative HPLC afforded the target compound. LC-MS (conditions A): $t_R$=0.90 min.; [M+H]$^+$: 432.88 g/mol.

Example 71

6-(2,6-dimethoxyphenyl)-1-((2-methylthiazol-4-yl)methyl)piperidin-2-one

Prepared according to the described general procedure 1 (GP1) by reaction of methyl 5-amino-5-(2,6-dimethoxyphenyl)pentanoate with commercially available 2-methylthiazole-4-carbaldehyde. Subsequent purification by preparative HPLC afforded the target compound. LC-MS (conditions A): $t_R$=0.65 min.; [M+H]$^+$: 346.85 g/mol.

Example 72

1-([1,1'-biphenyl]-3-ylmethyl)-7-(2,6-dimethoxyphenyl)azepan-2-one

Prepared according to the described general procedure 1 (GP1) by reaction of methyl 6-amino-6-(2,6-dimethoxyphenyl)hexanoate with commercially available [1,1'-biphenyl]-3-carbaldehyde. Subsequent purification by preparative HPLC afforded the target compound. LC-MS (conditions A): $t_R$=0.99 min.; [M+H]$^+$: 416.24 g/mol.

Example 73

7-(2,6-dimethoxyphenyl)-1-(4-phenoxybenzyl)azepan-2-one

Prepared according to the described general procedure 1 (GP1) by reaction of methyl 6-amino-6-(2,6-dimethoxyphenyl)hexanoate with commercially available 4-phenoxybenzaldehyde. Subsequent purification by preparative HPLC afforded the target compound. LC-MS (conditions A): $t_R$=1.00 min.; [M+H]$^+$: 432.27 g/mol.

Example 74

7-(2,6-dimethoxyphenyl)-1-(3-phenoxybenzyl)azepan-2-one

Prepared according to the described general procedure 1 (GP1) by reaction of methyl 6-amino-6-(2,6-dimethoxyphenyl)hexanoate with commercially available 3-phenoxybenzaldehyde. Subsequent purification by preparative HPLC afforded the target compound. LC-MS (conditions A): $t_R$=0.99 min.; [M+H]$^+$: 432.27 g/mol.

Example 75

7-(2,6-dimethoxyphenyl)-1-(naphthalen-2-ylmethyl)azepan-2-one

Prepared according to the described general procedure 1 (GP1) by reaction of methyl 6-amino-6-(2,6-dimethoxyphenyl)hexanoate with commercially available 2-naphthaldehyde. Subsequent purification by preparative HPLC afforded the target compound. LC-MS (conditions A): $t_R$=0.95 min.; [M+H]$^+$: 390.17 g/mol.

Example 76

7-(2,6-dimethoxyphenyl)-1-(naphthalen-1-ylmethyl)azepan-2-one

Prepared according to the described general procedure 1 (GP1) by reaction of methyl 6-amino-6-(2,6-dimethoxyphenyl)hexanoate with commercially available 1-naphthaldehyde. Subsequent purification by preparative HPLC afforded the target compound. LC-MS (conditions A): $t_R$=0.94 min.; [M+H]$^+$: 390.16 g/mol.

Example 77

1-([1,1'-biphenyl]-4-ylmethyl)-7-(2,6-dimethoxyphenyl)azepan-2-one

Prepared according to the described general procedure 1 (GP1) by reaction of methyl 6-amino-6-(2,6-dimethoxyphenyl)hexanoate with commercially available [1,1'-biphenyl]-4-carbaldehyde. Subsequent purification by preparative HPLC afforded the target compound. LC-MS (conditions A): $t_R$=1.00 min.; [M+H]$^+$: 416.23 g/mol.

Example 78

1-([1,1'-biphenyl]-2-ylmethyl)-7-(2,6-dimethoxyphenyl)azepan-2-one

Prepared according to the described general procedure 1 (GP1) by reaction of methyl 6-amino-6-(2,6-dimethoxyphenyl)hexanoate with commercially available [1,1'-biphenyl]-2-carbaldehyde. Subsequent purification by preparative HPLC afforded the target compound. LC-MS (conditions A): $t_R$=0.98 min.; [M+H]$^+$: 416.24 g/mol.

Example 79

7-(2,6-dimethoxyphenyl)-1-(quinolin-2-ylmethyl)azepan-2-one

Prepared according to the described general procedure 1 (GP1) by reaction of methyl 6-amino-6-(2,6-dimethoxyphenyl)hexanoate with commercially available quinoline-2-carbaldehyde. Subsequent purification by preparative HPLC afforded the target compound. LC-MS (conditions A): $t_R$=0.63 min.; [M+H]$^+$: 391.16 g/mol.

Example 80

7-(2,6-dimethoxyphenyl)-1-(quinolin-3-ylmethyl)azepan-2-one

Prepared according to the described general procedure 1 (GP1) by reaction of methyl 6-amino-6-(2,6-dimethoxyphenyl)hexanoate with commercially available quinoline-3-carbaldehyde. Subsequent purification by preparative HPLC afforded the target compound. LC-MS (conditions A): $t_R$=0.63 min.; [M+H]$^+$: 391.18 g/mol.

Example 81

7-(2,6-dimethoxyphenyl)-1-((2-phenylpyridin-4-yl)methyl)azepan-2-one

Prepared according to the described general procedure 1 (GP1) by reaction of methyl 6-amino-6-(2,6-dimethoxyphenyl)hexanoate with 2-phenylisonicotinaldehyde. Subsequent purification by preparative HPLC afforded the target compound. LC-MS (conditions A): $t_R$=0.68 min.; [M+H]$^+$: 417.21 g/mol.

Example 82

7-(2,6-dimethoxyphenyl)-1-((6-phenylpyridin-2-yl)methyl)azepan-2-one

Prepared according to the described general procedure 1 (GP1) by reaction of methyl 6-amino-6-(2,6-dimethoxyphenyl)hexanoate with 6-phenylpicolinaldehyde. Subsequent purification by preparative HPLC afforded the target compound. LC-MS (conditions A): $t_R$=0.76 min.; [M+H]$^+$: 417.22 g/mol.

Example 83

7-(2,6-dimethoxyphenyl)-1-(3-(pyrimidin-2-yl)benzyl)azepan-2-one

Prepared according to the described general procedure 1 (GP1) by reaction of methyl 6-amino-6-(2,6-dimethoxyphenyl)hexanoate with commercially available 3-(pyrimidin-2-yl)benzaldehyde. Subsequent purification by preparative HPLC afforded the target compound. LC-MS (conditions A): $t_R$=0.84 min.; [M+H]$^+$: 418.38 g/mol.

Example 84

7-(2,6-dimethoxyphenyl)-1-(3-(pyridin-2-yl)benzyl)azepan-2-one

Prepared according to the described general procedure 1 (GP1) by reaction of methyl 6-amino-6-(2,6-dimethoxyphenyl)hexanoate with commercially available 3-(pyridin-2-yl)benzaldehyde. Subsequent purification by preparative HPLC afforded the target compound. LC-MS (conditions A): $t_R$=0.67 min.; [M+H]$^+$: 417.04 g/mol.

Example 85

7-(2,6-dimethoxyphenyl)-1-(3-(thiazol-2-yl)benzyl)azepan-2-one

Prepared according to the described general procedure 1 (GP1) by reaction of methyl 6-amino-6-(2,6-dimethoxyphenyl)hexanoate with commercially available 3-(thiazol-2-yl) benzaldehyde. Subsequent purification by preparative HPLC afforded the target compound. LC-MS (conditions I): $t_R$=1.29 min.; [M+H]$^+$: 423.10 g/mol.

Example 86

7-(2,6-dimethoxyphenyl)-1-((9-methyl-9H-carbazol-3-yl)methyl)azepan-2-one

Prepared according to the described general procedure 1 (GP1) by reaction of methyl 6-amino-6-(2,6-dimethoxyphenyl)hexanoate with commercially available 9-methyl-9H-carbazole-3-carbaldehyde. Subsequent purification by preparative HPLC afforded the target compound. LC-MS (conditions I): $t_R$=1.49 min.; [M+H]$^+$: 443.14 g/mol.

Example 87

7-(2,6-dimethoxyphenyl)-1-(3-(pyridin-3-yl)benzyl) azepan-2-one

Prepared according to the described general procedure 1 (GP1) by reaction of methyl 6-amino-6-(2,6-dimethoxyphenyl)hexanoate with commercially available 3-(pyridin-3-yl) benzaldehyde. Subsequent purification by preparative HPLC afforded the target compound. LC-MS (conditions I): $t_R$=1.19 min.; [M+H]$^+$: 417.16 g/mol.

Example 88

7-(2,6-dimethoxyphenyl)-1-(3-(piperidin-1-yl)benzyl)azepan-2-one

Prepared according to the described general procedure 1 (GP1) by reaction of methyl 6-amino-6-(2,6-dimethoxyphenyl)hexanoate with commercially available 3-(piperidin-1-yl)benzaldehyde. Subsequent purification by preparative HPLC afforded the target compound. LC-MS (conditions A): $t_R$=0.65 min.; [M+H]$^+$: 423.10 g/mol.

Example 89

1-((5-chloro-6-(difluoromethoxy)pyridin-3-yl)methyl)-7-(2,6-dimethoxyphenyl)azepan-2-one Prepared according to the described general procedure 1 (GP1) by reaction of methyl 6-amino-6-(2,6-dimethoxyphenyl)hexanoate with 5-chloro-6-(difluoromethoxy)nicotinaldehyde. Subsequent purification by preparative HPLC afforded the target compound. LC-MS (conditions A): $t_R$=0.94 min.; [M+H]$^+$: 441.11 g/mol.

Example 90

1-(dibenzo[b,d]furan-2-ylmethyl)-7-(2,6-dimethoxyphenyl)azepan-2-one

Prepared according to the described general procedure 1 (GP1) by reaction of methyl 6-amino-6-(2,6-dimethoxyphenyl)hexanoate with commercially available dibenzo[b,d]furan-2-carbaldehyde. Subsequent purification by preparative HPLC afforded the target compound. LC-MS (conditions I): $t_R$=1.53 min.; [M+H]$^+$: 430.13 g/mol.

Example 91

7-(2,6-dimethoxyphenyl)-1-(3-(2-methylthiazol-4-yl) benzyl)azepan-2-one

Prepared according to the described general procedure 1 (GP1) by reaction of methyl 6-amino-6-(2,6-dimethoxyphenyl)hexanoate with commercially available 3-(2-methylthiazol-4-yl)benzaldehyde. Subsequent purification by preparative HPLC afforded the target compound. LC-MS (conditions I): $t_R$=1.37 min.; [M+H]$^+$: 437.10 g/mol.

Example 92

7-(2,6-dimethoxyphenyl)-1-((5-phenylpyridin-3-yl) methyl)azepan-2-one

Prepared according to the described general procedure 1 (GP1) by reaction of methyl 6-amino-6-(2,6-dimethoxyphenyl)hexanoate with 5-phenylnicotinaldehyde. Subsequent purification by preparative HPLC afforded the target compound. LC-MS (conditions I): $t_R$=1.26 min.; [M+H]$^+$: 417.20 g/mol.

Example 93

7-(2,6-dimethoxyphenyl)-1-(3-(pyrrolidin-1-yl)benzyl)azepan-2-one

Prepared according to the described general procedure 1 (GP1) by reaction of methyl 6-amino-6-(2,6-dimethoxyphenyl)hexanoate with commercially available 3-(pyrrolidin-1-yl)benzaldehyde. Subsequent purification by preparative HPLC afforded the target compound. LC-MS (conditions I): $t_R$=1.48 min.; [M+H]$^+$: 409.18 g/mol.

Example 94

7-(2,6-dimethoxyphenyl)-1-((1-phenyl-1H-pyrazol-4-yl)methyl)azepan-2-one

Prepared according to the described general procedure 1 (GP1) by reaction of methyl 6-amino-6-(2,6-dimethoxyphenyl)hexanoate with commercially available 1-phenyl-1H-pyrazole-4-carbaldehyde. Subsequent purification by preparative HPLC the target compound. LC-MS (conditions I): $t_R$=1.27 min.; [M+H]$^+$: 405.81 g/mol.

Example 95

7-(2,6-dimethoxyphenyl)-1-((2-methylbenzo[d]thiazol-5-yl)methyl)azepan-2-one

Prepared according to the described general procedure 1 (GP1) by reaction of methyl 6-amino-6-(2,6-dimethoxyphenyl)hexanoate with 2-methylbenzo[d]thiazole-5-carbaldehyde. Subsequent purification by preparative HPLC afforded the target compound. LC-MS (conditions I): $t_R$=1.23 min.; [M+H]$^+$: 411.11 g/mol.

Example 96

7-(2,6-dimethoxyphenyl)-1-(3-(pyridin-4-yl)benzyl) azepan-2-one

Prepared according to the described general procedure 1 (GP1) by reaction of methyl 6-amino-6-(2,6-dimethoxyphenyl)hexanoate with commercially available 3-(pyridin-4-yl) benzaldehyde. Subsequent purification by preparative HPLC afforded the target compound. LC-MS (conditions A): $t_R$=0.65 min.; [M+H]$^+$: 417.01 g/mol.

Example 97

1-(3-(1H-pyrazol-1-yl)benzyl)-7-(2,6-dimethoxyphenyl)azepan-2-one

Prepared according to the described general procedure 1 (GP1) by reaction of methyl 6-amino-6-(2,6-dimethoxyphenyl)hexanoate with commercially available 3-(1H-pyrazol-1-yl)benzaldehyde. Subsequent purification by preparative HPLC afforded the target compound. LC-MS (conditions A): $t_R$=0.86 min.; [M+H]$^+$: 406.12 g/mol.

Example 98

7-(2,6-dimethoxyphenyl)-1-((2-phenylthiazol-4-yl)methyl)azepan-2-one

Prepared according to the described general procedure 1 (GP1) by reaction of methyl 6-amino-6-(2,6-dimethoxyphenyl)hexanoate with commercially available 2-phenylthiazole-4-carbaldehyde. Subsequent purification by preparative HPLC afforded the target compound. LC-MS (conditions A): $t_R$=0.93 min.; [M+H]$^+$: 423.12 g/mol.

Example 99

7-(2,6-dimethoxyphenyl)-1-(3-(thiazol-5-yl)benzyl)azepan-2-one

Prepared according to the described general procedure 1 (GP1) by reaction of methyl 6-amino-6-(2,6-dimethoxyphenyl)hexanoate with 3-(thiazol-5-yl)benzaldehyde. Subsequent purification by preparative HPLC afforded the target compound. LC-MS (conditions A): $t_R$=0.84 min.; [M+H]$^+$: 423.08 g/mol.

Example 100

7-(2,6-dimethoxyphenyl)-1-(3-(5-methylthiazol-2-yl)benzyl)azepan-2-one

Prepared according to the described general procedure 1 (GP1) by reaction of methyl 6-amino-6-(2,6-dimethoxyphenyl)hexanoate with 3-(5-methylthiazol-2-yl)benzaldehyde. Subsequent purification by preparative HPLC afforded the target compound. LC-MS (conditions A): $t_R$=0.92 min.; [M+H]$^+$: 437.13 g/mol.

Example 101

1-(3-(2H-1,2,3-triazol-2-yl)benzyl)-7-(2,6-dimethoxyphenyl)azepan-2-one

Prepared according to the described general procedure 1 (GP1) by reaction of methyl 6-amino-6-(2,6-dimethoxyphenyl)hexanoate with 3-(2H-1,2,3-triazol-2-yl)benzaldehyde. Subsequent purification by preparative HPLC afforded the target compound. LC-MS (conditions A): $t_R$=0.88 min.; [M+H]$^+$: 407.09 g/mol.

Example 102

7-(2,6-dimethoxyphenyl)-1-(3-(thiazol-4-yl)benzyl)azepan-2-one

Prepared according to the described general procedure 1 (GP1) by reaction of methyl 6-amino-6-(2,6-dimethoxyphenyl)hexanoate with 3-(thiazol-4-yl)benzaldehyde. Subsequent purification by preparative HPLC afforded the target compound. LC-MS (conditions A): $t_R$=0.87 min.; [M+H]$^+$: 423.08 g/mol.

Example 103

1-((2-(1H-pyrazol-1-yl)pyridin-4-yl)methyl)-7-(2,6-dimethoxyphenyl)azepan-2-one

Prepared according to the described general procedure 1 (GP1) by reaction of methyl 6-amino-6-(2,6-dimethoxyphenyl)hexanoate with 2-(1H-pyrazol-1-yl)isonicotinaldehyde. Subsequent purification by preparative HPLC afforded the target compound. LC-MS (conditions A): $t_R$=0.83 min.; [M+H]$^+$: 407.11 g/mol.

Example 104

1-((6-(1H-pyrazol-1-yl)pyridin-2-yl)methyl)-7-(2,6-dimethoxyphenyl)azepan-2-one

Prepared according to the described general procedure 1 (GP1) by reaction of methyl 6-amino-6-(2,6-dimethoxyphenyl)hexanoate with 6-(1H-pyrazol-1-yl)picolinaldehyde. Subsequent purification by preparative HPLC afforded the target compound. LC-MS (conditions A): $t_R$=0.84 min.; [M+H]$^+$: 407.07 g/mol.

Example 105

7-(2,6-dimethoxyphenyl)-1-((2-methylbenzo[d]thiazol-6-yl)methyl)azepan-2-one

Prepared according to the described general procedure 1 (GP1) by reaction of methyl 6-amino-6-(2,6-dimethoxyphenyl)hexanoate with 2-methylbenzo[d]thiazole-6-carbaldehyde. Subsequent purification by preparative HPLC afforded the target compound. LC-MS (conditions A): $t_R$=0.83 min.; [M+H]$^+$: 411.03 g/mol.

Example 106

7-(2,6-dimethoxyphenyl)-1-(2-fluoro-3-(pyridin-2-yl)benzyl)azepan-2-one

Prepared according to the described general procedure 1 (GP1) by reaction of methyl 6-amino-6-(2,6-dimethoxyphenyl)hexanoate with 2-fluoro-3-(pyridin-2-yl)benzaldehyde.

Subsequent purification by preparative HPLC afforded the target compound. LC-MS (conditions A): $t_R$=0.72 min.; [M+H]$^+$: 435.13 g/mol.

Example 107

7-(2,6-dimethoxyphenyl)-1-(4-fluoro-3-(pyridin-2-yl)benzyl)azepan-2-one

Prepared according to the described general procedure 1 (GP1) by reaction of methyl 6-amino-6-(2,6-dimethoxyphenyl)hexanoate with 4-fluoro-3-(pyridin-2-yl)benzaldehyde. Subsequent purification by preparative HPLC afforded the target compound. LC-MS (conditions A): $t_R$=0.74 min.; [M+H]$^+$: 435.13 g/mol.

Example 108

1-(4-(trifluoromethoxy)benzyl)-5-(2,4,6-trimethoxyphenyl)pyrrolidin-2-one

Prepared according to the described general procedure 3 (GP3) by reaction of methyl 4-oxo-4-(2,4,6-trimethoxyphenyl)butanoate with commercially available (4-(trifluoromethoxy)phenyl)methanamine. Subsequent purification by preparative HPLC afforded the target compound. LC-MS (conditions D): $t_R$=1.08 min.; [M+H]$^+$: 425.72 g/mol.

Example 109

5-(2,6-dimethoxyphenyl)-1-(quinolin-3-ylmethyl)pyrrolidin-2-one

Prepared according to the described general procedure 1 (GP1) by reaction of methyl 4-amino-4-(2,6-dimethoxyphenyl)butanoate with commercially available quinoline-3-carbaldehyde. Subsequent purification by preparative HPLC afforded the target compound. LC-MS (conditions A): $t_R$=0.55 min.; [M+H]$^+$: 363.35 g/mol.

Example 110

5-(2,6-dimethoxyphenyl)-1-(quinolin-2-ylmethyl)pyrrolidin-2-one

Prepared according to the described general procedure 1 (GP1) by reaction of methyl 4-amino-4-(2,6-dimethoxyphenyl)butanoate with commercially available quinoline-2-carbaldehyde. Subsequent purification by preparative HPLC afforded the target compound. LC-MS (conditions A): $t_R$=0.57 min.; [M+H]$^+$: 363.36 g/mol.

Example 111

5-(2,6-dimethoxyphenyl)-1-(naphthalen-2-ylmethyl)pyrrolidin-2-one

Prepared according to the described general procedure 1 (GP1) by reaction of methyl 4-amino-4-(2,6-dimethoxyphenyl)butanoate with commercially available 2-naphthaldehyde. Subsequent purification by preparative HPLC afforded the target compound. LC-MS (conditions A): $t_R$=0.87 min.; [M+H]$^+$: 362.35 g/mol.

Example 112

1-((5-chloro-6-(difluoromethoxy)pyridin-3-yl)methyl)-5-(2,6-dimethoxyphenyl)pyrrolidin-2-one Prepared according to the described general procedure 2 (GP2) by reaction of methyl 4-amino-4-(2,6-dimethoxyphenyl)butanoate with 5-chloro-6-(difluoromethoxy)nicotinaldehyde. Subsequent purification by preparative HPLC afforded the target compound. LC-MS (conditions A): $t_R$=0.84 min.; [M+H]$^+$: 413.32 g/mol.

Example 113

1-([1,1'-biphenyl]-3-ylmethyl)-5-(2,6-dimethoxyphenyl)pyrrolidin-2-one

Prepared according to the described general procedure 2 (GP2) by reaction of methyl 4-amino-4-(2,6-dimethoxyphenyl)butanoate with commercially available [1,1'-biphenyl]-3-carbaldehyde. Subsequent purification by preparative HPLC afforded the target compound. LC-MS (conditions A): $t_R$=0.91 min.; [M+H]$^+$: 388.11 g/mol.

Example 114

1-([1,1'-biphenyl]-4-ylmethyl)-5-(2,6-dimethoxyphenyl)pyrrolidin-2-one

Prepared according to the described general procedure 2 (GP2) by reaction of methyl 4-amino-4-(2,6-dimethoxyphenyl)butanoate with commercially available [1,1'-biphenyl]-4-carbaldehyde. Subsequent purification by preparative HPLC afforded the target compound. LC-MS (conditions A): $t_R$=0.91 min.; [M+H]$^+$: 388.12 g/mol.

Example 115

5-(2,6-dimethoxyphenyl)-1-(3-(pyridin-3-yl)benzyl)pyrrolidin-2-one

Prepared according to the described general procedure 2 (GP2) by reaction of methyl 4-amino-4-(2,6-dimethoxyphenyl)butanoate with commercially available 3-(pyridin-3-yl)benzaldehyde. Subsequent purification by preparative HPLC afforded the target compound. LC-MS (conditions A): $t_R$=0.57 min.; [M+H]$^+$: 389.36 g/mol.

Example 116

5-(2,6-dimethoxyphenyl)-1-(naphthalen-1-ylmethyl)pyrrolidin-2-one

Prepared according to the described general procedure 2 (GP2) by reaction of methyl 4-amino-4-(2,6-dimethoxyphenyl)butanoate with commercially available 1-naphthaldehyde. Subsequent purification by preparative HPLC afforded the target compound. LC-MS (conditions A): $t_R$=0.87 min.; [M+H]$^+$: 362.17 g/mol.

Example 117

5-(2,6-dimethoxyphenyl)-1-(3-phenoxybenzyl)pyrrolidin-2-one

Prepared according to the described general procedure 2 (GP2) by reaction of methyl 4-amino-4-(2,6-dimethoxyphenyl)butanoate with commercially available 3-phenoxybenzaldehyde. Subsequent purification by preparative HPLC afforded the target compound. LC-MS (conditions A): $t_R$=0.92 min.; [M+H]$^+$: 404.17 g/mol.

Example 118

5-(2,6-dimethoxyphenyl)-1-(4-phenoxybenzyl)pyrrolidin-2-one

Prepared according to the described general procedure 2 (GP2) by reaction of methyl 4-amino-4-(2,6-dimethoxyphenyl)butanoate with commercially available 4-phenoxybenzaldehyde. Subsequent purification by preparative HPLC afforded the target compound. LC-MS (conditions A): $t_R$=0.92 min.; [M+H]$^+$: 404.15 g/mol.

Example 119

5-(2,6-dimethoxyphenyl)-1-(3-(pyridin-2-yl)benzyl)pyrrolidin-2-one

Prepared according to the described general procedure 2 (GP2) by reaction of methyl 4-amino-4-(2,6-dimethoxyphenyl)butanoate with commercially available 3-(pyridin-2-yl)benzaldehyde. Subsequent purification by preparative HPLC afforded the target compound. LC-MS (conditions A): $t_R$=0.60 min.; [M+H]$^+$: 389.15 g/mol.

Example 120

5-(2,6-dimethoxyphenyl)-1-((2-phenylpyridin-4-yl)methyl)pyrrolidin-2-one

Prepared according to the described general procedure 2 (GP2) by reaction of methyl 4-amino-4-(2,6-dimethoxyphenyl)butanoate with 2-phenylisonicotinaldehyde. Subsequent purification by preparative HPLC afforded the target compound. LC-MS (conditions A): $t_R$=0.61 min.; [M+H]$^+$: 389.16 g/mol.

Example 121

5-(2,6-dimethoxyphenyl)-1-((6-phenylpyridin-2-yl)methyl)pyrrolidin-2-one

Prepared according to the described general procedure 2 (GP2) by reaction of methyl 4-amino-4-(2,6-dimethoxyphenyl)butanoate with 6-phenylpicolinaldehyde. Subsequent purification by preparative HPLC afforded the target compound. LC-MS (conditions A): $t_R$=0.76 min.; [M+H]$^+$: 389.14 g/mol.

Example 122

1-([1,1'-biphenyl]-3-ylmethyl)-5-(2,6-dimethoxyphenyl)-3-methylpyrrolidin-2-one (Mixture of Stereoisomers)

Prepared according to the described general procedure 2 (GP2) by reaction of ethyl 4-amino-4-(2,6-dimethoxyphenyl)-2-methylbutanoate with commercially available [1,1'-biphenyl]-3-carbaldehyde. Subsequent purification by preparative HPLC afforded the target compound. LC-MS (conditions A): $t_R$=0.96 min.; [M+H]$^+$: 402.39 g/mol.

Example 123

5-(2,6-dimethoxyphenyl)-3-methyl-1-(3-(pyrrolidin-1-yl)benzyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with commercially available 3-(pyrrolidin-1-yl)benzaldehyde. Subsequent purification by preparative HPLC afforded the target compound. LC-MS (conditions A): $t_R$=0.82 min.; [M+H]$^+$: 395.20 g/mol.

Example 124

5-(2,6-dimethoxyphenyl)-1-(3-(thiazol-2-yl)benzyl)pyrrolidin-2-one

Prepared according to the described general procedure 2 (GP2) by reaction of methyl 4-amino-4-(2,6-dimethoxyphenyl)butanoate with commercially available 3-(thiazol-2-yl)benzaldehyde. Subsequent purification by preparative HPLC afforded the target compound. LC-MS (conditions A): $t_R$=0.79 min.; [M+H]$^+$: 395.12 g/mol.

Example 125

5-(2,6-dimethoxyphenyl)-1-(3-(2-methylthiazol-4-yl)benzyl)pyrrolidin-2-one

Prepared according to the described general procedure 2 (GP2) by reaction of methyl 4-amino-4-(2,6-dimethoxyphenyl)butanoate with commercially available 3-(2-methylthiazol-4-yl)benzaldehyde. Subsequent purification by preparative HPLC afforded the target compound. LC-MS (conditions A): $t_R$=0.81 min.; [M+H]$^+$: 409.15 g/mol.

Example 126

1-(3-(1H-pyrazol-1-yl)benzyl)-5-(2,6-dimethoxyphenyl)pyrrolidin-2-one

Prepared according to the described general procedure 2 (GP2) by reaction of methyl 4-amino-4-(2,6-dimethoxyphenyl)butanoate with commercially available 3-(1H-pyrazol-1-yl)benzaldehyde. Subsequent purification by preparative HPLC afforded the target compound. LC-MS (conditions A): $t_R$=0.76 min.; [M+H]$^+$: 378.17 g/mol.

Example 127

1-(dibenzo[b,d]furan-2-ylmethyl)-5-(2,6-dimethoxyphenyl)pyrrolidin-2-one

Prepared according to the described general procedure 2 (GP2) by reaction of methyl 4-amino-4-(2,6-dimethoxyphenyl)butanoate with commercially available dibenzo[b,d]furan-2-carbaldehyde. Subsequent purification by preparative HPLC afforded the target compound. LC-MS (conditions A): $t_R$=0.92 min.; [M+H]$^+$: δ 401.83 g/mol.

Example 128

1-(benzo[d]thiazol-2-ylmethyl)-5-(2,6-dimethoxyphenyl)pyrrolidin-2-one

Prepared according to the described general procedure 2 (GP2) by reaction of methyl 4-amino-4-(2,6-dimethoxyphenyl)butanoate with commercially available benzo[d]thiazole-2-carbaldehyde. Subsequent purification by preparative HPLC afforded the target compound. LC-MS (conditions A): $t_R$=0.77 min.; [M+H]$^+$: 369.10 g/mol.

Example 129

5-(2,6-dimethoxyphenyl)-1-(3-(piperidin-1-yl)benzyl)pyrrolidin-2-one

Prepared according to the described general procedure 2 (GP2) by reaction of methyl 4-amino-4-(2,6-dimethoxyphenyl)butanoate with commercially available 3-(piperidin-1-yl)benzaldehyde. Subsequent purification by preparative HPLC afforded the target compound. LC-MS (conditions A): $t_R$=0.57 min.; [M+H]$^+$: 394.99 g/mol.

Example 130

5-(2,6-dimethoxyphenyl)-1-((6-(piperidin-1-yl)pyridin-2-yl)methyl)pyrrolidin-2-one Prepared according to the described general procedure 2 (GP2) by reaction of methyl 4-amino-4-(2,6-dimethoxyphenyl)butanoate with commercially available 6-(piperidin-1-yl)picolinaldehyde. Subsequent purification by preparative HPLC afforded the target compound. LC-MS (conditions A): $t_R$=0.61 min.; [M+H]$^+$: 396.00 g/mol.

Example 131

5-(2,6-dimethoxyphenyl)-3-methyl-1-(naphthalen-2-ylmethyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with commercially available 2-naphthaldehyde. Subsequent purification by preparative HPLC afforded the target compound. LC-MS (conditions A): $t_R$=0.92 min.; [M+H]$^+$: 376.02 g/mol.

Example 132

5-(2,6-dimethoxyphenyl)-3-methyl-1-(3-(thiazol-2-yl)benzyl)pyrrolidin-2-one (Mixture of Stereoisomers)

Prepared according to the described general procedure 1 (GP1) by reaction of ethyl 4-amino-4-(2,6-dimethoxyphenyl)-2-methylbutanoate with commercially available 3-(thiazol-2-yl)benzaldehyde. Subsequent purification by preparative HPLC afforded the target compound. LC-MS (conditions A): $t_R$=0.84 min.; [M+H]$^+$: 409.16 g/mol.

Example 133

5-(2,6-dimethoxyphenyl)-3-methyl-1-(3-(2-methylthiazol-4-yl)benzyl)pyrrolidin-2-one (Mixture of Stereoisomers)

Prepared according to the described general procedure 1 (GP1) by reaction of ethyl 4-amino-4-(2,6-dimethoxyphenyl)-2-methylbutanoate with commercially available 3-(2-methylthiazol-4-yl)benzaldehyde. Subsequent purification by preparative HPLC afforded the target compound. LC-MS (conditions A): $t_R$=0.87 min.; [M+H]$^+$: 423.22 g/mol.

Example 134

5-(2,6-dimethoxyphenyl)-3-methyl-1-(3-(piperidin-1-yl)benzyl)pyrrolidin-2-one (mixture of stereoisomers)

Prepared according to the described general procedure 1 (GP1) by reaction of ethyl 4-amino-4-(2,6-dimethoxyphenyl)-2-methylbutanoate with commercially available 3-(piperidin-1-yl)benzaldehyde. Subsequent purification by preparative HPLC afforded the target compound. LC-MS (conditions A): $t_R$=0.61 min.; [M+H]$^+$: 409.11 g/mol.

Example 135

1-(3-(1H-pyrazol-1-yl)benzyl)-5-(2,6-dimethoxyphenyl)-3-methylpyrrolidin-2-one (Mixture of Stereoisomers)

Prepared according to the described general procedure 2 (GP2) by reaction of ethyl 4-amino-4-(2,6-dimethoxyphenyl)-2-methylbutanoate with commercially available 3-(1H-pyrazol-1-yl)benzaldehyde. Subsequent purification by preparative HPLC afforded the target compound. LC-MS (conditions A): $t_R$=0.81 min.; [M+H]$^+$: 392.18 g/mol.

Example 136

5-(2,6-dimethoxyphenyl)-1-(3-(5-methyl-1,2,4-oxadiazol-3-yl)benzyl)pyrrolidin-2-one Prepared according to the described general procedure 2 (GP2) by reaction of methyl 4-amino-4-(2,6-dimethoxyphenyl)butanoate with commercially available 3-(5-methyl-1,2,4-oxadiazol-3-yl)benzaldehyde. Subsequent purification by preparative HPLC afforded the target compound. LC-MS (conditions A): $t_R$=0.77 min.; [M+H]$^+$: 394.03 g/mol.

Example 137

1-(dibenzo[b,d]furan-2-ylmethyl)-5-(2,6-dimethoxyphenyl)-3-methylpyrrolidin-2-one (mixture of Stereoisomers)

Prepared according to the described general procedure 2 (GP2) by reaction of ethyl 4-amino-4-(2,6-dimethoxyphenyl)-2-methylbutanoate with commercially available dibenzo[b,d]furan-2-carbaldehyde. Subsequent purification by preparative HPLC afforded the target compound. LC-MS (conditions A): $t_R$=0.96 min.; [M+H]$^+$: 416.03 g/mol.

Example 138

5-(2,6-dimethoxyphenyl)-3-methyl-1-((6-phenylpyridin-2-yl)methyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 6-phenylpicolinaldehyde. Subsequent purification by preparative HPLC afforded the target compound. LC-MS (conditions A): $t_R$=0.82 min.; [M+H]$^+$: 403.00 g/mol.

Example 139

5-(2,6-dimethoxyphenyl)-3-methyl-1-((2-phenylpyridin-4-yl)methyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 2-phenylisonicotinaldehyde. Subsequent purification by preparative HPLC afforded the target compound. LC-MS (conditions A): $t_R$=0.65 min.; [M+H]$^+$: 402.99 g/mol.

Example 140

5-(2,6-dimethoxyphenyl)-3-methyl-1-(3-(pyridin-2-yl)benzyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with commercially available 3-(pyridin-2-yl)benzaldehyde. Subsequent purification by preparative HPLC afforded the target compound. LC-MS (conditions A): $t_R$=0.64 min.; [M+H]$^+$: 402.99 g/mol.

Example 141

5-(2,6-dimethoxyphenyl)-3-methyl-1-(3-(pyridin-3-yl)benzyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with commercially available 3-(pyridin-3-yl)benzaldehyde. Subsequent purification by preparative HPLC afforded the target compound. LC-MS (conditions A): $t_R$=0.61 min.; [M+H]$^+$: 403.00 g/mol.

Example 142

5-(2,6-dimethoxyphenyl)-3-methyl-1-(3-(pyrimidin-2-yl)benzyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with commercially available 3-(pyrimidin-2-yl)benzaldehyde. Subsequent purification by preparative HPLC afforded the target compound. LC-MS (conditions A): $t_R$=0.79 min.; [M+H]$^+$: 403.86 g/mol.

Example 143

5-(2,6-dimethoxyphenyl)-3-methyl-1-(3-(5-methyl-1,2,4-oxadiazol-3-yl)benzyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with commercially available 3-(5-methyl-1,2,4-oxadiazol-3-yl)benzaldehyde. Subsequent purification by preparative HPLC afforded the target compound. LC-MS (conditions A): $t_R$=0.82 min.; [M+H]$^+$: 408.01 g/mol.

Example 144

5-(2,6-dimethoxyphenyl)-3-methyl-1-((1-phenyl-1H-pyrazol-4-yl)methyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with commercially available 1-phenyl-1H-pyrazole-4-carbaldehyde. Subsequent purification by preparative HPLC afforded the target compound. LC-MS (conditions A): $t_R$=0.81 min.; [M+H]$^+$: 392.03 g/mol.

Example 145

5-(2,6-dimethoxyphenyl)-3-methyl-1-((2-phenylthiazol-4-yl)methyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with commercially available 2-phenylthiazole-4-carbaldehyde. Subsequent purification by preparative HPLC afforded the target compound. LC-MS (conditions A): $t_R$=0.89 min.; [M+H]$^+$: 409.09 g/mol.

Example 146

5-(2,6-dimethoxyphenyl)-1-(2-fluoro-3-(pyridin-2-yl)benzyl)-3-methylpyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 2-fluoro-3-(pyridin-2-yl)benzaldehyde. Subsequent purification by preparative HPLC afforded the target compound. LC-MS (conditions A): $t_R$=0.68 min.; [M+H]$^+$: 421.11 g/mol.

Example 147

5-(2,6-dimethoxyphenyl)-3-methyl-1-(3-(thiazol-5-yl)benzyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 3-(thiazol-5-yl)benzaldehyde.

Example 148

5-(2,6-dimethoxyphenyl)-3-methyl-1-(3-(5-methylthiazol-2-yl)benzyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 3-(5-methylthiazol-2-yl)benzaldehyde. Subsequent purification by preparative HPLC afforded the target compound. LC-MS (conditions A): $t_R$=0.89 min.; [M+H]$^+$: 423.09 g/mol.

Example 149

1-(3-(2H-1,2,3-triazol-2-yl)benzyl)-5-(2,6-dimethoxyphenyl)-3-methylpyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 3-(2H-1,2,3-triazol-2-yl)benzaldehyde. Subsequent purification by preparative HPLC afforded the target compound. LC-MS (conditions A): $t_R$=0.84 min.; [M+H]$^+$: 393.05 g/mol.

Example 150

5-(2,6-dimethoxyphenyl)-3-methyl-1-(3-(thiazol-4-yl)benzyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 3-(thiazol-4-yl)benzaldehyde. Subsequent purification by preparative HPLC afforded the target compound. LC-MS (conditions A): $t_R$=0.83 min.; [M+H]$^+$: 409.03 g/mol.

Example 151

5-(2,6-dimethoxyphenyl)-3-methyl-1-((2-methylbenzo[d]thiazol-6-yl)methyl)pyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 2-methylbenzo[d]thiazole-6-carbaldehyde. Subsequent purification by preparative HPLC afforded the target compound. LC-MS (conditions A): $t_R$=0.78 min.; [M+H]$^+$: 397.02 g/mol.

Example 152

1-(3-chloro-5-(pyridin-2-yl)benzyl)-5-(2,6-dimethoxyphenyl)-3-methylpyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 3-chloro-5-(pyridin-2-yl)benzaldehyde. Subsequent purification by preparative HPLC afforded the target compound. LC-MS (conditions A): $t_R$=0.76 min.; [M+H]$^+$: 437.09 g/mol.

Example 153

5-(2,6-dimethoxyphenyl)-1-(4-fluoro-3-(pyridin-2-yl)benzyl)-3-methylpyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 4-fluoro-3-(pyridin-2-yl)benzaldehyde. Subsequent purification by preparative HPLC afforded the target compound. LC-MS (conditions A): $t_R$=0.72 min.; [M+H]$^+$: 421.08 g/mol.

Example 154

1-((2-(1H-pyrazol-1-yl)pyridin-4-yl)methyl)-5-(2,6-dimethoxyphenyl)-3-methylpyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 2-(1H-pyrazol-1-yl)isonicotinaldehyde. Subsequent purification by preparative HPLC afforded the target compound. LC-MS (conditions A): $t_R$=0.80 min.; [M+H]$^+$: 392.88 g/mol.

Example 155

1-((6-(1H-pyrazol-1-yl)pyridin-2-yl)methyl)-5-(2,6-dimethoxyphenyl)-3-methylpyrrolidin-2-one (Mixture of Stereoisomers)

Prepared according to the described general procedure 2 (GP2) by reaction of ethyl 4-amino-4-(2,6-dimethoxyphenyl)-2-methylbutanoate with 6-(1H-pyrazol-1-yl)picolinaldehyde. Subsequent purification by preparative HPLC afforded the target compound. LC-MS (conditions A): $t_R$=0.80 min.; [M+H]$^+$: 393.10 g/mol.

Example 156

6-(2,6-dimethoxyphenyl)-1-(4-(trifluoromethoxy)benzyl)piperidin-2-one

Prepared according to the described general procedure 4 (GP4) by reaction of 6-(2,6-dimethoxyphenyl)piperidin-2-one with commercially available 1-(bromomethyl)-4-(trifluoromethoxy)benzene. Subsequent purification by preparative HPLC afforded the target compound. LC-MS (conditions E): $t_R$=0.82 min.; [M+H]$^+$: 410.08 g/mol.

Example 157

6-(2,6-dimethoxyphenyl)-1-(4-fluorobenzyl)piperidin-2-one

Prepared according to the described general procedure 4 (GP4) by reaction of 6-(2,6-dimethoxyphenyl)piperidin-2-one with commercially available 1-(bromomethyl)-4-fluorobenzene. Subsequent purification by preparative HPLC afforded the target compound. LC-MS (conditions E): $t_R$=0.73 min.; [M+H]$^+$: 344.22 g/mol.

Example 158

1-(4-chlorobenzyl)-6-(2,6-dimethoxyphenyl)piperidin-2-one

Prepared according to the described general procedure 4 (GP4) by reaction of 6-(2,6-dimethoxyphenyl)piperidin-2-one with commercially available 1-(bromomethyl)-4-chlorobenzene. Subsequent purification by preparative HPLC afforded the target compound. LC-MS (conditions E): $t_R$=0.77 min.; [M+H]$^+$: 360.18 g/mol.

Example 159

6-(2,6-dimethoxyphenyl)-1-(4-methoxybenzyl)piperidin-2-one

Prepared according to the described general procedure 4 (GP4) by reaction of 6-(2,6-dimethoxyphenyl)piperidin-2-one with commercially available 1-(chloromethyl)-4-methoxybenzene. Subsequent purification by preparative HPLC afforded the target compound. LC-MS (conditions E): $t_R$=0.72 min.; [M+H]$^+$: 356.26 g/mol.

Example 160

6-(2,6-dimethoxyphenyl)-1-(3-fluoro-4-(trifluoromethoxy)benzyl)piperidin-2-one

Prepared according to the described general procedure 4 (GP4) by reaction of 6-(2,6-dimethoxyphenyl)piperidin-2-one with commercially available 4-(bromomethyl)-2-fluoro-1-(trifluoromethoxy)benzene. Subsequent purification by preparative HPLC afforded the target compound. LC-MS (conditions E): $t_R$=0.81 min.; [M+H]$^+$: 428.21 g/mol.

Example 161

1-(3-chloro-4-(trifluoromethoxy)benzyl)-6-(2,6-dimethoxyphenyl)piperidin-2-one

Prepared according to the described general procedure 4 (GP4) by reaction of 6-(2,6-dimethoxyphenyl)piperidin-2-one with commercially available 4-(bromomethyl)-2-chloro-1-(trifluoromethoxy)benzene. Subsequent purification by preparative HPLC afforded the target compound. LC-MS (conditions E): $t_R$=0.83 min.; [M+H]$^+$: 444.11 g/mol.

Example 162

6-(2,6-dimethoxyphenyl)-1-(4-((trifluoromethyl)thio)benzyl)piperidin-2-one

Prepared according to the described general procedure 4 (GP4) by reaction of 6-(2,6-dimethoxyphenyl)piperidin-2-one with commercially available (4-(bromomethyl)phenyl)(trifluoromethyl)sulfane. Subsequent purification by preparative HPLC afforded the target compound. LC-MS (conditions E): $t_R$=0.83 min.; [M+H]$^+$: 426.20 g/mol.

Example 163

6-(2,6-dimethoxyphenyl)-1-(4-(trifluoromethyl)benzyl)piperidin-2-one

Prepared according to the described general procedure 4 (GP4) by reaction of 6-(2,6-dimethoxyphenyl)piperidin-2-one with commercially available 1-(bromomethyl)-4-(trifluoromethyl)benzene. Subsequent purification by preparative HPLC afforded the target compound. LC-MS (conditions E): $t_R$=0.79 min.; [M+H]$^+$: 394.17 g/mol.

Example 164

6-(2,6-dimethoxyphenyl)-1-(4-phenoxybenzyl)piperidin-2-one

Prepared according to the described general procedure 4 (GP4) by reaction of 6-(2,6-dimethoxyphenyl)piperidin-2-one with commercially available 1-(bromomethyl)-4-phenoxybenzene. Subsequent purification by preparative HPLC afforded the target compound. LC-MS (conditions E): $t_R$=0.82 min.; [M+H]$^+$: 417.72 g/mol.

Example 165

1-(4-(difluoromethoxy)benzyl)-6-(2,6-dimethoxyphenyl)piperidin-2-one

Prepared according to the described general procedure 4 (GP4) by reaction of 6-(2,6-dimethoxyphenyl)piperidin-2-one with commercially available 1-(bromomethyl)-4-(difluoromethoxy)benzene. Subsequent purification by preparative HPLC afforded the target compound. LC-MS (conditions E): $t_R$=0.76 min.; [M+H]$^+$: 392.16 g/mol.

Example 166

1-(benzo[d][1,3]dioxol-5-ylmethyl)-6-(2,6-dimethoxyphenyl)piperidin-2-one

Prepared according to the described general procedure 4 (GP4) by reaction of 6-(2,6-dimethoxyphenyl)piperidin-2-one with commercially available 5-(chloromethyl)benzo[d][1,3]dioxole. Subsequent purification by preparative HPLC afforded the target compound. LC-MS (conditions E): $t_R$=0.71 min.; [M+H]$^+$: 369.68 g/mol.

Example 167

6-(4-chloro-2,6-dimethoxyphenyl)-1-(4-(trifluoromethoxy)benzyl)piperidin-2-one

Prepared according to the described general procedure 4 (GP4) by reaction of 6-(4-chloro-2,6-dimethoxyphenyl)piperidin-2-one with commercially available 1-(bromomethyl)-4-(trifluoromethoxy)benzene. Subsequent purification by preparative HPLC afforded the target compound. LC-MS (conditions E): $t_R$=0.84 min.; [M+H]$^+$: 444.09 g/mol.

Example 168

1-(4-(1H-pyrazol-1-yl)benzyl)-6-(2,6-dimethoxyphenyl)piperidin-2-one

Prepared according to the described general procedure 4 (GP4) by reaction of 6-(2,6-dimethoxyphenyl)piperidin-2-one with commercially available 1-(4-(bromomethyl)phenyl)-1H-pyrazole. Subsequent purification by preparative HPLC afforded the target compound. LC-MS (conditions E): $t_R$=0.73 min.; [M+H]$^+$: 392.16 g/mol.

Example 169

1-(4-(1H-pyrrol-1-yl)benzyl)-6-(2,6-dimethoxyphenyl)piperidin-2-one

Prepared according to the described general procedure 4 (GP4) by reaction of 6-(2,6-dimethoxyphenyl)piperidin-2-one with commercially available 1-(4-(bromomethyl)phenyl)-1H-pyrrole. Subsequent purification by preparative HPLC afforded the target compound. LC-MS (conditions E): $t_R$=0.80 min.; [M+H]$^+$: 391.18 g/mol.

Example 170

1-(benzo[c][1,2,5]oxadiazol-5-ylmethyl)-6-(2,6-dimethoxyphenyl)piperidin-2-one

Prepared according to the described general procedure 4 (GP4) by reaction of 6-(2,6-dimethoxyphenyl)piperidin-2-one with commercially available 5-(bromomethyl)benzo[c][1,2,5]oxadiazole. Subsequent purification by preparative HPLC afforded the target compound. LC-MS (conditions E): $t_R$=0.74 min.; [M+H]$^+$: 368.1 g/mol.

Example 171

6-(2,6-dimethoxyphenyl)-1-((6-methoxynaphthalen-2-yl)methyl)piperidin-2-one

Prepared according to the described general procedure 4 (GP4) by reaction of 6-(2,6-dimethoxyphenyl)piperidin-2-one with 2-(chloromethyl)-6-methoxynaphthalene. Subsequent purification by preparative HPLC afforded the target compound. LC-MS (conditions E): $t_R$=0.80 min.; [M+H]$^+$: 406.18 g/mol.

Example 172

1-(4-(trifluoromethoxy)benzyl)-6-(2,4,6-trimethoxyphenyl)piperidin-2-one

Prepared according to the described general procedure 4 (GP4) by reaction of 6-(2,4,6-trimethoxyphenyl)piperidin-2-one with commercially available 1-(bromomethyl)-4-(trifluoromethoxy)benzene. Subsequent purification by preparative HPLC afforded the target compound. LC-MS (conditions D): $t_R$=1.10 min.; [M+H]$^+$: 439.78 g/mol.

Example 173

6-(2,6-dimethoxyphenyl)-4-methyl-1-(4-(trifluoromethoxy)benzyl)piperidin-2-one (Mixture of Stereoisomers)

Prepared according to the described general procedure 4 (GP4) by reaction of 6-(2,6-dimethoxyphenyl)-4-methylpiperidin-2-one with commercially available 1-(bromomethyl)-4-(trifluoromethoxy)benzene. Subsequent purification by preparative HPLC afforded the target compound. LC-MS (conditions D): $t_R$=1.13 min.; [M+H]$^+$: 423.91 g/mol.

Example 174

6-(2,6-dimethoxyphenyl)-4,4-dimethyl-1-(4(trifluoromethoxy)benzyl)piperidin-2-one Prepared according to the described general procedure 4 (GP4) by reaction of 6-(2,6-dimethoxyphenyl)-4,4-dimethylpiperidin-2-one with commercially available 1-(bromomethyl)-4-(trifluoromethoxy)benzene. Subsequent purification by preparative HPLC afforded the target compound. LC-MS (conditions D): $t_R$=1.14 min.; [M+H]$^+$: 437.96 g/mol.

Example 175

6-(2,6-dimethoxyphenyl)-1-(3-(trifluoromethoxy)benzyl)piperidin-2-one

Prepared according to the described general procedure 4 (GP4) by reaction of 6-(2,6-dimethoxyphenyl)piperidin-2-one with commercially available 1-(bromomethyl)-3-(trifluoromethoxy)benzene. Subsequent purification by preparative HPLC afforded the target compound. LC-MS (conditions D): $t_R$=1.10 min.; [M+H]$^+$: 410.4 g/mol.

Example 176

6-(2,6-dimethoxyphenyl)-1-(4-(2-fluoroethoxy)benzyl)piperidin-2-one

Prepared according to the described general procedure 4 (GP4) by reaction of 6-(2,6-dimethoxyphenyl)piperidin-2-one with 1-(bromomethyl)-4-(2-fluoroethoxy)benzene. Subsequent purification by preparative HPLC afforded the target compound. LC-MS (conditions F): $t_R$=0.80 min.; [M+H]$^+$: 388.23 g/mol.

Example 177

1-((6-(difluoromethoxy)pyridin-3-yl)methyl)-6-(2,6-dimethoxyphenyl)piperidin-2-one Prepared according to the described general procedure 4 (GP4) by reaction of 6-(2,6-dimethoxyphenyl)piperidin-2-one with 5-(bromomethyl)-2-(difluoromethoxy)pyridine. Subsequent purification by preparative HPLC afforded the target compound. LC-MS (conditions D): $t_R$=1.03 min.; [M+H]$^+$: 393.53 g/mol.

Example 178

1-(3-(difluoromethoxy)benzyl)-6-(2,6-dimethoxyphenyl)piperidin-2-one

Prepared according to the described general procedure 4 (GP4) by reaction of 6-(2,6-dimethoxyphenyl)piperidin-2-one with commercially available 1-(bromomethyl)-3-(difluoromethoxy)benzene. Subsequent purification by preparative HPLC afforded the target compound. LC-MS (conditions D): $t_R$=1.05 min.; [M+H]$^+$: 392.75 g/mol.

Example 179

6-(2,6-dimethoxyphenyl)-1-(3-phenoxybenzyl)piperidin-2-one

Prepared according to the described general procedure 4 (GP4) by reaction of 6-(2,6-dimethoxyphenyl)piperidin-2-

Example 180

1-(benzofuran-2-ylmethyl)-6-(2,6-dimethoxyphenyl)piperidin-2-one

Prepared according to the described general procedure 4 (GP4) by reaction of 6-(2,6-dimethoxyphenyl)piperidin-2-one with 2-(bromomethyl)benzofuran. Subsequent purification by preparative HPLC afforded the target compound. LC-MS (conditions F): $t_R$=0.83 min.; [M+H]$^+$: 366.15 g/mol.

Example 181

1-(benzo[b]thiophen-2-ylmethyl)-6-(2,6-dimethoxyphenyl)piperidin-2-one

Prepared according to the described general procedure 4 (GP4) by reaction of 6-(2,6-dimethoxyphenyl)piperidin-2-one with 2-(bromomethyl)benzo[b]thiophene. Subsequent purification by preparative HPLC afforded the target compound. LC-MS (conditions F): $t_R$=0.86 min.; [M+H]$^+$: 382.22 g/mol.

Example 182

1-((2,2-difluorobenzo[d][1,3]dioxol-5-yl)methyl)-6-(2,6-dimethoxyphenyl)piperidin-2-one Prepared according to the described general procedure 4 (GP4) by reaction of 6-(2,6-dimethoxyphenyl)piperidin-2-one with 5-(bromomethyl)-2,2-difluorobenzo[d][1,3]dioxole. Subsequent purification by preparative HPLC afforded the target compound. LC-MS (conditions A): $t_R$=0.91 min.; [M+H]$^+$: 406.17 g/mol.

Example 183

1-((6-(difluoromethoxy)pyridin-2-yl)methyl)-6-(2,6-dimethoxyphenyl)piperidin-2-one Prepared according to the described general procedure 4 (GP4) by reaction of 6-(2,6-dimethoxyphenyl)piperidin-2-one with 2-(bromomethyl)-6-(difluoromethoxy)pyridine. Subsequent purification by preparative HPLC afforded the target compound. LC-MS (conditions A): $t_R$=0.83 min.; [M+H]$^+$: 393.19 g/mol.

Example 184

6-(2,6-dimethoxyphenyl)-1-(1-(4-(trifluoromethoxy)phenyl)ethyl)piperidin-2-one (Mixture of Stereoisomers)

Prepared according to the described general procedure 4 (GP4) by reaction of 6-(2,6-dimethoxyphenyl)piperidin-2-one with 1-(1-bromoethyl)-4-(trifluoromethoxy)benzene. Subsequent purification by preparative HPLC afforded the target compound. LC-MS (conditions A): $t_R$=0.94 min.; [M+H]$^+$: 424.23 g/mol.

Example 185

1-(1-(5-chloro-6-(difluoromethoxy)pyridin-3-yl)ethyl)-6-(2,6-dimethoxyphenyl)piperidin-2-one (Mixture of Stereoisomers)

Prepared according to the described general procedure 4 (GP4) by reaction of 6-(2,6-dimethoxyphenyl)piperidin-2-one with 5-(1-bromoethyl)-3-chloro-2-(difluoromethoxy)pyridine. Subsequent purification by preparative HPLC afforded the target compound. LC-MS (conditions A): $t_R$=0.89 min., [M+H]$^+$: 441.23 g/mol; $t_R$=0.91 min., [M+H]$^+$: 441.22 g/mol (diastereomers).

Example 186

6-(2,6-dimethoxyphenyl)-1-(1-(4-(trifluoromethoxy)phenyl)propyl)piperidin-2-one (Mixture of Stereoisomers)

Prepared according to the described general procedure 4 (GP4) by reaction of 6-(2,6-dimethoxyphenyl)piperidin-2-one with 1-(1-bromopropyl)-4-(trifluoromethoxy)benzene. Subsequent purification by preparative HPLC afforded the target compound. LC-MS (conditions A): $t_R$=0.99 min.; [M+H]$^+$: 438.22 g/mol.

Example 187

1-((5-(difluoromethoxy)pyridin-2-yl)methyl)-6-(2,6-dimethoxyphenyl)piperidin-2-one Prepared according to the described general procedure 4 (GP4) by reaction of 6-(2,6-dimethoxyphenyl)piperidin-2-one with 2-(bromomethyl)-5-(difluoromethoxy)pyridine. Subsequent purification by preparative HPLC afforded the target compound. LC-MS (conditions B): $t_R$=0.82 min.; [M+H]$^+$: 393.28 g/mol.

Example 188

1-((4-(difluoromethoxy)pyridin-2-yl)methyl)-6-(2,6-dimethoxyphenyl)piperidin-2-one Prepared according to the described general procedure 4 (GP4) by reaction of 6-(2,6-dimethoxyphenyl)piperidin-2-one with 2-(bromomethyl)-4-(difluoromethoxy)pyridine. Subsequent purification by preparative HPLC afforded the target compound. LC-MS (conditions A): $t_R$=0.61 min.; [M+H]$^+$: 393.12 g/mol.

Example 189

1-([1,1'-biphenyl]-3-ylmethyl)-6-(2,6-dimethoxyphenyl)piperidin-2-one

Prepared according to the described general procedure 4 (GP4) by reaction of 6-(2,6-dimethoxyphenyl)piperidin-2-one with commercially available 3-(bromomethyl)-1,1'-biphenyl. Subsequent purification by preparative HPLC afforded the target compound. LC-MS (conditions A): $t_R$=0.95 min.; [M+H]$^+$: 402.16 g/mol.

(continued from previous page) one with commercially available 1-(bromomethyl)-3-phenoxybenzene. Subsequent purification by preparative HPLC afforded the target compound. LC-MS (conditions D): $t_R$=1.12 min.; [M+H]$^+$: 418.79 g/mol.

Example 190

1-([1,1'-biphenyl]-2-ylmethyl)-6-(2,6-dimethoxyphenyl)piperidin-2-one

Prepared according to the described general procedure 4 (GP4) by reaction of 6-(2,6-dimethoxyphenyl)piperidin-2-one with commercially available 2-(bromomethyl)-1,1'-biphenyl. Subsequent purification by preparative HPLC afforded the target compound. LC-MS (conditions A): $t_R$=0.92 min.; [M+H]$^+$: 402.15 g/mol.

Example 191

6-(2,6-dimethoxyphenyl)-1-(2-phenoxybenzyl)piperidin-2-one

Prepared according to the described general procedure 4 (GP4) by reaction of 6-(2,6-dimethoxyphenyl)piperidin-2-one with commercially available 1-(bromomethyl)-2-phenoxybenzene. Subsequent purification by preparative HPLC afforded the target compound. LC-MS (conditions A): $t_R$=0.93 min.; [M+H]$^+$: 418.01 g/mol.

Example 192

6-(2,6-dimethoxyphenyl)-1-((6-phenoxypyridin-3-yl)methyl)piperidin-2-one

Prepared according to the described general procedure 4 (GP4) by reaction of 6-(2,6-dimethoxyphenyl)piperidin-2-one with 5-(bromomethyl)-2-phenoxypyridine. Subsequent purification by preparative HPLC afforded the target compound. LC-MS (conditions A): $t_R$=0.84 min.; [M+H]$^+$: 419.25 g/mol.

Example 193

7-(2,6-dimethoxyphenyl)-1-(4-(trifluoromethoxy)benzyl)azepan-2-one

Prepared according to the described general procedure 4 (GP4) by reaction of 7-(2,6-dimethoxyphenyl)azepan-2-one with commercially available 1-(bromomethyl)-4-(trifluoromethoxy)benzene. Subsequent purification by preparative HPLC afforded the target compound. LC-MS (conditions A): $t_R$=0.98 min.; [M+H]$^+$: 424.20 g/mol.

Example 194

5-(2-ethoxyphenyl)-1-(4-fluorobenzyl)pyrrolidin-2-one

Prepared according to the described general procedure 4 (GP4) by reaction of 5-(2-ethoxyphenyl)pyrrolidin-2-one with commercially available 1-(bromomethyl)-4-fluorobenzene. Subsequent purification by preparative HPLC afforded the target compound. LC-MS (conditions D): $t_R$=1.01 min.; [M+H]$^+$: 313.99 g/mol.

Example 195

5-(2-ethoxyphenyl)-1-(4-(trifluoromethoxy)benzyl)pyrrolidin-2-one

Prepared according to the described general procedure 4 (GP4) by reaction of 5-(2-ethoxyphenyl)pyrrolidin-2-one with commercially available 1-(bromomethyl)-4-(trifluoromethoxy)benzene. Subsequent purification by preparative HPLC afforded the target compound. LC-MS (conditions D): $t_R$=1.08 min.; [M+H]$^+$: 379.99 g/mol.

Example 196

5-(2,6-dimethoxyphenyl)-1-(4-(trifluoromethoxy)benzyl)pyrrolidin-2-one

Prepared according to the described general procedure 4 (GP4) by reaction of 5-(2,6-dimethoxyphenyl)pyrrolidin-2-one with commercially available 1-(bromomethyl)-4-(trifluoromethoxy)benzene. Subsequent purification by preparative HPLC afforded the target compound. LC-MS (conditions E): $t_R$=0.80 min.; [M+H]$^+$: 396.00 g/mol.

Example 197

5-(2,6-dimethoxyphenyl)-1-(4-fluorobenzyl)pyrrolidin-2-one

Prepared according to the described general procedure 4 (GP4) by reaction of 5-(2,6-dimethoxyphenyl)pyrrolidin-2-one with commercially available 1-(bromomethyl)-4-fluorobenzene. Subsequent purification by preparative HPLC afforded the target compound. LC-MS (conditions E): $t_R$=0.71 min.; [M+H]$^+$: 330.24 g/mol.

Example 198

1-(3-(difluoromethoxy)benzyl)-5-(2,6-dimethoxyphenyl)-3-methylpyrrolidin-2-one (Mixture of Stereoisomers)

Prepared according to the described general procedure 4 (GP4) by reaction of 5-(2,6-dimethoxyphenyl)-3-methylpyrrolidin-2-one with commercially available 1-(bromomethyl)-3-(difluoromethoxy)benzene. Subsequent purification by preparative HPLC afforded the target compound. LC-MS (conditions F): $t_R$=0.84 min.; [M+H]$^+$: 392.16 g/mol.

Example 199

1-((6-(difluoromethoxy)pyridin-3-yl)methyl)-5-(2,6-dimethoxyphenyl)-3-methylpyrrolidin-2-one (Mixture of Stereoisomers)

Prepared according to the described general procedure 4 (GP4) by reaction of 5-(2,6-dimethoxyphenyl)-3-methylpyrrolidin-2-one with 5-(bromomethyl)-2-(difluoromethoxy)pyridine. Subsequent purification by preparative HPLC afforded the target compound. LC-MS (conditions F): $t_R$=0.82 min.; [M+H]$^+$: 393.28 g/mol.

Example 200

5-(2,6-dimethoxyphenyl)-3-methyl-1-(3-(trifluoromethoxy)benzyl)pyrrolidin-2-one (Mixture of Stereoisomers)

Prepared according to the described general procedure 4 (GP4) by reaction of 5-(2,6-dimethoxyphenyl)-3-methylpyrrolidin-2-one with commercially available 1-(bromomethyl)-3-(trifluoromethoxy)benzene. Subsequent purification by preparative HPLC afforded the target compound. LC-MS (conditions A): $t_R$=0.93 min.; [M+H]$^+$: 410.18 g/mol.

Example 201

1-((6-(difluoromethoxy)pyridin-2-yl)methyl)-5-(2,6-dimethoxyphenyl)-3-methylpyrrolidin-2-one (Mixture of Stereoisomers)

Prepared according to the described general procedure 4 (GP4) by reaction of 5-(2,6-dimethoxyphenyl)-3-methylpyrrolidin-2-one with 2-(bromomethyl)-6-(difluoromethoxy)pyridine. Subsequent purification by preparative HPLC afforded the target compound. LC-MS (conditions A): $t_R$=0.84 min.; [M+H]$^+$: 393.19 g/mol.

Example 202

1-((2-(difluoromethoxy)pyridin-4-yl)methyl)-5-(2,6-dimethoxyphenyl)-3-methylpyrrolidin-2-one (Mixture of Stereoisomers)

Prepared according to the described general procedure 4 (GP4) by reaction of 5-(2,6-dimethoxyphenyl)-3-methylpyrrolidin-2-one with 4-(bromomethyl)-2-(difluoromethoxy)pyridine. Subsequent purification by preparative HPLC afforded the target compound. LC-MS (conditions A): $t_R$=0.83 min.; [M+H]$^+$: 393.19 g/mol.

Example 203

5-(2,6-dimethoxyphenyl)-3-methyl-1-(1-(4-(trifluoromethoxy)phenyl)propyl)pyrrolidin-2-one (Mixture of Stereoisomers)

Prepared according to the described general procedure 4 (GP4) by reaction of 5-(2,6-dimethoxyphenyl)-3-methylpyrrolidin-2-one with 1-(1-bromopropyl)-4-(trifluoromethoxy)benzene. Subsequent purification by preparative HPLC afforded the target compound. LC-MS (conditions A): $t_R$=1.00 min.; [M+H]$^+$: 438.28 g/mol.

Example 204

1-((4-(difluoromethoxy)pyridin-2-yl)methyl)-5-(2,6-dimethoxyphenyl)-3-methylpyrrolidin-2-one (Mixture of Stereoisomers)

Prepared according to the described general procedure 4 (GP4) by reaction of 5-(2,6-dimethoxyphenyl)-3-methylpyrrolidin-2-one with 2-(bromomethyl)-4-(difluoromethoxy)pyridine. Subsequent purification by preparative HPLC afforded the target compound. LC-MS (conditions A): $t_R$=0.67 min.; [M+H]$^+$: 393.08 g/mol.

Example 205

6-(2,6-dimethoxyphenyl)-1-(4-ethoxybenzyl)piperidin-2-one

Prepared according to the described general procedure 7 (GP7) by O-alkylation of 6-(2,6-dimethoxyphenyl)-1-(4-hydroxybenzyl)piperidin-2-one with commercially available bromoethane. Subsequent purification by preparative HPLC afforded the target compound. LC-MS (conditions E): $t_R$=0.76 min.; [M+H]$^+$: 370.17 g/mol.

Example 206

6-(2,6-dimethoxyphenyl)-1-(4-isopropoxybenzyl)piperidin-2-one

Prepared according to the described general procedure 7 (GP7) by O-alkylation of 6-(2,6-dimethoxyphenyl)-1-(4-hydroxybenzyl)piperidin-2-one with commercially available 2-bromopropane. Subsequent purification by preparative HPLC afforded the target compound. LC-MS (conditions E): $t_R$=0.77 min.; [M+H]$^+$: 384.28 g/mol.

Example 207

6-(2,6-dimethoxyphenyl)-1-(4-propoxybenzyl)piperidin-2-one

Prepared according to the described general procedure 7 (GP7) by O-alkylation of 6-(2,6-dimethoxyphenyl)-1-(4-hydroxybenzyl)piperidin-2-one with commercially available 1-bromopropane. Subsequent purification by preparative HPLC afforded the target compound. LC-MS (conditions E): $t_R$=0.79 min.; [M+H]$^+$: 384.19 g/mol.

Example 208

1-(4-(cyclopropylmethoxy)benzyl)-6-(2,6-dimethoxyphenyl)piperidin-2-one

Prepared according to the described general procedure 7 (GP7) by O-alkylation of 6-(2,6-dimethoxyphenyl)-1-(4-hydroxybenzyl)piperidin-2-one with commercially available (bromomethyl)cyclopropane. Subsequent purification by preparative HPLC afforded the target compound. LC-MS (conditions E): $t_R$=0.78 min.; [M+H]$^+$: 396.27 g/mol.

Example 209

6-(2-(3-hydroxypropoxy)-6-methoxyphenyl)-1-(4-(trifluoromethoxy)benzyl)piperidin-2-one Prepared according to the described general procedure 7 (GP7) by O-alkylation of 6-(2-hydroxy-6-methoxyphenyl)-1-(4-(trifluoromethoxy)benzyl)piperidin-2-one with commercially available 3-bromopropan-1-ol. Subsequent purification by preparative HPLC afforded the target compound. LC-MS (conditions E): $t_R$=0.75 min.; [M+H]$^+$: 454.20 g/mol.

Example 210

6-(2-(cyclopropylmethoxy)-6-methoxyphenyl)-1-(4-(trifluoromethoxy)benzyl)piperidin-2-one Prepared according to the described general procedure 7 (GP7) by O-alkylation of 6-(2-hydroxy-6-methoxyphenyl)-1-(4-(trifluoromethoxy)benzyl)piperidin-2-one with commercially available (bromomethyl)cyclopropane. Subsequent purification by preparative HPLC afforded the target compound. LC-MS (conditions E): $t_R$=0.86 min.; [M+H]$^+$: 449.76 g/mol.

Example 211

6-(2-methoxy-6-(2-methoxyethoxy)phenyl)-1-(4-(trifluoromethoxy)benzyl)piperidin-2-one Prepared according to the described general procedure 7 (GP7) by O-alkylation of 6-(2-hydroxy-6-methoxyphenyl)-

1-(4-(trifluoromethoxy)benzyl)piperidin-2-one with commercially available 1-bromo-2-methoxyethane. Subsequent purification by preparative HPLC afforded the target compound. LC-MS (conditions E): $t_R$=0.80 min.; [M+H]$^+$: 454.25 g/mol.

Example 212

6-(2-ethoxy-6-methoxyphenyl)-1-(4-(trifluoromethoxy)benzyl)piperidin-2-one

Prepared according to the described general procedure 7 (GP7) by O-alkylation of 6-(2-hydroxy-6-methoxyphenyl)-1-(4-(trifluoromethoxy)benzyl)piperidin-2-one with commercially available iodoethane. Subsequent purification by preparative HPLC afforded the target compound. LC-MS (conditions E): $t_R$=0.83 min.; [M+H]$^+$: 424.17 g/mol.

Example 213

6-(2-(2-hydroxyethoxy)-6-methoxyphenyl)-1-(4-(trifluoromethoxy)benzyl)piperidin-2-one Prepared according to the described general procedure 7 (GP7) by O-alkylation of 6-(2-hydroxy-6-methoxyphenyl)-1-(4-(trifluoromethoxy)benzyl)piperidin-2-one with commercially available 2-bromoethanol. Subsequent purification by preparative HPLC afforded the target compound. LC-MS (conditions E): $t_R$=0.73 min.; [M+H]$^+$: 440.15 g/mol.

Example 214

6-(2-(2,3-dihydroxypropoxy)-6-methoxyphenyl)-1-(4-(trifluoromethoxy)benzyl)piperidin-2-one Prepared according to the described general procedure 7 (GP7) by O-alkylation of 6-(2-hydroxy-6-methoxyphenyl)-1-(4-(trifluoromethoxy)benzyl)piperidin-2-one with commercially available 3-chloropropane-1,2-diol. Subsequent purification by preparative HPLC afforded the target compound. LC-MS (conditions E): $t_R$=0.73 min.; [M+H]$^+$: 470.28 g/mol.

Example 215

6-(2,6-dimethoxyphenyl)-3,3-dimethyl-1-(4-(trifluoromethoxy)benzyl)piperidin-2-one Prepared according to the described general procedure 8 (GP8) by C-alkylation of 6-(2,6-dimethoxyphenyl)-1-(4-(trifluoromethoxy)benzyl)piperidin-2-one with commercially available iodomethane. Subsequent purification by preparative HPLC afforded the target compound. LC-MS (conditions E): $t_R$=0.87 min.; [M+H]$^+$: 438.17 g/mol.

Example 216

6-(2,6-dimethoxyphenyl)-3-methyl-1-(4-(trifluoromethoxy)benzyl)piperidin-2-one (Mixture of Stereoisomers)

Prepared according to the described general procedure 8 (GP8) by C-alkylation of 6-(2,6-dimethoxyphenyl)-1-(4-(trifluoromethoxy)benzyl)piperidin-2-one with commercially available iodomethane. Subsequent purification by preparative HPLC afforded the target compound. LC-MS (conditions E): $t_R$=0.84 min.; [M+H]$^+$: 424.22 g/mol.

Example 217

5-(2,6-dimethoxyphenyl)-3,3-dimethyl-1-(4-(trifluoromethoxy)benzyl)pyrrolidin-2-one Prepared according to the described general procedure 8 (GP8) by C-alkylation of 5-(2,6-dimethoxyphenyl)-1-(4-(trifluoromethoxy)benzyl)pyrrolidin-2-one with commercially available iodomethane. Subsequent purification by preparative HPLC afforded the target compound. LC-MS (conditions G): $t_R$=1.07 min.; [M+H]$^+$: 424.22 g/mol.

Example 218

5-(2,6-dimethoxyphenyl)-3-methyl-1-(4-(trifluoromethoxy)benzyl)pyrrolidin-2-one (Mixture of Stereoisomers)

Prepared according to the described general procedure 8 (GP8) by C-alkylation of 5-(2,6-dimethoxyphenyl)-1-(4-(trifluoromethoxy)benzyl)pyrrolidin-2-one with commercially available iodomethane. Subsequent purification by preparative HPLC afforded the target compound. LC-MS (conditions G): $t_R$=1.03 min.; [M+H]$^+$: 410.02 g/mol.

Example 219

6-(2,6-dimethoxyphenyl)-1-((2-(thiazol-2-yl)pyridin-4-yl)methyl)piperidin-2-one

A mixture of 1-((2-bromopyridin-4-yl)methyl)-6-(2,6-dimethoxyphenyl)piperidin-2-one (43 mg; 0.10 mmol; compound corresponding to example 36), commercially available 2-(tributylstannyl)thiazole (144 mg; 0.38 mmol), and PdCl$_2$(PPh$_3$)$_2$ (7.5 mg; 0.01 mmol) in anh. THF (3 ml) was heated to 75° C., under nitrogen, for 24 h. After cooling to rt, water and AcOEt were added. The separated aq. layer was further extracted with AcOEt. The mixed organic layers were washed with brine, dried over anh. MgSO$_4$, filtered, and concentrated to dryness under reduced pressure. Purification by preparative HPLC afforded the target compound. LC-MS (conditions A): $t_R$=0.75 min.; [M+H]$^+$: 410.00 g/mol.

Example 220

6-(2-fluoro-6-methoxyphenyl)-1-(4-(trifluoromethoxy)benzyl)piperidin-2-one

Prepared according to the described general procedure 5 (GP5) with commercially available 2-fluoro-6-methoxybenzaldehyde and commercially available 4-(trifluoromethoxy)benzaldehyde. Subsequent purification by preparative HPLC afforded the target compound. LC-MS (conditions E): $t_R$=0.80 min.; [M+H]$^+$: 398.09 g/mol.

Example 221

6-(2-chloro-6-methoxyphenyl)-1-(4-(trifluoromethoxy)benzyl)piperidin-2-one

Prepared according to the described general procedure 5 (GP5) with commercially available 2-chloro-6-methoxybenzaldehyde and commercially available 4-(trifluoromethoxy)benzaldehyde. Subsequent purification by preparative HPLC

Example 222

6-(2-methoxy-6-methylphenyl)-1-(4-(trifluoromethoxy)benzyl)piperidin-2-one

Prepared according to the described general procedure 5 (GP5) with commercially available 2-methoxy-6-methylbenzaldehyde and commercially available 4-(trifluoromethoxy)benzaldehyde. Subsequent purification by preparative HPLC afforded the target compound. LC-MS (conditions E): $t_R$=0.82 min.; $[M+H]^+$: 394.17 g/mol.

Example 223

6-(2-methoxy-6-(trifluoromethyl)phenyl)-1-(4-(trifluoromethoxy)benzyl)piperidin-2-one Prepared according to the described general procedure 5 (GP5) with commercially available 2-methoxy-6-(trifluoromethyl)benzaldehyde and commercially available 4-(trifluoromethoxy)benzaldehyde. Subsequent purification by preparative HPLC afforded the target compound. LC-MS (conditions E): $t_R$=0.84 min.; $[M+H]^+$: 448.22 g/mol.

Example 224

6-(2,6-difluorophenyl)-1-(4-(trifluoromethoxy)benzyl)piperidin-2-one

Prepared according to the described general procedure 5 (GP5) with commercially available 2,6-difluorobenzaldehyde and commercially available 4-(trifluoromethoxy)-benzaldehyde. Subsequent purification by preparative HPLC afforded the target compound. LC-MS (conditions E): $t_R$=0.79 min.; $[M+H]^+$: 385.65 g/mol.

Example 225

6-(2,6-difluoro-4-methoxyphenyl)-1-(4-(trifluoromethoxy)benzyl)piperidin-2-one

Prepared according to the described general procedure 5 (GP5) with commercially available 2,6-difluoro-4-methoxybenzaldehyde and commercially available 4-(trifluoromethoxy)benzaldehyde. Subsequent purification by preparative HPLC afforded the target compound. LC-MS (conditions E): $t_R$=0.81 min.; $[M+H]^+$: 416.08 g/mol.

Example 226

6-(2,6-difluoro-3-methylphenyl)-1-(4-(trifluoromethoxy)benzyl)piperidin-2-one

Prepared according to the described general procedure 5 (GP5) with commercially available 2,6-difluoro-3-methylbenzaldehyde and commercially available 4-(trifluoromethoxy)benzaldehyde. Subsequent purification by preparative HPLC afforded the target compound. LC-MS (conditions E): $t_R$=0.82 min.; $[M+H]^+$: 400.1 g/mol.

Example 227

6-(2-fluoro-6-(trifluoromethyl)phenyl)-1-(4-(trifluoromethoxy)benzyl)piperidin-2-one Prepared according to the described general procedure 5 (GP5) with commercially available 2-fluoro-6-(trifluoromethyl)benzaldehyde and commercially available 4-(trifluoromethoxy)benzaldehyde. Subsequent purification by preparative HPLC afforded the target compound. LC-MS (conditions E): $t_R$=0.83 min.; $[M+H]^+$: 436.26 g/mol.

Example 228

6-(2,6-dichlorophenyl)-1-(4-(trifluoromethoxy)benzyl)piperidin-2-one

Prepared according to the described general procedure 5 (GP5) with commercially available 2,6-dichlorobenzaldehyde and commercially available 4-(trifluoromethoxy)benzaldehyde. Subsequent purification by preparative HPLC afforded the target compound. LC-MS (conditions E): $t_R$=0.83 min.; $[M+H]^+$: 417.75 g/mol.

Example 229

6-(2-chloro-6-fluorophenyl)-1-(4-(trifluoromethoxy)benzyl)piperidin-2-one

Prepared according to the described general procedure 5 (GP5) with commercially available 2-chloro-6-fluorobenzaldehyde and commercially available 4-(trifluoromethoxy)benzaldehyde. Subsequent purification by preparative HPLC afforded the target compound. LC-MS (conditions E): $t_R$=0.82 min.; $[M+H]^+$: 401.82 g/mol.

Example 230

6-(2-isopropoxy-6-methoxyphenyl)-1-(4-(trifluoromethoxy)benzyl)piperidin-2-one

Prepared according to the described general procedure 5 (GP5) with commercially available 2-isopropoxy-6-methoxybenzaldehyde and commercially available 4-(trifluoromethoxy)benzaldehyde. Subsequent purification by preparative HPLC afforded the target compound. LC-MS (conditions E): $t_R$=0.86 min.; $[M+H]^+$: 438.21 g/mol.

Example 231

6-(2,6-diethoxyphenyl)-1-(4-(trifluoromethoxy)benzyl)piperidin-2-one

Prepared according to the described general procedure 5 (GP5) with 2,6-diethoxybenzaldehyde and commercially available 4-(trifluoromethoxy)benzaldehyde. Subsequent purification by preparative HPLC afforded the target compound. LC-MS (conditions E): $t_R$=0.86 min.; $[M+H]^+$: 438.27 g/mol.

Example 232

6-(4-fluoro-2,6-dimethoxyphenyl)-1-(4-(trifluoromethoxy)benzyl)piperidin-2-one

Prepared according to the described general procedure 5 (GP5) with 4-fluoro-2,6-dimethoxybenzaldehyde and commercially available 4-(trifluoromethoxy)benzaldehyde. Subsequent purification by preparative HPLC afforded the target compound. LC-MS (conditions E): $t_R$=0.81 min.; [M+H]$^+$: 428.3 g/mol.

Example 233

6-(2,6-dimethoxy-4-methylphenyl)-1-(4-(trifluoromethoxy)benzyl)piperidin-2-one

Prepared according to the described general procedure 5 (GP5) with commercially available 2,6-dimethoxy-4-methylbenzaldehyde and commercially available 4-(trifluoromethoxy)benzaldehyde. Subsequent purification by preparative HPLC afforded the target compound. LC-MS (conditions E): $t_R$=0.84 min.; [M+H]$^+$: 424.12 g/mol.

Example 234

1-([1,1'-biphenyl]-3-ylmethyl)-6-(4-fluoro-2,6-dimethoxyphenyl)piperidin-2-one

Prepared according to the described general procedure 5 (GP5) with 4-fluoro-2,6-dimethoxybenzaldehyde and commercially available [1,1'-biphenyl]-3-carbaldehyde. Subsequent purification by preparative HPLC afforded the target compound. LC-MS (conditions A): $t_R$=0.94 min.; [M+H]$^+$: 419.92 g/mol.

Example 235

1-([1,1'-biphenyl]-3-ylmethyl)-6-(6-methoxy-3-methylbenzo[d]isoxazol-7-yl)piperidin-2-one Prepared according to the described general procedure 5 (GP5) with 6-methoxy-3-methylbenzo[d]isoxazole-7-carbaldehyde and commercially available [1,1'-biphenyl]-3-carbaldehyde. Subsequent purification by preparative HPLC afforded the target compound. LC-MS (conditions A): $t_R$=0.89 min.; [M+H]$^+$: 426.91 g/mol.

Example 236

6-(2-methoxyphenyl)-1-(naphthalen-2-ylmethyl)piperidin-2-one

Prepared according to the described general procedure 6 (GP6) with commercially available naphthalen-2-ylmethanamine and commercially available 2-methoxybenzaldehyde. Subsequent purification by preparative HPLC afforded the target compound. LC-MS (conditions H): $t_R$=1.35 min.; [M+H]$^+$: 346.35 g/mol.

Example 237

6-(2-methoxyphenyl)-1-(4-(trifluoromethoxy)benzyl)piperidin-2-one

Prepared according to the described general procedure 6 (GP6) with commercially available (4-(trifluoromethoxy)phenyl)methanamine and commercially available 2-methoxybenzaldehyde. Subsequent purification by preparative HPLC afforded the target compound. LC-MS (conditions H): $t_R$=1.37 min.; [M+H]$^+$: 379.75 g/mol.

Example 238

6-(2,6-dimethoxyphenyl)-1-(naphthalen-2-ylmethyl)piperidin-2-one

Prepared according to the described general procedure 6 (GP6) with commercially available naphthalen-2-ylmethanamine and commercially available 2,6-dimethoxybenzaldehyde. Subsequent purification by preparative HPLC afforded the target compound. LC-MS (conditions H): $t_R$=1.35 min.; [M+H]$^+$: 375.79 g/mol.

Example 239

1-(naphthalen-2-ylmethyl)-6-(2-(trifluoromethyl)phenyl)piperidin-2-one

Prepared according to the described general procedure 6 (GP6) with commercially available naphthalen-2-ylmethanamine and commercially available 2-(trifluoromethyl)benzaldehyde. Subsequent purification by preparative HPLC afforded the target compound. LC-MS (conditions H): $t_R$=1.46 min.; [M+H]$^+$: 383.8 g/mol.

Example 240

6-(2,6-dimethoxyphenyl)-1-((1,2,3,4-tetrahydroquinolin-6-yl)methyl)piperidin-2-one Prepared according to the described general procedure 6 (GP6) with (1,2,3,4-tetrahydroquinolin-6-yl)methanamine and commercially available 2,6-dimethoxybenzaldehyde. Subsequent purification by preparative HPLC afforded the target compound. LC-MS (conditions E): $t_R$=0.53 min.; [M+H]$^+$: 381.15 g/mol.

Example 241

6-(2,6-dimethoxyphenyl)-1-((1-methyl-1H-indol-5-yl)methyl)piperidin-2-one

Prepared according to the described general procedure 6 (GP6) with commercially available (1-methyl-1H-indol-5-yl)methanamine and commercially available 2,6-dimethoxybenzaldehyde. Subsequent purification by preparative HPLC afforded the target compound. LC-MS (conditions E): $t_R$=0.76 min.; [M+H]$^+$: 379.12 g/mol.

Example 242

6-(2,6-dimethoxyphenyl)-1-(imidazo[1,2-a]pyridin-2-ylmethyl)piperidin-2-one

Prepared according to the described general procedure 6 (GP6) with commercially available imidazo[1,2-a]pyridin-2-ylmethanamine and commercially available 2,6-dimethoxybenzaldehyde. Subsequent purification by preparative HPLC afforded the target compound. LC-MS (conditions E): $t_R$=0.50 min.; [M+H]$^+$: 366.12 g/mol.

Example 243

6-(2,6-dimethoxyphenyl)-1-((1-methyl-1H-benzo[d][1,2,3]triazol-5-yl)methyl)piperidin-2-one Prepared according to the described general procedure 6 (GP6) with commercially available (1-methyl-1H-benzo[d]

[1,2,3]triazol-5-yl)methanamine and commercially available 2,6-dimethoxybenzaldehyde. Subsequent purification by preparative HPLC afforded the target compound. LC-MS (conditions E): $t_R$=0.65 min.; [M+H]$^+$: 381.09 g/mol.

Example 244

1-([1,1'-biphenyl]-4-ylmethyl)-6-(2,6-dimethoxyphenyl)piperidin-2-one

Prepared according to the described general procedure 6 (GP6) with commercially available [1,1'-biphenyl]-4-ylmethanamine and commercially available 2,6-dimethoxybenzaldehyde. Subsequent purification by preparative HPLC afforded the target compound. LC-MS (conditions E): $t_R$=0.84 min.; [M+H]$^+$: 401.85 g/mol.

Example 245

6-(2,6-dimethoxyphenyl)-1-(4-(pyrrolidin-1-yl)benzyl)piperidin-2-one

Prepared according to the described general procedure 6 (GP6) with commercially available (4-(pyrrolidin-1-yl)phenyl)methanamine and commercially available 2,6-dimethoxybenzaldehyde. Subsequent purification by preparative HPLC afforded the target compound. LC-MS (conditions E): $t_R$=0.62 min.; [M+H]$^+$: 395.25 g/mol.

Example 246

6-(2,6-dimethoxyphenyl)-1-(4-(2,2,2-trifluoroethoxy)benzyl)piperidin-2-one

Prepared according to the described general procedure 6 (GP6) with commercially available (4-(2,2,2-trifluoroethoxy)phenyl)methanamine and commercially available 2,6-dimethoxybenzaldehyde. Subsequent purification by preparative HPLC afforded the target compound. LC-MS (conditions E): $t_R$=0.80 min.; [M+H]$^+$: 424.08 g/mol.

Example 247

6-(2,6-dimethoxyphenyl)-1-((1-methyl-1H-indol-2-yl)methyl)piperidin-2-one

Prepared according to the described general procedure 6 (GP6) with commercially available (1-methyl-1H-indol-2-yl)methanamine and commercially available 2,6-dimethoxybenzaldehyde. Subsequent purification by preparative HPLC afforded the target compound. LC-MS (conditions E): $t_R$=0.78 min.; [M+H]$^+$: 379.31 g/mol.

Example 248

6-(2,6-dimethoxyphenyl)-1-(4-(methylsulfonyl)benzyl)piperidin-2-one

Prepared according to the described general procedure 6 (GP6) with commercially available (4-(methylsulfonyl)phenyl)methanamine and commercially available 2,6-dimethoxybenzaldehyde. Subsequent purification by preparative HPLC the target compound. LC-MS (conditions E): $t_R$=0.65 min.; [M+H]$^+$: 404.07 g/mol.

Example 249

6-(2,6-dimethoxyphenyl)-1-((2-methylbenzo[d]oxazol-5-yl)methyl)piperidin-2-one

Prepared according to the described general procedure 6 (GP6) with (2-methylbenzo[d]oxazol-5-yl)methanamine and commercially available 2,6-dimethoxybenzaldehyde. Subsequent purification by preparative HPLC afforded the target compound. LC-MS (conditions E): $t_R$=0.70 min.; [M+H]$^+$: 381.27 g/mol.

Example 250

1-(benzo[b]thiophen-5-ylmethyl)-6-(2,6-dimethoxyphenyl)piperidin-2-one

Prepared according to the described general procedure 6 (GP6) with commercially available benzo[b]thiophen-5-ylmethanamine and commercially available 2,6-dimethoxybenzaldehyde. Subsequent purification by preparative HPLC afforded the target compound. LC-MS (conditions E): $t_R$=0.79 min.; [M+H]$^+$: 382.09 g/mol.

Example 251

6-(2-ethoxyphenyl)-1-(4-(trifluoromethoxy)benzyl)piperidin-2-one

The detailed synthesis of example compound 251 can be found in section B.6.1 corresponding to the description of general procedure 9 (GP9).

Prepared according to the described general procedure 9 (GP9) with 6-oxo-1-(4-(trifluoromethoxy)benzyl)-1,4,5,6-tetrahydropyridin-2-yl diphenyl phosphate and commercially available (2-ethoxyphenyl)boronic acid. Subsequent hydrogenation and purification by preparative HPLC afforded the target compound. LC-MS (conditions E): $t_R$=0.82 min.; [M+H]$^+$: 394.22 g/mol.

Example 252

1-(4-(trifluoromethoxy)benzyl)-6-(2-(trifluoromethoxy)phenyl)piperidin-2-one

Prepared according to the described general procedure 9 (GP9) with 6-oxo-1-(4-(trifluoromethoxy)benzyl)-1,4,5,6-tetrahydropyridin-2-yl diphenyl phosphate and commercially available (2-(trifluoromethoxy)phenyl)boronic acid. Subsequent hydrogenation and purification by preparative HPLC afforded the target compound. LC-MS (conditions E): $t_R$=0.83 min.; [M+H]$^+$: 433.70 g/mol.

Example 253 rac-(3S*,5S*)-5-(2,6-dimethoxyphenyl)-3-hydroxy-1-(4-(trifluoromethoxy)benzyl)pyrrolidin-2-one The preparation is described in section B.7.2 corresponding to the description of general procedure 10B (GP10B). LC-MS (conditions A): $t_R$=0.81 min.; [M+H]$^+$: 412.27 g/mol.

Example 254 rac-(3S*,5S*)-5-(2,6-dimethoxyphenyl)-3-methoxy-1-(4-(trifluoromethoxy)benzyl)pyrrolidin-2-one The preparation is described in section B.7.3 corresponding to the description of general procedure 10C (GP10C). LC-MS (conditions A): $t_R$=0.88 min.; [M+H]$^+$: 426.19 g/mol.

Example 255 rac-(3R*,5S*)-5-(2,6-dimethoxyphenyl)-3-fluoro-1-(4-(trifluoromethoxy)benzyl)pyrrolidin-2-one Prepared according to general procedure 10I (GP10I) using rac-(3S*,5S*)-5-(2,6-dimethoxyphenyl)-3-hydroxy-1-(4-(trifluoromethoxy)benzyl)pyrrolidin-2-one (synthesis described in section B.7.2). LC-MS (conditions A): $t_R$=0.91 min.; [M+H]$^+$: 414.08 g/mol.

Example 256

5-(2,6-dimethoxyphenyl)-3,3-difluoro-1-(4-(trifluoromethoxy)benzyl)pyrrolidin-2-one The preparation is described in section B.7.7 corresponding to the description of general procedure 10G (GP10G). LC-MS (conditions A): $t_R$=0.96 min.; [M+H]$^+$: 432.22 g/mol.

Example 257 rac-(3R*,5S*)-3-chloro-5-(2,6-dimethoxyphenyl)-1-(4-(trifluoromethoxy)benzyl)pyrrolidin-2-one The preparation is described in section B.7.4 corresponding to the description of general procedure 10D (GP10D). LC-MS (conditions A): $t_R$=0.95 min.; [M+H]$^+$: 430.20 g/mol.

Example 258 rac-(3R*,5S*)-5-(2,6-dimethoxyphenyl)-3-hydroxy-1-(4-(trifluoromethoxy)benzyl)pyrrolidin-2-one The preparation is described in section B.7.6 corresponding to the description of general procedure 10F (GP10F). LC-MS (conditions A): $t_R$=0.80 min.; [M+H]$^+$: 412.10 g/mol.

Example 259 rac-(3S*,5S*)-5-(2,6-dimethoxyphenyl)-3-methyl-1-(4-(trifluoromethoxy)benzyl)pyrrolidin-2-one The preparation is described in section B.7.8 corresponding to the description of general procedure 10H (GP10H). LC-MS (conditions A): $t_R$=0.94 min.; [M+H]$^+$: 410.27 g/mol.

Example 260 rac-(3S*,5S*)-5-(2,6-dimethoxyphenyl)-3-fluoro-1-(4-(trifluoromethoxy)benzyl)pyrrolidin-2-one The preparation is described in section B.7.9 corresponding to the description of general procedure 10I (GP10I). LC-MS (conditions A): $t_R$=0.90 min.; [M+H]$^+$: 414.12 g/mol.

Example 261 rac-(3S*,5S*)-3-chloro-5-(2,6-dimethoxyphenyl)-1-(4-(trifluoromethoxy)benzyl)pyrrolidin-2-one Prepared according to general procedure 10D (GP10D) using rac-(3R*,5S*)-5-(2,6-dimethoxyphenyl)-3-hydroxy-1-(4-(trifluoromethoxy)benzyl)pyrrolidin-2-one (synthesis described in section B.7.6). LC-MS (conditions A): $t_R$=0.94 min.; [M+H]$^+$: 430.12 g/mol.

Example 262 rac-(3R*,5S*)-5-(2,6-dimethoxyphenyl)-3-methoxy-1-(4-(trifluoromethoxy)benzyl)pyrrolidin-2-one Prepared according to general procedure 10C (GP10C) using rac-(3R*,5S*)-5-(2,6-dimethoxyphenyl)-3-hydroxy-1-(4-(trifluoromethoxy)benzyl)pyrrolidin-2-one (synthesis described in section B.7.6). LC-MS (conditions A): $t_R$=0.89 min.; [M+H]$^+$: 426.17 g/mol.

Example 263 rac-(3S*,5S*)-5-(2,6-dimethoxyphenyl)-3-ethyl-1-(4-(trifluoromethoxy)benzyl)pyrrolidin-2-one Prepared according to general procedure 10H (GP10H) using 5-(2,6-dimethoxyphenyl)-1-(4-(trifluoromethoxy)benzyl)pyrrolidine-2,3-dione (synthesis described in section B.7.1 corresponding to general procedure 10A) and commercially available ethyltriphenylphosphonium bromide. LC-MS (conditions A): $t_R$=0.99 min.; [M+H]$^+$: 424.31 g/mol.

Example 264 rac-(3R*,5S*)-5-(2,6-dimethoxyphenyl)-3-methyl-1-(4-(trifluoromethoxy)benzyl)pyrrolidin-2-one The preparation is described in section B.7.5 corresponding to the description of general procedure 10E (GP10E). LC-MS (conditions A): $t_R$=0.94 min.; [M+H]$^+$: 410.32 g/mol.

Example 265 rac-(3S*,5S*)-5-(2-fluoro-6-methoxyphenyl)-3-hydroxy-1-(4-(trifluoromethoxy)benzyl)pyrrolidin-2-one Prepared according to general procedure 10A (GP10A) and general procedure 10B (GP10B) using commercially available (4-(trifluoromethoxy)phenyl)methanamine, commercially available 2-fluoro-6-methoxybenzaldehyde, and commercially available diethyl oxalacetate sodium salt. LC-MS (conditions A): $t_R$=0.80 min.; [M+H]$^+$: 400.22 g/mol.

Example 266

5-(2,6-dimethoxyphenyl)-4-(4-(trifluoromethoxy)benzyl)morpholin-3-one

The detailed synthesis for example compound 266 is described in section B.9 corresponding to the description of general procedure 12 (GP 12). Subsequent purification by preparative HPLC afforded the target compound. LC-MS (conditions E): $t_R$=0.79 min.; [M+H]$^+$: 412.06 g/mol.

Example 267

6-(2,6-dimethoxyphenyl)-1-(4-(trifluoromethoxy)benzyl)piperazin-2-one

The preparation is described in section B.8 corresponding to the description of general procedures GP11A, GP11B, and GP11C. LC-MS (conditions D): $t_R$=0.85 min.; [M+H]$^+$: 411.13 g/mol.

Example 268

6-(2,6-dimethoxyphenyl)-4-methyl-1-(4-(trifluoromethoxy)benzyl)piperazin-2-one

A cooled (0° C.) solution of 6-(2,6-dimethoxyphenyl)-1-(4-(trifluoromethoxy)benzyl)-piperazin-2-one (106 mg; 0.25 mmol) in anh. THF (1.5 ml) was treated with a solution of CH$_3$I (33 mg; 0.23 mmol) in anh. THF (0.5 ml). The resulting mixture was allowed to warm-up slowly to rt, and stirring at rt was then continued for 15 h. Brine was added, and the mixture was extracted with AcOEt (3×20 ml). The mixed organic layers were dried over anh. MgSO$_4$, filtered, and concentrated to dryness under reduced pressure. Subsequent purification by preparative HPLC afforded the target compound. LC-MS (conditions D): $t_R$=0.87 min.; [M+H]$^+$: 425.02 g/mol.

Example 269

6-(4,6-dimethoxypyrimidin-5-yl)-1-(3-(2-methylthiazol-4-yl)benzyl)piperidin-2-one Prepared according to the described general procedure 1 (GP1) by reaction of methyl 5-amino-5-(4,6-dimethoxypyrimidin-5-yl)pentanoate with commercially available 3-(2-methylthiazol-4-yl)benzaldehyde. Subsequent purification by preparative HPLC afforded the target compound. LC-MS (conditions A): $t_R$=0.74 min.; [M+H]$^+$: 424.92 g/mol.

Example 270

1-([1,1'-biphenyl]-3-ylmethyl)-6-(4,6-dimethoxypyrimidin-5-yl)piperidin-2-one

Prepared according to the described general procedure 1 (GP1) by reaction of methyl 5-amino-5-(4,6-dimethoxypyrimidin-5-yl)pentanoate with commercially available [1,1'-biphenyl]-3-carbaldehyde. Subsequent purification by preparative HPLC afforded the target compound. LC-MS (conditions A): $t_R$=0.86 min.; [M+H]$^+$: 403.96 g/mol.

Example 271

6-(4,6-dimethoxypyrimidin-5-yl)-1-((2-phenylthiazol-4-yl)methyl)piperidin-2-one

Prepared according to the described general procedure 1 (GP1) by reaction of methyl 5-amino-5-(4,6-dimethoxypyrimidin-5-yl)pentanoate with commercially available 2-phenylthiazole-4-carbaldehyde. Subsequent purification by preparative HPLC afforded the target compound. LC-MS (conditions A): $t_R$=0.77 min.; [M+H]$^+$: 410.79 g/mol.

Example 272

6-(2,3-dihydrobenzo[b][1,4]dioxin-5-yl)-1-(3-(2-methylthiazol-4-yl)benzyl)piperidin-2-one Prepared according to the described general procedure 1 (GP1) by reaction of methyl 5-amino-5-(2,3-dihydrobenzo[b][1,4]dioxin-5-yl)pentanoate with commercially available 3-(2-methylthiazol-4-yl)benzaldehyde. Subsequent purification by preparative HPLC afforded the target compound. LC-MS (conditions A): $t_R$=0.81 min.; [M+H]$^+$: 420.98 g/mol.

Example 273

1-([1,1'-biphenyl]-3-ylmethyl)-6-(2,3-dihydrobenzo[b][1,4]dioxin-5-yl)piperidin-2-one Prepared according to the described general procedure 1 (GP1) by reaction of methyl 5-amino-5-(2,3-dihydrobenzo[b][1,4]dioxin-5-yl)pentanoate with commercially available [1,1'-biphenyl]-3-carbaldehyde. Subsequent purification by preparative HPLC afforded the target compound. LC-MS (conditions A): $t_R$=0.91 min.; [M+H]$^+$: 400.01 g/mol.

Example 274

7-(3,5-dimethoxypyridin-4-yl)-1-(3-(2-methylthiazol-4-yl)benzyl)azepan-2-one

Prepared according to the described general procedure 1 (GP1) by reaction of methyl 6-amino-6-(3,5-dimethoxypyridin-4-yl)hexanoate with commercially available 3-(2-methylthiazol-4-yl)benzaldehyde. Subsequent purification by preparative HPLC afforded the target compound. LC-MS (conditions A): $t_R$=0.59 min.; [M+H]$^+$: 438.09 g/mol.

Example 275

1-([1,1'-biphenyl]-3-ylmethyl)-7-(3,5-dimethoxypyridin-4-yl)azepan-2-one

Prepared according to the described general procedure 1 (GP1) by reaction of methyl 6-amino-6-(3,5-dimethoxypyridin-4-yl)hexanoate with commercially available [1,1'-biphenyl]-3-carbaldehyde. Subsequent purification by preparative HPLC afforded the target compound. LC-MS (conditions A): $t_R$=0.68 min.; [M+H]$^+$: 416.99 g/mol.

Example 276

7-(3,5-dimethoxypyridin-4-yl)-1-((9-methyl-9H-carbazol-3-yl)methyl)azepan-2-one

Prepared according to the described general procedure 1 (GP1) by reaction of methyl 6-amino-6-(3,5-dimethoxypyridin-4-yl)hexanoate with commercially available 9-methyl-9H-carbazole-3-carbaldehyde. Subsequent purification by preparative HPLC afforded the target compound. LC-MS (conditions A): $t_R$=0.68 min.; [M+H]$^+$: 444.02 g/mol.

Example 277

7-(3,5-dimethoxypyridin-4-yl)-1-((2-phenylthiazol-4-yl)methyl)azepan-2-one

Prepared according to the described general procedure 1 (GP1) by reaction of methyl 6-amino-6-(3,5-dimethoxypyridin-4-yl)hexanoate with commercially available 2-phenylthiazole-4-carbaldehyde. Subsequent purification by preparative HPLC afforded the target compound. LC-MS (conditions A): $t_R$=0.61 min.; [M+H]$^+$: 423.86 g/mol.

Example 278

6-(2,6-dimethoxyphenyl)-1-((2-phenoxythiazol-4-yl)methyl)piperidin-2-one

Prepared according to the described general procedure 1 (GP1) by reaction of methyl 5-amino-5-(2,6-dimethoxyphenyl)pentanoate with 2-phenoxythiazole-4-carbaldehyde. Subsequent purification by preparative HPLC afforded the target compound. LC-MS (conditions A): $t_R$=0.86 min.; [M+H]$^+$: 424.82 g/mol.

Example 279

6-(6-methoxy-2-methylbenzo[d]oxazol-7-yl)-1-(quinolin-2-ylmethyl)piperidin-2-one A mixture of 6-(2,6-dimethoxyphenyl)-1-(quinolin-2-ylmethyl)piperidin-2-one (500 mg; 1.32 mmol; compound corresponding to example 4) and acetic acid (1.65 ml) was heated to 60° C., and 65% nitric acid HNO$_3$ (2.33 ml) was added dropwise. The resulting mixture was further stirred at 60° C. for 10 min. After cooling to rt, ice, 25% aq. NH$_4$OH, and DCM were added successively. The separated aq. layer was further extracted with DCM. The mixed organic layers were dried over anh. MgSO$_4$, filtered, and concentrated to dryness under reduced pressure. Subsequent purification by FC (DCM/MeOH=30/1) afforded 6-(2,6-dimethoxy-3-nitrophenyl)-1-(quinolin-2-ylmethyl)piperidin-2-one as a yellow-orange solid (363 mg; 65%). LC-MS (conditions A): $t_R$=0.61 min.; [M+H]$^+$: 422.07 g/mol.

A solution of 6-(2,6-dimethoxy-3-nitrophenyl)-1-(quinolin-2-ylmethyl)piperidin-2-one (403 mg; 0.95 mmol) in anh. DCM (9 ml) was treated dropwise at rt with a solution of boron tribromide BBr$_3$ (1 M in DCM; 4.4 ml; 4.4 mmol). The resulting mixture was further stirred at rt, under nitrogen, for 17 h. Water and ice were added, and the separated aq. layer was extracted with DCM. The mixed organic layers were washed with brine, dried over anh. MgSO$_4$, filtered, and concentrated to dryness under reduced pressure. Subsequent purification by FC (DCM/MeOH=30/1) afforded 6-(2-hydroxy-6-methoxy-3-nitrophenyl)-1-(quinolin-2-ylmethyl)-piperidin-2-one as a yellow solid (340 mg; 87%). LC-MS (conditions A): $t_R$=0.60 min.; [M+H]$^+$: 407.82 g/mol.

A mixture of 6-(2-hydroxy-6-methoxy-3-nitrophenyl)-1-(quinolin-2-ylmethyl)piperidin-2-one (340 mg; 0.83 mmol), and 10% Pd(C) (34 mg; 10% in mass) in anh. MeOH (15 ml) was stirred at rt, under hydrogen atmosphere (1 atm), for 5.5 h. Filtration over a pad of celite, concentration to dryness under reduced pressure, and additional drying under HV afforded 6-(3-amino-2-hydroxy-6-methoxyphenyl)-1-(quinolin-2-ylmethyl)piperidin-2-one as a red solid (302 mg; 96%). LC-MS (conditions A): $t_R$=0.41 min.; [M+H]$^+$: 378.38 g/mol.

A mixture of 6-(3-amino-2-hydroxy-6-methoxyphenyl)-1-(quinolin-2-ylmethyl)piperidin-2-one (100 mg; 0.26 mmol), commercially available p-TsOH (2 mg; 0.01 mmol), and commercially available triethyl orthoacetate (290 mg; 1.69 mmol) was refluxed (100° C.) for 25 min. After cooling to rt, AcOEt was added, and the obtained mixture was filtered over a pad of celite. The filtrate was then washed with water and brine, and the mixed aq. layers were further extracted with AcOEt. The mixed organic layers were then dried over anh. MgSO$_4$, filtered, and concentrated to dryness under reduced pressure. Subsequent purification by FC (DCM/MeOH=20/1) afforded the target compound. LC-MS (conditions A): $t_R$=0.54 min.; [M+H]$^+$: 401.73 g/mol.

Example 280

6-(6-methoxybenzo[d]oxazol-7-yl)-1-(quinolin-2-ylmethyl)piperidin-2-one

A mixture of 6-(3-amino-2-hydroxy-6-methoxyphenyl)-1-(quinolin-2-ylmethyl)piperidin-2-one (100 mg; 0.26 mmol; synthesis described in example 279), commercially available p-TsOH (2 mg; 0.01 mmol), and commercially available triethyl orthoformate (264 mg; 1.69 mmol) was refluxed (100° C.) for 1 h. After cooling to rt, AcOEt was added, and the obtained mixture was filtered over a pad of celite. The filtrate was then washed with water and brine, and the mixed aq. layers were further extracted with AcOEt. The mixed organic layers were then dried over anh. MgSO$_4$, filtered, and concentrated to dryness under reduced pressure. Subsequent purification by FC (DCM/MeOH=20/1) afforded the target compound. LC-MS (conditions A): $t_R$=0.53 min.; [M+H]$^+$: 388.05 g/mol.

Example 281

6-(3-chloro-2,6-dimethoxyphenyl)-1-(3-(2-methylthiazol-4-yl)benzyl)piperidin-2-one A mixture of 6-(2,6-dimethoxyphenyl)-1-(3-(2-methylthiazol-4-yl)benzyl)piperidin-2-one (60 mg; 0.14 mmol; compound corresponding to example 16), and NCS (21 mg; 0.15 mmol) in anh. DMF (1.5 ml) was stirred at rt, under nitrogen, for 24 h. Water (5 ml), and AcOEt (10 ml) were added, and the separated organic layer was washed with brine (5 ml), dried over anh. MgSO$_4$, filtered, and concentrated to dryness under reduced pressure.

Purification by preparative HPLC afforded the target compound. LC-MS (conditions A): $t_R$=0.90 min.; [M+H]$^+$: 456.94 g/mol.

Example 282

5-(2,6-dimethoxyphenyl)-1-(4-(thiazol-2-yloxy)benzyl)pyrrolidin-2-one 1-(4-(benzyloxy)benzyl)-5-(2,6-dimethoxyphenyl)pyrrolidin-2-one was prepared according to the described general procedure 2 (GP2) by reaction of methyl 4-amino-4-(2,6-dimethoxyphenyl)butanoate (400 mg; 1.38 mmol) with commercially available 4-(benzyloxy)benzaldehyde (293 mg; 1.38 mmol). Subsequent purification by preparative HPLC afforded 1-(4-(benzyloxy)benzyl)-5-(2,6-dimethoxyphenyl)pyrrolidin-2-one (316 mg; 55%). LC-MS (conditions A): $t_R$=0.91 min.; [M+H]$^+$: 417.76 g/mol.

A mixture of 1-(4-(benzyloxy)benzyl)-5-(2,6-dimethoxyphenyl)pyrrolidin-2-one (316 mg; 0.75 mmol), and 10% Pd(C) (90 mg) in anh. MeOH (4 ml) was stirred at rt, under hydrogen atmosphere (1 atm), for 24 h. Filtration over a pad of celite, concentration to dryness under reduced pressure, and additional drying under HV afforded 5-(2,6-dimethoxyphenyl)-1-(4-hydroxybenzyl)pyrrolidin-2-one as a colorless solid (120 mg; 48%). LC-MS (conditions A): $t_R$=0.67 min.; [M+H]$^+$: 328.10 g/mol.

In a microwave tube, a mixture of 5-(2,6-dimethoxyphenyl)-1-(4-hydroxybenzyl)pyrrolidin-2-one (60 mg; 0.18 mmol), commercially available 2-bromothiazole (60 mg; 0.36 mmol), Cs$_2$CO$_3$ (66 mg; 0.20 mmol), CuCl (9 mg; 0.09 mmol), and commercially available 2,2,6,6-tetramethylheptane-3,5-dione (34 mg; 0.18 mmol) in anh. NMP (1 ml) was sealed and irradiated by microwave (175° C.; 10 min.). Water (1 ml), AcOEt (2 ml), and toluene (1 ml) were added, and the resulting suspension was filtered over a pad of celite. The separated organic layer was dried over anh. MgSO$_4$, filtered, and concentrated to dryness under reduced pressure. Subsequent purification by preparative HPLC afforded the target compound. LC-MS (conditions A): t$_R$=0.79 min.; [M+H]$^+$: 411.07 g/mol.

Example 283

6-([1,1'-biphenyl]-2-yl)-1-(3-(2-methylthiazol-4-yl)benzyl)piperidin-2-one

Prepared according to the described general procedure 1 (GP1) by reaction of methyl 5-([1,1'-biphenyl]-2-yl)-5-aminopentanoate with commercially available 3-(2-methylthiazol-4-yl)benzaldehyde. Subsequent purification by preparative HPLC afforded the target compound. LC-MS (conditions A): t$_R$=0.95 min.; [M+H]$^+$: 439.10 g/mol.

Example 284

6-([1,1'-biphenyl]-2-yl)-1-([1,1'-biphenyl]-3-ylmethyl)piperidin-2-one

Prepared according to the described general procedure 1 (GP1) by reaction of methyl 5-([1,1'-biphenyl]-2-yl)-5-aminopentanoate with commercially available [1,1'-biphenyl]-3-carbaldehyde. Subsequent purification by preparative HPLC afforded the target compound. LC-MS (conditions A): t$_R$=1.03 min.; [M+H]$^+$: 417.81 g/mol.

Example 285

5-([1,1'-biphenyl]-2-yl)-1-([1,1'-biphenyl]-3-ylmethyl)pyrrolidin-2-one

Prepared according to the described general procedure 2 (GP2) by reaction of methyl 4-([1,1'-biphenyl]-2-yl)-4-aminobutanoate with commercially available [1,1'-biphenyl]-3-carbaldehyde. Subsequent purification by preparative HPLC afforded the target compound. LC-MS (conditions A): t$_R$=1.01 min.; [M+H]$^+$: 403.91 g/mol.

Example 286

5-([1,1'-biphenyl]-2-yl)-1-(3-(2-methylthiazol-4-yl)benzyl)pyrrolidin-2-one

Prepared according to the described general procedure 2 (GP2) by reaction of methyl 4-([1,1'-biphenyl]-2-yl)-4-aminobutanoate with commercially available 3-(2-methylthiazol-4-yl)benzaldehyde. Subsequent purification by preparative HPLC afforded the target compound. LC-MS (conditions A): t$_R$=0.92 min.; [M+H]$^+$: 425.01 g/mol.

Example 287

5-([1,1'-biphenyl]-2-yl)-1-(4-(trifluoromethoxy)benzyl)pyrrolidin-2-one

Prepared according to the described general procedure 2 (GP2) by reaction of methyl 4-([1,1'-biphenyl]-2-yl)-4-aminobutanoate with commercially available 4-(trifluoromethoxy)benzaldehyde. Subsequent purification by preparative HPLC afforded the target compound. LC-MS (conditions A): t$_R$=0.99 min.; [M+H]$^+$: 411.89 g/mol.

Example 288

5-([1,1'-biphenyl]-2-yl)-1-((2-phenylthiazol-4-yl)methyl)pyrrolidin-2-one

Prepared according to the described general procedure 2 (GP2) by reaction of methyl 4-([1,1'-biphenyl]-2-yl)-4-aminobutanoate with commercially available 2-phenylthiazole-4-carbaldehyde. Subsequent purification by preparative HPLC afforded the target compound. LC-MS (conditions A): t$_R$=0.96 min.; [M+H]$^+$: 410.81 g/mol.

Example 289

5-([1,1'-biphenyl]-2-yl)-1-([1,1'-biphenyl]-3-ylmethyl)-3-methylpyrrolidin-2-one Prepared according to the described general procedure 2 (GP2) by reaction of ethyl 4-([1,1'-biphenyl]-2-yl)-4-amino-2-methylbutanoate with commercially available [1,1'-biphenyl]-3-carbaldehyde. Subsequent purification by preparative HPLC afforded the target compound. LC-MS (conditions A): t$_R$=1.05 min.; [M+H]$^+$: 417.80 g/mol.

Example 290

5-([1,1'-biphenyl]-2-yl)-3-methyl-1-(3-(2-methylthiazol-4-yl)benzyl)pyrrolidin-2-one Prepared according to the described general procedure 2 (GP2) by reaction of ethyl 4-([1,1'-biphenyl]-2-yl)-4-amino-2-methylbutanoate with commercially available 3-(2-methylthiazol-4-yl)benzaldehyde. Subsequent purification by preparative HPLC afforded the target compound. LC-MS (conditions A): t$_R$=0.97 min.; [M+H]$^+$: 439.03 g/mol.

Example 291

5-([1,1'-biphenyl]-2-yl)-3-methyl-1-(4-(trifluoromethoxy)benzyl)pyrrolidin-2-one Prepared according to the described general procedure 2 (GP2) by reaction of ethyl 4-([1,1'-biphenyl]-2-yl)-4-amino-2-methylbutanoate with commercially available 4-(trifluoromethoxy)benzaldehyde. Subsequent purification by preparative HPLC afforded the target compound. LC-MS (conditions A): t$_R$=1.03 min.; [M+H]$^+$: 425.99 g/mol.

Example 292

5-(2,6-dimethoxyphenyl)-1-(4-((4-methylthiazol-2-yl)oxy)benzyl)pyrrolidin-2-one

In a microwave tube, a mixture of 5-(2,6-dimethoxyphenyl)-1-(4-hydroxybenzyl)pyrrolidin-2-one (prepared as described in example 282; 60 mg; 0.18 mmol), commercially available 2-bromo-4-methylthiazole (65 mg; 0.36 mmol), Cs$_2$CO$_3$ (66 mg; 0.20 mmol), CuCl (9 mg; 0.09 mmol), and commercially available 2,2,6,6-tetramethylheptane-3,5-dione (34 mg; 0.18 mmol) in anh. NMP (1 ml) was sealed and irradiated by microwave (175° C.; 10 min.). Water (1 ml), AcOEt (2 ml), and toluene (1 ml) were added, and the resulting suspension was filtered over a pad of celite. The separated organic layer was dried over anh. MgSO$_4$, filtered, and concentrated to dryness under reduced pressure. Subsequent purification by preparative HPLC afforded the target compound. LC-MS (conditions A): $t_R$=0.83 min.; [M+H]$^+$: 424.98 g/mol.

Example 293 rac-(3R*,5S*)-5-(2-fluoro-6-methoxyphenyl)-3-hydroxy-1-(4-(trifluoromethoxy)benzyl)pyrrolidin-2-one Prepared according to the described general procedures 10A2 (GP10A2), 10B (GP10B) and 10F (GP10F) using commercially available (4-(trifluoromethoxy)phenyl)methanamine and commercially available 2-fluoro-6-methoxybenzaldehyde. Subsequent purification by preparative HPLC afforded the target compound. LC-MS (conditions A): $t_R$=0.80 min.; [M+H]$^+$: 399.98 g/mol.

Example 294 rac-(3R*,5S*)-5-(2-chloro-6-methoxyphenyl)-3-hydroxy-1-(4-(trifluoromethoxy)benzyl)pyrrolidin-2-one Prepared according to the described general procedures 10A2 (GP10A2), 10B (GP10B) and 10F (GP10F) using commercially available (4-(trifluoromethoxy)phenyl)methanamine and commercially available 2-chloro-6-methoxybenzaldehyde. Subsequent purification by preparative HPLC afforded the target compound. LC-MS (conditions A): $t_R$=0.84 min.; [M+H]$^+$: 415.95 g/mol.

Example 295 rac-(3R*,5S*)-5-(2,3-dihydrobenzo[b][1,4]dioxin-5-yl)-3-hydroxy-1-(4-(trifluoromethoxy)benzyl)pyrrolidin-2-one Prepared according to the described general procedures 10A2 (GP10A2), 10B (GP10B) and 10F (GP10F) using commercially available (4-(trifluoromethoxy)phenyl)methanamine and commercially available 2,3-dihydrobenzo[b][1,4]dioxine-5-carbaldehyde. Subsequent purification by preparative HPLC afforded the target compound. LC-MS (conditions A): $t_R$=0.79 min.; [M+H]$^+$: 409.94 g/mol.

Example 296 rac-(3R*,5S*)-5-(4-fluoro-2-methoxyphenyl)-3-hydroxy-1-(4-(trifluoromethoxy)benzyl)pyrrolidin-2-one Prepared according to the described general procedures 10A2 (GP10A2), 10B (GP10B) and 10F (GP10F) using commercially available (4-(trifluoromethoxy)phenyl)methanamine and commercially available 4-fluoro-2-methoxybenzaldehyde. Subsequent purification by preparative HPLC afforded the target compound. LC-MS (conditions A): $t_R$=0.81 min.; [M+H]$^+$: 399.97 g/mol.

Example 297 rac-(3S*,5S*)-3-fluoro-5-(2-methoxyphenyl)-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and commercially available 2-methoxybenzaldehyde. Subsequent purification by preparative HPLC afforded the target compound. LC-MS (conditions A): $t_R$=0.90 min.; [M+H]$^+$: 383.97 g/mol.

Example 298 rac-(3S*,5S*)-3-chloro-5-(2-methoxyphenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and commercially available 2-methoxybenzaldehyde. Subsequent purification by preparative HPLC afforded the target compound. LC-MS (conditions A): $t_R$=0.94 min.; [M+H]$^+$: 399.94 g/mol.

Example 299 rac-(3R*,5S*)-5-(2-ethoxyphenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and commercially available 2-ethoxybenzaldehyde. Subsequent purification by preparative HPLC afforded the target compound. LC-MS (conditions A): $t_R$=0.85 min.; [M+H]$^+$: 396.01 g/mol.

Example 300 rac-(3S*,5S*)-5-(2-ethoxyphenyl)-3-fluoro-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and commercially available 2-ethoxybenzaldehyde. Subsequent purification by preparative HPLC afforded the target compound. LC-MS (conditions A): $t_R$=0.94 min.; [M+H]$^+$: 397.99 g/mol.

Example 301 rac-(3S*,5S*)-3-fluoro-5-(2-fluoro-6-methoxyphenyl)-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and commercially available 2-fluoro-6-methoxybenzaldehyde. Subsequent purification by preparative HPLC afforded the target compound. LC-MS (conditions A): $t_R$=0.89 min.; [M+H]$^+$: 401.72 g/mol.

Example 302 rac-(3S*,5S*)-5-(2-chloro-6-methoxyphenyl)-3-fluoro-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)

phenyl)methanamine and commercially available 2-chloro-6-methoxybenzaldehyde. Subsequent purification by preparative HPLC afforded the target compound. LC-MS (conditions A): $t_R$=0.93 min.; [M+H]$^+$: 417.78 g/mol.

Example 303 rac-(3S*,5S*)-3-fluoro-5-(4-fluoro-2-methoxyphenyl)-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and commercially available 4-fluoro-2-methoxybenzaldehyde. Subsequent purification by preparative HPLC afforded the target compound. LC-MS (conditions A): $t_R$=0.90 min.; [M+H]$^+$: 401.71 g/mol.

Example 304 rac-(3S*,5S*)-3-chloro-5-(2-ethoxyphenyl-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and commercially available 2-ethoxybenzaldehyde. Subsequent purification by preparative HPLC afforded the target compound. LC-MS (conditions A): $t_R$=0.98 min.; [M+H]$^+$: 413.94 g/mol.

Example 305 rac-(3S*,5S*)-3-chloro-5-(2-fluoro-6-methoxyphenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and commercially available 2-fluoro-6-methoxybenzaldehyde. Subsequent purification by preparative HPLC afforded the target compound. LC-MS (conditions A): $t_R$=0.93 min.; [M+H]$^+$: 417.67 g/mol.

Example 306 rac-(3S*,5S*)-3-chloro-5-(2-chloro-6-methoxyphenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and commercially available 2-chloro-6-methoxybenzaldehyde. Subsequent purification by preparative HPLC afforded the target compound. LC-MS (conditions A): $t_R$=0.97 min.; [M+H]$^+$: 433.71 g/mol.

Example 307 rac-(3S*,5S*)-3-chloro-5-(2,3-dihydrobenzo[b][1,4]dioxin-5-yl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and commercially available 2,3-dihydrobenzo[b][1,4]dioxine-5-carbaldehyde. Subsequent purification by preparative HPLC afforded the target compound. LC-MS (conditions A): $t_R$=0.91 min.; [M+H]$^+$: 427.84 g/mol.

Example 308 rac-(3S*,5S*)-3-chloro-5-(4-fluoro-2-methoxyphenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and commercially available 4-fluoro-2-methoxybenzaldehyde. Subsequent purification by preparative HPLC afforded the target compound. LC-MS (conditions A): $t_R$=0.94 min.; [M+H]$^+$: 417.67 g/mol.

Example 309 rac-(3R*,5S*)-3-hydroxy-5-(2-methoxy-6-methylphenyl)-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 2-methoxy-6-methylbenzaldehyde. Subsequent purification by preparative HPLC afforded the target compound. LC-MS (conditions A): $t_R$=0.83 min.; [M+H]$^+$: 395.97 g/mol.

Example 310 rac-(3R*,5S*)-5-(2-ethoxy-3-fluorophenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 2-ethoxy-3-fluorobenzaldehyde. Subsequent purification by preparative HPLC afforded the target compound. LC-MS (conditions A): $t_R$=0.86 min.; [M+H]$^+$: 413.96 g/mol.

Example 311 rac-(3R*,5S*)-5-(3-fluoro-2,6-dimethoxyphenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 3-fluoro-2,6-dimethoxybenzaldehyde. Subsequent purification by preparative HPLC afforded the target compound. LC-MS (conditions A): $t_R$=0.81 min.; [M+H]$^+$: 429.94 g/mol.

Example 312 rac-(3R*,5S*)-3-hydroxy-5-(2-methoxynaphthalen-1-yl)-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and commercially available 2-methoxy-1-naphthaldehyde. Subsequent purification by preparative HPLC afforded the target compound. LC-MS (conditions A): $t_R$=0.87 min.; [M+H]$^+$: 431.90 g/mol.

Example 313 rac-(3R*,5S*)-5-(3,6-difluoro-2-methoxyphenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 3,6-difluoro-2-methoxybenzaldehyde. Subsequent purification by preparative HPLC afforded the target compound. LC-MS (conditions A): $t_R$=0.81 min.; [M+H]$^+$: 417.69 g/mol.

Example 314 rac-(3R*,5S*)-5-(3-chloro-2,6-dimethoxyphenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 3-chloro-2,6-dimethoxybenzaldehyde. Subsequent purification by preparative HPLC afforded the target compound. LC-MS (conditions A): $t_R$=0.85 min.; [M+H]$^+$: 445.85 g/mol.

Example 315 rac-(3S*,5S*)-3-fluoro-5-(2-methoxynaphthalen-1-yl)-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and commercially available 2-methoxy-1-naphthaldehyde. Subsequent purification by preparative HPLC afforded the target compound. LC-MS (conditions A): $t_R$=0.96 min.; [M+H]$^+$: 433.67 g/mol.

Example 316 rac-(3S*,5S*)-3-chloro-5-(2-methoxynaphthalen-1-yl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and commercially available 2-methoxy-1-naphthaldehyde. Subsequent purification by preparative HPLC afforded the target compound. LC-MS (conditions A): $t_R$=0.98 min.; [M+H]$^+$: 449.66 g/mol.

Example 317 rac-(3R*,5S*)-3-chloro-5-(3,6-difluoro-2-methoxyphenyl)-1-(4-(trifluoromethoxy)benzyl)pyrrolidin-2-one Prepared according to the described general procedures 10A2 (GP10A2), 10B (GP10B), and 10D (GP10D) using commercially available (4-(trifluoromethoxy)phenyl)methanamine and synthesized 3,6-difluoro-2-methoxybenzaldehyde. Subsequent purification by preparative HPLC afforded the target compound. LC-MS (conditions A): $t_R$=0.95 min.; [M+H]$^+$: 435.86 g/mol.

Example 318 rac-(3S*,5S*)-3-chloro-5-(3-chloro-2,6-dimethoxyphenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 3-chloro-2,6-dimethoxybenzaldehyde. Subsequent purification by preparative HPLC afforded the target compound. LC-MS (conditions A): $t_R$=0.97 min.; [M+H]$^+$: 463.84 g/mol.

Example 319 rac-(3S*,5S*)-5-(3-chloro-2,6-dimethoxyphenyl)-3-fluoro-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and synthesized 3-chloro-2,6-dimethoxybenzaldehyde. Subsequent purification by preparative HPLC afforded the target compound. LC-MS (conditions A): $t_R$=0.94 min.; [M+H]$^+$: 447.84 g/mol.

Example 320 rac-(3S*,5S*)-3-chloro-5-(3,6-difluoro-2-methoxyphenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 3,6-difluoro-2-methoxybenzaldehyde. Subsequent purification by preparative HPLC afforded the target compound. LC-MS (conditions A): $t_R$=0.93 min.; [M+H]$^+$: 435.86 g/mol.

Example 321 rac-(3S*,5S*)-5-(3,6-difluoro-2-methoxyphenyl)-3-fluoro-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and synthesized 3,6-difluoro-2-methoxybenzaldehyde. Subsequent purification by preparative HPLC afforded the target compound. LC-MS (conditions A): $t_R$=0.90 min.; [M+H]$^+$: 419.85 g/mol.

Example 322 rac-(3R*,5S*)-3-chloro-5-(2,3-dihydrobenzo[b][1,4]dioxin-5-yl)-1-(4-(trifluoromethoxy)benzyl)pyrrolidin-2-one Prepared according to the described general procedures 10A2 (GP10A2), 10B (GP10B), and 10D (GP10D) using commercially available (4-(trifluoromethoxy)phenyl)methanamine and commercially available 2,3-dihydrobenzo[b][1,4]dioxine-5-carbaldehyde. Subsequent purification by preparative HPLC afforded the target compound. LC-MS (conditions A): $t_R$=0.92 min.; [M+H]$^+$: 427.85 g/mol.

Example 323 rac-(3R*,5S*)-3-chloro-5-(4-fluoro-2-methoxyphenyl)-1-(4-(trifluoromethoxy)benzyl)pyrrolidin-2-one Prepared according to the described general procedures 10A2 (GP10A2), 10B (GP10B), and 10D (GP10D) using commercially available (4-(trifluoromethoxy)phenyl)methanamine and commercially available 4-fluoro-2-methoxybenzaldehyde. Subsequent purification by preparative HPLC afforded the target compound. LC-MS (conditions A): $t_R$=0.94 min.; [M+H]$^+$: 417.67 g/mol.

Example 324 rac-(3R*,5S*)-3-chloro-5-(2-fluoro-6-methoxyphenyl)-1-(4-(trifluoromethoxy)benzyl)pyrrolidin-2-one Prepared according to the described general procedures 10A2 (GP10A2), 10B (GP10B), and 10D (GP10D) using commercially available (4-(trifluoromethoxy)phenyl)methanamine and commercially available 2-fluoro-6-methoxybenzaldehyde. Subsequent purification by preparative HPLC afforded the target compound. LC-MS (conditions A): $t_R$=0.94 min.; [M+H]$^+$: 417.69 g/mol.

Example 325 rac-(3S*,5S*)-3-fluoro-5-(2-methoxy-6-methylphenyl)-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and synthesized 2-methoxy-6-methylbenzaldehyde. Subsequent purification by preparative HPLC afforded the target compound. LC-MS (conditions A): $t_R$=0.92 min.; [M+H]$^+$: 397.92 g/mol.

Example 326 rac-(3S*,5S*)-3-chloro-5-(2-methoxy-6-methylphenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 2-methoxy-6-methylbenzaldehyde. Subsequent purification by preparative HPLC afforded the target compound. LC-MS (conditions A): $t_R$=0.96 min.; [M+H]$^+$: 413.91 g/mol.

Example 327 rac-(3R*,5S*)-3-chloro-5-(2-ethoxy-3-fluorophenyl)-1-(4-(trifluoromethoxy)benzyl)pyrrolidin-2-one Prepared according to the described general procedures 10A2 (GP10A2), 10B (GP10B), and 10D (GP10D) using commercially available (4-(trifluoromethoxy)phenyl)methanamine and synthesized 2-ethoxy-3-fluorobenzaldehyde. Subsequent purification by preparative HPLC afforded the target compound. LC-MS (conditions A): $t_R$=0.99 min.; [M+H]$^+$: 431.80 g/mol.

Example 328 rac-(3R*,5S*)-3-chloro-5-(3-fluoro-2,6-dimethoxyphenyl)-1-(4-(trifluoromethoxy)benzyl)pyrrolidin-2-one Prepared according to the described general procedures 10A2 (GP10A2), 10B (GP10B), and 10D (GP10D) using commercially available (4-(trifluoromethoxy)phenyl)methanamine and synthesized 3-fluoro-2,6-dimethoxybenzaldehyde. Subsequent purification by preparative HPLC afforded the target compound. LC-MS (conditions A): $t_R$=0.95 min.; [M+H]$^+$: 447.89 g/mol.

Example 329 rac-(3S*,5S*)-3-chloro-5-(2-ethoxy-3-fluorophenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 2-ethoxy-3-fluorobenzaldehyde. Subsequent purification by preparative HPLC afforded the target compound. LC-MS (conditions A): $t_R$=0.98 min.; [M+H]$^+$: 431.87 g/mol.

Example 330 rac-(3S*,5S*)-3-chloro-5-(3-fluoro-2,6-dimethoxyphenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 3-fluoro-2,6-dimethoxybenzaldehyde. Subsequent purification by preparative HPLC afforded the target compound. LC-MS (conditions A): $t_R$=0.94 min.; [M+H]$^+$: 447.86 g/mol.

Example 331 rac-(3S*,5S*)-5-(2-ethoxy-3-fluorophenyl)-3-fluoro-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and synthesized 2-ethoxy-3-fluorobenzaldehyde. Subsequent purification by preparative HPLC afforded the target compound. LC-MS (conditions A): $t_R$=0.95 min.; [M+H]$^+$: 415.87 g/mol.

Example 332 rac-(3S*,5S*)-3-fluoro-5-(3-fluoro-2,6-dimethoxyphenyl)-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)

phenyl)methanamine and synthesized 3-fluoro-2,6-dimethoxybenzaldehyde. Subsequent purification by preparative HPLC afforded the target compound. LC-MS (conditions A): $t_R$=0.90 min.; [M+H]$^+$: 431.90 g/mol.

Example 333 rac-(3R*,5S*)-3-chloro-5-(2-ethoxy-6-fluorophenyl)-1-(4-(trifluoromethoxy)benzyl)pyrrolidin-2-one Prepared according to the described general procedures 10A2 (GP10A2), 10B (GP10B), and 10D (GP10D) using commercially available (4-(trifluoromethoxy)phenyl)methanamine and synthesized 2-ethoxy-6-fluorobenzaldehyde. Subsequent purification by preparative HPLC afforded the target compound. LC-MS (conditions A): $t_R$=0.98 min.; [M+H]$^+$: 431.76 g/mol.

Example 334 rac-(3R*,5S*)-5-(2-ethoxy-6-fluorophenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 2-ethoxy-6-fluorobenzaldehyde. Subsequent purification by preparative HPLC afforded the target compound. LC-MS (conditions A): $t_R$=0.83 min.; [M+H]$^+$: 414.37 g/mol.

Example 335 rac-(3R*,5S*)-5-(2-ethoxy-4-fluorophenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 2-ethoxy-4-fluorobenzaldehyde. Subsequent purification by preparative HPLC afforded the target compound. LC-MS (conditions A): $t_R$=0.84 min.; [M+H]$^+$: 414.36 g/mol.

Example 336

1-([1,1'-biphenyl]-3-ylmethyl)-5-(2,6-dimethoxyphenyl)-3,3-difluoropyrrolidin-2-one Prepared according to the described general procedures 10A2 (GP10A2), and 10G (GP10G) using commercially available [1,1'-biphenyl]-3-ylmethanamine and commercially available 2,6-dimethoxybenzaldehyde. Subsequent purification by preparative HPLC afforded the target compound. LC-MS (conditions A): $t_R$=0.97 min.; [M+H]$^+$: 424.41 g/mol.

Example 337

1-([1,1'-biphenyl]-3-ylmethyl)-5-(2-ethoxy-6-methoxyphenyl)-3,3-difluoropyrrolidin-2-one Prepared according to the described general procedures 10A2 (GP10A2), and 10G (GP10G) using commercially available [1,1'-biphenyl]-3-ylmethanamine and synthesized 2-ethoxy-6-methoxybenzaldehyde. Subsequent purification by preparative HPLC afforded the target compound. LC-MS (conditions A): $t_R$=1.01 min.; [M+H]$^+$: 438.45 g/mol.

Example 338 rac-(3R*,5S*)-5-(6-ethoxy-2,3-difluorophenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 6-ethoxy-2,3-difluorobenzaldehyde. Subsequent purification by preparative HPLC afforded the target compound. LC-MS (conditions A): $t_R$=0.84 min.; [M+H]$^+$: 431.93 g/mol.

Example 339 rac-(3S*,5S*)-3-chloro-5-(6-ethoxy-2,3-difluorophenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 6-ethoxy-2,3-difluorobenzaldehyde. Subsequent purification by preparative HPLC afforded the target compound. LC-MS (conditions A): $t_R$=0.96 min.; [M+H]$^+$: 450.17 g/mol.

Example 340 rac-(3S*,5S*)-5-(6-ethoxy-2,3-difluorophenyl)-3-fluoro-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and synthesized 6-ethoxy-2,3-difluorobenzaldehyde. Subsequent purification by preparative HPLC afforded the target compound. LC-MS (conditions A): $t_R$=0.92 min.; [M+H]$^+$: 434.18 g/mol.

Example 341 rac-(3R*,5S*)-3-chloro-5-(2-ethoxy-4-fluor phenyl)-1-(4-(trifluoromethoxy)benzyl)pyrrolidin-2-one Prepared according to the described general procedures 10A2 (GP10A2), 10B (GP10B), and 10D (GP10D) using commercially available (4-(trifluoromethoxy)phenyl)methanamine and synthesized 2-ethoxy-4-fluorobenzaldehyde. Subsequent purification by preparative HPLC afforded the target compound. LC-MS (conditions A): $t_R$=0.97 min.; [M+H]$^+$: 432.35 g/mol.

Example 342 rac-(3S*,5S*)-5-(2-ethoxy-6-fluorophenyl)-3-fluoro-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and synthesized 2-ethoxy-6-fluorobenzaldehyde. Subsequent purification by preparative HPLC afforded the target compound. LC-MS (conditions A): $t_R$=0.93 min.; [M+H]⁺: 416.36 g/mol.

Example 343 rac-(3S*,5S*)-3-chloro-5-(2-ethoxy-6-fluorophenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 2-ethoxy-6-fluorobenzaldehyde. Subsequent purification by preparative HPLC afforded the target compound. LC-MS (conditions A): $t_R$=0.96 min.; [M+H]⁺: 432.34 g/mol.

Example 344 rac-(3S*,5S*)-5-(2-ethoxy-4-fluorophenyl)-3-fluoro-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and synthesized 2-ethoxy-4-fluorobenzaldehyde. Subsequent purification by preparative HPLC afforded the target compound. LC-MS (conditions A): $t_R$=0.93 min.; [M+H]⁺: 416.34 g/mol.

Example 345 rac-(3S*,5S*)-3-chloro-5-(6-ethoxy-2,3-difluorophenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 2-ethoxy-4-fluorobenzaldehyde. Subsequent purification by preparative HPLC afforded the target compound. LC-MS (conditions A): $t_R$=0.97 min.; [M+H]⁺: 432.34 g/mol.

Example 346 rac-(3R*,5S*)-3-chloro-5-(6-ethoxy-2,3-difluorophenyl)-1-(4-(trifluoromethoxy)benzyl)pyrrolidin-2-one Prepared according to the described general procedures 10A2 (GP10A2), 10B (GP10B), and 10D (GP10D) using commercially available (4-(trifluoromethoxy)phenyl)methanamine and synthesized 6-ethoxy-2,3-difluorobenzaldehyde. Subsequent purification by preparative HPLC afforded the target compound. LC-MS (conditions A): $t_R$=0.97 min.; [M+H]⁺: 450.18 g/mol.

Example 347

5-(2,6-dimethoxyphenyl)-3-methyl-1-(quinolin-3-ylmethyl)pyrrolidin-2-one

Prepared according to the described general procedure 2 (GP2) by reaction of ethyl 4-amino-4-(2,6-dimethoxyphenyl)-2-methylbutanoate with commercially available quinoline-3-carbaldehyde. Subsequent purification by preparative HPLC afforded the target compound. LC-MS (conditions A): $t_R$=0.60 min.; [M+H]⁺: 376.75 g/mol.

Example 348

5-(2,6-dimethoxyphenyl)-3-methyl-1-(quinolin-2-ylmethyl)pyrrolidin-2-one

Prepared according to the described general procedure 2 (GP2) by reaction of ethyl 4-amino-4-(2,6-dimethoxyphenyl)-2-methylbutanoate with commercially available quinoline-2-carbaldehyde. Subsequent purification by preparative HPLC afforded the target compound. LC-MS (conditions A): $t_R$=0.63 min.; [M+H]⁺: 377.04 g/mol.

Example 349

5-(2,4-dimethoxypyridin-3-yl)-3-methyl-1-(3-(5-methylthiazol-2-yl)benzyl)pyrrolidin-2-one Prepared according to the described general procedure 2 (GP2) by reaction of methyl 4-amino-4-(2,4-dimethoxypyridin-3-yl)-2-methylbutanoate with 3-(5-methylthiazol-2-yl)benzaldehyde. Subsequent purification by preparative HPLC afforded the target compound. LC-MS (conditions A): $t_R$=0.75 min.; [M+H]⁺: 423.87 g/mol.

Example 350

5-(2,4-dimethoxypyridin-3-yl)-3-methyl-1-((2-(p-tolyl)thiazol-4-yl)methyl)pyrrolidin-2-one Prepared according to the described general procedure 2 (GP2) by reaction of methyl 4-amino-4-(2,4-dimethoxypyridin-3-yl)-2-methylbutanoate with commercially available 2-(p-tolyl)thiazole-4-carbaldehyde. Subsequent purification by preparative HPLC afforded the target compound. LC-MS (conditions A): $t_R$=0.82 min.; [M+H]⁺: 423.98 g/mol.

Example 351

5-(2,6-dimethoxyphenyl)-3-methyl-1-((2-(5-methylthiazol-2-yl)pyridin-4-yl)methyl)pyrrolidin-2-one Prepared according to the described general procedure 2 (GP2) by reaction of ethyl 4-amino-4-(2,6-dimethoxyphenyl)-2-methylbutanoate with synthesized 2-(5-methylthiazol-2-yl)isonicotinaldehyde. Subsequent purification by preparative HPLC afforded the target compound. LC-MS (conditions A): $t_R$=0.82 min.; [M+H]⁺: 424.03 g/mol.

Example 352

1-(dibenzo[b,d]furan-2-ylmethyl)-5-(2,4-dimethoxypyridin-3-yl)-3-methylpyrrolidin-2-one Prepared according to the described general procedure 2 (GP2) by reaction of methyl 4-amino-4-(2,4-dimethoxypyridin-3-yl)-2-methylbutanoate with commercially available dibenzo[b,d]furan-2-carbaldehyde. Subsequent purification by preparative HPLC afforded the target compound. LC-MS (conditions A): $t_R$=0.85 min.; [M+H]⁺: 416.90 g/mol.

Example 353

1-(dibenzo[b,d]furan-2-ylmethyl)-5-(2,6-dimethoxyphenyl)-3,3-difluoropyrrolidin-2-one Prepared according to the described general procedures 10A2 (GP10A2), and 10G (GP10G) using synthesized dibenzo[b,d]furan-2-ylmethanamine and commercially available 2,6-dimethoxybenzaldehyde. Subsequent purification by preparative HPLC afforded the target compound. LC-MS (conditions A): $t_R$=0.98 min.; [M+H]$^+$: 437.90 g/mol.

Example 354

1-([1,1'-biphenyl]-3-ylmethyl)-5-(2,4-dimethoxypyridin-3-yl)-3-methylpyrrolidin-2-one Prepared according to the described general procedure 2 (GP2) by reaction of methyl 4-amino-4-(2,4-dimethoxypyridin-3-yl)-2-methylbutanoate with commercially available [1,1'-biphenyl]-3-carbaldehyde. Subsequent purification by preparative HPLC afforded the target compound. LC-MS (conditions A): $t_R$=0.85 min.; [M+H]$^+$: 402.99 g/mol.

Example 355

1-(3-(4-chlorothiazol-2-yl)benzyl)-5-(2,4-dimethoxypyridin-3-yl)-3-methylpyrrolidin-2-one Prepared according to the described general procedure 2 (GP2) by reaction of methyl 4-amino-4-(2,4-dimethoxypyridin-3-yl)-2-methylbutanoate with synthesized 3-(4-chlorothiazol-2-yl)benzaldehyde. Subsequent purification by preparative HPLC afforded the target compound. LC-MS (conditions A): $t_R$=0.81 min.; [M+H]$^+$: 443.85 g/mol.

Example 356

5-(2,4-dimethoxypyridin-3-yl)-3-methyl-1-(3-(2-methylthiazol-4-yl)benzyl)pyrrolidin-2-one Prepared according to the described general procedure 2 (GP2) by reaction of methyl 4-amino-4-(2,4-dimethoxypyridin-3-yl)-2-methylbutanoate with commercially available 3-(2-methylthiazol-4-yl)benzaldehyde. Subsequent purification by preparative HPLC afforded the target compound. LC-MS (conditions A): $t_R$=0.73 min.; [M+H]$^+$: 424.03 g/mol.

Example 357 rac-(3R*,5S*)-1-(dibenzo[b,d]furan-2-ylmethyl)-5-(2,6-dimethoxyphenyl)-3-hydroxypyrrolidin-2-one Prepared according to the described general procedures 10A2 (GP10A2), 10B (GP10B), and 10F (GP10F) using synthesized dibenzo[b,d]furan-2-ylmethanamine and commercially available 2,6-dimethoxybenzaldehyde. Subsequent purification by preparative HPLC afforded the target compound. LC-MS (conditions A): $t_R$=0.82 min.; [M+H]$^+$: 417.71 g/mol.

Example 358

5-(2-fluoro-6-methoxyphenyl)-3-methyl-1-(quinolin-3-ylmethyl)pyrrolidin-2-one

Prepared according to the described general procedure 2 (GP2) by reaction of ethyl 4-amino-4-(2-fluoro-6-methoxyphenyl)-2-methylbutanoate with commercially available quinoline-3-carbaldehyde. Subsequent purification by preparative HPLC afforded the target compound. LC-MS (conditions A): $t_R$=0.60 min.; [M+H]$^+$: 365.01 g/mol.

Example 359

5-(2-fluoro-6-methoxyphenyl)-3-methyl-1-(quinolin-2-ylmethyl)pyrrolidin-2-one

Prepared according to the described general procedure 2 (GP2) by reaction of ethyl 4-amino-4-(2-fluoro-6-methoxyphenyl)-2-methylbutanoate with commercially available quinoline-2-carbaldehyde. Subsequent purification by preparative HPLC afforded the target compound. LC-MS (conditions A): $t_R$=0.65 min.; [M+H]$^+$: 365.02 g/mol.

Example 360

5-(2-fluoro-6-methoxyphenyl)-3-methyl-1-((2-(5-methylthiazol-2-yl)pyridin-4-yl)methyl)pyrrolidin-2-one Prepared according to the described general procedure 2 (GP2) by reaction of ethyl 4-amino-4-(2-fluoro-6-methoxyphenyl)-2-methylbutanoate with 2-(5-methylthiazol-2-yl)isonicotinaldehyde. Subsequent purification by preparative HPLC afforded the target compound. LC-MS (conditions A): $t_R$=0.81 min.; [M+H]$^+$: 412.01 g/mol.

Example 361

1-((2-(1H-pyrazol-1-yl)pyridin-4-yl)methyl)-5-(2-fluoro-6-methoxyphenyl)-3-methylpyrrolidin-2-one Prepared according to the described general procedure 2 (GP2) by reaction of ethyl 4-amino-4-(2-fluoro-6-methoxyphenyl)-2-methylbutanoate with 2-(1H-pyrazol-1-yl)isonicotinaldehyde. Subsequent purification by preparative HPLC afforded the target compound. LC-MS (conditions A): $t_R$=0.79 min.; [M+H]$^+$: 381.04 g/mol.

Example 362

1-(dibenzo[b,d]furan-2-ylmethyl)-5-(2-fluoro-6-methoxyphenyl)-3-methylpyrrolidin-2-one Prepared according to the described general procedure 2 (GP2) by reaction of ethyl 4-amino-4-(2-fluoro-6-methoxyphenyl)-2-methylbutanoate with commercially available dibenzo[b,d]furan-2-carbaldehyde. Subsequent purification by preparative HPLC afforded the target compound. LC-MS (conditions A): $t_R$=0.96 min.; [M+H]$^+$: 403.87 g/mol.

Example 363

5-(2-fluoro-6-methoxyphenyl)-3-methyl-1-((2-(p-tolyl)thiazol-4-yl)methyl)pyrrolidin-2-one Prepared according to the described general procedure 2 (GP2) by reaction of ethyl 4-amino-4-(2-fluoro-6-methoxyphenyl)-2-methylbutanoate with commercially available 2-(p-tolyl)thiazole-4-carbaldehyde. Subsequent purification by preparative HPLC afforded the target compound. LC-MS (conditions A): $t_R$=0.94 min.; [M+H]$^+$: 411.02 g/mol.

Example 364

5-(2-fluoro-6-methoxyphenyl)-3-methyl-1-(3-(5-methylthiazol-2-yl)benzyl)pyrrolidin-2-one Prepared according to the described general procedure 2 (GP2) by reaction of ethyl 4-amino-4-(2-fluoro-6-methoxyphenyl)-2-methylbutanoate with 3-(5-methylthiazol-2-yl)benzaldehyde. Subsequent purification by preparative HPLC afforded the target compound. LC-MS (conditions A): $t_R$=0.88 min.; [M+H]$^+$: 411.00 g/mol.

Example 365

1-(3-(4-chlorothiazol-2-yl)benzyl)-5-(2-fluoro-6-methoxyphenyl)-3-methylpyrrolidin-2-one Prepared according to the described general procedure 2 (GP2) by reaction of ethyl 4-amino-4-(2-fluoro-6-methoxyphenyl)-2-methylbutanoate with 3-(4-chlorothiazol-2-yl)benzaldehyde. Subsequent purification by preparative HPLC afforded the target compound. LC-MS (conditions A): $t_R$=0.93 min.; [M+H]$^+$: 430.96 g/mol.

Example 366

5-(2-fluoro-6-methoxyphenyl)-3-methyl-1-((2-(4-methylthiazol-2-yl)pyridin-4-yl)methyl)pyrrolidin-2-one Prepared according to the described general procedure 2 (GP2) by reaction of ethyl 4-amino-4-(2-fluoro-6-methoxyphenyl)-2-methylbutanoate with 2-(4-methylthiazol-2-yl)isonicotinaldehyde. Subsequent purification by preparative HPLC afforded the target compound. LC-MS (conditions A): $t_R$=0.81 min.; [M+H]$^+$: 411.99 g/mol.

Example 367 rac-(3S*,5S*)-1-(dibenzo[b,d]furan-2-ylmethyl)-5-(2,6-dimethoxyphenyl)-3-fluoropyrrolidin-2-one Prepared according to the described general procedures 10A2 (GP10A2), 10B (GP10B), 10F (GP10F), and 10I (GP10I) using synthesized dibenzo[b,d]furan-2-ylmethanamine and commercially available 2,6-dimethoxybenzaldehyde. Subsequent purification by preparative HPLC afforded the target compound. LC-MS (conditions A): $t_R$=0.92 min.; [M+H]$^+$: 419.98 g/mol.

Example 368 rac-(3R*,5S*)-1-(dibenzo[b,d]furan-2-ylmethyl)-5-(2,6-dimethoxyphenyl)-3-fluoropyrrolidin-2-one Prepared according to the described general procedures 10A2 (GP10A2), 10B (GP10B), and 10I (GP10I) using synthesized dibenzo[b,d]furan-2-ylmethanamine and commercially available 2,6-dimethoxybenzaldehyde. Subsequent purification by preparative HPLC afforded the target compound. LC-MS (conditions A): $t_R$=0.93 min.; [M+H]$^+$: 419.94 g/mol.

Example 369 rac-(3S*,5S*)-3-chloro-1-(dibenzo[b,d]furan-2-ylmethyl)-5-(2,6-dimethoxyphenyl)pyrrolidin-2-one Prepared according to the described general procedures 10A2 (GP10A2), 10B (GP10B), 10F (GP10F), and 10D (GP10D) using synthesized dibenzo[b,d]furan-2-ylmethanamine and commercially available 2,6-dimethoxybenzaldehyde. Subsequent purification by preparative HPLC afforded the target compound. LC-MS (conditions A): $t_R$=0.96 min.; [M+H]$^+$: 435.86 g/mol.

Example 370

5-(2-ethoxy-6-fluorophenyl)-3-methyl-1-(4-(trifluoromethoxy)benzyl)pyrrolidin-2-one Prepared according to the described general procedure 2 (GP2) by reaction of ethyl 4-amino-4-(2-ethoxy-6-fluorophenyl)-2-methylbutanoate with commercially available 4-(trifluoromethoxy)benzaldehyde. Subsequent purification by preparative HPLC afforded the target compound. LC-MS (conditions A): $t_R$=0.97 min.; [M+H]$^+$: 411.97 g/mol.

Example 371

5-(2-ethoxy-6-fluorophenyl)-3-methyl-1-(3-(trifluoromethoxy)benzyl)pyrrolidin-2-one Prepared according to the described general procedure 2 (GP2) by reaction of ethyl 4-amino-4-(2-ethoxy-6-fluorophenyl)-2-methylbutanoate with commercially available 3-(trifluoromethoxy)benzaldehyde. Subsequent purification by preparative HPLC afforded the target compound. LC-MS (conditions A): $t_R$=0.97 min.; [M+H]$^+$: 411.84 g/mol.

Example 372

5-(2-ethoxy-6-fluorophenyl)-1-(3-fluoro-4-(trifluoromethoxy)benzyl)-3-methylpyrrolidin-2-one Prepared according to the described general procedure 2 (GP2) by reaction of ethyl 4-amino-4-(2-ethoxy-6-fluorophenyl)-2-methylbutanoate with commercially available 3-fluoro-4-(trifluoromethoxy)benzaldehyde. Subsequent purification by preparative HPLC afforded the target compound. LC-MS (conditions A): $t_R$=0.98 min.; [M+H]$^+$: 429.97 g/mol.

Example 373

1-(4-(difluoromethoxy)benzyl)-5-(2-ethoxy-6-fluorophenyl)-3-methylpyrrolidin-2-one Prepared according to the described general procedure 2 (GP2) by reaction of ethyl 4-amino-4-(2-ethoxy-6-fluorophenyl)-2-methylbutanoate with commercially available 4-(difluoromethoxy)benzaldehyde. Subsequent purification by preparative HPLC afforded the target compound. LC-MS (conditions A): $t_R$=0.90 min.; [M+H]$^+$: 394.01 g/mol.

Example 374

1-(3-(difluoromethoxy)benzyl)-5-(2-ethoxy-6-fluorophenyl)-3-methylpyrrolidin-2-one Prepared according to the described general procedure 2 (GP2) by reaction of ethyl 4-amino-4-(2-ethoxy-6-fluorophenyl)-2-methylbutanoate with commercially available 3-(difluoromethoxy)benzaldehyde. Subsequent purification by preparative HPLC afforded the target compound. LC-MS (conditions A): $t_R$=0.90 min.; [M+H]$^+$: 394.02 g/mol.

Example 375

1-(3-chloro-4-(difluoromethoxy)benzyl)-5-(2-ethoxy-6-fluorophenyl)-3-methylpyrrolidin-2-one Prepared according to the described general procedure 2 (GP2) by reaction of ethyl 4-amino-4-(2-ethoxy-6-fluorophenyl)-2-methylbutanoate with commercially available 3-chloro-4-(difluoromethoxy)benzaldehyde. Subsequent purification by preparative HPLC afforded the target compound. LC-MS (conditions A): $t_R$=0.93 min.; [M+H]$^+$: 427.96 g/mol.

Example 376

5-(2-ethoxy-6-fluorophenyl)-1-(3-ethoxybenzyl)-3-methylpyrrolidin-2-one

Prepared according to the described general procedure 2 (GP2) by reaction of ethyl 4-amino-4-(2-ethoxy-6-fluorophenyl)-2-methylbutanoate with commercially available 3-ethoxybenzaldehyde. Subsequent purification by preparative HPLC afforded the target compound. LC-MS (conditions A): $t_R$=0.92 min.; [M+H]$^+$: 372.03 g/mol.

Example 377

5-(2-ethoxy-6-fluorophenyl)-3-methyl-1-(4-propoxybenzyl)pyrrolidin-2-one

Prepared according to the described general procedure 2 (GP2) by reaction of ethyl 4-amino-4-(2-ethoxy-6-fluorophenyl)-2-methylbutanoate with commercially available 4-propoxybenzaldehyde. Subsequent purification by preparative HPLC afforded the target compound. LC-MS (conditions A): $t_R$=0.97 min.; [M+H]$^+$: 385.81 g/mol.

Example 378

5-(2-ethoxy-6-fluorophenyl)-3-methyl-1-(quinolin-3-ylmethyl)pyrrolidin-2-one

Prepared according to the described general procedure 2 (GP2) by reaction of ethyl 4-amino-4-(2-ethoxy-6-fluorophenyl)-2-methylbutanoate with commercially available quinoline-3-carbaldehyde. Subsequent purification by preparative HPLC afforded the target compound. LC-MS (conditions A): $t_R$=0.64 min.; [M+H]$^+$: 379.06 g/mol.

Example 379

5-(2-ethoxy-6-fluorophenyl)-3-methyl-1-(quinolin-2-ylmethyl)pyrrolidin-2-one

Prepared according to the described general procedure 2 (GP2) by reaction of ethyl 4-amino-4-(2-ethoxy-6-fluorophenyl)-2-methylbutanoate with commercially available quinoline-2-carbaldehyde. Subsequent purification by preparative HPLC afforded the target compound. LC-MS (conditions A): $t_R$=0.71 min.; [M+H]$^+$: 379.04 g/mol.

Example 380

5-(2-ethoxy-6-fluorophenyl)-3-methyl-1-((2-(5-methylthiazol-2-yl)pyridin-4-yl)methyl)pyrrolidin-2-one Prepared according to the described general procedure 2 (GP2) by reaction of ethyl 4-amino-4-(2-ethoxy-6-fluorophenyl)-2-methylbutanoate with 2-(5-methylthiazol-2-yl)isonicotinaldehyde. Subsequent purification by preparative HPLC afforded the target compound. LC-MS (conditions A): $t_R$=0.86 min.; [M+H]$^+$: 425.99 g/mol.

Example 381

1-((2-(1H-pyrazol-1-yl)pyridin-4-yl)methyl)-5-(2-ethoxy-6-fluorophenyl)-3-methylpyrrolidin-2-one Prepared according to the described general procedure 2 (GP2) by reaction of ethyl 4-amino-4-(2-ethoxy-6-fluorophenyl)-2-methylbutanoate with 2-(1H-pyrazol-1-yl)isonicotinaldehyde. Subsequent purification by preparative HPLC afforded the target compound. LC-MS (conditions A): $t_R$=0.84 min.; [M+H]$^+$: 394.85 g/mol.

Example 382

1-(dibenzo[b,d]furan-2-ylmethyl)-5-(2-ethoxy-6-fluorophenyl)-3-methylpyrrolidin-2-one Prepared according to the described general procedure 2 (GP2) by reaction of ethyl 4-amino-4-(2-ethoxy-6-fluorophenyl)-2-methylbutanoate with commercially available dibenzo[b,d]furan-2-carbaldehyde. Subsequent purification by preparative HPLC afforded the target compound. LC-MS (conditions A): $t_R$=1.00 min.; [M+H]$^+$: 417.81 g/mol.

Example 383

5-(2-ethoxy-6-fluorophenyl)-3-methyl-1-((2-(p-tolyl)thiazol-4-yl)methyl)pyrrolidin-2-one Prepared according to the described general procedure 2 (GP2) by reaction of ethyl 4-amino-4-(2-ethoxy-6-fluorophenyl)-2-methylbutanoate with commercially available 2-(p-tolyl)thiazole-4-carbaldehyde. Subsequent purification by preparative HPLC afforded the target compound. LC-MS (conditions A): $t_R$=0.98 min.; [M+H]$^+$: 425.01 g/mol.

Example 384

5-(2-ethoxy-6-fluorophenyl)-3-methyl-1-(3-(5-methylthiazol-2-yl)benzyl)pyrrolidin-2-one Prepared according to the described general procedure 2 (GP2) by reaction of ethyl 4-amino-4-(2-ethoxy-6-fluorophenyl)-2-methylbutanoate with 3-(5-methylthiazol-2-yl)benzaldehyde. Subsequent purification by preparative HPLC afforded the target compound. LC-MS (conditions A): $t_R$=0.92 min.; [M+H]$^+$: 425.02 g/mol.

Example 385

1-(3-(4-chlorothiazol-2-yl)benzyl)-5-(2-ethoxy-6-fluorophenyl)-3-methylpyrrolidin-2-one Prepared according to the described general procedure 2 (GP2) by reaction of ethyl 4-amino-4-(2-ethoxy-6-fluorophenyl)-2-methylbutanoate with 3-(4-chlorothiazol-2-yl)benzaldehyde. Subsequent purification by preparative HPLC afforded the target compound. LC-MS (conditions A): $t_R$=0.97 min.; [M+H]$^+$: 444.95 g/mol.

Example 386

5-(2-ethoxy-6-fluorophenyl)-3-methyl-1-((2-(4-methylthiazol-2-yl)pyridin-4-yl)methyl)pyrrolidin-2-one Prepared according to the described general procedure 2 (GP2) by reaction of ethyl 4-amino-4-(2-ethoxy-6-fluorophenyl)-2-methylbutanoate with 2-(4-methylthiazol-2-yl)isonicotinaldehyde. Subsequent purification by preparative HPLC afforded the target compound. LC-MS (conditions A): $t_R$=0.86 min.; [M+H]$^+$: 426.01 g/mol.

Example 387

5-(2,6-dimethoxyphenyl)-3-methyl-1-((9-methyl-9H-carbazol-3-yl)methyl)pyrrolidin-2-one Prepared according to the described general procedure 2 (GP2) by reaction of ethyl 4-amino-4-(2,6-dimethoxyphenyl)-2-methylbutanoate with commercially available 9-methyl-9H-carbazole-3-carbaldehyde. Subsequent purification by preparative HPLC afforded the target compound. LC-MS (conditions A): $t_R$=0.94 min.; [M+H]$^+$: 429.05 g/mol.

Example 388

5-(2,6-dimethoxyphenyl)-3-methyl-1-((1-methyl-1H-indol-2-yl)methyl)pyrrolidin-2-one Prepared according to the described general procedure 2 (GP2) by reaction of ethyl 4-amino-4-(2,6-dimethoxyphenyl)-2-methylbutanoate with commercially available 1-methyl-1H-indole-2-carbaldehyde. Subsequent purification by preparative HPLC afforded the target compound. LC-MS (conditions A): $t_R$=0.90 min.; [M+H]$^+$: 379.05 g/mol.

Example 389

1-((1H-indol-2-yl)methyl)-5-(2,6-dimethoxyphenyl)-3-methylpyrrolidin-2-one

Prepared according to the described general procedure 2 (GP2) by reaction of ethyl 4-amino-4-(2,6-dimethoxyphenyl)-2-methylbutanoate with commercially available 1H-indole-2-carbaldehyde. Subsequent purification by preparative HPLC afforded the target compound. LC-MS (conditions A): $t_R$=0.87 min.; [M+H]$^+$: 365.03 g/mol.

Example 390

5-(2,6-dimethoxyphenyl)-1-((5-fluoro-1-methyl-1H-indol-2-yl)methyl)-3-methylpyrrolidin-2-one Prepared according to the described general procedure 2 (GP2) by reaction of ethyl 4-amino-4-(2,6-dimethoxyphenyl)-2-methylbutanoate with commercially available 5-fluoro-1-methyl-1H-indole-2-carbaldehyde. Subsequent purification by preparative HPLC afforded the target compound. LC-MS (conditions A): $t_R$=0.90 min.; [M+H]$^+$: 397.08 g/mol.

Example 391

5-(2,6-dimethoxyphenyl)-3-methyl-1-((1-methyl-1H-indol-5-yl)methyl)pyrrolidin-2-one Prepared according to the described general procedure 2 (GP2) by reaction of ethyl 4-amino-4-(2,6-dimethoxyphenyl)-2-methylbutanoate with commercially available 1-methyl-1H-indole-5-carbaldehyde. Subsequent purification by preparative HPLC afforded the target compound. LC-MS (conditions A): $t_R$=0.84 min.; [M+H]$^+$: 378.93 g/mol.

Example 392

1-((1H-indol-5-yl)methyl)-5-(2,6-dimethoxyphenyl)-3-methylpyrrolidin-2-one

Prepared according to the described general procedure 2 (GP2) by reaction of ethyl 4-amino-4-(2,6-dimethoxyphenyl)-2-methylbutanoate with commercially available 1H-indole-5-carbaldehyde. Subsequent purification by preparative HPLC afforded the target compound. LC-MS (conditions A): $t_R$=0.77 min.; [M+H]$^+$: 365.00 g/mol.

Example 393

5-(2,6-dimethoxyphenyl)-3-methyl-1-((2-methylbenzo[d]thiazol-5-yl)methyl)pyrrolidin-2-one Prepared according to the described general procedure 2 (GP2) by reaction of ethyl 4-amino-4-(2,6-dimethoxyphenyl)-2-methylbutanoate with 2-methylbenzo[d]thiazole-5-carbaldehyde. Subsequent purification by preparative HPLC afforded the target compound. LC-MS (conditions A): $t_R$=0.79 min.; [M+H]$^+$: 396.76 g/mol.

Example 394 rac-(3R*,5S*)-5-(2-fluoro-6-isopropoxyphenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 2-fluoro-6-isopropoxybenzaldehyde. Subsequent purification by preparative HPLC afforded the target compound. LC-MS (conditions A): $t_R$=0.87 min.; [M+H]$^+$: 427.92 g/mol.

Example 395 rac-(3R*,5S*)-1-(dibenzo[b,d]furan-2-ylmethyl)-3-fluoro-5-(2-fluoro-6-methoxyphenyl)pyrrolidin-2-one Prepared according to the described general procedures 10A2 (GP10A2), 10B (GP10B), and 10I (GP10I) using synthesized dibenzo[b,d]furan-2-ylmethanamine and commercially available 2-fluoro-6-methoxybenzaldehyde. Subsequent purification by preparative HPLC afforded the target compound. LC-MS (conditions A): $t_R$=0.93 min.; [M+H]$^+$: 407.88 g/mol.

Example 396 rac-(3R*,5S*)-3-chloro-1-(dibenzo[b,d]furan-2-ylmethyl)-5-(2-fluoro-6-methoxyphenyl)pyrrolidin-2-one Prepared according to the described general procedures 10A2 (GP10A2), 10B (GP10B), and 10D (GP10D) using synthesized dibenzo[b,d]furan-2-ylmethanamine and commercially available 2-fluoro-6-methoxybenzaldehyde. Subsequent purification by preparative HPLC afforded the target compound. LC-MS (conditions A): $t_R$=0.97 min.; [M+H]$^+$: 423.83 g/mol.

Example 397

5-(2,6-dimethoxyphenyl)-1-(4-isopropoxybenzyl)-3-methylpyrrolidin-2-one

Prepared according to the described general procedure 2 (GP2) by reaction of ethyl 4-amino-4-(2,6-dimethoxyphenyl)-2-methylbutanoate with commercially available 4-isopropoxybenzaldehyde. Subsequent purification by preparative HPLC afforded the target compound. LC-MS (conditions A): $t_R$=0.90 min.; [M+H]$^+$: 384.12 g/mol.

Example 398

5-(2,6-dimethoxyphenyl)-3-methyl-1-(4-((trifluoromethyl)thio)benzyl)pyrrolidin-2-one Prepared according to the described general procedure 2 (GP2) by reaction of ethyl 4-amino-4-(2,6-dimethoxyphenyl)-2-methylbutanoate with commercially available 4-((trifluoromethyl)thio)benzaldehyde. Subsequent purification by preparative HPLC afforded the target compound. LC-MS (conditions A): $t_R$=0.97 min.; [M+H]$^+$: 425.95 g/mol.

Example 399

5-(2,6-dimethoxyphenyl)-3-methyl-1-(4-(1,1,2,2-tetrafluoroethoxy)benzyl)pyrrolidin-2-one Prepared according to the described general procedure 2 (GP2) by reaction of ethyl 4-amino-4-(2,6-dimethoxyphenyl)-2-methylbutanoate with commercially available 4-(1,1,2,2-tetrafluoroethoxy)benzaldehyde. Subsequent purification by preparative HPLC afforded the target compound. LC-MS (conditions A): $t_R$=0.90 min.; [M+H]$^+$: 441.83 g/mol.

Example 400

5-(2,6-dimethoxyphenyl)-1-(3-fluoro-4-(trifluoromethoxy)benzyl)-3-methylpyrrolidin-2-one Prepared according to the described general procedure 2 (GP2) by reaction of ethyl 4-amino-4-(2,6-dimethoxyphenyl)-2-methylbutanoate with commercially available 3-fluoro-4-(trifluoromethoxy)benzaldehyde. Subsequent purification by preparative HPLC afforded the target compound. LC-MS (conditions A): $t_R$=0.94 min.; [M+H]$^+$: 427.98 g/mol.

Example 401

1-(3-chloro-4-(difluoromethoxy)benzyl)-5-(2,6-dimethoxyphenyl)-3-methylpyrrolidin-2-one Prepared according to the described general procedure 2 (GP2) by reaction of ethyl 4-amino-4-(2,6-dimethoxyphenyl)-2-methylbutanoate with commercially available 3-chloro-4-(difluoromethoxy)benzaldehyde. Subsequent purification by preparative HPLC afforded the target compound. LC-MS (conditions A): $t_R$=0.90 min.; [M+H]$^+$: 425.86 g/mol.

Example 402

1-(4-(difluoromethoxy)benzyl)-5-(2,6-dimethoxyphenyl)-3-methylpyrrolidin-2-one

Prepared according to the described general procedure 2 (GP2) by reaction of ethyl 4-amino-4-(2,6-dimethoxyphenyl)-2-methylbutanoate with commercially available 4-(difluoromethoxy)benzaldehyde. Subsequent purification by preparative HPLC afforded the target compound. LC-MS (conditions A): $t_R$=0.86 min.; [M+H]$^+$: 391.78 g/mol.

Example 403

5-(2,6-dimethoxyphenyl)-1-(2-methoxy-5-(trifluoromethoxy)benzyl)-3-methylpyrrolidin-2-one Prepared according to the described general procedure 2 (GP2) by reaction of ethyl 4-amino-4-(2,6-dimethoxyphenyl)-2-methylbutanoate with commercially available 2-methoxy-5-(trifluoromethoxy)benzaldehyde. Subsequent purification by preparative HPLC afforded the target compound. LC-MS (conditions A): $t_R$=0.92 min.; [M+H]$^+$: 440.07 g/mol.

Example 404

5-(2,6-dimethoxyphenyl)-1-(4-methoxy-3-(trifluoromethoxy)benzyl)-3-methylpyrrolidin-2-one Prepared according to the described general procedure 2 (GP2) by reaction of ethyl 4-amino-4-(2,6-dimethoxyphenyl)-2-methylbutanoate with commercially available 4-methoxy-3-(trifluoromethoxy)benzaldehyde. Subsequent purification by preparative HPLC afforded the target compound. LC-MS (conditions A): $t_R$=0.91 min.; [M+H]$^+$: 439.85 g/mol.

Example 405

5-(2,6-dimethoxyphenyl)-3-methyl-1-(2-(trifluoromethoxy)benzyl)pyrrolidin-2-one

Prepared according to the described general procedure 2 (GP2) by reaction of ethyl 4-amino-4-(2,6-dimethoxyphenyl)-2-methylbutanoate with commercially available 2-(trifluoromethoxy)benzaldehyde. Subsequent purification by preparative HPLC afforded the target compound. LC-MS (conditions A): $t_R$=0.91 min.; [M+H]$^+$: 410.01 g/mol.

Example 406 rac-(3S*,5S*)-1-(dibenzo[b,d]furan-2-ylmethyl)-3-fluoro-5-(2-fluoro-6-methoxyphenyl)pyrrolidin-2-one Prepared according to the described general procedures 10A2 (GP10A2), 10B (GP10B), 10F (GP10F), and 10I (GP10I) using synthesized dibenzo[b,d]furan-2-ylmethanamine and commercially available 2-fluoro-6-methoxybenzaldehyde. Subsequent purification by preparative HPLC afforded the target compound. LC-MS (conditions A): $t_R$=0.91 min.; [M+H]$^+$: 407.96 g/mol.

Example 407 rac-(3S*,5S*)-3-fluoro-5-(2-fluoro-6-isopropoxyphenyl)-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and synthesized 2-fluoro-6-isopropoxybenzaldehyde. Subsequent purification by preparative HPLC afforded the target compound. LC-MS (conditions A): $t_R$=0.96 min.; [M+H]$^+$: 429.91 g/mol.

Example 408 rac-(3S*,5S*)-3-chloro-1-(dibenzo[b,d]furan-2-ylmethyl)-5-(2-fluoro-6-methoxyphenyl)pyrrolidin-2-one Prepared according to the described general procedures 10A2 (GP10A2), 10B (GP10B), 10F (GP10F), and 10D (GP10D) using synthesized dibenzo[b,d]furan-2-ylmethanamine and commercially available 2-fluoro-6-methoxybenzaldehyde. Subsequent purification by preparative HPLC afforded the target compound. LC-MS (conditions A): $t_R$=0.95 min.; [M+H]$^+$: 423.92 g/mol.

Example 409 rac-(3S*,5S*)-3-chloro-5-(2-fluoro-6-isopropoxyphenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 2-fluoro-6-isopropoxybenzaldehyde. Subsequent purification by preparative HPLC afforded the target compound. LC-MS (conditions A): $t_R$=0.99 min.; [M+H]$^+$: 445.93 g/mol.

Example 410

1-(dibenzo[b,d]furan-2-ylmethyl)-3,3-difluoro-5-(2-fluoro-6-methoxyphenyl)pyrrolidin-2-one Prepared according to the described general procedures 10A2 (GP10A2), and 10G (GP10G) using synthesized dibenzo[b,d]furan-2-ylmethanamine and commercially available 2-fluoro-6-methoxybenzaldehyde. Subsequent purification by preparative HPLC afforded the target compound. LC-MS (conditions A): $t_R$=0.98 min.; [M+H]$^+$: 426.20 g/mol.

Example 411

3,3-difluoro-5-(2-fluoro-6-isopropoxyphenyl)-1-(4-(trifluoromethoxy)benzyl)pyrrolidin-2-one Prepared according to the described general procedures 10A2 (GP10A2), and 10G (GP10G) using commercially available (4-(trifluoromethoxy)phenyl)methanamine and synthesized 2-fluoro-6-isopropoxybenzaldehyde. Subsequent purification by preparative HPLC afforded the target compound. LC-MS (conditions A): $t_R$=1.01 min.; [M+H]$^+$: 448.20 g/mol.

Example 412 rac-(3R*,5S*)-1-(dibenzo[b,d]furan-2-ylmethyl)-5-(2-fluoro-6-methoxyphenyl)-3-hydroxypyrrolidin-2-one Prepared according to the described general procedures 10A2 (GP10A2), 10B (GP10B), and 10F (GP10F) using synthesized dibenzo[b,d]furan-2-ylmethanamine and commercially available 2-fluoro-6-methoxybenzaldehyde. Subsequent purification by preparative HPLC afforded the target compound. LC-MS (conditions A): $t_R$=0.82 min.; [M+H]$^+$: 405.95 g/mol.

Example 413

5-(2-fluoro-6-isopropoxyphenyl)-3-methyl-1-(4-(trifluoromethoxy)benzyl)pyrrolidin-2-one 5-(2-Fluoro-6-methoxyphenyl)-3-methyl-1-(4-(trifluoromethoxy)benzyl)pyrrolidin-2-one was prepared according to the described general procedure 2 (GP2) by reaction of ethyl 4-amino-4-(2-fluoro-6-methoxyphenyl)-2-methylbutanoate with commercially available 4-(trifluoromethoxy)benzaldehyde. Subsequent purification by FC (heptane/AcOEt=1/1) afforded the compound. LC-MS (conditions A): $t_R$=0.93 min.; [M+H]$^+$: 398.00 g/mol.

A cooled (−78° C.) solution of 5-(2-fluoro-6-methoxyphenyl)-3-methyl-1-(4-(trifluoromethoxy)benzyl)pyrrolidin-2-one (518 mg; 1.30 mmol) in anh. DCM (7 ml) was treated dropwise with a solution of boron tribromide BBr$_3$ (1.0 M in DCM; 6.52 ml; 6.52 mmol). The resulting mixture was further stirred at rt, under nitrogen, for 17 h. Water was added dropwise, and the separated aq. layer was extracted with DCM. The mixed organic layers were washed with brine, dried over anh. MgSO$_4$, filtered and concentrated to dryness under reduced pressure affording 5-(2-fluoro-6-hydroxyphenyl)-3-methyl-1-(4-(trifluoromethoxy)benzyl)pyrrolidin-2-one. LC-MS (conditions A): $t_R$=0.84 min.; [M+H]$^+$: 383.89 g/mol.

A mixture of 5-(2-fluoro-6-hydroxyphenyl)-3-methyl-1-(4-(trifluoromethoxy)benzyl)pyrrolidin-2-one (50 mg; 0.13 mmol), 2-iodopropane (66 mg; 0.39 mmol), potassium carbonate (36 mg; 0.26 mmol), and cesium carbonate (8.5 mg; 0.026 mmol) in anh. DMF (0.7 ml) was stirred at rt, under nitrogen, for 17 h. Subsequent filtration and purification by preparative HPLC afforded the target compound 5-(2-fluoro-6-isopropoxyphenyl)-3-methyl-1-(4-(trifluoromethoxy)benzyl)pyrrolidin-2-one. LC-MS (conditions A): $t_R$=1.00 min.; [M+H]$^+$: 426.01 g/mol.

Example 414

5-(2-fluoro-6-(2-fluoroethoxy)phenyl)-3-methyl-1-(4-(trifluoromethoxy)benzyl)pyrrolidin-2-one A mixture of 5-(2-fluoro-6-hydroxyphenyl)-3-methyl-1-(4-(trifluoromethoxy)benzyl)pyrrolidin-2-one (preparation described in example 413; 50 mg; 0.13 mmol), 1-fluoro-2-iodoethane (23 mg; 0.13 mmol), potassium carbonate (36 mg; 0.26 mmol), and cesium carbonate (8.5 mg; 0.026 mmol) in anh. DMF (0.7 ml) was stirred at rt, under nitrogen, for 17 h. Subsequent filtration and purification by preparative HPLC afforded the target compound. LC-MS (conditions A): $t_R$=0.92 min.; [M+H]$^+$: 429.96 g/mol.

Example 415

5-(2-fluoro-6-propoxyphenyl)-3-methyl-1-(4-(trifluoromethoxy)benzyl)pyrrolidin-2-one A mixture of 5-(2-fluoro-6-hydroxyphenyl)-3-methyl-1-(4-(trifluoromethoxy)benzyl)pyrrolidin-2-one (preparation described in example 413; 50 mg; 0.13 mmol), 1-iodopropane (22 mg; 0.13 mmol), potassium carbonate (36 mg; 0.26 mmol), and cesium carbonate (8.5 mg; 0.026 mmol) in anh. DMF (0.7 ml) was stirred at rt, under nitrogen, for 17 h. Subsequent filtration and purification by preparative HPLC afforded the target compound. LC-MS (conditions A): $t_R$=1.01 min.; [M+H]$^+$: 425.99 g/mol.

Example 416

5-(2-fluoro-6-(2-hydroxyethoxy)phenyl)-3-meetthyl-1-(4-(trifluoromethoxy)benzyl)pyrrolidin-2-one A mixture of 5-(2-fluoro-6-hydroxyphenyl)-3-methyl-1-(4-(trifluoromethoxy)benzyl)pyrrolidin-2-one (preparation described in example 413; 50 mg; 0.13 mmol), ((2-bromoethoxy)methyl)benzene (28 mg; 0.13 mmol), potassium carbonate (36 mg; 0.26 mmol), and cesium carbonate (8.5 mg; 0.026 mmol) in anh. DMF (0.7 ml) was stirred at rt, under nitrogen, for 17 h. Water was added, and the separated aq. layer was extracted with Et$_2$O. The mixed organic layers were washed with water, dried over anh. MgSO$_4$, filtered and concentrated to dryness under reduced pressure affording 5-(2-(2-(benzyloxy)ethoxy)-6-fluorophenyl)-3-methyl-1-(4-(trifluoromethoxy)benzyl)pyrrolidin-2-one. LC-MS (conditions A): $t_R$=1.04 min.; [M+H]$^+$: 518.47 g/mol. A mixture of 5-(2-(2-(benzyloxy)ethoxy)-6-fluorophenyl)-3-methyl-1-(4-(trifluoromethoxy)benzyl)pyrrolidin-2-one 55 mg; 0.10 mmol), and platinum (IV) oxide hydrate PtO$_2$ (24 mg; 0.10 mmol) in anh. MeOH (2 ml) was stirred at rt, under hydrogen atmosphere (1 atm), for 16 h. Filtration over a pad of celite, concentration to dryness under reduced pressure, and subsequent purification by preparative HPLC afforded the target compound. LC-MS (conditions A): $t_R$=0.84 min.; [M+H]$^+$: 427.92 g/mol.

Example 417

5-(2,6-dimethoxyphenyl)-3-methyl-1-(3-(2,2,2-trifluoroethoxy)benzyl)pyrrolidin-2-one Prepared according to the described general procedure 2 (GP2) by reaction of ethyl 4-amino-4-(2,6-dimethoxyphenyl)-2-methylbutanoate with 3-(2,2,2-trifluoroethoxy)benzaldehyde. Subsequent purification by preparative HPLC afforded the target compound. LC-MS (conditions A): $t_R$=0.90 min.; [M+H]$^+$: 424.43 g/mol.

Example 418

5-(2,6-dimethoxyphenyl)-3-methyl-1-(4-(2,2,2-trifluoroethoxy)benzyl)pyrrolidin-2-one Prepared according to the described general procedure 2 (GP2) by reaction of ethyl 4-amino-4-(2,6-dimethoxyphenyl)-2-methylbutanoate with 4-(2,2,2-trifluoroethoxy)benzaldehyde. Subsequent purification by preparative HPLC afforded the target compound. LC-MS (conditions A): $t_R$=0.89 min.; [M+H]$^+$: 424.45 g/mol.

Example 419

1-(3-(2,2-difluoroethoxy)benzyl)-5-(2,6-dimethoxyphenyl)-3-methylpyrrolidin-2-one Prepared according to the described general procedure 2 (GP2) by reaction of ethyl 4-amino-4-(2,6-dimethoxyphenyl)-2-methylbutanoate with 3-(2,2-difluoroethoxy)benzaldehyde. Subsequent purification by preparative HPLC afforded the target compound. LC-MS (conditions A): $t_R$=0.85 min.; [M+H]$^+$: 406.06 g/mol.

Example 420

1-(4-(2,2-difluoroethoxy)benzyl)-5-(2,6-dimethoxyphenyl)-3-methylpyrrolidin-2-one Prepared according to the described general procedure 2 (GP2) by reaction of ethyl 4-amino-4-(2,6-dimethoxyphenyl)-2-methylbutanoate with 4-(2,2-difluoroethoxy)benzaldehyde. Subsequent purification by preparative HPLC afforded the target compound. LC-MS (conditions A): $t_R$=0.84 min.; [M+H]$^+$: 406.02 g/mol.

Example 421

5-(2,6-dimethoxyphenyl)-1-(3-(2-fluoroethoxy)benzyl)-3-methylpyrrolidin-2-one

Prepared according to the described general procedure 2 (GP2) by reaction of ethyl 4-amino-4-(2,6-dimethoxyphenyl)-2-methylbutanoate with 3-(2-fluoroethoxy)benzaldehyde. Subsequent purification by preparative HPLC afforded the target compound. LC-MS (conditions A): $t_R$=0.82 min.; [M+H]$^+$: 388.02 g/mol.

Example 422

5-(2,6-dimethoxyphenyl)-1-(4-(2-fluoroethoxy)benzyl)-3-methylpyrrolidin-2-one

Prepared according to the described general procedure 2 (GP2) by reaction of ethyl 4-amino-4-(2,6-dimethoxyphenyl)-2-methylbutanoate with 4-(2-fluoroethoxy)benzaldehyde. Subsequent purification by preparative HPLC afforded the target compound. LC-MS (conditions A): $t_R$=0.81 min.; [M+H]$^+$: 388.05 g/mol.

Example 423

5-(2,6-dimethoxyphenyl)-1-(3-isopropoxybenzyl)-3-methylpyrrolidin-2-one

Prepared according to the described general procedure 2 (GP2) by reaction of ethyl 4-amino-4-(2,6-dimethoxyphenyl)-2-methylbutanoate with 3-isopropoxybenzaldehyde. Subsequent purification by preparative HPLC afforded the target compound. LC-MS (conditions A): $t_R$=0.91 min.; [M+H]$^+$: 384.08 g/mol.

Example 424

5-(2,6-dimethoxyphenyl)-3-methyl-1-(3-(1,1,2,2-tetrafluoroethoxy)benzyl)pyrrolidin-2-one Prepared according to the described general procedure 2 (GP2) by reaction of ethyl 4-amino-4-(2,6-dimethoxyphenyl)-2-methylbutanoate with commercially available 3-(1,1,2,2-tetrafluoroethoxy)benzaldehyde. Subsequent purification by preparative HPLC afforded the target compound. LC-MS (conditions A): $t_R$=0.90 min.; [M+H]$^+$: 441.98 g/mol.

Example 425

1-(4-(difluoromethoxy)-3-methoxybenzyl)-5-(2,6-dimethoxyphenyl)-3-methylpyrrolidin-2-one Prepared according to the described general procedure 2 (GP2) by reaction of ethyl 4-amino-4-(2,6-dimethoxyphenyl)-2-methylbutanoate with commercially available 4-(difluoromethoxy)-3-methoxybenzaldehyde. Subsequent purification by preparative HPLC afforded the target compound. LC-MS (conditions A): $t_R$=0.85 min.; [M+H]$^+$: 422.01 g/mol.

Example 426

1-(dibenzo[b,d]thiophen-2-ylmethyl)-5-(2,6-dimethoxyphenyl)-3-methylpyrrolidin-2-one Prepared according to the described general procedure 2 (GP2) by reaction of ethyl 4-amino-4-(2,6-dimethoxyphenyl)-2-methylbutanoate with synthesized dibenzo[b,d]thiophene-2-carbaldehyde. Subsequent purification by preparative HPLC afforded the target compound. LC-MS (conditions A): $t_R$=0.99 min.; [M+H]$^+$: 431.87 g/mol.

Example 427 rac-(3R*,5S*)-5-(2-chloro-6-ethoxyphenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 2-chloro-6-ethoxybenzaldehyde. Subsequent purification by preparative HPLC afforded the target compound. LC-MS (conditions A): $t_R$=0.87 min.; [M+H]$^+$: 429.91 g/mol.

Example 428 rac-(3R*,5S*)-5-(2-ethoxy-6-fluorophenyl)-1-(3-fluoro-4-(trifluoromethoxy)benzyl)-3-hydroxypyrrolidin-2-one Prepared according to the described general procedures 10A2 (GP10A2), 10B (GP10B), and 10F (GP10F) using commercially available (3-fluoro-4-(trifluoromethoxy)phenyl)methanamine and synthesized 2-ethoxy-6-fluorobenzaldehyde. Subsequent purification by preparative HPLC afforded the target compound. LC-MS (conditions A): $t_R$=0.84 min.; [M+H]$^+$: 431.77 g/mol.

Example 429 rac-(3R*,5S*)-(3-chloro-4-(trifluoromethoxy)benzyl)-5-(2-ethoxy-6-fluorophenyl)-3-hydroxypyrrolidin-2-one Prepared according to the described general procedures 10A2 (GP10A2), 10B (GP10B), and 10F (GP10F) using commercially available (3-chloro-4-(trifluoromethoxy)phenyl)methanamine and synthesized 2-ethoxy-6-fluorobenzaldehyde. Subsequent purification by preparative HPLC afforded the target compound. LC-MS (conditions A): $t_R$=0.87 min.; [M+H]$^+$: 447.94 g/mol.

Example 430 rac-(3R*,5S*)-5-(2-fluoro-6-methoxyphenyl)-3-hydroxy-1-(3-(trifluoromethoxy)benzyl)pyrrolidin-2-one Prepared according to the described general procedures 10A2 (GP10A2), 10B (GP10B), and 10F (GP10F) using commercially available (3-(trifluoromethoxy)phenyl)methanamine and 2-fluoro-6-methoxybenzaldehyde. Subsequent purification by preparative HPLC afforded the target compound. LC-MS (conditions A): $t_R$=0.79 min.; [M+H]$^+$: 399.98 g/mol.

Example 431 rac-(3R*,5S*)-5-(2-ethoxy-4,6-difluorophenyl)-3-hydroxy-1-(4-(trifluoromethoxy)benzyl)pyrrolidin-2-one Prepared according to the described general procedures 10A2 (GP10A2), 10B (GP10B), and 10F (GP10F) using commercially available (4-(trifluoromethoxy)phenyl)methanamine and synthesized 2-ethoxy-4,6-difluorobenzaldehyde. Subsequent purification by preparative HPLC afforded the target compound. LC-MS (conditions A): $t_R$=0.84 min.; [M+H]$^+$: 431.95 g/mol.

Example 432 rac-(3R*,5S*)-5-(2-fluoro-6-(2-fluoroethoxy)phenyl)-3-hydroxy-1-(4-(trifluoromethoxy)benzyl)pyrrolidin-2-one A cooled (–78° C.) solution of rac-(3R*,5S*)-5-(2-fluoro-6-methoxyphenyl)-3-hydroxy-1-(4-(trifluoromethoxy)benzyl)pyrrolidin-2-one (compound corresponding to example 293; 355 mg; 0.88 mmol) in anh. DCM (8 ml) was treated dropwise with a solution of boron tribromide BBr$_3$ (1.0 M in DCM; 4.45 ml; 4.45 mmol). The resulting mixture was further stirred at rt, under nitrogen, for 17 h. Water was added dropwise to the cooled (0° C.) reaction mixture, and the separated aq. layer was extracted with DCM. The mixed organic layers were washed with brine, dried over anh. MgSO$_4$, filtered and concentrated to dryness under reduced pressure affording rac-(3R*,5S*)-5-(2-fluoro-6-hydroxyphenyl)-3-hydroxy-1-(4-(trifluoromethoxy)benzyl)pyrrolidin-2-one. LC-MS (conditions A): $t_R$=0.83 min.; [M+H]$^+$: 386.05 g/mol.

A mixture of rac-(3R*,5S*)-5-(2-fluoro-6-hydroxyphenyl)-3-hydroxy-1-(4-(trifluoromethoxy)benzyl)pyrrolidin-2-one (50 mg; 0.13 mmol), 1-fluoro-2-iodoethane (23 mg; 0.13 mmol), potassium carbonate (36 mg; 0.26 mmol), and cesium carbonate (8.5 mg; 0.026 mmol) in anh. DMF (1.3 ml) was stirred at rt, under nitrogen, for 72 h. Filtration of the reaction mixture, and subsequent purification by preparative HPLC afforded the target compound. LC-MS (conditions A): $t_R$=0.79 min.; [M+H]$^+$: 431.96 g/mol.

Example 433 rac-(3R*,5S*)-5-(2-ethoxy-6-fluorophenyl)-3-hydroxy-1-(2-(trifluoromethoxy)benzyl)pyrrolidin-2-one Prepared according to the described general procedures 10A2 (GP10A2), 10B (GP10B), and 10F (GP10F) using commercially available (2-(trifluoromethoxy)phenyl)methanamine and synthesized 2-ethoxy-6-fluorobenzaldehyde. Subsequent purification by preparative HPLC afforded the target compound. LC-MS (conditions A): $t_R$=0.82 min.; [M+H]$^+$: 413.98 g/mol.

Example 434 rac-(3S*,5S*)-5-(2-ethoxy-6-fluorophenyl)-3-fluoro-1-(3-fluoro-4-(trifluoromethoxy)benzyl)pyrrolidin-2-one Prepared according to the described general procedures 10A2 (GP10A2), 10B (GP10B), 10F (GP10F), and 10I (GP10I) using commercially available (3-fluoro-4-(trifluoromethoxy)phenyl)methanamine and synthesized 2-ethoxy-6-fluorobenzaldehyde. Subsequent purification by preparative HPLC afforded the target compound. LC-MS (conditions A): $t_R$=0.93 min.; [M+H]$^+$: 433.92 g/mol.

Example 435 rac-(3S*,5S*)-3-chloro-5-(2-ethoxy-6-fluorophenyl)-1-(3-fluoro-4-(trifluoromethoxy)benzyl)pyrrolidin-2-one Prepared according to the described general procedures 10A2 (GP10A2), 10B (GP10B), 10F (GP10F), and 10D (GP10D) using commercially available (3-fluoro-4-(trifluoromethoxy)phenyl)methanamine and synthesized 2-ethoxy-6-fluorobenzaldehyde. Subsequent purification by preparative HPLC afforded the target compound. LC-MS (conditions A): $t_R$=0.97 min.; [M+H]$^+$: 449.85 g/mol.

Example 436 rac-(3S*,5S*)-5-(2-chloro-6-ethoxyphenyl)-3-fuoro-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and synthesized 2-chloro-6-ethoxybenzaldehyde. Subsequent purification by preparative HPLC afforded the target compound. LC-MS (conditions A): $t_R$=0.97 min.; [M+H]$^+$: 431.89 g/mol.

Example 437 rac-(3S*,5S*)-3-chloro-5-(2-chloro-6-ethoxyphenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 2-chloro-6-ethoxybenzaldehyde. Subsequent purification by preparative HPLC afforded the target compound. LC-MS (conditions A): $t_R$=1.00 min.; [M+H]$^+$: 447.88 g/mol.

Example 438 rac-(3S*,5S*)-5-(2-ethoxy-4,6-difluorophenyl)-3-fluoro-1-(4-(trifluoromethoxy)benzyl)pyrrolidin-2-one Prepared according to the described general procedures 10A2 (GP10A2), 10B (GP10B), 10F (GP10F), and 10I (GP10I) using commercially available (4-(trifluoromethoxy)phenyl)methanamine and synthesized 2-ethoxy-4,6-difluorobenzaldehyde. Subsequent purification by preparative HPLC afforded the target compound. LC-MS (conditions A): $t_R$=0.93 min.; [M+H]$^+$: 433.89 g/mol.

Example 439 rac-(3S*,5S*)-3-chloro-5-(2-ethoxy-4,6-difluorophenyl)-1-(4-(trifluoromethoxy)benzyl)pyrrolidin-2-one Prepared according to the described general procedures 10A2 (GP10A2), 10B (GP10B), 10F (GP10F), and 10D (GP10D) using commercially available (4-(trifluoromethoxy)phenyl)methanamine and synthesized 2-ethoxy-4,6-difluorobenzaldehyde. Subsequent purification by preparative HPLC afforded the target compound. LC-MS (conditions A): $t_R$=0.97 min.; [M+H]$^+$: 449.84 g/mol.

Example 440

1-([1,1'-biphenyl]-3-ylmethyl)-6-(6-methoxy-2-methylbenzo[d]oxazol-7-yl)piperidin-2-one Prepared according to the procedure described for example 279 starting with 1-([1,1'-biphenyl]-3-ylmethyl)-6-(2,6-dimethoxyphenyl)piperidin-2-one (compound from example 189). Subsequent purification by preparative HPLC afforded the target compound. LC-MS (conditions A): $t_R$=0.84 min.; [M+H]$^+$: 426.99 g/mol.

Example 441

6-(6-methoxy-2-methylbenzo[d]oxazol-7-yl)-1-(3-(2-methylthiazol-4-yl)benzyl)piperidin-2-one Prepared according to the procedure described for example 279 starting with 6-(2,6-dimethoxyphenyl)-1-(3-(2-methylthiazol-4-yl)benzyl)piperidin-2-one (compound from example 16). Subsequent purification by preparative HPLC afforded the target compound. LC-MS (conditions A): $t_R$=0.73 min.; [M+H]$^+$: 447.97 g/mol.

Example 442

6-(2-ethyl-6-methoxybenzo[d]oxazol-7-yl)-1-(3-(2-methylthiazol-4-yl)benzyl)piperidin-2-one Prepared according to the procedure described for example 279 starting with 6-(2,6-dimethoxyphenyl)-1-(3-(2-methylthiazol-4-yl)benzyl)piperidin-2-one (compound from example 16) and using commercially available 1,1,1-triethoxypropane for the last step. Subsequent purification by preparative HPLC afforded the target compound. LC-MS (conditions A): $t_R$=0.78 min.; [M+H]$^+$: 462.04 g/mol.

Example 443

6-(6-methoxy-2,3-dihydrobenzo[b][1,4]dioxin-5-yl)-1-(3-(2-methylthiazol-4-yl)benzyl)piperidin-2-one Prepared according to general procedure 5 (GP5) using 6-methoxy-2,3-dihydrobenzo[b][1,4]dioxine-5-carbaldehyde and commercially available 3-(2-methylthiazol-4-yl)benzaldehyde. Subsequent purification by preparative HPLC afforded the target compound. LC-MS (conditions A): $t_R$=0.82 min.; [M+H]$^+$: 450.93 g/mol.

Example 444

6-(6-methoxy-2,3-dihydrobenzo[b][1,4]dioxin-5-yl)-1-(3-(5-methylthiazol-2-yl)benzyl)piperidin-2-one Prepared according to general procedure 5 (GP5) using 6-methoxy-2,3-dihydrobenzo[b][1,4]dioxine-5-carbaldehyde and 3-(5-methylthiazol-2-yl)benzaldehyde. Subsequent purification by preparative HPLC afforded the target compound. LC-MS (conditions A): $t_R$=0.83 min.; [M+H]$^+$: 451.18 g/mol.

Example 445

6-(2-methoxynaphthalen-1-yl)-1-(3-(pyrimidin-2-yl)benzyl)piperidin-2-one

Prepared according to general procedure 1 (GP1) using methyl 5-amino-5-(2-methoxynaphthalen-1-yl)pentanoate and commercially available 3-(pyrimidin-2-yl)benzaldehyde. Subsequent purification by preparative HPLC afforded the target compound. LC-MS (conditions A): $t_R$=0.84 min.; [M+H]$^+$: 424.10 g/mol.

Example 446

6-(2-methoxynaphthalen-1-yl)-1-(3-(5-methylthiazol-2-yl)benzyl)piperidin-2-one

Prepared according to general procedure 1 (GP1) using methyl 5-amino-5-(2-methoxynaphthalen-1-yl)pentanoate and 3-(5-methylthiazol-2-yl)benzaldehyde. Subsequent purification by preparative HPLC afforded the target compound. LC-MS (conditions A): $t_R$=0.92 min.; [M+H]$^+$: 443.13 g/mol.

Example 447

6-(2-methoxynaphthalen-1-yl)-1-(3-phenoxybenzyl)piperidin-2-one

Prepared according to general procedure 1 (GP1) using methyl 5-amino-5-(2-methoxynaphthalen-1-yl)pentanoate and commercially available 3-phenoxybenzaldehyde. Subsequent purification by preparative HPLC afforded the target compound. LC-MS (conditions A): $t_R$=0.99 min.; [M+H]$^+$: 438.14 g/mol.

Example 448

6-(5-methoxybenzo[d][1,3]dioxol-4-yl)-1-(3-(2-methylthiazol-4-yl)benzyl)piperidin-2-one Prepared according to general procedure 5 (GP5) using 5-methoxybenzo[d][1,3]dioxole-4-carbaldehyde and commercially available 3-(2-methylthiazol-4-yl)benzaldehyde. Subsequent purification by preparative HPLC afforded the target compound. LC-MS (conditions A): $t_R$=0.82 min.; [M+H]$^+$: 436.84 g/mol.

Example 449

6-(5-methoxybenzo[d][1,3]dioxol-4-yl)-1-(4-(trifluoromethoxy)benzyl)piperidin-2-one Prepared according to general procedure 5 (GP5) using 5-methoxybenzo[d][1,3]dioxole-4-carbaldehyde and commercially available 4-(trifluoromethoxy)benzaldehyde. Subsequent purification by preparative HPLC afforded the target compound. LC-MS (conditions A): $t_R$=0.90 min.; [M+H]$^+$: 423.97 g/mol.

Example 450

7-(2-(pyridin-4-yl)phenyl)-1-(3-(thiazol-2-yl)benzyl)azepan-2-one

The azepan-2-one derivative 7-(2-bromophenyl)-1-(3-(thiazol-2-yl)benzyl)azepan-2-one [LC-MS (conditions A): $t_R$=0.90 min.; [M+H]$^+$: 441.05 g/mol] was prepared according to a modified general procedure 5 (GP5) starting with commercially available 2-bromobenzaldehyde and using commercially available 3-(thiazol-2-yl)benzaldehyde for step 4. For the addition of the Grignard reagent on the activated imine (step 2), a commercially available solution of but-3-en-1-ylmagnesium bromide (0.5 M in THF; 1.2 equivalents) was used, and the reaction was performed at 60° C. The hydrogenation of the olefin (step 7) was carried out in EtOH with the catalyst platinum(IV) oxide $PtO_2$ (0.32 equivalent).

A mixture of 7-(2-bromophenyl)-1-(3-(thiazol-2-yl)benzyl)azepan-2-one (50 mg; 0.11 mmol), commercially available pyridin-4-ylboronic acid (14 mg; 0.11 mmol), and $Pd(PPh_3)_4$ (7 mg; 0.006 mmol) in THF (2 ml), and aq. 2 M $Na_2CO_3$ (0.2 ml) was heated to 80° C., under nitrogen, for 24 h. After cooling to rt, water and AcOEt were added. The separated aq. layer was further extracted with AcOEt. The mixed organic layers were washed with brine, dried over anh. $MgSO_4$, filtered, and concentrated to dryness under reduced pressure. Subsequent purification by preparative HPLC afforded 7-(2-(pyridin-4-yl)phenyl)-1-(3-(thiazol-2-yl)benzyl)azepan-2-one. LC-MS (conditions A): $t_R$=0.62 min.; $[M+H]^+$: 440.15 g/mol.

Example 451

1-(3-(thiazol-2-yl)benzyl)-7-(2-(thiazol-5-yl)phenyl)azepan-2-one

A mixture of 7-(2-bromophenyl)-1-(3-(thiazol-2-yl)benzyl)azepan-2-one (preparation described in example 450; 50 mg; 0.11 mmol), commercially available 5-(tributylstannyl)thiazole (51 mg; 0.13 mmol), and $PdCl_2(PPh_3)_2$ (8 mg; 0.011 mmol) in THF (1 ml) was heated to 75° C., under nitrogen, for 17 h. After cooling to rt, water and AcOEt were added. The separated aq. layer was further extracted with AcOEt. The mixed organic layers were washed with brine, dried over anh. $MgSO_4$, filtered, and concentrated to dryness under reduced pressure. Subsequent purification by preparative HPLC afforded the target compound. LC-MS (conditions A): $t_R$=0.80 min.; $[M+H]^+$: 446.11 g/mol.

Example 452

1-(3-(thiazol-2-yl)benzyl)-7-(2-(thiazol-4-yl)phenyl)azepan-2-one

A mixture of 7-(2-bromophenyl)-1-(3-(thiazol-2-yl)benzyl)azepan-2-one (preparation described in example 450; 50 mg; 0.11 mmol), commercially available 4-(tributylstannyl)thiazole (51 mg; 0.13 mmol), and $PdCl_2(PPh_3)_2$ (8 mg; 0.011 mmol) in THF (1 ml) was heated to 75° C., under nitrogen, for 18 h. After cooling to rt, water and AcOEt were added. The separated aq. layer was further extracted with AcOEt. The mixed organic layers were washed with brine, dried over anh. $MgSO_4$, filtered, and concentrated to dryness under reduced pressure. Subsequent purification by preparative HPLC afforded the target compound. LC-MS (conditions A): $t_R$=0.84 min.; $[M+H]^+$: 446.14 g/mol.

Example 453

7-(2-(pyridin-3-yl)phenyl)-1-(3-(thiazol-2-yl)benzyl)azepan-2-one

A mixture of 7-(2-bromophenyl)-1-(3-(thiazol-2-yl)benzyl)azepan-2-one (preparation described in example 450; 50 mg; 0.11 mmol), commercially available pyridin-3-ylboronic acid (14 mg; 0.11 mmol), and $Pd(PPh_3)_4$ (7 mg; 0.006 mmol) in THF (2 ml), and aq. 2 M $Na_2CO_3$ (0.2 ml) was heated to 80° C., under nitrogen, for 24 h. After cooling to rt, water and AcOEt were added. The separated aq. layer was further extracted with AcOEt. The mixed organic layers were washed with brine, dried over anh. $MgSO_4$, filtered, and concentrated to dryness under reduced pressure. Subsequent purification by preparative HPLC afforded the target compound. LC-MS (conditions A): $t_R$=0.63 min.; $[M+H]^+$: 440.15 g/mol.

Example 454

7-([1,1'-biphenyl]-2-yl)-1-(3-(thiazol-2-yl)benzyl)azepan-2-one

A mixture of 7-(2-bromophenyl)-1-(3-(thiazol-2-yl)benzyl)azepan-2-one (preparation described in example 450; 50 mg; 0.11 mmol), commercially available phenylboronic acid (15 mg; 0.12 mmol), and $Pd(PPh_3)_4$ (7 mg; 0.006 mmol) in THF (2 ml), and aq. 2 M $Na_2CO_3$ (0.2 ml) was heated to 80° C., under nitrogen, for 24 h. After cooling to rt, water and AcOEt were added. The separated aq. layer was further extracted with AcOEt. The mixed organic layers were washed with brine, dried over anh. $MgSO_4$, filtered, and concentrated to dryness under reduced pressure. Subsequent purification by preparative HPLC afforded the target compound. LC-MS (conditions A): $t_R$=0.98 min.; $[M+H]^+$: 439.16 g/mol.

Example 455

6-(6-methoxybenzo[d]oxazol-7-yl)-1-(3-(2-methylthiazol-4-yl)benzyl)piperidin-2-one Prepared according to the procedure described for example 279 starting with 6-(2,6-dimethoxyphenyl)-1-(3-(2-methylthiazol-4-yl)benzyl)piperidin-2-one (compound from example 16) and using commercially available triethoxymethane for the last step. Subsequent purification by preparative HPLC afforded the target compound. LC-MS (conditions A): $t_R$=0.73 min.; $[M+H]^+$: 433.71 g/mol.

Example 456

1-([1,1'-biphenyl]-3-ylmethyl)-6-(1-phenyl-1H-pyrazol-5-yl)piperidin-2-one

Prepared according to general procedure 5 (GP5) using commercially available 1-phenyl-1H-pyrazole-5-carbaldehyde and commercially available [1,1'-biphenyl]-3-carbaldehyde. Subsequent purification by preparative HPLC afforded the target compound. LC-MS (conditions A): $t_R$=0.84 min.; $[M+H]^+$: 408.17 g/mol.

Example 457

1-([1,1'-biphenyl]-3-ylmethyl)-6-(5-methoxybenzo[d][1,3]dioxol-4-yl)piperidin-2-one Prepared according to general procedure 5 (GP5) using 5-methoxybenzo[d][1,3]dioxole-4-carbaldehyde and commercially available [1,1'-biphenyl]-3-carbaldehyde. Subsequent purification by preparative HPLC afforded the target compound. LC-MS (conditions A): $t_R$=0.92 min.; $[M+H]^+$: 415.90 g/mol.

Example 458

6-(5-methoxybenzo[d][1,3]dioxol-4-yl)-1-(3-phenoxybenzyl)piperidin-2-one

Prepared according to general procedure 5 (GP5) using 5-methoxybenzo[d][1,3]dioxole-4-carbaldehyde and commercially available 3-phenoxybenzaldehyde. Subsequent purification by preparative HPLC afforded the target compound. LC-MS (conditions A): $t_R$=0.92 min.; $[M+H]^+$: 431.97 g/mol.

Example 459

6-(5-methoxybenzo[d][1,3]dioxol-4-yl)-1-((2-phenylthiazol-4-yl)methyl)piperidin-2-one Prepared according to general procedure 5 (GP5) using 5-methoxybenzo[d][1,3]dioxole-4-carbaldehyde and commercially available 2-phenylthiazole-4-carbaldehyde. Subsequent purification by preparative HPLC afforded the target compound. LC-MS (conditions A): $t_R$=0.85 min.; $[M+H]^+$: 422.80 g/mol.

Example 460 rac-(3S*,5S*)-3-chloro-5-(2-fluoro-6-methoxyphenyl)-1-(3-(trifluoromethoxy)benzyl)pyrrolidin-2-one Prepared according to the described general procedures 10A2 (GP10A2), 10B (GP10B), 10F (GP10F), and 10D (GP10D) using commercially available (3-(trifluoromethoxy)phenyl)methanamine and 2-fluoro-6-methoxybenzaldehyde. Subsequent purification by preparative HPLC afforded the target compound. LC-MS (conditions A): $t_R$=0.92 min.; $[M+H]^+$: 417.87 g/mol.

Example 461 rac-(3S*,5S*)-1-(3-chloro-4-(trifluoromethoxy)benzyl)-5-(2-ethoxy-6-fluorophenyl)-3-fluoropyrrolidin-2-one Prepared according to the described general procedures 10A2 (GP10A2), 10B (GP10B), 10F (GP10F), and 10I (GP10I) using commercially available (3-chloro-4-(trifluoromethoxy)phenyl)methanamine and synthesized 2-ethoxy-6-fluorobenzaldehyde. Subsequent purification by preparative HPLC afforded the target compound. LC-MS (conditions A): $t_R$=0.96 min.; $[M+H]^+$: 449.84 g/mol.

Example 462 rac-(3S*,5S*)-3-chloro-1-(3-chloro-4-(trifluoromethoxy)benzyl)-5-(2-ethoxy-6-fluorophenyl)pyrrolidin-2-one Prepared according to the described general procedures 10A2 (GP10A2), 10B (GP10B), 10F (GP10F), and 10D (GP10D) using commercially available (3-chloro-4-(trifluoromethoxy)phenyl)methanamine and synthesized 2-ethoxy-6-fluorobenzaldehyde. Subsequent purification by preparative HPLC afforded the target compound. LC-MS (conditions A): $t_R$=1.00 min.; $[M+H]^+$: 465.77 g/mol.

Example 463 rac-(3S*,5S*)-3-fluoro-5-(2-fluoro-6-methoxyphenyl)-1-(3-(trifluoromethoxy)benzyl)pyrrolidin-2-one Prepared according to the described general procedures 10A2 (GP10A2), 10B (GP10B), 10F (GP10F), and 10I (GP10I) using commercially available (3-(trifluoromethoxy)phenyl)methanamine and 2-fluoro-6-methoxybenzaldehyde. Subsequent purification by preparative HPLC afforded the target compound. LC-MS (conditions A): $t_R$=0.88 min.; $[M+H]^+$: 401.89 g/mol.

II. Biological Assays

Antagonistic activities on both orexin receptors have been measured for each example compound using the following procedure:

In Vitro Assay: Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 g/ml G418, 100 U/ml penicillin, 100 g/ml streptomycin and 10% heat inactivated fetal calf serum (FCS). The cells are seeded at 20,000 cells/well into 384-well black clear bottom sterile plates (Greiner). The seeded plates are incubated overnight at 37° C. in 5% $CO_2$.

Human orexin-A as an agonist is prepared as 1 mM stock solution in MeOH:water (1:1), diluted in HBSS containing 0.1% bovine serum albumin (BSA), $NaHCO_3$: 0.375 g/l and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), $NaHCO_3$: 0.375 g/l and 20 mM HEPES. On the day of the assay, 50 µl of staining buffer (HBSS containing 1% FCS, 20 mM HEPES, $NaHCO_3$: 0.375 g/l, 5 mM probenecid (Sigma) and 3 M of the fluorescent calcium indicator fluo-4 AM (1 mM stock solution in DMSO, containing 10% pluronic) is added to each well. The 384-well cell-plates are incubated for 50 min at 37° C. in 5% $CO_2$ followed by equilibration at RT for 30 min before measurement.

Within the Fluorescent Imaging Plate Reader (FLIPR Tetra, Molecular Devices), antagonists are added to the plate in a volume of 10 µl/well, incubated for 120 min or (where explicitly indicated) for 10 min and finally 10 µl/well of agonist is added. Fluorescence is measured for each well at 1 second intervals, and the height of each fluorescence peak is compared to the height of the fluorescence peak induced by 3 nM orexin-A with vehicle in place of antagonist. The $IC_{50}$ value (the concentration of compound needed to inhibit 50% of the agonistic response) is determined and may be normalized using the obtained $IC_{50}$ value of a on-plate reference compound. Optimized conditions were achieved by adjustment of pipetting speed and cell splitting regime. The calculated $IC_{50}$ values may fluctuate depending on the daily cellular assay performance. Fluctuations of this kind are known to those skilled in the art.

Antagonistic activities of example compounds are displayed in Table 1.

TABLE 1

Antagonistic activities of Example compounds with respect to $OX_1$ and $OX_2$ receptors.

| Example | $IC_{50}$ OX1 [nM] | $IC_{50}$ OX2 [nM] | Example | $IC_{50}$ OX1 [nM] | $IC_{50}$ OX2 [nM] | Example | $IC_{50}$ OX1 [nM] | $IC_{50}$ OX2 [nM] |
|---|---|---|---|---|---|---|---|---|
| 1 | 643*3# | 209*3# | 95 | 8 | 29 | 191 | 373# | 50# |
| 2 | 26 | 13 | 96 | 16*2 | 85*2 | 192 | 361# | 29# |
| 3 | 154 | 1002 | 97 | 5*2 | 20*2 | 193 | 257*3# | 66*3# |

TABLE 1-continued

Antagonistic activities of Example compounds with respect to $OX_1$ and $OX_2$ receptors.

| Example | IC$_{50}$ OX1 [nM] | IC$_{50}$ OX2 [nM] | Example | IC$_{50}$ OX1 [nM] | IC$_{50}$ OX2 [nM] | Example | IC$_{50}$ OX1 [nM] | IC$_{50}$ OX2 [nM] |
|---|---|---|---|---|---|---|---|---|
| 4a | 16 | 41 | 98 | 6*2 | 6*2 | 194 | >12700# | 669# |
| 4b | 1418 | 329 | 99 | 7 | 34 | 195 | 821# | 240# |
| 4 | 174 | 58 | 100 | 1 | 3 | 196 | 724# | 158# |
| 5 | 224*2 | 38*2 | 101 | 3 | 33 | 197 | >10360# | 1305# |
| 6 | 119 | 142 | 102 | 6 | 19 | 198 | 117# | 96# |
| 7 | 71 | 55 | 103 | 8 | 86 | 199 | 351# | 621# |
| 8 | 1700 | 700 | 104 | 38 | 429 | 200 | 108*3# | 108*3# |
| 9 | 29 | 64 | 105 | 155 | 258 | 201 | 955*3# | 192*3# |
| 10 | 9 | 8 | 106 | 14 | 60 | 202 | 224# | 923# |
| 11 | 34 | 43 | 107 | 4 | 22 | 203 | 451# | 1170# |
| 12 | 25 | 34 | 108 | 1930# | 271# | 204 | 6380# | 1260# |
| 13 | 22 | 46 | 109 | 227# | 44# | 205 | 202# | 65# |
| 14 | 4 | 4 | 110 | 409# | 136# | 206 | 383# | 16# |
| 15 | 210 | 23 | 111 | 168# | 113# | 207 | 169# | 35# |
| 16 | 3 | 2 | 112 | 646# | 107# | 208 | 1113# | 39# |
| 17 | 210 | 661 | 113 | 29 | 34 | 209 | 1062# | 286# |
| 18 | 117 | 38 | 114 | 149 | 184 | 210 | 2552# | 4137# |
| 19 | 25 | 26 | 115 | 217 | 249 | 211 | 2783# | 664# |
| 20 | 952 | 864 | 116 | 789 | 291 | 212 | 216# | 37# |
| 21 | 951 | 366 | 117 | 211 | 65 | 213 | 1379# | 85# |
| 22 | 166 | 131 | 118 | 233 | 58 | 214 | 3537# | 735# |
| 23 | 312 | 471 | 119 | 57 | 56 | 215 | 1407# | 1291# |
| 24 | 22 | 31 | 120 | 64 | 121 | 216 | 40# | 894# |
| 25 | 688 | 902 | 121 | 183 | 105 | 217 | 22# | 252# |
| 26 | 167 | 115 | 122 | 18 | 70 | 218 | 107# | 133# |
| 27 | 136 | 181 | 123 | 13 | 74 | 219 | 19 | 9 |
| 28 | 21 | 11 | 124 | 23 | 89 | 220 | 1342*5# | 156*2# |
| 29 | 14 | 28 | 125 | 11 | 82 | 221 | 4883# | 154# |
| 30 | 2 | 4 | 126 | 165 | 839 | 222 | 4385# | 268# |
| 31 | 941 | 858 | 127 | 14 | 20 | 223 | >21570# | 2950# |
| 32 | 50 | 132 | 128 | 3880 | 2050 | 224 | 3192*5# | 2466*2# |
| 33 | 39 | 50 | 129 | 198 | 858 | 225 | 4208*4# | 5479*2# |
| 34 | 1050 | 2060 | 130 | 636 | 690 | 226 | 5184# | 2437# |
| 35 | 28*3 | 5*3 | 131 | 27 | 455 | 227 | 3501*5# | 5896*2# |
| 36 | 1570 | 1150 | 132 | 4 | 44 | 228 | 2970*4# | 456*2# |
| 37 | 72 | 64 | 133 | 2 | 24 | 229 | 2917*6# | 1193*3# |
| 38 | 153 | 87 | 134 | 37*3 | 157*3 | 230 | 363# | 85# |
| 39 | 179 | 147 | 135 | 23 | 264 | 231 | 550# | 395# |
| 40 | 75 | 696 | 136 | 219 | 547 | 232 | 270# | 27# |
| 41 | 18 | 26 | 137 | 2 | 5 | 233 | 400*4# | 107*2# |
| 42 | 25*4 | 17*4 | 138 | 32 | 29 | 234 | 262 | 232 |
| 43 | 6*2 | 6*2 | 139 | 35 | 172 | 235 | 288 | 194 |
| 44 | 14*2 | 19*2 | 140 | 10 | 73 | 236 | 1769# | 369# |
| 45 | 12*2 | 17*2 | 141 | 35 | 28 | 237 | 3486# | 635# |
| 46 | 440*2 | 239*2 | 142 | 11 | 40 | 238 | 77# | 47# |
| 47 | 187 | 165 | 143 | 27 | 46 | 239 | 6415# | 3585# |
| 48 | 169 | 625 | 144 | 223 | 318 | 240 | 2045# | 596# |
| 49 | 28 | 11 | 145 | 28*2 | 54*2 | 241 | 426# | 275# |
| 50 | 39 | 119 | 146 | 39 | 230 | 242 | 17670# | 1390# |
| 51 | 154 | 213 | 147 | 20 | 114 | 243 | 10090# | 311# |
| 52 | 14 | 80 | 148 | 3 | 21 | 244 | 1086# | 72# |
| 53 | 33 | 22 | 149 | 6 | 77 | 245 | 1067# | 132# |
| 54 | 15 | 13 | 150 | 7 | 47 | 246 | 665# | 11# |
| 55 | 96 | 95 | 151 | 125 | 703 | 247 | 132# | 41# |
| 56 | 141 | 6 | 152 | 74 | 270 | 248 | 7254# | 1710# |
| 57 | 5 | 3 | 153 | 8 | 122 | 249 | 334*3 | 223*3 |
| 58 | 2560 | 1530 | 154 | 10 | 204 | 250 | 204# | 140# |
| 59 | 207 | 135 | 155 | 134 | 1180 | 251 | 4072# | 426# |
| 60 | 39 | 34 | 156 | 259*3# | 22*3# | 252 | 9367# | 2662# |
| 61 | 40 | 26 | 157 | 1465# | 231# | 253 | 899# | 670# |
| 62 | 25 | 33 | 158 | 702# | 154# | 254 | 191# | 168# |
| 63 | 135 | 90 | 159 | 684# | 397# | 255 | 299# | 242# |
| 64 | 618 | 246 | 160 | 238*2# | 18*2# | 256 | 193# | 133# |
| 65 | 6 | 1 | 161 | 147# | 62# | 257 | 177# | 563# |
| 66 | 3100 | 3700 | 162 | 1311# | 62# | 258 | 927# | 59# |
| 67 | 163 | 156 | 163 | 1193# | 171# | 259 | 110*2# | 126*2# |
| 68 | 45 | 31 | 164 | 409*2# | 27*2# | 260 | 75# | 19# |
| 69 | 247 | 77 | 165 | 224*2# | 31*2# | 261 | 65# | 41# |
| 70 | 1780 | 400 | 166 | 1721# | 549# | 262 | 3380# | 6940# |
| 71 | >12600 | 6190 | 167 | 231# | 28# | 263 | 619# | 3610# |
| 72 | 3 | 12 | 168 | 1819# | 453# | 264 | 44# | 19# |
| 73 | 186 | 187 | 169 | 1587# | 190# | 265 | 730# | 1090# |
| 74 | 137 | 98 | 170 | 2390# | 766# | 266 | 412# | 86# |

TABLE 1-continued

Antagonistic activities of Example compounds with respect to $OX_1$ and $OX_2$ receptors.

| Example | $IC_{50}$ OX1 [nM] | $IC_{50}$ OX2 [nM] | Example | $IC_{50}$ OX1 [nM] | $IC_{50}$ OX2 [nM] | Example | $IC_{50}$ OX1 [nM] | $IC_{50}$ OX2 [nM] |
|---|---|---|---|---|---|---|---|---|
| 75 | 12 | 32 | 171 | 122# | 66# | 267 | 2680# | 589# |
| 76 | 68 | 27 | 172 | 330# | 106# | 268 | 1270# | 410# |
| 77 | 305 | 188 | 173 | 537# | 297# | 269 | 1026*2 | 619*2 |
| 78 | 323 | 806 | 174 | 1800# | 1080# | 270 | 568 | 412 |
| 79 | 21 | 82 | 175 | 136# | 94# | 271 | 5690 | 256 |
| 80 | 715 | 1041 | 176 | 327# | 61# | 272 | 510 | 229 |
| 81 | 7 | 58 | 177 | 354# | 92# | 273 | 795 | 296 |
| 82 | 7 | 26 | 178 | 215# | 78# | 274 | 23 | 64 |
| 83 | 3*2 | 19*2 | 179 | 225# | 42# | 275 | 50 | 80 |
| 84 | 3 | 7 | 180 | 1450# | 170# | 276 | 347 | 222 |
| 85 | 2 | 3 | 181 | 805*2# | 252*2# | 277 | 214 | 182 |
| 86 | 45 | 71 | 182 | 283# | 178# | 278 | 250 | 172 |
| 87 | 21 | 46 | 183 | 644*3# | 64*3# | 279 | 623 | 1030 |
| 88 | 12 | 58 | 184 | 66 | 6 | 280 | 1817*2 | 1805*2 |
| 89 | 385 | 85 | 185 | 323# | 34# | 281 | 42 | 115 |
| 90 | 1 | 3 | 186 | 2770# | 5650# | 282 | 139 | 213 |
| 91 | 1 | 3 | 187 | 235# | 70# | 283 | 275 | 548 |
| 92 | 1060 | 455 | 188 | 4180# | 484# | 284 | 1450 | 722 |
| 93 | 3 | 16 | 189 | 17 | 12 | 285 | 243*3 | 533*3 |
| 94 | 121 | 378 | 190 | 1950# | 507# | 286 | 104 | 462 |
| 287 | 922 | 585 | 346 | 2850 | 212 | 405 | 555*2 | 87*2 |
| 288 | 825 | 1370 | 347 | 1400 | 777 | 406 | 81 | 2 |
| 289 | 420*4 | 596*4 | 348 | 206 | 474 | 407 | 678 | 11 |
| 290 | 103*5 | 455*5 | 349 | 104*3 | 120*3 | 408 | 86 | 5 |
| 291 | 2052*2 | 457*2 | 350 | 665 | 51 | 409 | 323 | 25 |
| 292 | 214 | 125 | 351 | 16 | 51 | 410 | 143 | 12 |
| 293 | 2754*2 | 338*2 | 352 | 7*3 | 13*3 | 411 | 1490 | 98 |
| 294 | 2442*2 | 294*2 | 353 | 4*3 | 19*3 | 412 | 288 | 4 |
| 295 | 3970 | 5010 | 354 | 56*2 | 113*2 | 413 | 1498*2 | 68*2 |
| 296 | 1300 | 2210 | 355 | 34 | 103 | 414 | 1497*2 | 44*2 |
| 297 | 1050 | 568 | 356 | 30 | 113 | 415 | 978*2 | 291*2 |
| 298 | 1630 | 901 | 357 | 20*2 | 4*2 | 416 | 2940*2 | 59*2 |
| 299 | 1856*2 | 170*2 | 358 | 959 | 1260 | 417 | 123*3 | 110*3 |
| 300 | 1259*2 | 98*2 | 359 | 1710 | 334 | 418 | 430 | 323 |
| 301 | 1701*2 | 66*2 | 360 | 352 | 12 | 419 | 143*2 | 173*2 |
| 302 | 1380*3 | 103*3 | 361 | 849*3 | 87*3 | 420 | 586 | 549 |
| 303 | 1376*2 | 143*2 | 362 | 85 | 6 | 421 | 498 | 237 |
| 304 | 615*2 | 129*2 | 363 | 424 | 49 | 422 | 863 | 1040 |
| 305 | 396*2 | 96*2 | 364 | 121 | 11 | 423 | 101*3 | 93*3 |
| 306 | 740 | 108 | 365 | 114 | 9 | 424 | 27*2 | 13*2 |
| 307 | 563 | 397 | 366 | 158 | 8 | 425 | 311 | 235 |
| 308 | 567 | 585 | 367 | 3 | 1 | 426 | 6*2 | 8*2 |
| 309 | 2220 | 887 | 368 | 23 | 40 | 427 | 1230 | 75 |
| 310 | 1200 | 1680 | 369 | 2 | 5 | 428 | 1710 | 53 |
| 311 | 1370 | 742 | 370 | 872*3 | 30*3 | 429 | 1160 | 15 |
| 312 | 2200 | 826 | 371 | 386*2 | 19*2 | 430 | 5360 | 152 |
| 313 | 1460 | 1030 | 372 | 1494*2 | 115*2 | 431 | 1490 | 255 |
| 314 | 1100 | 920 | 373 | 956 | 65 | 432 | 3960 | 57 |
| 315 | 1200 | 552 | 374 | 976*2 | 41*2 | 433 | 1710 | 3920 |
| 316 | 329 | 1040 | 375 | 715 | 65 | 434 | 655 | 21 |
| 317 | 1070 | 1410 | 376 | 515*3 | 25*3 | 435 | 660 | 30 |
| 318 | 167 | 444 | 377 | 1281*3 | 95*3 | 436 | 965 | 31 |
| 319 | 971 | 1020 | 378 | 1640 | 690 | 437 | 782 | 46 |
| 320 | 1050 | 219 | 379 | 1003*3 | 71*3 | 438 | 921 | 37 |
| 321 | 1430 | 405 | 380 | 131 | 2 | 439 | 575 | 63 |
| 322 | 1080 | 1480 | 381 | 418 | 9 | 440 | 46*2 | 91*2 |
| 323 | 986 | 2150 | 382 | 88 | 2 | 441 | 16*4 | 62*4 |
| 324 | 968 | 1210 | 383 | 234 | 9 | 442 | 10 | 33 |
| 325 | 1380 | 178 | 384 | 111 | 2 | 443 | 5 | 13 |
| 326 | 1517*3 | 126*3 | 385 | 64 | 2 | 444 | 7 | 8 |
| 327 | 1060 | 1760 | 386 | 39 | 2 | 445 | 21 | 90 |
| 328 | 739 | 1790 | 387 | 100*3 | 111*3 | 446 | 12 | 59 |
| 329 | 885 | 528 | 388 | 83*2 | 132*2 | 447 | 112 | 92 |
| 330 | 227*3 | 197*3 | 389 | 466 | 1190 | 448 | 17 | 11 |
| 331 | 1150 | 434 | 390 | 80*2 | 142*2 | 449 | 351*2 | 23*2 |
| 332 | 1018*2 | 296*2 | 391 | 175 | 529 | 450 | 561 | 15 |
| 333 | 965 | 184 | 392 | 810 | 1780 | 451 | 427 | 19 |
| 334 | 2122*5 | 33*5 | 393 | 32*2 | 121*2 | 452 | 105 | 15 |
| 335 | 5350 | 1360 | 394 | 2547*2 | 77*2 | 453 | 381 | 93 |
| 336 | 16*3 | 81*3 | 395 | 209 | 7 | 454 | 182*4 | 77*4 |
| 337 | 12*3 | 63*3 | 396 | 214 | 29 | 455 | 57 | 102 |
| 338 | 2468*3 | 58*3 | 397 | 265 | 370 | 456 | 654*2 | 716*2 |
| 339 | 816*2 | 35*2 | 398 | 277 | 428 | 457 | 59*2 | 30*2 |

TABLE 1-continued

Antagonistic activities of Example compounds with respect to $OX_1$ and $OX_2$ receptors.

| Example | $IC_{50}$ OX1 [nM] | $IC_{50}$ OX2 [nM] | Example | $IC_{50}$ OX1 [nM] | $IC_{50}$ OX2 [nM] | Example | $IC_{50}$ OX1 [nM] | $IC_{50}$ OX2 [nM] |
|---|---|---|---|---|---|---|---|---|
| 340 | 981*² | 17*² | 399 | 172*² | 124*² | 458 | 142*² | 14*² |
| 341 | 3340 | 1630 | 400 | 151 | 183 | 459 | 108 | 40 |
| 342 | 1110*² | 8*² | 401 | 164 | 155 | 460 | 798 | 22 |
| 343 | 603*² | 15*² | 402 | 271 | 621 | 461 | 724 | 4 |
| 344 | 1804*³ | 392*³ | 403 | 532 | 449 | 462 | 405 | 22 |
| 345 | 745*³ | 462*³ | 404 | 965 | 513 | 463 | 1260 | 93 |

*²geometric mean n = 2 values; *³n = 3 values; *⁴n = 4 values; *⁵n = 5 values; *⁶n = 6 values
$IC_{50}$ values measured using a compound incubation time of 10 min.

The invention claimed is:
1. A compound of formula (I)

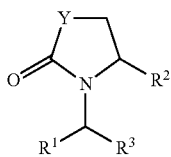

Formula (I)

wherein

Y represents a group —$(CH_2)_m$—, wherein m represents the integer 1, 2, or 3, wherein said group is optionally substituted with one or two substituents independently selected from the group consisting of $(C_{1-3})$alkyl, $(C_{1-3})$alkoxy, hydroxy, and halogen;

$R^1$ represents aryl or heteroaryl, wherein the aryl or heteroaryl independently is:
  substituted with one, two, or three substituents, wherein the substituents are independently selected from the group consisting of:
    $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, $(C_{1-3})$fluoroalkyl-thio-, $(C_{1-4})$alkyl-sulfonyl, $(C_{3-6})$cycloalkyl-$(C_{1-4})$alkoxy, $(C_{1-4})$alkoxy-$(C_{1-4})$alkoxy;
    —$NR^4R^5$, wherein $R^4$ and $R^5$ are independently selected from hydrogen, $(C_{1-4})$alkyl, or, $R^4$ and $R^5$ together with the nitrogen atom to which they are attached form a saturated 5-, 6-, or 7-membered ring optionally containing an oxygen atom;
    phenyl or 5- or 6-membered heteroaryl, wherein said phenyl or 5- or 6-membered heteroaryl is independently unsubstituted, or mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy; and
    phenyloxy or 5- or 6-membered heteroaryloxy, wherein said phenyl or 5- or 6-membered heteroaryl is independently unsubstituted, or mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;
  wherein at maximum one substituent selected from phenyl or 5- or 6-membered heteroaryl, and phenyloxy or 5- or 6-membered heteroaryloxy is present;
  or said aryl or heteroaryl is fused to a non-aromatic 5- or 6-membered ring, wherein said ring optionally contains one or two heteroatoms independently selected from oxygen and nitrogen; wherein said ring is optionally substituted with one or two substituents independently selected from $(C_{1-3})$alkyl, oxo, and halogen;
  or, in the specific case wherein said aryl is naphthyl, or said heteroaryl is a bicyclic or tricyclic ring, said aryl or heteroaryl may additionally be unsubstituted;

$R^2$ represents aryl or 5- to 10-membered heteroaryl, wherein the aryl or heteroaryl is independently substituted with one, two, or three substituents, wherein at least one substituent is attached in ortho-position to the point of attachment of $R^2$ to the rest of the molecule; wherein
  the substituents are independently selected from the group consisting of:
    $(C_{1-4})$alkyl, $(C_{1-4})$alkoxy, halogen, cyano, $(C_{1-3})$fluoroalkyl, $(C_{1-3})$fluoroalkoxy; hydroxy-$(C_{1-4})$alkoxy, dihydroxy-$(C_{1-4})$alkoxy, $(C_{3-6})$cycloalkyl-$(C_{1-4})$alkoxy, $(C_{1-4})$alkoxy-$(C_{1-4})$alkoxy; and
    phenyl or 5- or 6-membered heteroaryl, wherein said phenyl or 5- or 6-membered heteroaryl is independently unsubstituted, or mono-, di-, or tri-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy;
  wherein at maximum one phenyl or 5- or 6-membered heteroaryl substituent is present;
  or two of said substituents form a non-aromatic 5- or 6-membered ring fused to said aryl or heteroaryl, wherein said ring optionally contains one or two heteroatoms independently selected from oxygen and nitrogen, wherein said ring in turn is optionally substituted with one or two substituents independently selected from $(C_{1-3})$alkyl, oxo, and halogen;
  and the remaining of said substituents, if present, is selected from the group consisting of $(C_{1-4})$alkyl, $(C_{1-4})$alkoxy, halogen, cyano, $(C_{1-3})$fluoroalkyl, $(C_{1-3})$fluoroalkoxy, hydroxy-$(C_{1-4})$alkoxy, dihydroxy-$(C_{1-4})$alkoxy, $(C_{3-6})$cycloalkyl-$(C_{1-4})$alkoxy, and $(C_{1-4})$alkoxy-$(C_{1-4})$alkoxy; and $R^3$ represents hydrogen, methyl or ethyl;
with the exception of the following compound:
5-(2-Methoxyphenyl)-1-[(4-methoxyphenyl)methyl]-3-methyl-2-pyrrolidinone;
or a pharmaceutically acceptable salt thereof.

2. The compound according to claim 1; wherein Y represents —CH$_2$—, —CH(CH$_3$)—, —CH(C$_2$H$_5$)—, —CHF—, —CHCl—, —CH(OCH$_3$)—, —CH(OH)—, —C(CH$_3$)$_2$—, —CF$_2$—, —CH$_2$—CH$_2$—, *—CH(CH$_3$)—CH$_2$—, *—CH$_2$—CH(CH$_3$)—, *—C(CH$_3$)$_2$—CH$_2$—, *—CH$_2$—C(CH$_3$)$_2$—, or —CH$_2$—CH$_2$—CH$_2$—; wherein the asterisks indicate the bond which is attached to the carbonyl group of the ring;
or a pharmaceutically acceptable salt thereof.

3. The compound according to claim 1; wherein R$^1$ represents Ar$^1$ or Ar$^3$—X—Ar$^2$—* wherein the asterisk indicates the bond that is attached to the rest of the molecule; wherein
Ar$^1$ represents aryl or heteroaryl, wherein the aryl or heteroaryl independently is:
  substituted with one, two, or three substituents, wherein the substituents are independently selected from the group consisting of:
    (C$_{1-4}$)alkyl, (C$_{1-4}$)alkoxy, (C$_{3-6}$)cycloalkyl, halogen, cyano, (C$_{1-3}$)fluoroalkyl, (C$_{1-3}$)fluoroalkoxy, (C$_{1-3}$)fluoroalkyl-thio-, (C$_{1-4}$)alkyl-sulfonyl, (C$_{3-6}$)cycloalkyl-(C$_{1-4}$)alkoxy, (C$_{1-4}$)alkoxy-(C$_{1-4}$)alkoxy; and
    —NR$^4$R$^5$, wherein R$^4$ and R$^5$ are independently selected from hydrogen, (C$_{1-4}$)alkyl, or, R$^4$ and R$^5$ together with the nitrogen atom to which they are attached form a saturated 5-, 6-, or 7-membered ring optionally containing an oxygen atom;
  or said aryl or heteroaryl is fused to a non-aromatic 5- or 6-membered ring, wherein said ring optionally contains one or two heteroatoms independently selected from oxygen and nitrogen; wherein said ring is optionally substituted with one or two substituents independently selected from (C$_{1-3}$)alkyl, oxo, and halogen;
  or, in the specific case wherein said aryl is naphthyl, or said heteroaryl is a bicyclic or tricyclic ring, said aryl or heteroaryl may additionally be unsubstituted;
Ar$^2$ represents phenyl or 5- or 6-membered heteroaryl; wherein the phenyl or 5- or 6-membered heteroaryl independently is
unsubstituted, or substituted with one, or two substituents, wherein the substituents are independently selected from the group consisting of:
  (C$_{1-4}$)alkyl, (C$_{1-4}$)alkoxy, (C$_{3-6}$)cycloalkyl, halogen, cyano, (C$_{1-3}$)fluoro alkyl, (C$_{1-3}$)fluoroalkoxy, (C$_{1-3}$)fluoroalkyl-thio-, (C$_{1-4}$)alkyl-sulfonyl, (C$_{3-6}$)cycloalkyl-(C$_{1-4}$)alkoxy, (C$_{1-4}$)alkoxy-(C$_{1-4}$)alkoxy;
Ar$^3$ represents phenyl or 5- or 6-membered heteroaryl, wherein said phenyl or 5- or 6-membered heteroaryl is independently unsubstituted, or mono-, di-, or tri-substituted, wherein the substituents are independently selected from the group consisting of (C$_{1-4}$)alkyl, (C$_{1-4}$)alkoxy, halogen, cyano, (C$_{1-3}$)fluoroalkyl, and (C$_{1-3}$)fluoroalkoxy; and
X represents a bond, or oxygen;
or a pharmaceutically acceptable salt thereof.

4. The compound according to claim 3; wherein,
R$^1$ represents naphthyl, or bicyclic or tricyclic heteroaryl; wherein said naphthyl or bicyclic or tricyclic heteroaryl independently are unsubstituted or substituted with a substituent independently selected from the group consisting of (C$_{1-4}$)alkyl, and (C$_{1-4}$)alkoxy;
or R$^1$ represents a group selected from the group consisting of:

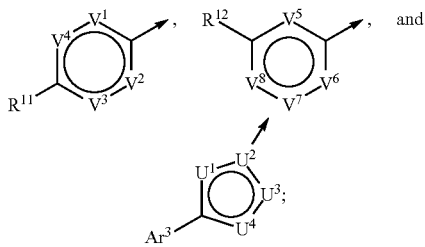

wherein
R$^{11}$ represents Ar$^3$—X, (C$_{1-3}$)alkoxy, or (C$_{1-3}$)fluoroalkoxy;
R$^{12}$ represents Ar$^3$—X, or —NR$^4$R$^5$, wherein R$^4$ and R$^5$ together with the nitrogen atom to which they are attached form a saturated 5-, or 6-membered ring optionally containing an oxygen atom;
independently one or two of V$^1$, V$^2$, V$^3$ and V$^4$ are N or CH, and the remaining are CH; wherein one of V$^1$, V$^2$, V$^3$ and V$^4$ being CH may optionally be substituted with halogen;
independently one or two of V$^5$, V$^6$, V$^7$ and V$^8$ are N or CH, and the remaining are CH; wherein one of V$^5$, V$^6$, V$^7$ and V$^8$ being CH may optionally be substituted with halogen;
U$^2$ is C or N, and U$^1$, U$^3$, and U$^4$ independently are CH, N, O, or S; provided that at least one of U$^2$, U$^1$, U$^3$, and U$^4$ is different from CH; wherein one of U$^1$, U$^3$, and U$^4$ being CH may optionally be substituted with methyl;
or a pharmaceutically acceptable salt thereof.

5. The compound according to claim 3; wherein Ar$^3$ represents phenyl or 5- or 6-membered heteroaryl, wherein said phenyl or 5- or 6-membered heteroaryl is independently unsubstituted, or mono-substituted with (C$_{1-4}$)alkyl, or halogen;
or a pharmaceutically acceptable salt thereof.

6. The compound according to claim 3; wherein Ar$^3$—X—Ar$^2$—* is a group selected from the group consisting of 3-biphenyl, 3-(thiazolyl)-phenyl, 2-(thiazolyl)-pyridin-4-yl, 3-(pyrazolyl)-phenyl, 2-(pyrazolyl)-pyridin-4-yl, 3-(triazolyl)-phenyl, 3-(oxadiazolyl)-phenyl, 2-phenyl-thiazolyl, 3-(pyridinyl)-phenyl, 3-(pyrimidinyl)-phenyl, 2-phenyl-pyridin-4-yl, and 6-phenyl-pyridin-2-yl; wherein said groups are optionally mono-substituted with methyl or halogen;
or a pharmaceutically acceptable salt thereof.

7. The compound according to claim 1; wherein
R$^2$ represents phenyl or 5- or 6-membered heteroaryl, wherein the phenyl or 5- or 6-membered heteroaryl is independently substituted with one, two, or three substituents, wherein at least one substituent is attached in ortho-position to the point of attachment of R$^2$ to the rest of the molecule; wherein the substituents are independently selected from the group consisting of:
(C$_{1-4}$)alkyl, (C$_{1-4}$)alkoxy, halogen, (C$_{1-3}$)fluoroalkyl, (C$_{1-3}$)fluoroalkoxy; hydroxy-(C$_{1-4}$)alkoxy, dihydroxy-(C$_{1-4}$)alkoxy, (C$_{3-6}$)cycloalkyl-(C$_{1-4}$)alkoxy, (C$_{1-4}$)alkoxy-(C$_{1-4}$)alkoxy; and
phenyl or 5- or 6-membered heteroaryl, wherein said phenyl or 5- or 6-membered heteroaryl is independently unsubstituted, or mono-substituted, wherein the substituent is independently selected from the group consisting of (C$_{1-4}$)alkyl, (C$_{1-4}$)alkoxy, halogen, cyano, (C$_{1-3}$)fluoroalkyl, and (C$_{1-3}$)fluoroalkoxy;

wherein at maximum one phenyl or 5- or 6-membered heteroaryl substituent is present;

or R² represents naphthyl or 8- to 10-membered bicyclic heteroaryl, wherein the naphthyl or 8- to 10-membered bicyclic heteroaryl is attached in alpha position to a bridgehead atom; and wherein the naphthyl or 8- to 10-membered bicyclic heteroaryl is independently substituted with one, or two substituents, wherein one substituent is $(C_{1-4})$alkoxy which is attached in ortho-position to the point of attachment of R² to the rest of the molecule; and the remaining substituent, if present, is $(C_{1-4})$alkyl;

or R² represents a group selected from the group consisting of 2,3-dihydrobenzofuranyl, chromanyl, chromenyl, benzo[1,3]dioxolyl, 2,3-dihydro-benzo[1,4]dioxinyl, benzo[b][1,4]dioxinyl, and 2,3-dihydro-[1,4]dioxinopyridinyl; wherein said groups are attached to the rest of the molecule on the aromatic ring, in alpha position to a bridgehead atom; and wherein said groups are optionally substituted in the aromatic moiety with a substituent selected from $(C_{1-4})$alkoxy;

or a pharmaceutically acceptable salt thereof.

8. The compound according to claim 1; wherein R² represents a group selected from the group consisting of:

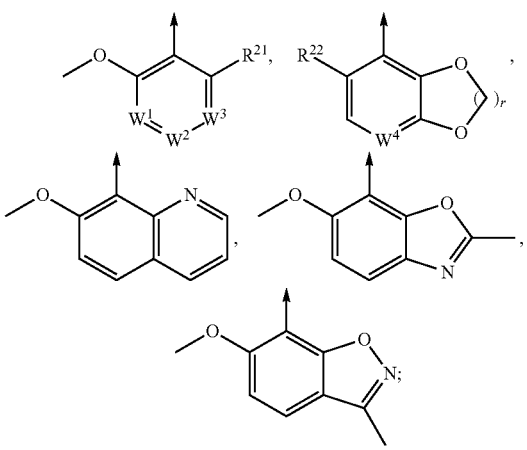

wherein
W¹ and W³ represent CH, and W² represents CR²³ or N; or one or two of W¹ and W³ represent N, and W² represents CH;
R²¹ represents methyl, $(C_{1-3})$alkoxy, halogen, $(C_{1-2})$ fluoroalkoxy, or trifluoromethyl;
R²² represents hydrogen or methoxy;
R²³ represents hydrogen, methyl, methoxy, fluoro, or chloro; and
W⁴ represents CH, or N;
r represents the integer 1 or 2;
or a pharmaceutically acceptable salt thereof.

9. The compound according to claim 1; wherein, R³ represents hydrogen or methyl;
or a pharmaceutically acceptable salt thereof.

10. The compound according to claim 1 selected from the group consisting of:
6-(2,6-dimethoxyphenyl)-1-((2-methylbenzo[d]thiazol-5-yl)methyl)piperidin-2-one;
6-(2,6-dimethoxyphenyl)-1-(quinolin-6-ylmethyl)piperidin-2-one;
(R)-6-(2,6-dimethoxyphenyl)-1-(quinolin-2-ylmethyl)piperidin-2-one;
(S)-6-(2,6-dimethoxyphenyl)-1-(quinolin-2-ylmethyl)piperidin-2-one;
1-((5-chloro-6-(difluoromethoxy)pyridin-3-yl)methyl)-6-(2,6-dimethoxyphenyl)piperidin-2-one;
6-(2,6-dimethoxyphenyl)-1-((6-(4-fluorophenyl)pyridin-2-yl)methyl)piperidin-2-one;
6-(2,6-dimethoxyphenyl)-1-(3-(pyridin-3-yl)benzyl)piperidin-2-one;
6-(2,6-dimethoxyphenyl)-1-(3-(pyridin-4-yl)benzyl)piperidin-2-one;
6-(2,6-dimethoxyphenyl)-1-(3-(pyridin-2-yl)benzyl)piperidin-2-one;
6-(2,6-dimethoxyphenyl)-1-((6-phenylpyridin-2-yl)methyl)piperidin-2-one;
6-(2,6-dimethoxyphenyl)-1-((2-phenylpyridin-4-yl)methyl)piperidin-2-one;
6-(2,6-dimethoxyphenyl)-1-(3-(piperidin-1-yl)benzyl)piperidin-2-one;
6-(2,6-dimethoxyphenyl)-1-(3-(thiazol-2-yl)benzyl)piperidin-2-one;
6-(2,6-dimethoxyphenyl)-1-(naphthalen-1-ylmethyl)piperidin-2-one;
6-(2,6-dimethoxyphenyl)-1-(3-(2-methylthiazol-4-yl)benzyl)piperidin-2-one;
6-(2,6-dimethoxyphenyl)-1-((5-phenylthiophen-2-yl)methyl)piperidin-2-one;
1-(3-(1H-pyrazol-1-yl)benzyl)-6-(2,6-dimethoxyphenyl)piperidin-2-one;
6-(2,6-dimethoxyphenyl)-1-((4-phenylpyridin-2-yl)methyl)piperidin-2-one;
6-(2,6-dimethoxyphenyl)-1-(3-(pyrrolidin-1-yl)benzyl)piperidin-2-one;
6-(2,6-dimethoxyphenyl)-1-((1-phenyl-1H-pyrazol-4-yl)methyl)piperidin-2-one;
1-(3-(1H-imidazol-1-yl)benzyl)-6-(2,6-dimethoxyphenyl)piperidin-2-one;
6-(2,6-dimethoxyphenyl)-1-((6-(piperidin-1-yl)pyridin-2-yl)methyl)piperidin-2-one;
6-(2,6-dimethoxyphenyl)-1-(3-(pyrimidin-2-yl)benzyl)piperidin-2-one;
1-(dibenzo[b,d]furan-2-ylmethyl)-6-(2,6-dimethoxyphenyl)piperidin-2-one;
6-(2,6-dimethoxyphenyl)-1-((9-methyl-9H-carbazol-3-yl)methyl)piperidin-2-one;
6-(2,6-dimethoxyphenyl)-1-(3-(5-methyl-1,2,4-oxadiazol-3-yl)benzyl)piperidin-2-one;
6-(2,6-dimethoxyphenyl)-1-((2-phenylthiazol-4-yl)methyl)piperidin-2-one;
6-(2,6-dimethoxyphenyl)-1-(2-fluoro-3-(pyridin-2-yl)benzyl)piperidin-2-one;
1-([2,2'-bipyridin]-6-ylmethyl)-6-(2,6-dimethoxyphenyl)piperidin-2-one;
6-(2,6-dimethoxyphenyl)-1-((6-(thiazol-2-yl)pyridin-2-yl)methyl)piperidin-2-one;
6-(2,6-dimethoxyphenyl)-1-(2-fluoro-5-(pyridin-2-yl)benzyl)piperidin-2-one;
6-(2,6-dimethoxyphenyl)-1-(4-fluoro-3-(pyridin-2-yl)benzyl)piperidin-2-one;
6-(2,6-dimethoxyphenyl)-1-(3-(thiazol-5-yl)benzyl)piperidin-2-one;
6-(2,6-dimethoxyphenyl)-1-(3-(5-methylthiazol-2-yl)benzyl)piperidin-2-one;
1-(3-(2H-1,2,3-triazol-2-yl)benzyl)-6-(2,6-dimethoxyphenyl)piperidin-2-one;
6-(2,6-dimethoxyphenyl)-1-(3-(thiazol-4-yl)benzyl)piperidin-2-one;

6-(2,6-dimethoxyphenyl)-1-((2-methylbenzo[d]thiazol-6-yl)methyl)piperidin-2-one;
1-(2-chloro-5-(pyridin-2-yl)benzyl)-6-(2,6-dimethoxyphenyl)piperidin-2-one;
1-(3-chloro-5-(pyridin-2-yl)benzyl)-6-(2,6-dimethoxyphenyl)piperidin-2-one;
1-([2,2'-bipyridin]-4-ylmethyl)-6-(2,6-dimethoxyphenyl)piperidin-2-one;
1-((6-(1H-pyrazol-1-yl)pyridin-2-yl)methyl)-6-(2,6-dimethoxyphenyl)piperidin-2-one;
1-((2-(1H-pyrazol-1-yl)pyridin-4-yl)methyl)-6-(2,6-dimethoxyphenyl)piperidin-2-one;
6-(2,4-dimethoxypyridin-3-yl)-1-(3-(thiazol-2-yl)benzyl)piperidin-2-one;
6-(2,4-dimethoxypyridin-3-yl)-1-(3-(2-methylthiazol-4-yl)benzyl)piperidin-2-one;
6-(2,4-dimethoxypyridin-3-yl)-1-(3-(pyridin-2-yl)benzyl)piperidin-2-one;
6-(2,4-dimethoxypyridin-3-yl)-1-((2-phenylthiazol-4-yl)methyl)piperidin-2-one;
1-(dibenzo[b,d]furan-2-ylmethyl)-6-(2,4-dimethoxypyridin-3-yl)piperidin-2-one;
6-(2,4-dimethoxypyridin-3-yl)-1-(4-fluoro-3-(pyridin-2-yl)benzyl)piperidin-2-one;
1-([1,1'-biphenyl]-3-ylmethyl)-6-(2,4-dimethoxypyridin-3-yl)piperidin-2-one;
6-(3,5-dimethoxypyridin-4-yl)-1-(3-(thiazol-2-yl)benzyl)piperidin-2-one;
6-(3,5-dimethoxypyridin-4-yl)-1-(3-(2-methylthiazol-4-yl)benzyl)piperidin-2-one;
6-(3,5-dimethoxypyridin-4-yl)-1-(3-(pyridin-2-yl)benzyl)piperidin-2-one;
1-(dibenzo[b,d]furan-2-ylmethyl)-6-(3,5-dimethoxypyridin-4-yl)piperidin-2-one;
1-(3-(2H-1,2,3-triazol-2-yl)benzyl)-6-(3,5-dimethoxypyridin-4-yl)piperidin-2-one;
1-([1,1'-biphenyl]-3-ylmethyl)-6-(3,5-dimethoxypyridin-4-yl)piperidin-2-one;
1-((6-(difluoromethoxy)-5-methylpyridin-3-yl)methyl)-6-(2,6-dimethoxyphenyl)piperidin-2-one;
1-([1,1'-biphenyl]-3-ylmethyl)-7-(2,6-dimethoxyphenyl)azepan-2-one;
7-(2,6-dimethoxyphenyl)-1-(4-phenoxybenzyl)azepan-2-one;
7-(2,6-dimethoxyphenyl)-1-(3-phenoxybenzyl)azepan-2-one;
7-(2,6-dimethoxyphenyl)-1-(naphthalen-2-ylmethyl)azepan-2-one;
7-(2,6-dimethoxyphenyl)-1-(naphthalen-1-ylmethyl)azepan-2-one;
1-([1,1'-biphenyl]-4-ylmethyl)-7-(2,6-dimethoxyphenyl)azepan-2-one;
7-(2,6-dimethoxyphenyl)-1-(quinolin-2-ylmethyl)azepan-2-one;
7-(2,6-dimethoxyphenyl)-1-((2-phenylpyridin-4-yl)methyl)azepan-2-one;
7-(2,6-dimethoxyphenyl)-1-((6-phenylpyridin-2-yl)methyl)azepan-2-one;
7-(2,6-dimethoxyphenyl)-1-(3-(pyrimidin-2-yl)benzyl)azepan-2-one;
7-(2,6-dimethoxyphenyl)-1-(3-(pyridin-2-yl)benzyl)azepan-2-one;
7-(2,6-dimethoxyphenyl)-1-(3-(thiazol-2-yl)benzyl)azepan-2-one;
7-(2,6-dimethoxyphenyl)-1-((9-methyl-9H-carbazol-3-yl)methyl)azepan-2-one;
7-(2,6-dimethoxyphenyl)-1-(3-(pyridin-3-yl)benzyl)azepan-2-one;
7-(2,6-dimethoxyphenyl)-1-(3-(piperidin-1-yl)benzyl)azepan-2-one;
1-((5-chloro-6-(difluoromethoxy)pyridin-3-yl)methyl)-7-(2,6-dimethoxyphenyl)azepan-2-one;
1-(dibenzo[b,d]furan-2-ylmethyl)-7-(2,6-dimethoxyphenyl)azepan-2-one;
7-(2,6-dimethoxyphenyl)-1-(3-(2-methylthiazol-4-yl)benzyl)azepan-2-one;
7-(2,6-dimethoxyphenyl)-1-(3-(pyrrolidin-1-yl)benzyl)azepan-2-one;
7-(2,6-dimethoxyphenyl)-1-((1-phenyl-1H-pyrazol-4-yl)methyl)azepan-2-one;
7-(2,6-dimethoxyphenyl)-1-((2-methylbenzo[d]thiazol-5-yl)methyl)azepan-2-one;
7-(2,6-dimethoxyphenyl)-1-(3-(pyridin-4-yl)benzyl)azepan-2-one;
1-(3-(1H-pyrazol-1-yl)benzyl)-7-(2,6-dimethoxyphenyl)azepan-2-one;
7-(2,6-dimethoxyphenyl)-1-((2-phenylthiazol-4-yl)methyl)azepan-2-one;
7-(2,6-dimethoxyphenyl)-1-(3-(thiazol-5-yl)benzyl)azepan-2-one;
7-(2,6-dimethoxyphenyl)-1-(3-(5-methylthiazol-2-yl)benzyl)azepan-2-one;
1-(3-(2H-1,2,3-triazol-2-yl)benzyl)-7-(2,6-dimethoxyphenyl)azepan-2-one;
7-(2,6-dimethoxyphenyl)-1-(3-(thiazol-4-yl)benzyl)azepan-2-one;
1-((2-(1H-pyrazol-1-yl)pyridin-4-yl)methyl)-7-(2,6-dimethoxyphenyl)azepan-2-one;
1-((6-(1H-pyrazol-1-yl)pyridin-2-yl)methyl)-7-(2,6-dimethoxyphenyl)azepan-2-one;
7-(2,6-dimethoxyphenyl)-1-((2-methylbenzo[d]thiazol-6-yl)methyl)azepan-2-one;
7-(2,6-dimethoxyphenyl)-1-(2-fluoro-3-(pyridin-2-yl)benzyl)azepan-2-one;
7-(2,6-dimethoxyphenyl)-1-(4-fluoro-3-(pyridin-2-yl)benzyl)azepan-2-one;
5-(2,6-dimethoxyphenyl)-1-(quinolin-3-ylmethyl)pyrrolidin-2-one;
5-(2,6-dimethoxyphenyl)-1-(quinolin-2-ylmethyl)pyrrolidin-2-one;
5-(2,6-dimethoxyphenyl)-1-(naphthalen-2-ylmethyl)pyrrolidin-2-one;
1-((5-chloro-6-(difluoromethoxy)pyridin-3-yl)methyl)-5-(2,6-dimethoxyphenyl)pyrrolidin-2-one;
1-([1,1'-biphenyl]-3-ylmethyl)-5-(2,6-dimethoxyphenyl)pyrrolidin-2-one;
1-([1,1'-biphenyl]-4-ylmethyl)-5-(2,6-dimethoxyphenyl)pyrrolidin-2-one;
5-(2,6-dimethoxyphenyl)-1-(3-phenoxybenzyl)pyrrolidin-2-one;
5-(2,6-dimethoxyphenyl)-1-(4-phenoxybenzyl)pyrrolidin-2-one;
5-(2,6-dimethoxyphenyl)-1-(3-(pyridin-2-yl)benzyl)pyrrolidin-2-one;
5-(2,6-dimethoxyphenyl)-1-((2-phenylpyridin-4-yl)methyl)pyrrolidin-2-one;
5-(2,6-dimethoxyphenyl)-1-((6-phenylpyridin-2-yl)methyl)pyrrolidin-2-one;
1-([1,1'-biphenyl]-3-ylmethyl)-5-(2,6-dimethoxyphenyl)-3-methylpyrrolidin-2-one;
5-(2,6-dimethoxyphenyl)-3-methyl-1-(3-(pyrrolidin-1-yl)benzyl)pyrrolidin-2-one;

5-(2,6-dimethoxyphenyl)-1-(3-(thiazol-2-yl)benzyl)pyrrolidin-2-one;
5-(2,6-dimethoxyphenyl)-1-(3-(2-methylthiazol-4-yl)benzyl)pyrrolidin-2-one;
1-(3-(1H-pyrazol-1-yl)benzyl)-5-(2,6-dimethoxyphenyl)pyrrolidin-2-one;
1-(dibenzo[b,d]furan-2-ylmethyl)-5-(2,6-dimethoxyphenyl)pyrrolidin-2-one;
5-(2,6-dimethoxyphenyl)-1-(3-(piperidin-1-yl)benzyl)pyrrolidin-2-one;
5-(2,6-dimethoxyphenyl)-3-methyl-1-(naphthalen-2-ylmethyl)pyrrolidin-2-one;
5-(2,6-dimethoxyphenyl)-3-methyl-1-(3-(thiazol-2-yl)benzyl)pyrrolidin-2-one;
5-(2,6-dimethoxyphenyl)-3-methyl-1-(3-(2-methylthiazol-4-yl)benzyl)pyrrolidin-2-one;
5-(2,6-dimethoxyphenyl)-3-methyl-1-(3-(piperidin-1-yl)benzyl)pyrrolidin-2-one;
1-(3-(1H-pyrazol-1-yl)benzyl)-5-(2,6-dimethoxyphenyl)-3-methylpyrrolidin-2-one;
1-(dibenzo[b,d]furan-2-ylmethyl)-5-(2,6-dimethoxyphenyl)-3-methylpyrrolidin-2-one;
5-(2,6-dimethoxyphenyl)-3-methyl-1-((6-phenylpyridin-2-yl)methyl)pyrrolidin-2-one;
5-(2,6-dimethoxyphenyl)-3-methyl-1-((2-phenylpyridin-4-yl)methyl)pyrrolidin-2-one;
5-(2,6-dimethoxyphenyl)-3-methyl-1-(3-(pyridin-2-yl)benzyl)pyrrolidin-2-one;
5-(2,6-dimethoxyphenyl)-3-methyl-1-(3-(pyridin-3-yl)benzyl)pyrrolidin-2-one;
5-(2,6-dimethoxyphenyl)-3-methyl-1-(3-(pyrimidin-2-yl)benzyl)pyrrolidin-2-one;
5-(2,6-dimethoxyphenyl)-3-methyl-1-(3-(5-methyl-1,2,4-oxadiazol-3-yl)benzyl)pyrrolidin-2-one;
5-(2,6-dimethoxyphenyl)-3-methyl-1-((2-phenylthiazol-4-yl)methyl)pyrrolidin-2-one;
5-(2,6-dimethoxyphenyl)-1-(2-fluoro-3-(pyridin-2-yl)benzyl)-3-methylpyrrolidin-2-one;
5-(2,6-dimethoxyphenyl)-3-methyl-1-(3-(thiazol-5-yl)benzyl)pyrrolidin-2-one;
5-(2,6-dimethoxyphenyl)-3-methyl-1-(3-(5-methylthiazol-2-yl)benzyl)pyrrolidin-2-one;
1-(3-(2H-1,2,3-triazol-2-yl)benzyl)-5-(2,6-dimethoxyphenyl)-3-methylpyrrolidin-2-one;
5-(2,6-dimethoxyphenyl)-3-methyl-1-(3-(thiazol-4-yl)benzyl)pyrrolidin-2-one;
5-(2,6-dimethoxyphenyl)-3-methyl-1-((2-methylbenzo[d]thiazol-6-yl)methyl)pyrrolidin-2-one;
1-(3-chloro-5-(pyridin-2-yl)benzyl)-5-(2,6-dimethoxyphenyl)-3-methylpyrrolidin-2-one;
5-(2,6-dimethoxyphenyl)-1-(4-fluoro-3-(pyridin-2-yl)benzyl)-3-methylpyrrolidin-2-one;
1-((2-(1H-pyrazol-1-yl)pyridin-4-yl)methyl)-5-(2,6-dimethoxyphenyl)-3-methylpyrrolidin-2-one;
1-((6-(1H-pyrazol-1-yl)pyridin-2-yl)methyl)-5-(2,6-dimethoxyphenyl)-3-methylpyrrolidin-2-one;
6-(2,6-dimethoxyphenyl)-1-(4-(trifluoromethoxy)benzyl)piperidin-2-one;
1-(4-chlorobenzyl)-6-(2,6-dimethoxyphenyl)piperidin-2-one;
6-(2,6-dimethoxyphenyl)-1-(3-fluoro-4-(trifluoromethoxy)benzyl)piperidin-2-one;
1-(3-chloro-4-(trifluoromethoxy)benzyl)-6-(2,6-dimethoxyphenyl)piperidin-2-one;
6-(2,6-dimethoxyphenyl)-1-(4-((trifluoromethyl)thio)benzyl)piperidin-2-one;
6-(2,6-dimethoxyphenyl)-1-(4-(trifluoromethyl)benzyl)piperidin-2-one;
6-(2,6-dimethoxyphenyl)-1-(4-phenoxybenzyl)piperidin-2-one;
1-(4-(difluoromethoxy)benzyl)-6-(2,6-dimethoxyphenyl)piperidin-2-one;
6-(4-chloro-2,6-dimethoxyphenyl)-1-(4-(trifluoromethoxy)benzyl)piperidin-2-one;
1-(4-(1H-pyrrol-1-yl)benzyl)-6-(2,6-dimethoxyphenyl)piperidin-2-one;
6-(2,6-dimethoxyphenyl)-1-((6-methoxynaphthalen-2-yl)methyl)piperidin-2-one;
1-(4-(trifluoromethoxy)benzyl)-6-(2,4,6-trimethoxyphenyl)piperidin-2-one;
6-(2,6-dimethoxyphenyl)-1-(3-(trifluoromethoxy)benzyl)piperidin-2-one;
6-(2,6-dimethoxyphenyl)-1-(4-(2-fluoroethoxyl)benzyl)piperidin-2-one;
1-((6-(difluoromethoxy)pyridin-3-yl)methyl)-6-(2,6-dimethoxyphenyl)piperidin-2-one;
1-(3-(difluoromethoxy)benzyl)-6-(2,6-dimethoxyphenyl)piperidin-2-one;
6-(2,6-dimethoxyphenyl)-1-(3-phenoxybenzyl)piperidin-2-one;
1-(benzofuran-2-ylmethyl)-6-(2,6-dimethoxyphenyl)piperidin-2-one;
1-((2,2-difluorobenzo[d][1,3]dioxol-5-yl)methyl)-6-(2,6-dimethoxyphenyl)piperidin-2-one;
1-((6-(difluoromethoxy)pyridin-2-yl)methyl)-6-(2,6-dimethoxyphenyl)piperidin-2-one;
6-(2,6-dimethoxyphenyl)-1-(1-(4-(trifluoromethoxy)phenyl)ethyl)piperidin-2-one;
1-(1-(5-chloro-6-(difluoromethoxy)pyridin-3-yl)ethyl)-6-(2,6-dimethoxyphenyl)piperidin-2-one;
1-(5-(difluoromethoxy)pyridin-2-yl)methyl)-6-(2,6-dimethoxyphenyl)piperidin-2-one;
1-([1,1'-biphenyl]-3-ylmethyl)-6-(2,6-dimethoxyphenyl)piperidin-2-one;
6-(2,6-dimethoxyphenyl)-1-(2-phenoxybenzyl)piperidin-2-one;
6-(2,6-dimethoxyphenyl)-1-((6-phenoxypyridin-3-yl)methyl)piperidin-2-one;
7-(2,6-dimethoxyphenyl)-1-(4-(trifluoromethoxy)benzyl)azepan-2-one;
5-(2,6-dimethoxyphenyl)-1-(4-(trifluoromethoxy)benzyl)pyrrolidin-2-one;
1-(3-(difluoromethoxy)benzyl)-5-(2,6-dimethoxyphenyl)-3-methylpyrrolidin-2-one;
5-(2,6-dimethoxyphenyl)-3-methyl-1-(3-(trifluoromethoxy)benzyl)pyrrolidin-2-one;
1-((6-(difluoromethoxy)pyridin-2-yl)methyl)-5-(2,6-dimethoxyphenyl)-3-methylpyrrolidin-2-one;
6-(2,6-dimethoxyphenyl)-1-(4-ethoxybenzyl)piperidin-2-one;
6-(2,6-dimethoxyphenyl)-1-(4-isopropoxybenzyl)piperidin-2-one;
6-(2,6-dimethoxyphenyl)-1-(4-propoxybenzyl)piperidin-2-one;
1-(4-(cyclopropylmethoxy)benzyl)-6-(2,6-dimethoxyphenyl)piperidin-2-one;
6-(2-ethoxy-6-methoxyphenyl)-1-(4-(trifluoromethoxy)benzyl)piperidin-2-one;
6-(2-(2-hydroxyethoxy)-6-methoxyphenyl)-1-(4-(trifluoromethoxy)benzyl)piperidin-2-one;
6-(2,6-dimethoxyphenyl)-3-methyl-1-(4-(trifluoromethoxy)benzyl)piperidin-2-one;

5-(2,6-dimethoxyphenyl)-3,3-dimethyl-1-(4-(trifluoromethoxy)benzyl)pyrrolidin-2-one;
5-(2,6-dimethoxyphenyl)-3-methyl-1-(4-(trifluoromethoxy)benzyl)pyrrolidin-2-one;
6-(2,6-dimethoxyphenyl)-1-((2-(thiazol-2-yl)pyridin-4-yl)methyl)piperidin-2-one;
6-(2-fluoro-6-methoxyphenyl)-1-(4-(trifluoromethoxy)benzyl)piperidin-2-one;
6-(2-chloro-6-methoxyphenyl)-1-(4-(trifluoromethoxy)benzyl)piperidin-2-one;
6-(2-isopropoxy-6-methoxyphenyl)-1-(4-(trifluoromethoxy)benzyl)piperidin-2-one;
6-(4-fluoro-2,6-dimethoxyphenyl)-1-(4-(trifluoromethoxy)benzyl)piperidin-2-one;
6-(2,6-dimethoxy-4-methylphenyl)-1-(4-(trifluoromethoxy)benzyl)piperidin-2-one;
1-([1,1'-biphenyl]-3-ylmethyl)-6-(6-methoxy-3-methylbenzo[d]isoxazol-7-yl)piperidin-2-one;
6-(2,6-dimethoxyphenyl)-1-(naphthalen-2-ylmethyl)piperidin-2-one;
1-([1,1'-biphenyl]-4-ylmethyl)-6-(2,6-dimethoxyphenyl)piperidin-2-one;
6-(2,6-dimethoxyphenyl)-1-(4-(pyrrolidin-1-yl)benzyl)piperidin-2-one;
6-(2,6-dimethoxyphenyl)-1-(4-(2,2,2-trifluoroethoxyl)benzyl)piperidin-2-one;
6-(2,6-dimethoxyphenyl)-1-((1-methyl-1H-indol-2-yl)methyl)piperidin-2-one;
6-(2,6-dimethoxyphenyl)-1-((2-methylbenzo[d]oxazol-5-yl)methyl)piperidin-2-one;
1-(benzo[b]thiophen-5-ylmethyl)-6-(2,6-dimethoxyphenyl)piperidin-2-one;
(3S*,5S*)-5-(2,6-dimethoxyphenyl)-3-methoxy-1-(4-(trifluoromethoxy)benzyl)pyrrolidin-2-one;
5-(2,6-dimethoxyphenyl)-3,3-difluoro-1-(4-(trifluoromethoxy)benzyl)pyrrolidin-2-one;
(3R*,5S*)-3-chloro-5-(2,6-dimethoxyphenyl)-1-(4-(trifluoromethoxy)benzyl)pyrrolidin-2-one;
(3R*,5S*)-5-(2,6-dimethoxyphenyl)-3-hydroxy-1-(4-(trifluoromethoxy)benzyl)pyrrolidin-2-one;
(3S*,5S*)-5-(2,6-dimethoxyphenyl)-3-methyl-1-(4-(trifluoromethoxy)benzyl)pyrrolidin-2-one;
(3S*,5S*)-5-(2,6-dimethoxyphenyl)-3-fluoro-1-(4-(trifluoromethoxy)benzyl)pyrrolidin-2-one;
(3S*,5S*)-3-chloro-5-(2,6-dimethoxyphenyl)-1-(4-(trifluoromethoxy)benzyl)pyrrolidin-2-one;
(3R*,5S*)-5-(2,6-dimethoxyphenyl)-3-methyl-1-(4-(trifluoromethoxy)benzyl)pyrrolidin-2-one;
7-(3,5-dimethoxypyridin-4-yl)-1-(3-(2-methylthiazol-4-yl)benzyl)azepan-2-one;
1-([1,1'-biphenyl]-3-ylmethyl)-7-(3,5-dimethoxypyridin-4-yl)azepan-2-one;
7-(3,5-dimethoxypyridin-4-yl)-1-((2-phenylthiazol-4-yl)methyl)azepan-2-one;
6-(2,6-dimethoxyphenyl)-1-((2-phenoxythiazol-4-yl)methyl)piperidin-2-one;
6-(3-chloro-2,6-dimethoxyphenyl)-1-(3-(2-methylthiazol-4-yl)benzyl)piperidin-2-one; and
5-(2,6-dimethoxyphenyl)-1-(4-(thiazol-2-yloxy)benzyl)pyrrolidin-2-one;
or a pharmaceutically acceptable salt thereof.

11. The compound according to claim 1 selected from the group consisting of:
5-([1,1'-biphenyl]-2-yl)-1-(3-(2-methylthiazol-4-yl)benzyl)pyrrolidin-2-one;
5-([1,1'-biphenyl]-2-yl)-3-methyl-1-(3-(2-methylthiazol-4-yl)benzyl)pyrrolidin-2-one;
5-(2,6-dimethoxyphenyl)-1-(4-((4-methylthiazol-2-yl)oxy)benzyl)pyrrolidin-2-one;
(3R*,5S*)-5-(2-ethoxyphenyl)-3-hydroxy-1-(4-(trifluoromethoxy)benzyl)pyrrolidin-2-one;
(3S*,5S*)-5-(2-ethoxyphenyl)-3-fluoro-1-(4-(trifluoromethoxy)benzyl)pyrrolidin-2-one;
(3S*,5S*)-3-fluoro-5-(2-fluoro-6-methoxyphenyl)-1-(4-(trifluoromethoxy)benzyl)pyrrolidin-2-one;
(3S*,5S*)-5-(2-chloro-6-methoxyphenyl)-3-fluoro-1-(4-(trifluoromethoxy)benzyl)pyrrolidin-2-one;
(3S*,5S*)-3-fluoro-5-(4-fluoro-2-methoxyphenyl)-1-(4-(trifluoromethoxy)benzyl)pyrrolidin-2-one;
(3S*,5S*)-3-chloro-5-(2-ethoxyphenyl)-1-(4-(trifluoromethoxy)benzyl)pyrrolidin-2-one;
(3S*,5S*)-3-chloro-5-(2-fluoro-6-methoxyphenyl)-1-(4-(trifluoromethoxy)benzyl)pyrrolidin-2-one;
(3S*,5S*)-3-chloro-5-(2-chloro-6-methoxyphenyl)-1-(4-(trifluoromethoxy)benzyl)pyrrolidin-2-one;
(3S*,5S*)-3-chloro-5-(3-chloro-2,6-dimethoxyphenyl)-1-(4-(trifluoromethoxy)benzyl)pyrrolidin-2-one;
(3S*,5S*)-3-fluoro-5-(2-methoxy-6-methylphenyl)-1-(4-(trifluoromethoxy)benzyl)pyrrolidin-2-one;
(3S*,5S*)-3-chloro-5-(2-methoxy-6-methylphenyl)-1-(4-(trifluoromethoxy)benzyl)pyrrolidin-2-one;
(3S*,5S*)-3-chloro-5-(3-fluoro-2,6-dimethoxyphenyl)-1-(4-(trifluoromethoxy)benzyl)pyrrolidin-2-one;
(3R*,5S*)-3-chloro-5-(2-ethoxy-6-fluorophenyl)-1-(4-(trifluoromethoxy)benzyl)pyrrolidin-2-one;
(3R*,5S*)-5-(2-ethoxy-6-fluorophenyl)-3-hydroxy-1-(4-(trifluoromethoxy)benzyl)pyrrolidin-2-one;
1-([1,1'-biphenyl]-3-ylmethyl)-5-(2,6-dimethoxyphenyl)-3,3-difluoropyrrolidin-2-one;
1-([1,1'-biphenyl]-3-ylmethyl)-5-(2-ethoxy-6-methoxyphenyl)-3,3-difluoropyrrolidin-2-one;
(3R*,5S*)-5-(6-ethoxy-2,3-difluorophenyl)-3-hydroxy-1-(4-(trifluoromethoxy)benzyl)pyrrolidin-2-one;
(3S*,5S*)-3-chloro-5-(6-ethoxy-2,3-difluorophenyl)-1-(4-(trifluoromethoxy)benzyl)pyrrolidin-2-one;
(3S*,5S*)-5-(6-ethoxy-2,3-difluorophenyl)-3-fluoro-1-(4-(trifluoromethoxy)benzyl)pyrrolidin-2-one;
(3S*,5S*)-5-(2-ethoxy-6-fluorophenyl)-3-fluoro-1-(4-(trifluoromethoxy)benzyl)pyrrolidin-2-one;
(3S*,5S*)-3-chloro-5-(2-ethoxy-6-fluorophenyl)-1-(4-(trifluoromethoxy)benzyl)pyrrolidin-2-one;
5-(2,4-dimethoxypyridin-3-yl)-3-methyl-1-(3-(5-methylthiazol-2-yl)benzyl)pyrrolidin-2-one;
5-(2,4-dimethoxypyridin-3-yl)-3-methyl-1-((2-(p-tolyl)thiazol-4-yl)methyl)pyrrolidin-2-one;
5-(2,6-dimethoxyphenyl)-3-methyl-1-((2-(5-methylthiazol-2-yl)pyridin-4-yl)methyl)pyrrolidin-2-one;
1-(dibenzo[b,d]furan-2-ylmethyl)-5-(2,4-dimethoxypyridin-3-yl)-3-methylpyrrolidin-2-one;
1-(dibenzo[b,d]furan-2-ylmethyl)-5-(2,6-dimethoxyphenyl)-3,3-difluoropyrrolidin-2-one;
1-([1,1'-biphenyl]-3-ylmethyl)-5-(2,4-dimethoxypyridin-3-yl)-3-methylpyrrolidin-2-one;
1-(3-(4-chlorothiazol-2-yl)benzyl)-5-(2,4-dimethoxypyridin-3-yl)-3-methylpyrrolidin-2-one;
5-(2,4-dimethoxypyridin-3-yl)-3-methyl-1-(3-(2-methylthiazol-4-yl)benzyl)pyrrolidin-2-one;
(3R*,5S*)-1-(dibenzo[b,d]furan-2-ylmethyl)-5-(2,6-dimethoxyphenyl)-3-hydroxypyrrolidin-2-one;
5-(2-fluoro-6-methoxyphenyl)-3-methyl-1-((2-(5-methylthiazol-2-yl)pyridin-4-yl)methyl)pyrrolidin-2-one;
1-((2-(1H-pyrazol-1-yl)pyridin-4-yl)methyl)-5-(2-fluoro-6-methoxyphenyl)-3-methylpyrrolidin-2-one;

1-(dibenzo[b,d]furan-2-ylmethyl)-5-(2-fluoro-6-methoxyphenyl)-3-methylpyrrolidin-2-one;
5-(2-fluoro-6-methoxyphenyl)-3-methyl-1-((2-(p-tolyl)thiazol-4-yl)methyl)pyrrolidin-2-one;
5-(2-fluoro-6-methoxyphenyl)-3-methyl-1-(3-(5-methylthiazol-2-yl)benzyl)pyrrolidin-2-one;
1-(3-(4-chlorothiazol-2-yl)benzyl)-5-(2-fluoro-6-methoxyphenyl)-3-methylpyrrolidin-2-one;
5-(2-fluoro-6-methoxyphenyl)-3-methyl-1-((2-(4-methylthiazol-2-yl)pyridin-4-yl)methyl)pyrrolidin-2-one;
(3S*,5S*)-1-(dibenzo[b,d]furan-2-ylmethyl)-5-(2,6-dimethoxyphenyl)-3-fluoropyrrolidin-2-one;
(3R*,5S*)-1-(dibenzo[b,d]furan-2-ylmethyl)-5-(2,6-dimethoxyphenyl)-3-fluoropyrrolidin-2-one;
(3S*,5S*)-3-chloro-1-(dibenzo[b,d]furan-2-ylmethyl)-5-(2,6-dimethoxyphenyl)pyrrolidin-2-one;
5-(2-ethoxy-6-fluorophenyl)-3-methyl-1-(4-(trifluoromethoxy)benzyl)pyrrolidin-2-one;
5-(2-ethoxy-6-fluorophenyl)-3-methyl-1-(3-(trifluoromethoxy)benzyl)pyrrolidin-2-one;
5-(2-ethoxy-6-fluorophenyl)-1-(3-fluoro-4-(trifluoromethoxy)benzyl)-3-methylpyrrolidin-2-one;
1-(4-(difluoromethoxy)benzyl)-5-(2-ethoxy-6-fluorophenyl)-3-methylpyrrolidin-2-one;
1-(3-(difluoromethoxy)benzyl)-5-(2-ethoxy-6-fluorophenyl)-3-methylpyrrolidin-2-one;
1-(3-chloro-4-(difluoromethoxy)benzyl)-5-(2-ethoxy-6-fluorophenyl)-3-methylpyrrolidin-2-one;
5-(2-ethoxy-6-fluorophenyl)-1-(3-ethoxybenzyl)-3-methylpyrrolidin-2-one;
5-(2-ethoxy-6-fluorophenyl)-3-methyl-1-(4-propoxybenzyl)pyrrolidin-2-one;
5-(2-ethoxy-6-fluorophenyl)-3-methyl-1-(quinolin-2-ylmethyl)pyrrolidin-2-one;
5-(2-ethoxy-6-fluorophenyl)-3-methyl-1-((2-(5-methylthiazol-2-yl)pyridin-4-yl)methyl)pyrrolidin-2-one;
1-((2-(1H-pyrazol-1-yl)pyridin-4-yl)methyl)-5-(2-ethoxy-6-fluorophenyl)-3-methylpyrrolidin-2-one;
1-(dibenzo[b,d]furan-2-ylmethyl)-5-(2-ethoxy-6-fluorophenyl)-3-methylpyrrolidin-2-one;
5-(2-ethoxy-6-fluorophenyl)-3-methyl-1-((2-(p-tolyl)thiazol-4-yl)methyl)pyrrolidin-2-one;
5-(2-ethoxy-6-fluorophenyl)-3-methyl-1-(3-(5-methylthiazol-2-yl)benzyl)pyrrolidin-2-one;
1-(3-(4-chlorothiazol-2-yl)benzyl)-5-(2-ethoxy-6-fluorophenyl)-3-methylpyrrolidin-2-one;
5-(2-ethoxy-6-fluorophenyl)-3-methyl-1-((2-(4-methylthiazol-2-yl)pyridin-4-yl)methyl)pyrrolidin-2-one;
5-(2,6-dimethoxyphenyl)-3-methyl-1-((9-methyl-9H-carbazol-3-yl)methyl)pyrrolidin-2-one;
5-(2,6-dimethoxyphenyl)-3-methyl-1-((1-methyl-1H-indol-2-yl)methyl)pyrrolidin-2-one;
5-(2,6-dimethoxyphenyl)-1-((5-fluoro-1-methyl-1H-indol-2-yl)methyl)-3-methylpyrrolidin-2-one;
5-(2,6-dimethoxyphenyl)-3-methyl-1-((1-methyl-1H-indol-5-yl)methyl)pyrrolidin-2-one;
5-(2,6-dimethoxyphenyl)-3-methyl-1-((2-methylbenzo[d]thiazol-5-yl)methyl)pyrrolidin-2-one;
(3R*,5S*)-5-(2-fluoro-6-isopropoxyphenyl)-3-hydroxy-1-(4-(trifluoromethoxy)benzyl)pyrrolidin-2-one;
(3R*,5S*)-1-(dibenzo[b,d]furan-2-ylmethyl)-3-fluoro-5-(2-fluoro-6-methoxyphenyl)pyrrolidin-2-one;
(3R*,5S*)-3-chloro-1-(dibenzo[b,d]furan-2-ylmethyl)-5-(2-fluoro-6-methoxyphenyl)pyrrolidin-2-one;
5-(2,6-dimethoxyphenyl)-3-methyl-1-(4-(1,1,2,2-tetrafluoroethoxy)benzyl)pyrrolidin-2-one;
5-(2,6-dimethoxyphenyl)-1-(3-fluoro-4-(trifluoromethoxy)benzyl)-3-methylpyrrolidin-2-one;
1-(3-chloro-4-(difluoromethoxy)benzyl)-5-(2,6-dimethoxyphenyl)-3-methylpyrrolidin-2-one;
5-(2,6-dimethoxyphenyl)-3-methyl-1-(2-(trifluoromethoxy)benzyl)pyrrolidin-2-one;
(3S*,5S*)-1-(dibenzo[b,d]furan-2-ylmethyl)-3-fluoro-5-(2-fluoro-6-methoxyphenyl)pyrrolidin-2-one;
(3S*,5S*)-3-fluoro-5-(2-fluoro-6-isopropoxyphenyl)-1-(4-(trifluoromethoxy)benzyl)pyrrolidin-2-one;
(3S*,5S*)-3-chloro-1-(dibenzo[b,d]furan-2-ylmethyl)-5-(2-fluoro-6-methoxyphenyl)pyrrolidin-2-one;
(3S*,5S*)-3-chloro-5-(2-fluoro-6-isopropoxyphenyl)-1-(4-(trifluoromethoxy)benzyl)pyrrolidin-2-one;
1-(dibenzo[b,d]furan-2-ylmethyl)-3,3-difluoro-5-(2-fluoro-6-methoxyphenyl)pyrrolidin-2-one;
3,3-difluoro-5-(2-fluoro-6-isopropoxyphenyl)-1-(4-(trifluoromethoxy)benzyl)pyrrolidin-2-one;
(3R*,5S*)-1-(dibenzo[b,d]furan-2-ylmethyl)-5-(2-fluoro-6-methoxyphenyl)-3-hydroxypyrrolidin-2-one;
5-(2-fluoro-6-isopropoxyphenyl)-3-methyl-1-(4-(trifluoromethoxy)benzyl)pyrrolidin-2-one;
5-(2-fluoro-6-(2-fluoroethoxyl)phenyl)-3-methyl-1-(4-(trifluoromethoxy)benzyl)pyrrolidin-2-one;
5-(2-fluoro-6-(2-hydroxyethoxy)phenyl)-3-methyl-1-(4-(trifluoromethoxy)benzyl)pyrrolidin-2-one;
5-(2,6-dimethoxyphenyl)-3-methyl-1-(3-(2,2,2-trifluoroethoxyl)benzyl)pyrrolidin-2-one;
1-(3-(2,2-difluoroethoxyl)benzyl)-5-(2,6-dimethoxyphenyl)-3-methylpyrrolidin-2-one;
5-(2,6-dimethoxyphenyl)-1-(3-isopropoxybenzyl)-3-methylpyrrolidin-2-one;
5-(2,6-dimethoxyphenyl)-3-methyl-1-(3-(1,1,2,2-tetrafluoroethoxy)benzyl)pyrrolidin-2-one;
1-(dibenzo[b,d]thiophen-2-ylmethyl)-5-(2,6-dimethoxyphenyl)-3-methylpyrrolidin-2-one;
(3R*,5S*)-5-(2-chloro-6-ethoxyphenyl)-3-hydroxy-1-(4-(trifluoromethoxy)benzyl)pyrrolidin-2-one;
(3R*,5S*)-5-(2-ethoxy-6-fluorophenyl)-1-(3-fluoro-4-(trifluoromethoxy)benzyl)-3-hydroxypyrrolidin-2-one;
(3R*,5S*)-1-(3-chloro-4-(trifluoromethoxy)benzyl)-5-(2-ethoxy-6-fluorophenyl)-3-hydroxypyrrolidin-2-one;
(3R*,5S*)-5-(2-fluoro-6-methoxyphenyl)-3-hydroxy-1-(3-(trifluoromethoxy)benzyl)pyrrolidin-2-one;
(3R*,5S*)-5-(2-fluoro-6-(2-fluoroethoxyl)phenyl)-3-hydroxy-1-(4-(trifluoromethoxy)benzyl)pyrrolidin-2-one;
(3S*,5S*)-5-(2-ethoxy-6-fluorophenyl)-3-fluoro-1-(3-fluoro-4-(trifluoromethoxy)benzyl)pyrrolidin-2-one;
(3S*,5S*)-3-chloro-5-(2-ethoxy-6-fluorophenyl)-1-(3-fluoro-4-(trifluoromethoxy)benzyl)pyrrolidin-2-one;
(3S*,5S*)-5-(2-chloro-6-ethoxyphenyl)-3-fluoro-1-(4-(trifluoromethoxy)benzyl)pyrrolidin-2-one;
(3S*,5S*)-3-chloro-5-(2-chloro-6-ethoxyphenyl)-1-(4-(trifluoromethoxy)benzyl)pyrrolidin-2-one;
(3S*,5S*)-5-(2-ethoxy-4,6-difluorophenyl)-3-fluoro-1-(4-(trifluoromethoxy)benzyl)pyrrolidin-2-one;
(3S*,5S*)-3-chloro-5-(2-ethoxy-4,6-difluorophenyl)-1-(4-(trifluoromethoxy)benzyl)pyrrolidin-2-one;
1-([1,1'-biphenyl]-3-ylmethyl)-6-(6-methoxy-2-methylbenzo[d]oxazol-7-yl)piperidin-2-one;
6-(6-methoxy-2-methylbenzo[d]oxazol-7-yl)-1-(3-(2-methylthiazol-4-yl)benzyl)piperidin-2-one;
6-(2-ethyl-6-methoxybenzo[d]oxazol-7-yl)-1-(3-(2-methylthiazol-4-yl)benzyl)piperidin-2-one;
6-(6-methoxy-2,3-dihydrobenzo[b][1,4]dioxin-5-yl)-1-(3-(2-methylthiazol-4-yl)benzyl)piperidin-2-one;

6-(6-methoxy-2,3-dihydrobenzo[b][1,4]dioxin-5-yl)-1-(3-(5-methylthiazol-2-yl)benzyl)piperidin-2-one;
6-(2-methoxynaphthalen-1-yl)-1-(3-(pyrimidin-2-yl)benzyl)piperidin-2-one;
6-(2-methoxynaphthalen-1-yl)-1-(3-(5-methylthiazol-2-yl)benzyl)piperidin-2-one;
6-(2-methoxynaphthalen-1-yl)-1-(3-phenoxybenzyl)piperidin-2-one;
6-(5-methoxybenzo[d][1,3]dioxol-4-yl)-1-(3-(2-methylthiazol-4-yl)benzyl)piperidin-2-one;
6-(5-methoxybenzo[d][1,3]dioxol-4-yl)-1-(4-(trifluoromethoxy)benzyl)piperidin-2-one;
7-(2-(pyridin-4-yl)phenyl)-1-(3-(thiazol-2-yl)benzyl)azepan-2-one;
1-(3-(thiazol-2-yl)benzyl)-7-(2-(thiazol-5-yl)phenyl)azepan-2-one;
1-(3-(thiazol-2-yl)benzyl)-7-(2-(thiazol-4-yl)phenyl)azepan-2-one;
7-(2-(pyridin-3-yl)phenyl)-1-(3-(thiazol-2-yl)benzyl)azepan-2-one;
7-([1,1'-biphenyl]-2-yl)-1-(3-(thiazol-2-yl)benzyl)azepan-2-one;
6-(6-methoxybenzo[d]oxazol-7-yl)-1-(3-(2-methylthiazol-4-yl)benzyl)piperidin-2-one;
1-([1,1'-biphenyl]-3-ylmethyl)-6-(5-methoxybenzo[d][1,3]dioxol-4-yl)piperidin-2-one;
6-(5-methoxybenzo[d][1,3]dioxol-4-yl)-1-(3-phenoxybenzyl)piperidin-2-one;
6-(5-methoxybenzo[d][1,3]dioxol-4-yl)-1-((2-phenylthiazol-4-yl)methyl)piperidin-2-one;
(3S*,5S*)-3-chloro-5-(2-fluoro-6-methoxyphenyl)-1-(3-(trifluoromethoxy)benzyl)pyrrolidin-2-one;
(3S*,5S*)-1-(3-chloro-4-(trifluoromethoxy)benzyl)-5-(2-ethoxy-6-fluorophenyl)-3-fluoropyrrolidin-2-one;
(3S*,5S*)-3-chloro-1-(3-chloro-4-(trifluoromethoxy)benzyl)-5-(2-ethoxy-6-fluorophenyl)pyrrolidin-2-one; and
(3S*,5S*)-3-fluoro-5-(2-fluoro-6-methoxyphenyl)-1-(3-(trifluoromethoxy)benzyl)pyrrolidin-2-one;
or a pharmaceutically acceptable salt thereof.

12. A pharmaceutical composition comprising, as active principle, one or more compounds according to claim 1, or a pharmaceutically acceptable salt thereof, and at least one pharmaceutically acceptable carrier.

* * * * *